(12) United States Patent
Minor, Jr. et al.

(10) Patent No.: US 9,862,684 B2
(45) Date of Patent: Jan. 9, 2018

(54) MODULATION OF K2P CHANNELS

(71) Applicant: The Regents of the University of California, Oakland, CA (US)

(72) Inventors: Daniel L. Minor, Jr., San Francisco, CA (US); Sviatoslav N. Bagriantsev, Guilford, CT (US); Adam R. Renslo, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/815,480

(22) Filed: Jul. 31, 2015

(65) Prior Publication Data

US 2016/0031814 A1    Feb. 4, 2016

Related U.S. Application Data

(63) Continuation of application No. PCT/US2014/027611, filed on Mar. 14, 2014.

(60) Provisional application No. 61/785,155, filed on Mar. 14, 2013.

(51) Int. Cl.
| | |
|---|---|
| *C07D 209/88* | (2006.01) |
| *C07D 401/06* | (2006.01) |
| *A61K 31/5415* | (2006.01) |
| *A61K 31/404* | (2006.01) |
| *A61K 31/4045* | (2006.01) |
| *A61K 31/405* | (2006.01) |

(52) U.S. Cl.
CPC .......... *C07D 209/88* (2013.01); *A61K 31/404* (2013.01); *A61K 31/405* (2013.01); *A61K 31/4045* (2013.01); *A61K 31/5415* (2013.01); *C07D 401/06* (2013.01)

(58) Field of Classification Search
CPC ........................... C07D 209/88; C07D 401/06
USPC ....................................................... 514/297
See application file for complete search history.

(56) References Cited

U.S. PATENT DOCUMENTS

| | | | | |
|---|---|---|---|---|
| 3,498,986 A * | 3/1970 | Storni | ..................... | A61K 31/00 546/104 |
| 4,861,760 A | 8/1989 | Mazuel et al. | | |
| 4,911,920 A | 3/1990 | Jani et al. | | |
| 5,212,162 A | 5/1993 | Missel et al. | | |
| 5,403,841 A | 4/1995 | Lang et al. | | |
| 7,781,588 B1 * | 8/2010 | Wang | ................... | C07D 219/04 546/102 |
| 2004/0076648 A1 | 4/2004 | Williams et al. | | |
| 2012/0039804 A1 | 2/2012 | Diaz et al. | | |
| 2012/0252740 A1 | 10/2012 | Kozikowski et al. | | |
| 2012/0322060 A1 | 12/2012 | Mazella et al. | | |
| 2013/0040298 A1 | 2/2013 | Feinmark et al. | | |

FOREIGN PATENT DOCUMENTS

| | | | |
|---|---|---|---|
| WO | WO-2013/144931 A2 | 10/2013 | |
| WO | WO-2013/144931 A3 | 10/2013 | |

OTHER PUBLICATIONS

Yang et al. Organic Letters, (2006), 8(25), p. 5721-23.*
Maati et al. PLoSONE, (2011), 6(10), p. 1-10.*
Abu-Elfotoh, A.M. et al. (Nov. 2, 2010). "Asymmetric inter- and intramolecular cyclopropanation reactions catalyzed by a reusable macroporous-polymer-supported chiral ruthenium(II)/phenyloxazoline complex," *Angew Chem Int Engl* 49(45):8439-8443.
Bagriantsev, S.N. et al. (Aug. 16, 2013, e-published Jun. 17, 2013). "A high-throughput functional screen identifies small molecule regulators of temperature- and mechano-sensitive K2P channels," *ACS Chem Biol* 8(8):1841-1851.
Bagriantsev, S.N. et al. (Aug. 1, 2012; e-published Jun. 22, 2012). "Metabolic and thermal stimuli control K(2P)2.1 (TREK-1) through modular sensory and gating domains," *EMBO J* 31(15):3297-3308.
Bagriantsev, S.N. et al. (Jul. 15, 2011). "Multiple modalities converge on a common gate to control K2P channel function," *EMBO J* 30(17):3594-3606.
Bansode, T.N. et al. (Jun. 1, 2009). "Synthesis, antibacterial and antifungal activity of 1, 3-di(2-substituted 10H-phenothiazin-10-yl)propan-1-one," *Pharmaceutical Chemistry Journal* 43(6):311-314.
Belei, D. et al. (Jul. 15, 2012, e-published Jun. 9, 2012). "New farnesyltransferase inhibitors in the phenothiazine series," *Bioorg Med Chem Lett* 22(14):4517-4522.
Bøgesø, K.P. et al. (Jan. 1, 1971). "Some Tetrazole Derivatives of Phenothiazone," *Acta Chemica Scandinavica* 25(5):1889-1930.
Cadaveira-Mosquera, A. et al. (Jan. 26, 2011). "Activation of TREK currents by the neuroprotective agent riluzole in mouse sympathetic neurons," *J Neurosci* 31(4):1375-1385.
Chanthamath, S. et al. (Aug. 11, 2012, e-published Jun. 29, 2012). "Highly stereoselective Ru(II)-Pheox catalyzed asymmetric cyclopropanation of terminal olefins with succinimidyl diazoacetate," *Chem Commun (Camb)* 48(62):7750-7752.
Chen, C. et al. (Jan. 1, 2012). "Metal-free organic dyes derived from triphenylethylene for dye-sensitized solar cells: tuning of the performance by phenothiazine and carbazole," *Journal of Materials Chemistry* 22(18):8994.
Duprat, F. et al. (May 2000). "The neuroprotective agent riluzole activates the two P domain K(+) channels TREK-1 and TRAAK," *Mol Pharmacol* 57(5):906-912.
Enyedi, P. et al. (Apr. 2010). "Molecular background of leak K+ currents: two-pore domain potassium channels," *Physiol Rev* 90(20:559-605.
Ferorelli, S. et al. (Mar. 29, 2007). "Design and evaluation of naphthol- and carbazole-containing fluorescent sigma ligands as potential probes for receptor binding studies," *J Med Chem* 50(19):4648-4655.
Franks, N.P. et al. (Nov. 2004). "The TREK K2P channels and their role in general anaesthesia and neuroprotection," *Trends Pharmacol Sci* 25(11):601-608.

(Continued)

*Primary Examiner* — Yong Chu
(74) *Attorney, Agent, or Firm* — Mintz Levin Cohn Ferris Glovsky and Popeo, P.C.

(57) ABSTRACT

Disclosed herein inter alia are compositions and methods useful in the treatment of diseases, for example pain, neurodegeneration, or mood disorders, and for modulating the activity of a $K_{2P}$ channel.

20 Claims, 29 Drawing Sheets

(56) References Cited

OTHER PUBLICATIONS

Godefroi, E.F. et al. (Oct. 1, 1956). "The Preparation of Some Derivatives of β-(10-Phenothiazinyl) propionic Acid and β-(2-Chloro-10-phenothiazinyl) propionic Acid," *The Journal of Organic Chemistry* 21:1163-1168.

Gruss, M. et al. (Feb. 2004). "Two-pore-domain K+ channels are a novel target for the anesthetic gases xenon, nitrous oxide, and cyclopropane," *Mol Pharmacol* 65(2):443-452.

Heurteaux, C. et al. (Jul. 7, 2004, e-published Jun. 3, 2004). "TREK-1, a K+ channel involved in neuroprotection and general anesthesia," *Embo J* 23(13):2684-2695.

Heurteaux, C. et al. (Sep. 2006, e-published Aug. 13, 2006). "Deletion of the background potassium channel TREK-1 results in a depression-resistant phenotype," *Nat Neurosci* 9(9):1134-1141.

Honore, E. (Apr. 2007). "The neuronal background K2P channels: focus on TREK1," *Nat rev Neurosci* 8(4):251-261.

Hu, L. et al. (Oct. 19, 2006). "Synthesis and structure-activity relationships of carbazole sulfonamides as a novel class of antimitotic agents against solid tumors," *J Med Chem* 49(21):6273-6282.

Infelta, P.P. et al. (Feb. 27, 1980). "Aspects of Artificial Photosynthesis, Photosensitized Electron Transfer and Charge Separation in Cationic Surfactant Vesicles," *Journal of the American Chemical Society* 102(5):1479-1483.

International Search Report dated Apr. 2, 2015, for PCT Application No. PCT/US2014/027611, filed on Mar. 14, 2014, 2 pages.

Judge, S. et al. (Apr. 2009). "Patents related to therapeutic activation of K(ATP) and K(2P) potassium channels for neuroprotection: ischemic/hypoxic/anoxic injury and general anesthetics," *Expert Opin Ther Pat* 19(4):433-460.

Kennard, L.E. et al. (Mar. 20050. "Inhibition of the human two-pore domain potassium channel, TREK-1, by fluoxetine and its metabolite norfluoxetine," *Br J. Pharmacol* 144(6):821-829.

Lehmann, F. et al. (Sep. 6, 2004). "Discovery of inhibitors of human adipocyte fatty acid-binding protein, a potential type 2 diabetes target," *Bioorg Med Chem Lett* 14(17):4445-4448.

Lesage, F. et al. (Dec. 2011). "Molecular physiology of pH-sensitive background K(2P) channels," *Physiology* (Bethesda) 26(6):424-437.

Lotshaw, D.P. (2007). "Biophysical, pharmacological, and functional characteristics of cloned and native mammalian two-pore domain K+ channels," *Cell Biochem Biophys* 47(2):209-256.

Mathie, A. et al. (2007). "Therapeutic potential of neuronal two-pore domain potassium-channel modulators," *Curr Opin Investig Drugs* 8(7):555-562.

Minor, D.L. Jr. Aug. 2009, e-published Jun. 19, 2009). "Searching for interesting channels: pairing selection and molecular evolution methods to study ion channel structure and function," *Mol Biosyst* 5(8);802-810.

Molnar, I. et al. (Jan. 1, 1965). "Snythese von in 10-Stellung basisch substituierten 9,9-Dialkylacridanen)" *Helvetica Chimica Acta* 1782-1791.

Noel, J. et al. (Sep.-Oct. 2011, e-published Sep. 1, 2011). "Molecular regulations governing TREK and TRAAK channel functions," *Channels* (Austin) 5(5):402-409.

Park, J.H. et al. (Nov. 2012, e-published Oct. 12, 2012). "Photocatalysis by phenothiazine dyes: visible-light-driven oxidative coupling of primary amines at ambient temperature," *Org Lett* 14(21):5502-5505.

Peterson, J.R. et al. (Jul. 4, 2004, e-published Jul. 4, 2004). "Chemical inhibition of N-WASP by stabilization of a native autoinhibited conformation," Nat Struct Mol Biol 11(8):747-755.

Petrov, V.A. et al. (Jun. 18, 2011). "Simple synthesis of 1,1-bis(trifluoromethyl) cyclopropanes," *Journal of Fluorine Chemistry* 133:61-66.

Pilger, B.D. et al. (May 2004). "Identification of a Small Molecule that Inhibits Herpes Simplex Virus DNA Polymerase Subunit Interactions and Viral Replication," *Chemistry & Biology* 11:647-654.

Punke, M.A. et al. (Jun. 2003). "Inhibition of human TREK-1 channels by bupivacaine," *Anesth Analg* 96(6):1665-1673.

Sailer, M. et al. (Sep. 1, 2003). "Practical synthesis of iodo phenothiazines. A facile access to electrophore building blocks," *J Org Chem* 68(19):7509-7512.

Su, L. et al. (Jul. 2006, e-published May 23, 2006). "Synthesis and self-assembly of dichalcone substituted carbazole-based low-molecular mass organogel," *Org Biomol Chem* 4(13):2591-2594.

Takahira, M. et al. (Dec. 2005, e-published Aug. 2, 2005). "Fenamates and diltiazem modulate lipid-sensitive mechano-gated 2P domain K(+) channels," *Plfugers Arch: Eur J Physiol* 451;474-478.

Tang, W. et al. (Sep. 1995). "Functional expression of a vertebrate inwardly rectifying K+ channel in yeast," *Mol Biol Cell* 6(9):1231-1240.

Tertyshnikova, S. et al. (Apr. 2005, e-published Dec. 17, 2004). "BL-1249 [(5,6,7,8-tetrahydro-naphthalen-1-yl)-[2-(1H-tetrazol-5-yl)-phenyl]-amine]: a putative potassium channel opener with bladder-relaxant properties," *J Pharmacol Exp Ther* 313(1):250-259.

Tian, Y. et al. (Apr. 1, 2004). Two Novel Two-Photon Polymerization Initiators with Extensive Application Prospects, Chemical Physics Letters 388:4-6.

Written Opinion dated Apr. 2, 2015, for PCT Application No. PCT/US2014/027611, filed on Mar. 14, 2014, 6 pages.

Zaks-Makhina, E. et al. Jan. 2004). "Novel neuroprotective K+ channel inhibitor identified by high-throughput screening in yeast," *Mol Pharmacol* 65(1);214-219.

Zhang, Y. et al. (Feb. 1, 2007, e-published Nov. 2, 2006). "Design, synthesis, and evaluation of efflux substrate-metal chelator conjugates as potential antimicrobial agents," *Bioorg Med Chem Lett* 17(3):707-711.

Molnar, I. et al. (May 1, 1965). "Synthesis of 9,9-Dialkylacridans with Alkaline Substitution in Position 10," *Helvetica Chimica Acta* 48(7):1782-1791. (English Translation).

* cited by examiner

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| A | 0 | 5 | 20 | 21 | 1 | 4 | -7 | 16 | -13 | 97 | -6 | -1 | -8 | 3 | -18 | 71 | -12 | 11 | 15 | 31 | 17 | -13 | 102 |
| B | 10 | 2 | 27 | -7 | -111 | -8 | -1 | 17 | 4 | 25 | 17 | 16 | -47 | -3 | 23 | 10 | 29 | -2 | -5 | 14 | 24 | -32 | 101 |
| C | -5 | 3 | -22 | -1 | -8 | -2 | -11 | 24 | -10 | -5 | 89 | 7 | 6 | -8 | -7 | 3 | -14 | -8 | 24 | 22 | -30 | 57 | 102 |
| D | 7 | -1 | -2 | -1 | 11 | 17 | 6 | -1 | -1 | -6 | 5 | -9 | -10 | -9 | 1 | -7 | -8 | -3 | 10 | 15 | -43 | 84 | 101 |
| E | -10 | -8 | -17 | 29 | -27 | -25 | -23 | -13 | -12 | 40 | -5 | 9 | -19 | -120 | -13 | 18 | -40 | -12 | 2 | 14 | 3 | -30 | 97 |
| F | -5 | -3 | -6 | 4 | -3 | -34 | -28 | -16 | 17 | 22 | -5 | -21 | -6 | -13 | 11 | -13 | -12 | -26 | -9 | -13 | 28 | -11 | 98 |
| G | -2 | 3 | -4 | -13 | -13 | -1389 | 10 | 10 | 15 | 20 | 20 | 18 | 11 | 93 | -2 | 14 | 5 | 15 | -14 | 1 | -13 | 26 | 98 |
| H | 17 | 4 | 50 | -4 | 35 | -9 | 6 | -2 | 5 | -19 | 27 | 17 | 98 | -6 | 14 | 12 | 4 | -12 | 24 | -15 | 22 | -34 | 101 |
| I | 1 | -2 | -6 | -8 | 10 | 22 | -6 | -11 | -8 | 19 | -7 | -8 | 31 | 53 | -9 | -9 | 12 | 26 | -11 | 0 | 22 | 6 | 101 |
| J | 9 | -5 | 19 | -6 | 2 | -2 | -3 | -12 | 17 | -11 | 11 | -11 | -2 | 8 | -6 | -5 | -6 | -12 | -14 | -9 | 12 | -32 | 100 |
| K | -4 | -7 | -16 | -15 | -9 | 3 | -24 | -8 | 10 | -14 | 2 | -16 | -15 | -7 | 15 | 48 | -12 | -25 | -16 | 24 | 19 | 29 | 99 |
| L | -2 | -2 | 84 | -6 | -106 | -15 | 13 | -17 | 8 | -3 | -16 | -12 | 7 | -22 | -6 | -21 | 38 | -23 | -10 | -8 | 6 | -42 | 101 |
| M | -5 | 6 | 23 | 1 | -3 | 3 | -1 | 12 | 18 | 2 | -2 | -4 | 0 | 23 | -10 | -4 | -2 | 3 | 2 | 12 | 21 | -33 | 101 |
| N | 14 | 0 | 3 | 0 | 96 | -5 | 17 | 1 | 42 | 2 | 2 | -8 | -523 | -4 | 36 | -13 | 32 | -4 | 6 | 29 | 16 | -13 | 100 |
| O | -9 | 4 | -15 | -4 | -3 | 3 | -5 | 2 | 4 | 6 | -15 | -9 | 3 | 14 | -26 | -6 | 1 | 53 | -12 | 13 | 18 | -21 | 98 |
| P | -6 | -8 | -5 | -9 | 14 | -6 | -9 | -18 | -2 | -3 | 55 | 7 | 10 | -15 | -11 | -8 | -12 | 1 | -1 | -1 | 2 | 17 | 98 |

0% inhibition control (1% DMSO), columns 1-2
Library Compounds, columns 3-22
100% inhibition control (0.1% SDS), column 23 numbers: % growth inhibition

|  | 0% inhibition control | 100% inhibition control | Z' |
|---|---|---|---|
| Alamar Blue mean fluorescence, AU | 60.6 | 14.4 | 0.76 |
| s.d. | 3.05 | 0.712 |  |

HTS score    SMILES and chemical names

66%    Cc1cccc(c1)n1ncc2c(NCCc3CCCCC3)ncnc12

N-phenethyl-1-(m-tolyl)-1H-pyrazolo[3,4-d]
pyrimidine-4-amine

B

HTS score: 57%

SMILES and chemical names

Clc1ccc(cc1)CNC(=O)c1c(sc(C)c1C)n1cccc1

N-[(4-chlorophenyl)methyl]-4,5-dimethyl-2-(1H-pyrrol-1-yl)thiophene-3-carboxamide

Functional Test

A

HTS score   SMILES and chemical names

59%   Fc1ccc(cc1)/C=C\1SC(=O)N(CN2CCCCC2)C1=O 5-(4-fluorobenzylidene(-3-(1-piperidinylmethyl)-1,3-thiazolidine-2,4-dione

B

ML42

HTS score   SMILES and chemical names

65%   OC(=O)COC=CC=C(C=C1)C12CC3CC(CC(CC(C3)C1)C2

2-[4-(adamantan-1-yl)phenoxy]acetic acid

Functional Test

HTS score    SMILES and chemical names

66%     ClC1=CC=C(N(CCC(O)C3=C2C=C(Cl)C=C3)C2=C1

3-(3,6-Dichloro-carbazol-9-yl)propionic acid i) Me$_2$SO$_4$, K$_2$CO$_3$, acetone; ii) 3M MeLi, DEM; iii) 85% H$_3$PO$_4$;
iv) acrylonitrile, triton-B; v) SO$_2$Cl$_2$, DCM; vi) NaN$_3$, NH$_4$Cl, DMF.

MODULATION OF K2P CHANNELS

CROSS-REFERENCES TO RELATED APPLICATIONS

This application is a continuation of PCT Application No. PCT/US2014/027611, filed Mar. 14, 2014, which claims the benefit of U.S. Provisional Patent Application No. 61/785,155, filed Mar. 14, 2013, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. R01 MH093603 and R01 NS049272 awarded by the National Institutes of Health. The government has certain rights in the invention.

BACKGROUND OF THE INVENTION $K_{2P}$ channels regulate electrical activity in various tissues through generation of a plasma membrane background 'leak' potassium conductance {Enyedi, 2010; Lesage, 2011}. Channels from this family are found in both excitable and non-excitable cells and have been implicated vasodilation, respiratory control, nociception, neuroprotection, anesthesia, and anti-depressant responses {Es-Salah-Lamoureux, 2010; Enyedi, 2010; Lesage, 2011}. Due to their involvement in pain, ischemia, and migraine, $K_{2P}$s have been proposed as therapeutic targets for a range of cardiovascular and neurological disorders {Mathie, 2007 #867; Bayliss, 2008; Es-Salah-Lamoureux, 2010}; however, despite this considerable interest, the $K_{2P}$ family is poorly responsive to classic potassium channel blockers {Lotshaw, 2007} and remains practically pharmacologically orphaned {Es-Salah-Lamoureux, 2010; Lesage, 2011; Bayliss, 2008}. Further, the development of specific $K_{2P}$ pharmacology has been hindered by the scarcity of facile methods to detect potassium flux in cells and by the fact that the channels produce a 'leak' current that is a challenge for conventional electrophysiological screening assays. Thus, there has been a need to develop new, robust screening strategies that could identify $K_{2P}$ modulators. Disclosed herein, inter alia, are solutions to these and other problems in the art.

BRIEF SUMMARY OF THE INVENTION

In a first aspect is provided a method of treating a disease in a patient in need of such treatment, the method including administering a therapeutically effective amount of a compound to the patient, wherein the disease is selected from the group consisting of a neurological disease, pain, migraine, ischemic injury, brain ischemia, stroke, a neurodegenerative disease, a mood disorder, depression, and decompression sickness; and wherein the compound is a compound described herein, including embodiments (e.g. compound of formula I, II, III, IV, V, or VI).

In a second aspect is provided a method of modulating the level of activity of TREK-1 in a cell including contacting the cell with an effective amount of a compound as described herein, including embodiments (e.g. compound of formula I, II, III, IV, V, or VI).

In a third aspect is provided a compound, or a pharmaceutically acceptable salt thereof, having the formula:

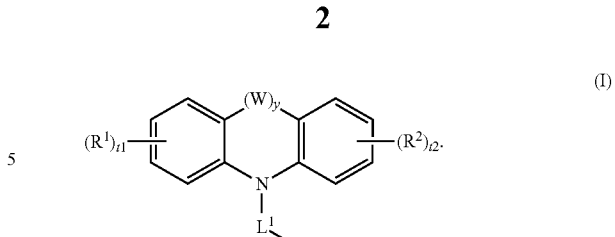

$L^1$ is a substituted or unsubstituted $C_1$-$C_{10}$ alkylene, substituted or unsubstituted 2 to 10 membered heteroalkylene, or substituted or unsubstituted $C_3$-$C_6$ cycloalkylene. $L^2$ is a bond, —O—, —S—, —NH—, —C(O)—, —C(O)NH—, —NHC(O)—, —S(O)—, or —S(O)$_2$—. $R^1$, $R^2$, $R^4$, and $R^5$ are independently hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

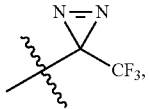 [SMILES: *C1(C(F)(F)F)N=N1]

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^4$ and $R^5$ may optionally be joined to form a substituted or unsubstituted cycloalkyl or substituted or unsubstituted heterocycloalkyl. $R^3$ is hydrogen, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$) C=(O)R$^9$, —NR$^7$C(O)—OR$^9$, —NR$^7$OR$^9$, —OCX$_3$, —OCHX$_2$, —OPO(OH)$_2$, —PO(OH)$_2$, —SO$_3$H, —SO$_4$H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$, are independently hydrogen, oxo, halogen, —C(O)CH$_3$, —CF$_3$, —CCl$_3$, —CN, —OH, —NH$_2$, —COOH, —CONH$_2$, —NO$_2$, —SO$_2$Cl, —SO$_3$H, —SO$_4$H, —SO$_2$NH$_2$, —NHNH$_2$, —ONH$_2$, —NHC=(O)NHNH$_2$, —NHC=(O)CH$_3$, —NHC=(O)NH$_2$, —NHSO$_2$H, —NHC=(O)H, —NHC(O)—OH, —NHOH, —OCF$_3$, —OCHF$_2$, —N$_3$,

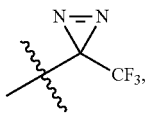 [SMILES: *C1(C(F)(F)F)N=N1]

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. The symbol W is —O—, —S—, —S(O)—, —S(O)₂—, or —C(R⁴)(R⁵)—. The symbol y is 0 or 1. The symbols t1 and t2 are independently 1 to 4.

In a fourth aspect is provided a compound, or a pharmaceutically acceptable salt thereof, having the formula:

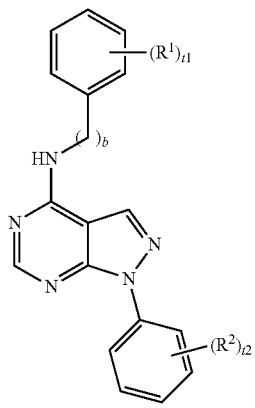
(III)

wherein R¹ and R² are independently halogen, —CF₃, —CCl₃, —CN, —OH, —NH₂, —COOH, —CONH₂, —NO₂, —SH, —OCF₃, —OCHF₂, unsubstituted $C_1$-$C_5$ alkyl, or unsubstituted 2 to 5 membered heteroalkyl; the symbol b is an integer from 1 to 5, the symbol t1 is an integer from 0 to 5; and the symbol t2 is an integer from 0 to 5.

In a fifth aspect is provided a compound, or a pharmaceutically acceptable salt thereof, having the formula:

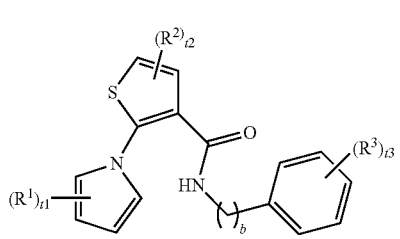
(IV)

wherein R¹, R², and R³ are independently halogen, —CF₃, —CCl₃, —CN, —OH, —NH₂, —COOH, —CONH₂, —NO₂, —SH, —OCF₃, —OCHF₂, unsubstituted $C_1$-$C_5$ alkyl, or unsubstituted 2 to 5 membered heteroalkyl; the symbol b is an integer from 1 to 5, the symbol t1 is an integer from 0 to 4; the symbol t2 is an integer from 0 to 2; and the symbol t3 is an integer from 0 to 5.

In a sixth aspect is provided a compound, or a pharmaceutically acceptable salt thereof, having the formula:

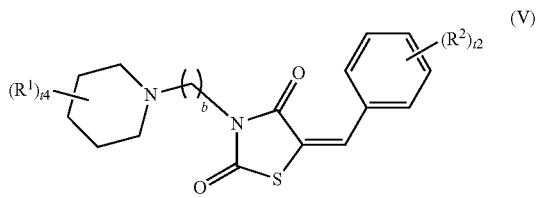
(V)

wherein R¹ and R² are independently halogen, —CF₃, —CCl₃, —CN, —OH, —NH₂, —COOH, —CONH₂, —NO₂, —SH, —OCF₃, —OCHF₂, unsubstituted $C_1$-$C_5$ alkyl, or unsubstituted 2 to 5 membered heteroalkyl; the symbol b is an integer from 1 to 5, the symbol t4 is an integer from 0 to 10; and the symbol t2 is an integer from 0 to 5.

In a seventh aspect is provided a compound, or a pharmaceutically acceptable salt thereof, having the formula:

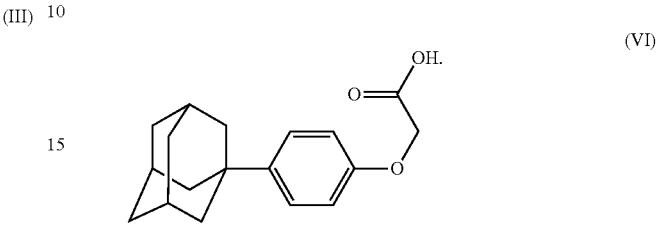
(VI)

In an eighth aspect is provided a pharmaceutical composition including a pharmaceutically acceptable excipient and a compound, or pharmaceutically acceptable salt thereof, as described herein, including embodiments (e.g. compound of formula I, II, III, IV, V, or VI).

BRIEF DESCRIPTION OF THE DRAWINGS

FIG. 8 Upper panel, A 384-well plate showing calculated growth of SGY1528 yeast expressing $K_{2P}2.1$ (TREK-1) after 48 hour incubation in 2 mM KCl media in the presence of library compounds (10 µM, 1% DMSO) and controls. Growth was assessed by measuring fluorescence (560 nm excitation/590 nm emission) after the addition of the vital dye Alamar Blue at the end of incubation. The numbers show percent of growth inhibition caused by the compounds relative to 1% DMSO or 0.1% SDS (0 and 100% inhibition controls, respectively). Lower panel, A summary table showing assay performance statistics.

Figure 1:
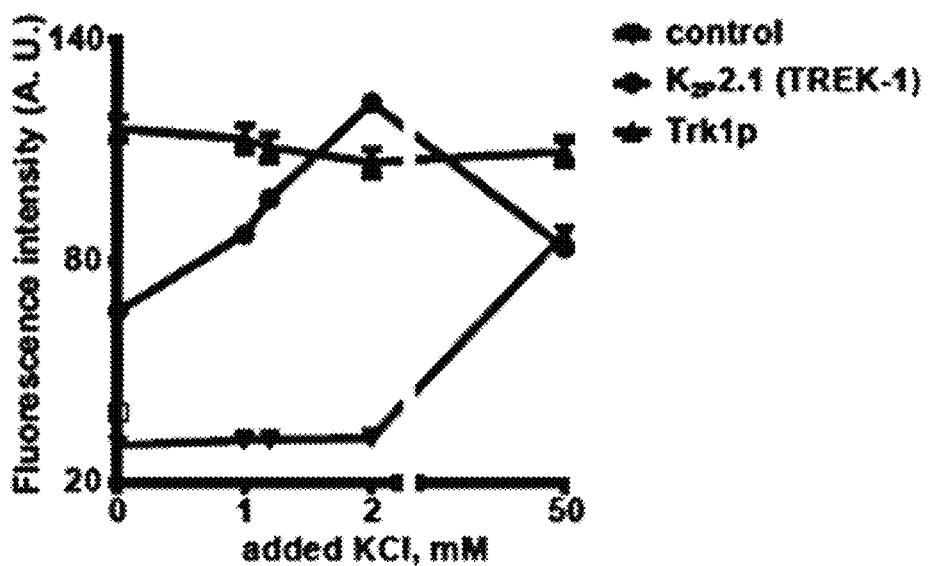
FIG. 1 Yeast screen identifies small molecule modulators of $K_{2P}2.1$ (TREK-1) a, resazurin (Alamar blue) measurement of the effect of potassium concentration on growth of SGY1528 yeast expressing indicated constructs in 386-well plates for 24 hours; error bars show ±s.e., n=16; for some points, the error bars are smaller than the symbols. b, scatter plot showing distribution of growth inhibition scores from a representative 384-well screening plate; each point represents quantification of growth of $K_{2P}2.1$ (TREK-1)-expressing yeast in a single well supplemented with 2 mM KCl; end-point Resazurin fluorescence was measured in each well and normalized to 0 and 100% growth inhibition controls (1% DMSO and 0.1% SDS, respectively) from the same 384-well plate. Error bars show ±s.d; c, and d, dose-response comparison of the effects of c, ML67 and d, ML45 on growth inhibition of yeast expressing $K_{2P}2.1$ (TREK-1) (filled circles) or TRK1p (triangles); compound structures are shown.
Figure 1:
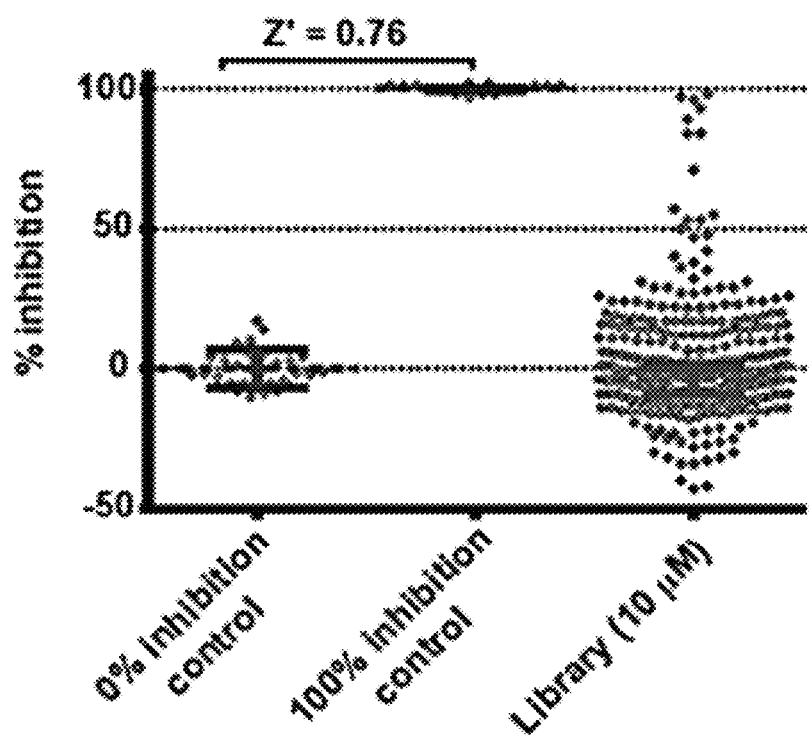
Figure 1:
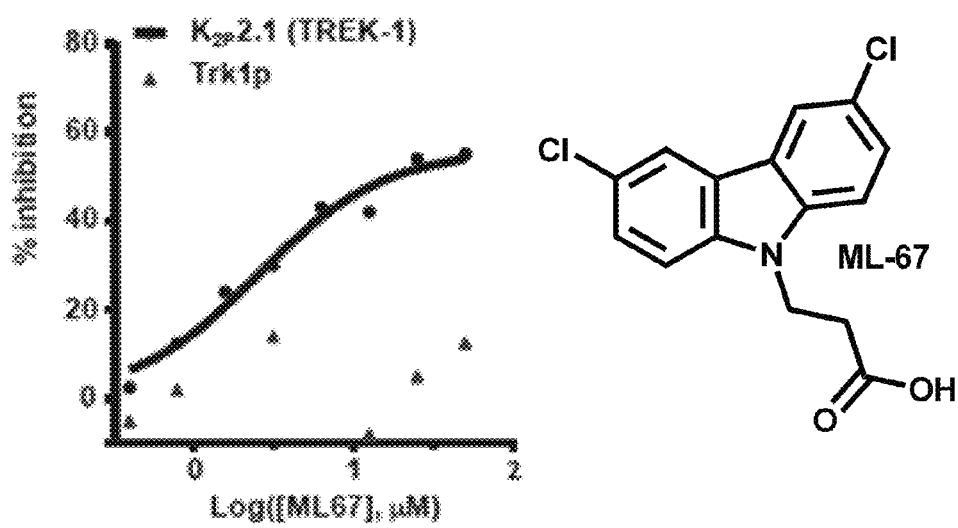
Figure 1:
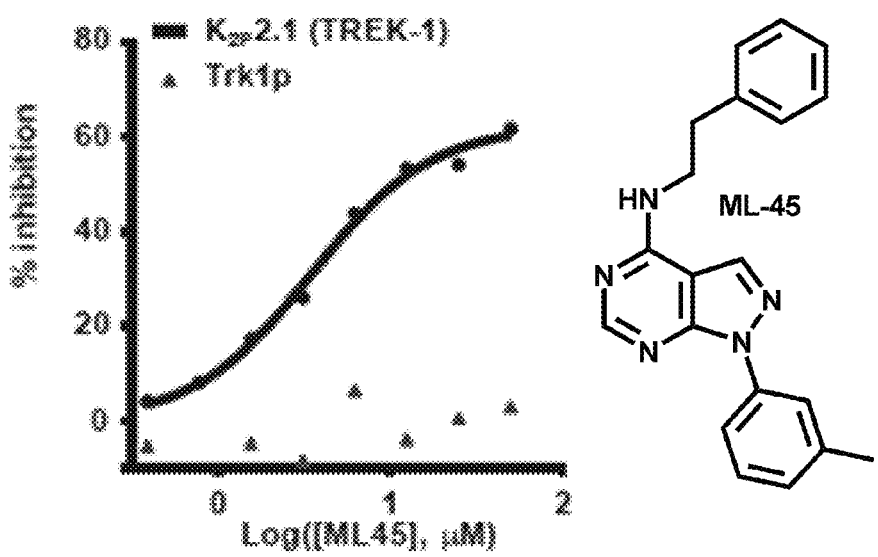

DETAILED DESCRIPTION OF THE INVENTION $K_{2P}$ potassium channels generate potassium currents that are active over the entire membrane potential range. This 'leak' behavior strongly influences cellular excitability and contributes to pain perception, somatosensation, anesthesia, and mood. Despite the physiological importance of this channel class, $K_{2P}$s lack specific pharmacology. This situation is complicated further by the challenge posed by the leak nature of $K_{2P}$ currents for electrophysiology-based high throughput screening strategies. Here, we present a yeast based high-throughput screening assay that avoids this problem. Using a simple growth-based functional readout, we screened a library of 105,863 compounds and identified two new inhibitors and three new activators of the mammalian $K_{2P}$ channel, $K_{2P}2.1$ (TREK 1). Combination of biophysical analysis, structure-activity studies, and mechanistic analysis produced ML67-33, a low micromolar selective activator of heat- and mechano-sensitive $K_{2P}$ channels that acts on the extracellular selectivity filter-based C-type gate and that reversibly increases channel currents by >10 fold. These new $K_{2P}$ modulators, together with the yeast-based assay, should facilitate both mechanistic and physiological tests of $K_{2P}$ activity as well as the further discovery of other $K_{2P}$ small molecule modulators.

A. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a non-cyclic straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —NRNR"R'", —ONR'R", —NR'C=(O)NR"NR'"R"", —CN, —$NO_2$, —R', —$N_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C''R''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, —OPO(OH)$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, —OPO(OH)$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, —OPO(OH)$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, —OPO(OH)$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomic mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "~" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat pain, depression, a mood disorder, ischemic injury, stroke, neurodegeneration (e.g. due to disease, ischemic injury, stroke, or traumatic brain injury), migraine, and/or decompression sickness. For example certain methods herein treat pain by decreasing the perception of pain or reducing the severity of pain, treat neurodegeneration by improving mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival, treat decompression sickness by reducing a symptom of decompression sickness, treat depression by decreasing a symptom of depression, treat a mood disorder by decreasing a symptom of a mood disorder, treat pain by decreasing a symptom of pain, treat migraine by decreasing a symptom of migraine (e.g. pain), treat neurodegeneration by treating a symptom of neurodegeneration, treat ischemic injury by treating a symptom of ischemic injury, treat stroke by decreasing a symptom of stroke. Symptoms of pain, migraine, depression, a mood disorder, ischemic injury, stroke, neurodegeneration (e.g. due to disease, ischemic injury, stroke, or traumatic brain injury), decompression sickness would be known or may be determined by a person of ordinary skill in the art. The term "treating" and conjugations thereof, include prevention of an injury, pathology, condition, or disease (e.g. preventing the development of one or more symptoms of pain, migraine, depression, a mood disorder, ischemic injury, stroke, neurodegeneration (e.g. due to ischemic injury, stroke, or traumatic brain injury), or decompression sickness).

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. neurological disease, pain, migraine, depression, a mood disorder, ischemic injury, stroke, neurodegeneration (e.g. due to disease, ischemic injury, stroke, or traumatic brain injury), or decompression sickness) means that the disease (e.g. neurological disease, pain, migraine, depression, a mood disorder, ischemic injury, stroke, neurodegeneration (e.g. due to ischemic injury, stroke, or traumatic brain injury), or decompression sickness) is caused by (in whole or in part), or a symptom of the disease is caused by (in whole or in part) the substance or substance activity or function. For example, a symptom of a disease or condition associated with a reduction in the level of TREK-1 activity may be a symptom that results (entirely or partially) from a reduction in the level of TREK-1 activity (e.g. loss of function mutation or gene deletion or modulation of TREK-1 signal transduction pathway). As used herein, what is described as being associated with a disease, if a causative agent, could be a target for treatment of the disease. For example, a disease associated with TREK-1, may be treated with an agent (e.g. compound as described herein) effective for increasing the level of activity of TREK-1. For example, a disease associated with TREK-1, may be treated with an agent (e.g. compound as described herein) effective for decreasing the level of activity of TREK-1.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. TREK-1). In some embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein (e.g. TREK-1) relative to the activity or function of the protein in the absence of the activator (e.g. compound described herein). In some embodiments, activation refers to an increase in the activity of a signal transduction pathway or signaling pathway (e.g. TREK-1 pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of TREK-1 activity or protein associated with pain, migraine, depression, a mood disorder, ischemic injury, stroke, neurodegeneration (e.g. due to ischemic injury, stroke, or traumatic brain injury), or decompression sickness). Activation may include, at least in part, partially or totally increasing stimulation, increasing or enabling activation, or activating, sensitizing, or up-regulating signal transduction or enzymatic activity or the amount of a protein (e.g. TREK-1) that may modulate the level of another protein or increase cell survival (e.g. increase in TREK-1 activity may increase cell survival in cells that may or may not have a reduction in TREK-1 activity relative to a non-disease control).

The term "modulator" refers to a composition that increases or decreases the level of a target molecule or the function of a target molecule. In some embodiments, a modulator of TREK-1 is a compound that reduces the severity of one or more symptoms of a disease associated with TREK-1 (e.g. disease associated with a reduction of the level of TREK-1 activity or protein, for example neurological disease, pain, migraine, depression, a mood disorder, ischemic injury, stroke, neurodegeneration (e.g. due to ischemic injury, stroke, or traumatic brain injury), or decompression sickness) or a disease that is not caused by TREK-1 (e.g. loss of TREK-1 function) but may benefit from modulation of TREK-1 activity (e.g. increase in level of TREK-1 or TREK-1 activity). In embodiments, a modulator of TREK-1 is an analgesic. In embodiments, a modulator of TREK-1 is an anesthetic. In embodiments, a modulator of TREK-1 is a neuroprotectant. In embodiments, a modulator of TREK-1 is an anti-depressant. In embodiments, a modulator of TREK-1 is a mood altering composition.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with a compound, pharmaceutical composition, or method provided herein. In some embodiments, the disease is a disease related to (e.g. caused by) a reduction in the level of TREK-1. In some embodiments, the disease is a disease related to (e.g. caused by) neurodegeneration. In some embodiments, the disease is a disease related to (e.g. caused by) neural cell death. In some embodiments, the disease is a disease related to (e.g. caused by) a reduction in the level of TREK-1 activity. In some embodiments, the disease is stroke. In some embodiments, the disease is a neurodegenerative disease. In some embodiments, the disease is pain. In some embodiments, the disease is a migraine. In some embodiments, the disease is ischemic injury. In some embodiments, the disease is decompression sickness. In some embodiments, the disease is a neurological disease, wherein the term neurological disease is used in accordance with its common meaning and refers to a disease of the nervous system (e.g. brain, spinal cord, and/or nerves). Examples of neurological diseases include neurodegenerative diseases (e g Alzheimer's disease, prion diseases, Parkinson's disease, Huntington's disease), diseases of the blood vessels of the brain (e.g. stroke), traumatic injuries to the brain or spinal cord, brain ischemia, and epilepsy.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, stroke, ischemic injury, or decompression sickness.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. neurological disease therapies, anesthetics, analgesics, neuroprotectants). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. TREK-1), and/or reducing, eliminating, or slowing the progression of disease symptoms (e.g. symptoms of pain, migraine, depression, a mood disorder, ischemic injury, stroke, neurodegeneration (e.g. due to disease, ischemic injury, stroke, or traumatic brain injury), or decompression sickness). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms neurological disease, pain, neurodegeneration, decompression sickness, depression, a mood disorder, ischemia, and severity of such symptoms), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating pain, migraine, depression, a mood disorder, ischemic injury, stroke, neurodegeneration (e.g. due to disease, ischemic injury, stroke, or traumatic brain injury), or decompression sickness, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for pain, migraine, depression, a mood disorder, ischemic injury, stroke, neurodegeneration (e.g. due to disease, ischemic injury, stroke, or traumatic brain injury), or decompression sickness such as surgery.

The term "TREK-1" or "KCNK2" refers to the protein "Potassium channel subfamily K member 2". In embodiments, TREK-1 refers to the human protein TREK-1. In embodiments, TREK-1 refers to a homolog of the human protein TREK-1. Included in the term TREK-1 are the wildtype and mutant forms of the protein. In embodiments, TREK-1 refers to the protein associated with Entrez Gene 3776, OMIM 603219, UniProt O95069, and/or RefSeq (protein) NP 001017424. In embodiments, TREK-1 refers to the protein associated with one or more of the database entries listed immediately above at the time of filing of the present application.

The term "TREK-2" or "KCNK10" refers to the protein "Potassium channel subfamily K member 10". In embodiments, TREK-2 refers to the human protein TREK-2. In embodiments, TREK-2 refers to a homolog of the human protein TREK-2. Included in the term TREK-2 are the wildtype and mutant forms of the protein. In embodiments, TREK-2 refers to the protein associated with Entrez Gene 54207, OMIM 605873, UniProt P57789, and/or RefSeq (protein) NP 066984. In embodiments, TREK-2 refers to the protein associated with one or more of the database entries listed immediately above at the time of filing of the present application.

The term "TRAAK" or "KCNK4" refers to the protein "Potassium channel subfamily K member 4". In embodiments, TRAAK refers to the human protein TRAAK. In embodiments, TRAAK refers to a homolog of the human protein TRAAK. Included in the term TRAAK are the wildtype and mutant forms of the protein. In embodiments, TRAAK refers to the protein associated with Entrez Gene 50801, OMIM 605720, UniProt Q9NYG8, and/or RefSeq (protein) NP 201567. In embodiments, TRAAK refers to the protein associated with one or more of the database entries listed immediately above at the time of filing of the present application.

A. Methods of Treatment

In a first aspect is provided a method of treating a disease in a patient in need of such treatment, the method including administering a therapeutically effective amount of a compound to the patient, wherein the disease is selected from the group consisting of a neurological disease, pain, ischemic injury, brain ischemia, stroke, a neurodegenerative disease, a mood disorder, depression, and decompression sickness; and wherein the compound is a compound described herein, including embodiments (e.g. compound of formula I, II, III, IV, V, or VI).

In embodiments, the compound has the formula:

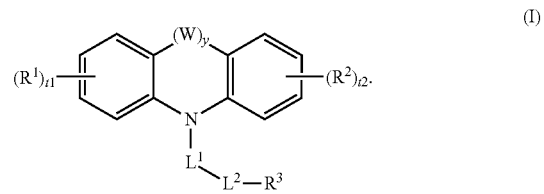

(I)

$L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is a bond, —O—, —S—, —NH—, —C(O)—, —C(O)NH—, —NHC(O)—, —S(O)—, or —S(O)$_2$—. $R^1$, $R^2$, $R^4$, and $R^5$ are independently hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

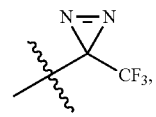 [SMILES: *C1(C(F)(F)F)N=N1]

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, —CCH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^4$ and $R^5$ may optionally be joined to form a substituted or unsubstituted cycloalkyl or substituted or unsubstituted heterocycloalkyl. $R^3$ is hydrogen, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$)C=(O)R$^9$, —NR$^7$C(O)—OR$^9$, —NR$^7$OR$^9$, —OCX$_3$, —OCHX$_2$, —OPO(OH)$_2$, —PO(OH)$_2$, —C(O)NR$^7$S(O)$_2$R$^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$, are independently hydrogen, oxo, halogen, —C(O)CH$_3$, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)CH$_3$, —NHC=(O)NH$_2$, —NHSO$_2$H, —NHC=(O)H, —NHC(O)—OH, —NHOH, —OCHF$_2$, —N$_3$,

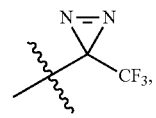 [SMILES: *C1(C(F)(F)F)N=N1]

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. The symbol W is —O—, —S—, —S(O)—, —S(O)$_2$—, or —C(R$^4$)(R$^5$)—. The symbol y is 0 or 1. The symbols m and v are independently 1 or 2. The symbol n is independently 0 to 4. The symbols t1 and t2 are independently 1 to 4. The symbol X is independently —Cl, —Br, —I, or —F.

In embodiments, the compound has the formula:

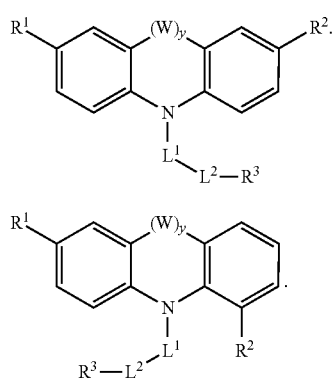

In embodiments, the compound has the formula:

In embodiments, $L^1$ is an unsubstituted $C_1$-$C_{10}$ alkylene. In embodiments, $L^1$ is an unsubstituted $C_1$-$C_8$ alkylene. In embodiments, $L^1$ is an unsubstituted $C_1$-$C_6$ alkylene. In embodiments, $L^1$ is an unsubstituted $C_1$-$C_4$ alkylene. In embodiments, $L^1$ is an unsubstituted saturated $C_1$-$C_{10}$ alkylene. In embodiments, $L^1$ is an unsubstituted $C_1$-$C_{10}$ alkenylene. In embodiments, $L^1$ is an unsubstituted polyunsaturated $C_1$-$C_{10}$ alkenylene. In embodiments, $L^1$ is an unsubstituted $C_3$-$C_6$ cycloalkylene. In embodiments, $L^1$ is an unsubstituted $C_4$-$C_6$ cycloalkylene. In embodiments, $L^1$ is an unsubstituted $C_5$-$C_6$ cycloalkylene. In embodiments, $L^1$ is an unsubstituted $C_3$-$C_5$ cycloalkylene. In embodiments, $L^1$ is an unsubstituted $C_3$-$C_4$ cycloalkylene. In embodiments, $L^1$ is an unsubstituted cyclobutylene. In embodiments, $L^1$ is an unsubstituted 2 to 10 membered heteroalkylene. In embodiments, $L^1$ is an unsubstituted 2 to 8 membered heteroalkylene. In embodiments, $L^1$ is an unsubstituted 2 to 6 membered heteroalkylene. In embodiments, $L^1$ is an unsubstituted 2 to 4 membered heteroalkylene. In embodiments, $L^1$ is a substituted $C_1$-$C_{10}$ alkylene. In embodiments, $L^1$ is a substituted $C_1$-$C_8$ alkylene. In embodiments, $L^1$ is a substituted $C_1$-$C_6$ alkylene. In embodiments, $L^1$ is a substituted $C_1$-$C_4$ alkylene. In embodiments, $L^1$ is a substituted saturated $C_1$-$C_{10}$ alkylene. In embodiments, $L^1$ is a substituted $C_1$-$C_{10}$ alkenylene. In embodiments, $L^1$ is a substituted polyunsaturated $C_1$-$C_{10}$ alkenylene. In embodiments, $L^1$ is a substituted $C_3$-$C_6$ cycloalkylene. In embodiments, $L^1$ is a substituted $C_4$-$C_6$ cycloalkylene. In embodiments, $L^1$ is a substituted $C_5$-$C_6$ cycloalkylene. In embodiments, $L^1$ is a substituted $C_3$-$C_5$ cycloalkylene. In embodiments, $L^1$ is a substituted $C_3$-$C_4$ cycloalkylene. In embodiments, $L^1$ is a substituted cyclobutylene. In embodiments, $L^1$ is a substituted 2 to 10 membered heteroalkylene. In embodiments, $L^1$ is a substituted 2 to 8 membered heteroalkylene. In embodiments, $L^1$ is a substituted 2 to 6 membered heteroalkylene. In embodiments, $L^1$ is a substituted 2 to 4 membered heteroalkylene. In embodiments, $L^1$ is substituted with oxo. In embodiments, $L^1$ is substituted with —OH.

In embodiments, $L^2$ is a bond. In embodiments, $L^2$ is —O—. In embodiments, $L^2$ is —S—. In embodiments, $L^2$ is —NH—. In embodiments, $L^2$ is —C(O)—. In embodiments, $L^2$ is —S(O)—. In embodiments, $L^2$ is —S(O)$_2$—. In embodiments, $L^2$ is —C(O)NH—. In embodiments, $L^2$ is —NHC(O)—.

In embodiments, $R^1$ is hydrogen, halogen, substituted or unsubstituted $C_1$-$C_3$ alkyl, or —N$_3$. In embodiments, $R^1$ is hydrogen, halogen, —CH$_2$OH, or —N$_3$. In embodiments, $R^1$ is halogen. In embodiments, $R^1$ is —Br. In embodiments, $R^1$ is —Cl. In embodiments, $R^2$ is hydrogen, halogen, substituted or unsubstituted $C_1$-$C_3$ alkyl, or —N$_3$. In embodiments, $R^2$ is hydrogen, halogen, —CH$_2$OH, or —N$_3$. In embodiments, $R^2$ is halogen. In embodiments, $R^2$ is —Br. In embodiments, $R^2$ is —Cl.

In embodiments, $R^1$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCH$_3$, —OCF$_3$, —OCHF$_2$, —N$_3$,

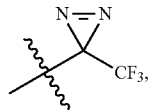 [SMILES: *C1(C(F)(F)F)N=N1]

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, —CCH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently halogen. In embodiments, $R^1$ is —F. In embodiments, $R^1$ is —Cl. In embodiments, $R^1$ is —Br. In embodiments, $R^1$ is —I. In embodiments, $R^1$ is —CF$_3$. In embodiments, $R^1$ is independently substituted or unsubstituted alkyl. In embodiments, $R^1$ is independently substituted or unsubstituted $C_1$-$C_{10}$ alkyl. In embodiments, $R^1$ is independently substituted or unsubstituted $C_1$-$C_8$ alkyl. In embodiments, $R^1$ is independently substituted or unsubstituted $C_1$-$C_6$ alkyl. In embodiments, $R^1$ is independently substituted or unsubstituted $C_1$-$C_4$ alkyl. In embodiments, $R^1$ is independently substituted or unsubstituted $C_1$-$C_3$ alkyl. In embodiments, $R^1$ is independently unsubstituted alkyl. In embodiments, $R^1$ is independently unsubstituted $C_1$-$C_{10}$ alkyl. In embodiments, $R^1$ is independently unsubstituted $C_1$-$C_8$ alkyl. In embodiments, $R^1$ is independently unsubstituted $C_1$-$C_6$ alkyl. In embodiments, $R^1$ is independently unsubstituted $C_1$-$C_4$ alkyl. In embodiments, $R^1$ is independently unsubstituted $C_1$-$C_3$ alkyl. In embodiments, $R^1$ is unsubstituted methyl. In embodiments, $R^1$ is unsubstituted ethyl. In embodiments, $R^1$ is unsubstituted propyl. In embodiments, $R^1$ is unsubstituted butyl. In embodiments, $R^1$ is unsubstituted isopropyl. In embodiments, $R^1$ is unsubstituted tert-butyl. In embodiments, $R^1$ is

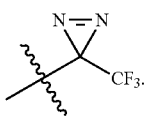

In embodiments, R¹ is —N₃. In embodiments, R¹ is —OCH₂CCH. In embodiments, R¹ is —CCH.

In embodiments, R² is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCH₃, —OCF₃, —OCHF₂, —N₃,

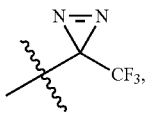

—C(CH₃)₃, —OCH₂CCH, —NHCH₂CCH, —NHCH₃, —N(CH₃)₂, —NHS(O)CH₃, —C(O)CH₃, —CH₃, —CH₂CCH, —NHC(O)CH₃, —CCH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R² is independently halogen. In embodiments, R² is —F. In embodiments, R² is —Cl. In embodiments, R² is —Br. In embodiments, R² is —I. In embodiments, R² is —CF₃. In embodiments, R² is independently substituted or unsubstituted alkyl. In embodiments, R² is independently substituted or unsubstituted $C_1$-$C_{10}$ alkyl. In embodiments, R² is independently substituted or unsubstituted $C_1$-$C_8$ alkyl. In embodiments, R² is independently substituted or unsubstituted $C_1$-$C_6$ alkyl. In embodiments, R² is independently substituted or unsubstituted $C_1$-$C_4$ alkyl. In embodiments, R² is independently substituted or unsubstituted $C_1$-$C_3$ alkyl. In embodiments, R² is independently unsubstituted alkyl. In embodiments, R² is independently unsubstituted $C_1$-$C_{10}$ alkyl. In embodiments, R² is independently unsubstituted $C_1$-$C_8$ alkyl. In embodiments, R² is independently unsubstituted $C_1$-$C_6$ alkyl. In embodiments, R² is independently unsubstituted $C_1$-$C_4$ alkyl. In embodiments, R² is independently unsubstituted $C_1$-$C_3$ alkyl. In embodiments, R² is unsubstituted methyl. In embodiments, R² is unsubstituted ethyl. In embodiments, R² is unsubstituted propyl. In embodiments, R² is unsubstituted butyl. In embodiments, R² is unsubstituted isopropyl. In embodiments, R² is unsubstituted tert-butyl. In embodiments, R² is

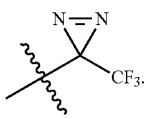 [SMILES: *C1(C(F)(F)F)N=N1]

In embodiments, R² is —N₃. In embodiments, R² is —OCH₂CCH. In embodiments, R² is —CCH. In embodiments, at least one of R¹ or R² is not hydrogen.

In embodiments, R³ is —C(O)OR⁹, —C(O)NR⁷R⁸, —SO₂R¹⁰, —OPO(OH)₂, —PO(OH)₂, —SO₃H, —SO₄H, substituted or unsubstituted sulfonate, substituted or unsubstituted phosphate, substituted or unsubstituted $C_1$-$C_{10}$ alkyl, substituted or unsubstituted 2 to 10 membered heteroalkyl, substituted or unsubstituted cycloalkyl, substituted or unsubstituted heterocycloalkyl, or substituted or unsubstituted heteroaryl. In embodiments, R³ is —C(O)OR⁹, —C(O)NR⁷R⁸, —SO₂R¹⁰, —OPO(OH)₂, —PO(OH)₂, —SO₃H, —SO₄H, substituted or unsubstituted $C_1$-$C_{10}$ alkyl, substituted or unsubstituted 2 to 10 membered heteroalkyl, substituted or unsubstituted heterocycloalkyl, or substituted or unsubstituted heteroaryl. In embodiments, R³ is —C(O)OH. In embodiments, R³ is —C(O)NH₂. In embodiments, R³ is substituted or unsubstituted $C_1$-$C_{10}$ alkyl. In embodiments, R³ is substituted or unsubstituted $C_1$-$C_8$ alkyl. In embodiments, R³ is substituted or unsubstituted $C_1$-$C_6$ alkyl. In embodiments, R³ is substituted or unsubstituted $C_1$-$C_4$ alkyl. In embodiments, R³ is substituted or unsubstituted $C_1$-$C_3$ alkyl. In embodiments, R³ is unsubstituted $C_1$-$C_{10}$ alkyl. In embodiments, R³ is unsubstituted $C_1$-$C_8$ alkyl. In embodiments, R³ is unsubstituted $C_1$-$C_6$ alkyl. In embodiments, R³ is unsubstituted $C_1$-$C_4$ alkyl. In embodiments, R³ is unsubstituted $C_1$-$C_3$ alkyl. In embodiments, R³ is substituted or unsubstituted $C_3$-$C_7$ cycloalkyl. In embodiments, R³ is substituted or unsubstituted $C_3$-$C_6$ cycloalkyl. In embodiments, R³ is substituted or unsubstituted $C_3$-$C_5$ cycloalkyl. In embodiments, R³ is substituted or unsubstituted $C_3$-$C_4$ cycloalkyl. In embodiments, R³ is substituted or unsubstituted $C_4$-$C_6$ cycloalkyl. In embodiments, R³ is unsubstituted $C_3$-$C_8$ cycloalkyl. In embodiments, R³ is unsubstituted $C_3$-$C_6$ cycloalkyl. In embodiments, R³ is unsubstituted $C_3$-$C_5$ cycloalkyl. In embodiments, R³ is unsubstituted $C_3$-$C_4$ cycloalkyl. In embodiments, R³ is unsubstituted $C_4$-$C_6$ cycloalkyl. In embodiments, R³ is —OPO(OH)₂. In embodiments, R³ is —PO(OH)₂. In embodiments, R³ is —SO₃H. In embodiments, R³ is —SO₄H. In embodiments, R³ is substituted or unsubstituted 3 to 8 membered heterocycloalkyl. In embodiments, R³ is substituted or unsubstituted 3 to 6 membered heterocycloalkyl. In embodiments, R³ is substituted or unsubstituted 3 to 5 membered heterocycloalkyl. In embodiments, R³ is unsubstituted 3 to 8 membered heterocycloalkyl. In embodiments, R³ is unsubstituted 3 to 6 membered heterocycloalkyl. In embodiments, R³ is unsubstituted 3 to 5 membered heterocycloalkyl. In embodiments, R³ is substituted or unsubstituted 2 to 10 membered heteroalkyl. In embodiments, R³ is substituted or unsubstituted 2 to 8 membered heteroalkyl. In embodiments, R³ is substituted or unsubstituted 2 to 6 membered heteroalkyl. In embodiments, R³ is substituted or unsubstituted 2 to 4 membered heteroalkyl. In embodiments, R³ is unsubstituted 2 to 8 membered heteroalkyl. In embodiments, R³ is unsubstituted 2 to 6 membered heteroalkyl. In embodiments, R³ is unsubstituted 2 to 4 membered heteroalkyl. In embodiments, R³ is substituted 2 to 10 membered heteroalkyl. In embodiments, R³ is substituted 2 to 8 membered heteroalkyl. In embodiments, R³ is substituted 2 to 6 membered heteroalkyl. In embodiments, R³ is substituted 2 to 4 membered heteroalkyl. In embodiments, R³ is substituted or unsubstituted 5 to 10 membered heteroaryl. In embodiments, R³ is substituted or unsubstituted 5 to 9 membered heteroaryl. In embodiments, R³ is substituted or unsubstituted 5 to 6 membered heteroaryl. In embodiments, R³ is substituted or unsubstituted 5 membered heteroaryl. In embodiments, R³ is substituted or unsubstituted 6 membered heteroaryl. In embodiments, R³ is unsubstituted 5 to 10 membered heteroaryl. In embodiments, R³ is unsubstituted 5 to 9 membered heteroaryl. In embodiments, R³ is unsubstituted 5 to 6 membered heteroaryl. In embodiments, R³ is unsubstituted 5 membered heteroaryl. In embodiments, R³ is unsubstituted 6 membered heteroaryl. In embodiments, R³ is substituted or unsubstituted tetrazolyl. In embodiments, R³ is unsubstituted tetrazolyl. In embodiments, R³ is substituted tetrazolyl. In embodiments, R³ is unsubstituted phosphate. In embodiments, R³ is unsubstituted sulfonate. In embodiments, R³ is unsubstituted phosphonate. In embodiments, R³ is unsubstituted sulfate. In embodiments, R³ is substituted or unsubstituted triazolyl. In embodiments, R³ is substituted or unsubstituted imidazolyl. In embodiments, R³ is substituted or unsubstituted pyrazolyl. In embodiments, R³ is substituted or unsubstituted oxazolyl. In embodiments, R³ is substituted or unsubstituted isoxazolyl. In embodiments, R³ is substituted or unsubstituted thiazolyl. In embodiments, R³ is substituted or unsubstituted triazinyl. In embodiments, R³ is substituted or unsubstituted pyridazinyl. In embodiments, R³ is substituted or unsubstituted pyrimidinyl. In embodiments, R³ is substituted or unsubstituted pyridinyl. In embodiments, R³ is substituted or unsubstituted furanyl. In embodiments, R³ is substituted or unsubstituted pyrrolyl. In embodiments, R³ is substituted or unsubstituted thienyl. In embodiments, R³ is substituted or unsubstituted isoxazolyl. In embodiments, R³ is substituted or unsubstituted 1,2,5-oxadiazolyl. In embodiments, R³ is substituted or unsubstituted 1,3,4-oxadiazolyl. In embodiments, R³ is substituted or unsubstituted 1H-1,2,4-triazolyl. In embodiments, R³ is substituted or unsubstituted isothiazolyl. In embodiments, R³ is substituted or unsubstituted 1,2,5-thiadiazolyl. In embodiments, R³ is substituted or unsubstituted 4,5-dihydro-1H-tetrazolyl. In embodiments, R³ is substituted or unsubstituted 2H-tetrazolyl. In embodiments, R³ is substituted or unsubstituted 1,2,4-oxadiazolidinyl. In embodiments, R³ is substituted or unsubstituted 4,5-dihydro-1,2,4-oxadiazolyl. In embodiments, R³ is substituted or unsubstituted 4,5-dihydro-1H-1,2,4-triazolyl. In embodiments, R³ is substituted or unsubstituted 4H-1,2,4-triazolyl. In embodiments, R³ is substituted or unsubstituted 1H-pyrazolyl. In embodiments, R³ is substituted or unsubstituted 1H-1,2,3-triazolyl. In embodiments, R³ is substituted or unsubstituted 1H-imidazolyl. In embodiments, R³ is substituted or unsubstituted 1,2,5-thiadiazolidinyl. In embodiments, R³ is substituted or unsubstituted 1,2,5-thiadiazolidinyl 1,1-dioxide. In embodiments, R³ is substituted or unsubstituted 1,2,4-thiadiazolidinyl. In embodiments, R³ is substituted or unsubstituted 1,2,4-thiadiazolidinyl 1,1-dioxide. In embodiments, R³ is substituted or unsubstituted thiazolidinyl. In embodiments, R³ is substituted or unsubstituted oxazolidinyl. In embodiments, R³ is substituted or unsubstituted pyrrolidinyl. In embodiments, R³ is substituted or unsubstituted 2,5-dihydrofuranyl. In embodiments, R³ is substituted or unsubstituted cyclobutenyl.

In embodiments, R³ is substituted or unsubstituted

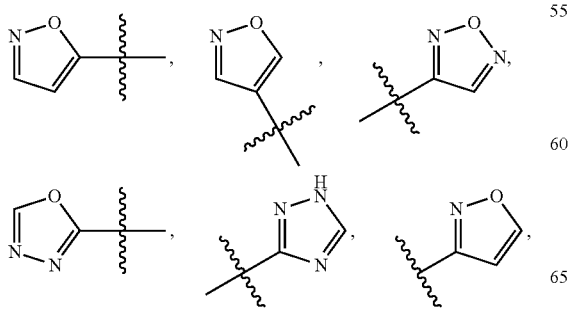

-continued

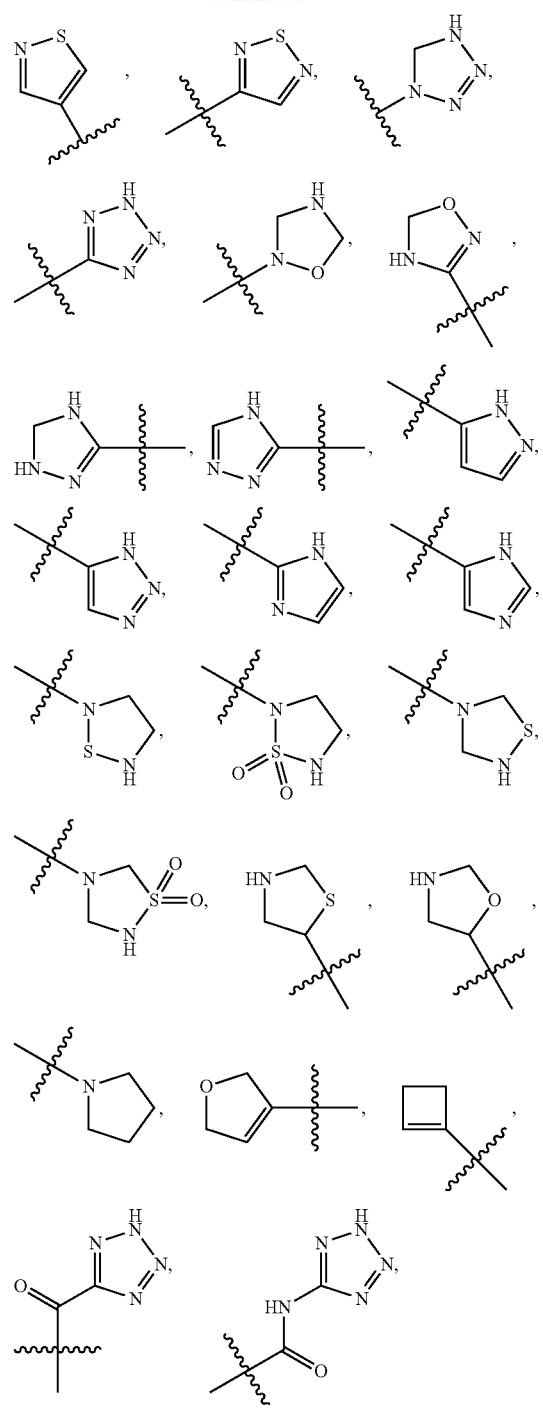

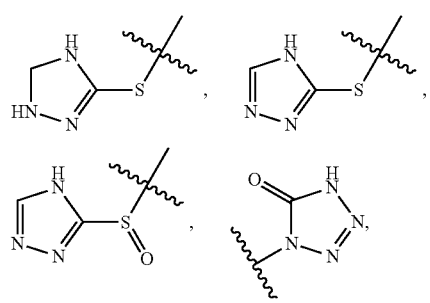

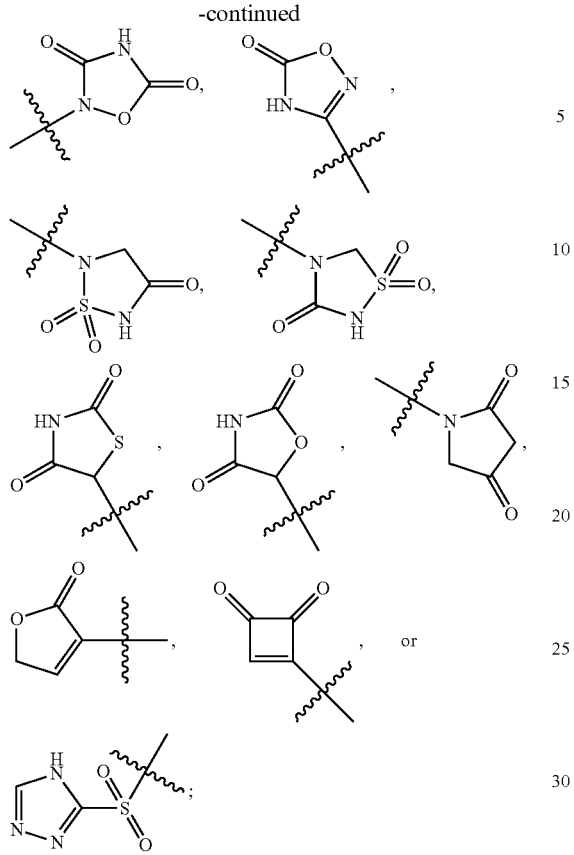

wherein a substituted $R^3$ may optionally have one or more substituents in place of one or more of the ring hydrogens in the structures immediately above. A "ring hydrogen" as used herein refers to a hydrogen attached to an atom that forms part of a chemical ring (e.g. an aryl, heteroaryl, cycloalkyl or heterocycloalkyl). In embodiments, $R^3$ is substituted or unsubstituted

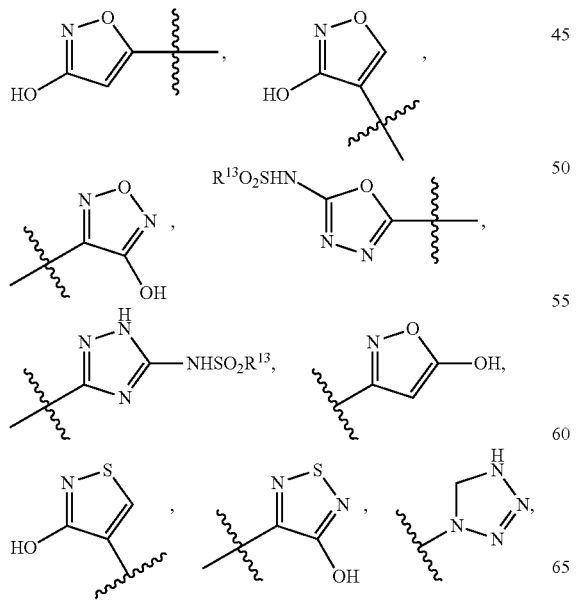

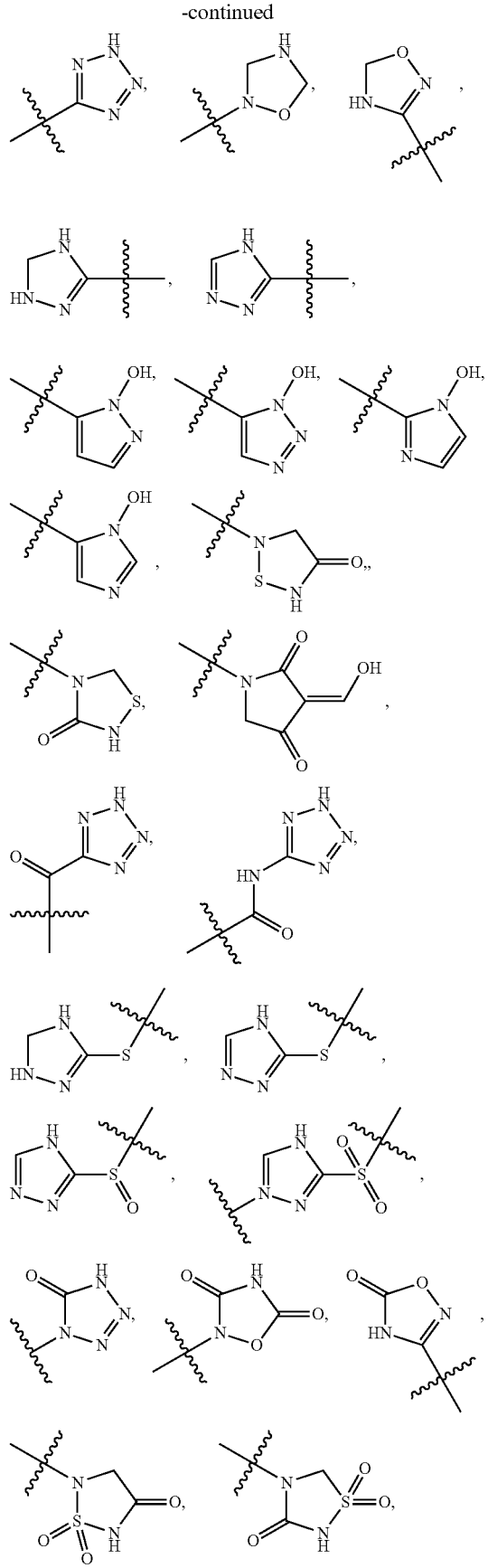

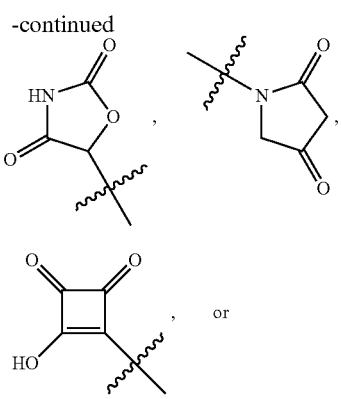

wherein a substituted $R^3$ may optionally have one or more substituents in place of one or more of the ring hydrogens in the structures immediately above. A "ring hydrogen" as used herein refers to a hydrogen attached to an atom that forms part of a chemical ring (e.g. an aryl, heteroaryl, cycloalkyl or heterocycloalkyl). In embodiments, $R^3$ is —S(O)$_2$CH$_3$, —S(O)$_2$NHC(O)CH$_3$, or —S(O)$_2$OH. In embodiments, $R^3$ is —C(O)NR$^7$S(O)$_2$R$^{10}$.

In embodiments, $R^4$ is substituted or unsubstituted alkyl or substituted or unsubstituted heteroalkyl. In embodiments, $R^4$ is substituted or unsubstituted $C_1$-$C_8$ alkyl. In embodiments, $R^4$ is substituted or unsubstituted $C_1$-$C_6$ alkyl. In embodiments, $R^4$ is substituted or unsubstituted $C_1$-$C_4$ alkyl. In embodiments, $R^4$ is substituted or unsubstituted $C_1$-$C_3$ alkyl. In embodiments, $R^4$ is unsubstituted $C_1$-$C_8$ alkyl. In embodiments, $R^4$ is unsubstituted $C_1$-$C_6$ alkyl. In embodiments, $R^4$ is unsubstituted $C_1$-$C_4$ alkyl. In embodiments, $R^4$ is unsubstituted $C_1$-$C_3$ alkyl. In embodiments, $R^4$ is unsubstituted methyl. In embodiments, $R^4$ is unsubstituted ethyl. In embodiments, $R^4$ is unsubstituted propyl. In embodiments, $R^4$ is unsubstituted isopropyl. In embodiments, $R^4$ is

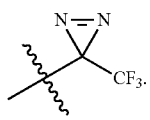

In embodiments, $R^4$ is —N$_3$. In embodiments, $R^4$ is —OCH$_2$CCH. In embodiments, $R^4$ is —CF$_3$. In embodiments, $R^4$ is —NHC(O)CH$_3$. In embodiments, $R^4$ is —OH. In embodiments, $R^4$ is —OCH$_3$. In embodiments, $R^4$ is —NHCH$_3$. In embodiments, $R^4$ is —NHC(S)CH$_3$. In embodiments, $R^4$ is —N(CH$_3$)$_2$. In embodiments, $R^4$ is —C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, or —NHC(O)CH$_3$.

In embodiments, $R^5$ is substituted or unsubstituted alkyl or substituted or unsubstituted heteroalkyl. In embodiments, $R^5$ is substituted or unsubstituted $C_1$-$C_8$ alkyl. In embodiments, $R^5$ is substituted or unsubstituted $C_1$-$C_6$ alkyl. In embodiments, $R^5$ is substituted or unsubstituted $C_1$-$C_4$ alkyl. In embodiments, $R^5$ is substituted or unsubstituted $C_1$-$C_3$ alkyl. In embodiments, $R^5$ is unsubstituted $C_1$-$C_8$ alkyl. In embodiments, $R^5$ is unsubstituted $C_1$-$C_6$ alkyl. In embodiments, $R^5$ is unsubstituted $C_1$-$C_4$ alkyl. In embodiments, $R^5$ is unsubstituted $C_1$-$C_3$ alkyl. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted isopropyl. In embodiments, $R^5$ is

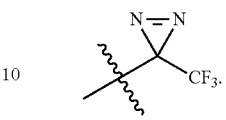

In embodiments, $R^5$ is —N$_3$. In embodiments, $R^5$ is —OCH$_2$CCH. In embodiments, $R^5$ is —CF$_3$. In embodiments, $R^5$ is —NHC(O)CH$_3$. In embodiments, $R^5$ is —OH. In embodiments, $R^5$ is —OCH$_3$. In embodiments, $R^5$ is —NHCH$_3$. In embodiments, $R^5$ is —NHC(S)CH$_3$. In embodiments, $R^5$ is —N(CH$_3$)$_2$. In embodiments, $R^5$ is —C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, or —NHC(O)CH$_3$.

In embodiments, $R^4$ and $R^5$ are joined to form a substituted or unsubstituted cycloalkyl, substituted or unsubstituted heterocycloalkyl, substituted or unsubstituted aryl, or substituted or unsubstituted heteroaryl. In embodiments, $R^4$ and $R^5$ are joined to form a substituted or unsubstituted cycloalkyl or substituted or unsubstituted heterocycloalkyl. In embodiments, $R^4$ and $R^5$ are joined to form a substituted or unsubstituted cycloalkyl. In embodiments, $R^4$ and $R^5$ are joined to form a substituted or unsubstituted $C_3$-$C_8$ cycloalkyl. In embodiments, $R^4$ and $R^5$ are joined to form a substituted or unsubstituted $C_3$-$C_6$ cycloalkyl. In embodiments, $R^4$ and $R^5$ are joined to form a substituted or unsubstituted $C_3$-$C_5$ cycloalkyl. In embodiments, $R^4$ and $R^5$ are joined to form an unsubstituted cycloalkyl. In embodiments, $R^4$ and $R^5$ are joined to form an unsubstituted $C_3$-$C_8$ cycloalkyl. In embodiments, $R^4$ and $R^5$ are joined to form an unsubstituted $C_3$-$C_6$ cycloalkyl. In embodiments, $R^4$ and $R^5$ are joined to form an unsubstituted $C_3$-$C_5$ cycloalkyl. In embodiments, $R^4$ and $R^5$ are joined to form an unsubstituted $C_4$ cycloalkyl. In embodiments, $R^4$ and $R^5$ are joined to form a substituted $C_4$ cycloalkyl. In embodiments, $R^4$ and $R^5$ are joined to form an unsubstituted $C_5$ cycloalkyl. In embodiments, $R^4$ and $R^5$ are joined to form a substituted $C_5$ cycloalkyl. In embodiments, $R^4$ and $R^5$ are joined to form an unsubstituted $C_6$ cycloalkyl. In embodiments, $R^4$ and $R^5$ are joined to form a substituted $C_6$ cycloalkyl. In embodiments, $R^4$ and $R^5$ are joined to form an unsubstituted $C_7$ cycloalkyl. In embodiments, $R^4$ and $R^5$ are joined to form a substituted $C_7$ cycloalkyl. In embodiments, $R^4$ and $R^5$ are joined to form an unsubstituted $C_8$ cycloalkyl. In embodiments, $R^4$ and $R^5$ are joined to form a substituted $C_8$ cycloalkyl. In embodiments, $R^4$ and $R^5$ are joined to form an unsubstituted cyclopropyl. In embodiments, $R^4$ and $R^5$ are joined to form an unsubstituted cyclobutyl. In embodiments, $R^4$ and $R^5$ are joined to form an unsubstituted cyclopentyl. In embodiments, $R^4$ and $R^5$ are joined to form an unsubstituted cyclohexyl. In embodiments, $R^4$ and $R^5$ are joined to form a substituted cyclopropyl. In embodiments, $R^4$ and $R^5$ are joined to form a substituted cyclobutyl. In embodiments, $R^4$ and $R^5$ are joined to form a substituted cyclopentyl. In embodiments, $R^4$ and $R^5$ are joined to form a substituted cyclohexyl. In embodiments, $R^4$ and $R^5$ are joined to form a substituted cyclohexyl. In embodiments, $R^4$ and $R^5$ are joined to form a substituted cycloheptyl. In embodiments, $R^4$ and $R^5$ are joined to form an unsubstituted cycloheptyl.

In embodiments, $R^4$ and $R^5$ are joined to form a substituted cyclooctyl. In embodiments, $R^4$ and $R^5$ are joined to form an unsubstituted cyclooctyl. In embodiments, $R^4$ and $R^5$ are joined to form a substituted or unsubstituted heterocycloalkyl. In embodiments, $R^4$ and $R^5$ are joined to form a substituted or unsubstituted 3 to 10 membered heterocycloalkyl. In embodiments, $R^4$ and $R^5$ are joined to form a substituted or unsubstituted 3 to 8 membered heterocycloalkyl. In embodiments, $R^4$ and $R^5$ are joined to form a substituted or unsubstituted 3 to 6 membered heterocycloalkyl. In embodiments, $R^4$ and $R^5$ are joined to form a substituted or unsubstituted 3 to 5 membered heterocycloalkyl. In embodiments, $R^4$ and $R^5$ are joined to form a substituted or unsubstituted 3 to 4 membered heterocycloalkyl. In embodiments, $R^4$ and $R^5$ are joined to form a substituted or unsubstituted piperidinyl. In embodiments, $R^4$ and $R^5$ are joined to form an N-substituted piperidinyl. In embodiments, $R^4$ and $R^5$ are joined to form a piperidinyl substituted with —$CH_3$, —$CH_2CCH$, —$C(O)CH_3$, —NHC(O)$CH_3$, unsubstituted alkyl, or unsubstituted heteroalkyl. In embodiments, $R^4$ and $R^5$ are joined to form a substituted or unsubstituted tetrahydropyranyl.

In embodiments, $R^7$, $R^8$, $R^9$, and $R^{10}$, are independently hydrogen, oxo, halogen, —$C(O)CH_3$, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$CH_3$, —NHC=(O)$NH_2$, —$NHSO_2H$, —NHC=(O)H, —NHC(O)—OH, —NHOH, —$OCF_3$, —$OCHF_2$, —$N_3$,

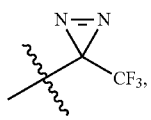 [SMILES: *C1(C(F)(F)F)N=N1]

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. In embodiments, $R^7$, $R^8$, $R^9$, and $R^{10}$, are independently hydrogen. In embodiments, $R^7$, $R^8$, $R^9$, and $R^{10}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$, $R^8$, $R^9$, and $R^{10}$, are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$, $R^8$, $R^9$, and $R^{10}$, are independently unsubstituted alkyl, unsubstituted heteroalkyl, unsubstituted cycloalkyl, unsubstituted heterocycloalkyl, unsubstituted aryl, or unsubstituted heteroaryl.

In embodiments, the symbol W is —O—. In embodiments, the symbol W is —S—. In embodiments, the symbol W is —$C(R^4)(R^5)$—. In embodiments, the symbol W is —S(O)—. In embodiments, the symbol W is —$S(O)_2$—. In embodiments, the symbol y is 0. In embodiments, the symbol y is 1. In embodiments, the symbols m and v are independently 1. In embodiments, the symbols m and v are independently 2. In embodiments, the symbol n is independently 0. In embodiments, the symbol n is independently 1. In embodiments, the symbol n is independently 2. In embodiments, the symbol n is independently 3. In embodiments, the symbol n is independently 4. In embodiments, the symbol t1 is independently 0. In embodiments, the symbol t1 is independently 1. In embodiments, the symbol t1 is independently 2. In embodiments, the symbol t1 is independently 3. In embodiments, the symbol t1 is independently 4. In embodiments, the symbol t2 is independently 0. In embodiments, the symbol t2 is independently 1. In embodiments, the symbol t2 is independently 2. In embodiments, the symbol t2 is independently 3. In embodiments, the symbol t2 is independently 4. In embodiments, the symbol X is independently —Cl. In embodiments, the symbol X is independently —Br. In embodiments, the symbol X is independently —I. In embodiments, the symbol X is independently —F.

In embodiments, the compound is not a compound having the formula:

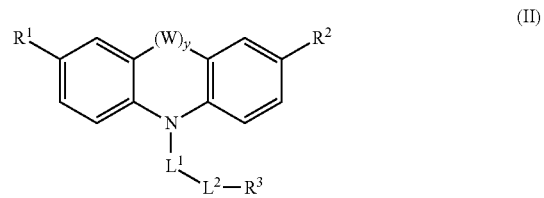

wherein y is 0, $R^1$ and $R^2$ are independently halide, $L^1$-$L^2$ is unsubstituted ethylene, and $R^3$ is —COOH. In embodiments, the compound is not a compound of formula (II) wherein y is 0, $R^1$ and $R^2$ are independently hydrogen, $L^1$-$L^2$ is unsubstituted ethylene, and $R^3$ is —COOH. In embodiments, the compound is not a compound of formula (II) wherein y is 0, $R^1$ and $R^2$ are independently hydrogen or halide, $L^1$-$L^2$ is unsubstituted ethylene, and $R^3$ is —COOH. In embodiments, the compound is not a compound of formula (II) wherein y is 0, $R^1$ and $R^2$ are independently hydrogen or halide, $L^1$-$L^2$ is unsubstituted ethylene, and $R^3$ is —COOH or —CN. In embodiments, the compound is not a compound of formula (II) wherein y is 0, $R^1$ and $R^2$ are independently hydrogen or halide, $L^1$-$L^2$ is unsubstituted ethylene, and $R^3$ is —CN. In embodiments, the compound is not a compound of formula (II) wherein y is 0, $R^1$ and $R^2$ are independently hydrogen or halide, $L^1$-$L^2$ is unsubstituted ethylene, and $R^3$ is —COOH or —CN or —C(O)$NHNH_2$. In embodiments, the compound is not a compound of formula (II) wherein y is 0, $R^1$ and $R^2$ are independently hydrogen or halide, $L^1$-$L^2$ is unsubstituted ethylene, and $R^3$ is C(O)$NHNH_2$. In embodiments, the compound is not a compound of formula (II) wherein y is 0, $R^1$ and $R^2$ are independently hydrogen or halide, $L^1$-$L^2$ is unsubstituted $C_1$-$C_4$ alkylene, and $R^3$ is —COOH or —CN or —C(O)$NHNH_2$. In embodiments, the compound is not a compound of formula (II) wherein y is 0, $R^1$ and $R^2$ are independently hydrogen or halide, $L^1$-$L^2$ is $C_1$-$C_4$ alkylene substituted with —OH, and $R^3$ is —OH or —COOH or —CN or —C(O)$NHNH_2$. In embodiments, the compound is not a compound of formula (II) wherein y is 0, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)$NHNH_2$.

In embodiments, the compound is not a compound of formula (I) wherein y is 0, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)NHNH$_2$. In embodiments, the compound is not a compound of formula (I) wherein t1 and t2 are 1, y is 1, W is —S—, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)NHNH$_2$. In embodiments, the compound is not a compound of formula (I) wherein t1 and t2 are 1, y is 1, W is —S— or —O—, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)NHNH$_2$. In embodiments, the compound is not a compound of formula (I) wherein t1 and t2 are 1, y is 0 or 1, W is —S— or —O—, $R^1$ and $R^2$ are independently hydrogen or halide, $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (I) wherein t1 and t2 are 1, $R^1$ and $R^2$ are independently hydrogen or halide, $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (I) wherein t1 and t2 are 1, $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (I) wherein $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (I) wherein $R^3$ is —OH or —COOH or —CN or —C(O)NHNH$_2$. In embodiments, the compound is not a compound of formula (II) wherein y is 0, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)NHNH$_2$. In embodiments, the compound is not a compound of formula (II) wherein t1 and t2 are 1, y is 1, W is —S—, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)NHNH$_2$. In embodiments, the compound is not a compound of formula (II) wherein t1 and t2 are 1, y is 1, W is —S— or —O—, $R^1$ and $R^2$ are independently hydrogen or halide, $L^1$-$L^2$ is —OH substituted or unsubstituted $C_1$-$C_4$ alkylene, and $R^3$ is —OH or —COOH or —CN or —C(O)NHNH$_2$. In embodiments, the compound is not a compound of formula (II) wherein t1 and t2 are 1, y is 0 or 1, W is —S— or —O—, $R^1$ and $R^2$ are independently hydrogen or halide, $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (II) wherein t1 and t2 are 1, $R^1$ and $R^2$ are independently hydrogen or halide, $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (II) wherein t1 and t2 are 1, $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (II) wherein $L^1$-$L^2$ is substituted or unsubstituted $C_1$-$C_4$ alkylene, and $R^3$ is —OH or —COOH or —CN or —C(O)NHNH$_2$. In embodiments, the compound is not a compound of formula (II) wherein $R^3$ is —OH or —COOH or —CN or —C(O)NHNH$_2$.

In embodiments, the compound is not a compound selected from the group consisting of

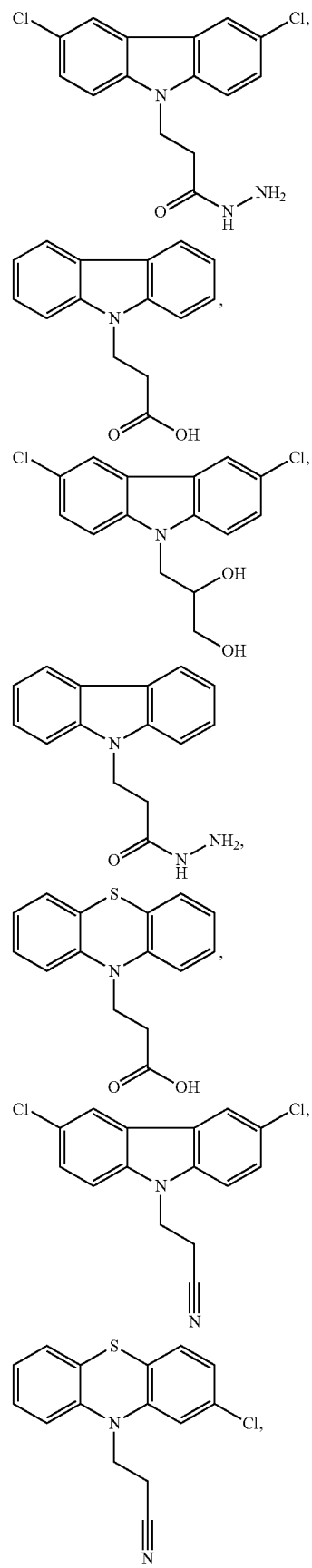

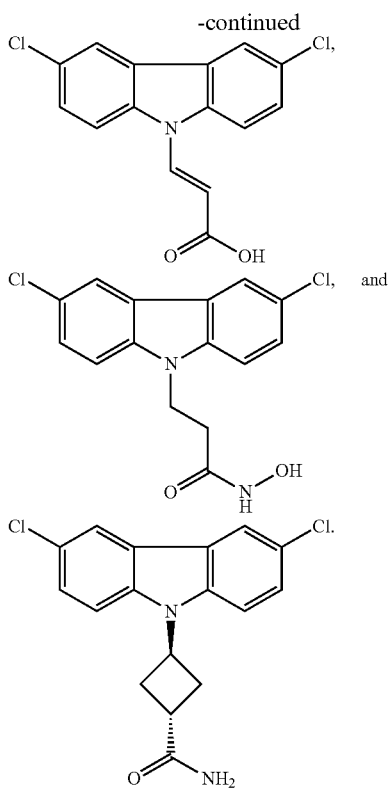

In embodiments, the compound is a TREK-1 agonist. In embodiments, the compound is a TREK-1 antagonist. In embodiments, the compound is selective for binding TREK-1 over other potassium channels. In embodiments, the compound is about 2-fold, 3-fold, 4-fold, 5-fold, 6-fold, 7-fold, 8-fold, 9-fold, 10-fold, or 100-fold selective for binding TREK-1 over other potassium channels. In embodiments, the compound is 2-fold, 3-fold, 4-fold, 5-fold, 6-fold, 7-fold, 8-fold, 9-fold, 10-fold, or 100-fold selective for binding TREK-1 over other potassium channels. In embodiments, the compound is selective for binding to TREK-1, TREK-2, and TRAAK over other potassium channels. In embodiments, the compound binds the C-type gate of TREK-1. In embodiments, the compound binds the extracellular portion of TREK-1. In embodiments, the compound does not bind the intracellular C terminal domain of TREK-1. In embodiments, the compound is an analgesic. In embodiments, the compound is an anesthetic. In embodiments, the compound is a neuroprotectant. In embodiments, the compound is a mood modifier. In embodiments, the compound is an anti-depressant. In embodiments, the compound treats decompression sickness. In embodiments, the compound increases TREK-1 activity. In embodiments, the compound decreases TREK-1 activity. In embodiments, the compound is a TREK-2 agonist. In embodiments, the compound is a TREK-2 antagonist. In embodiments, the compound is selective for binding TREK-2 over other potassium channels. In embodiments, the compound is about 2-fold, 3-fold, 4-fold, 5-fold, 6-fold, 7-fold, 8-fold, 9-fold, 10-fold, or 100-fold selective for binding TREK-2 over other potassium channels. In embodiments, the compound is 2-fold, 3-fold, 4-fold, 5-fold, 6-fold, 7-fold, 8-fold, 9-fold, 10-fold, or 100-fold selective for binding TREK-2 over other potassium channels. In embodiments, the compound binds the C-type gate of TREK-2. In embodiments, the compound binds the extracellular portion of TREK-2. In embodiments, the compound does not bind the intracellular C terminal domain of TREK-2. In embodiments, the compound increases TREK-2 activity. In embodiments, the compound decreases TREK-2 activity. In embodiments, the compound is a TRAAK agonist. In embodiments, the compound is a TRAAK antagonist. In embodiments, the compound is selective for binding TRAAK over other potassium channels. In embodiments, the compound is about 2-fold, 3-fold, 4-fold, 5-fold, 6-fold, 7-fold, 8-fold, 9-fold, 10-fold, or 100-fold selective for binding TRAAK over other potassium channels. In embodiments, the compound is 2-fold, 3-fold, 4-fold, 5-fold, 6-fold, 7-fold, 8-fold, 9-fold, 10-fold, or 100-fold selective for binding TRAAK over other potassium channels. In embodiments, the compound binds the C-type gate of TRAAK. In embodiments, the compound binds the extracellular portion of TRAAK. In embodiments, the compound does not bind the intracellular C terminal domain of TRAAK. In embodiments, the compound is an analgesic. In embodiments, the compound increases TRAAK activity. In embodiments, the compound decreases TRAAK activity.

In embodiments, the disease is a neurodegenerative disease selected from the group consisting of Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, and Tabes dorsalis. In embodiments, the disease is stroke. In embodiments, the disease is ischemia. In embodiments, the disease is stroke. In embodiments, the disease is brain ischemia. In embodiments, the disease is a mood disorder. In embodiments, the disease is depression. In embodiments, the disease is a neurodegenerative disease. In embodiments, the disease is pain. In embodiments, the disease is decompression sickness. In embodiments, the compound is in a pharmaceutical composition including a pharmaceutically acceptable excipient. In embodiments, the compound is in a pharmaceutically acceptable salt. In embodiments of the method, the compound is co-administered with a second agent (e.g. therapeutic agent). In embodiments of the method, the second agent is administered in a therapeutically effective amount.

In embodiments of the method, the compound is a compound described herein, including embodiments (e.g. compound of formula I, II, III, IV, V, or VI), for example in the Compounds section below, figures, tables, or Examples section below.

B. Methods of Modulating Enzymatic Activity

In a second aspect is provided a method of modulating the level of activity of TREK-1 in a cell including contacting the cell with an effective amount of a compound as described herein, including embodiments and including the compounds described for use in treating a disease as disclosed herein above or the compounds described in the Compounds section below or in any examples, tables, or figures (e.g. compound of formula I, II, III, IV, V, or VI).

In embodiments, the method includes increasing the activity of TREK-1. In embodiments, the method includes decreasing the activity of TREK-1. In embodiments of the method, the cell is in a patient. In embodiments of the method, the cell is isolated from a patient. In embodiments of the method, the cell is in cell culture. In embodiments of the method, the cell is a neuron. In embodiments of the method, the cell is a brain cell. In embodiments of the method, the cell is associated with a disease caused by a decrease in TREK-1 activity relative to a person without the disease. In embodiments of the method, the cell is associated with a neurological disease caused by a decrease in TREK-1 activity relative to a person without the neurological disease. In embodiments of the method, the cell is associated with a neurodegenerative disease caused by a decrease in TREK-1 activity relative to a person without the neurodegenerative disease. In embodiments of the method, the cell is associated with a disease associated with a decrease in TREK-1 activity relative to a person without the disease. In embodiments of the method, the cell is associated with a disease caused by an increase in TREK-1 activity relative to a person without the disease. In embodiments of the method, the cell is associated with a neurodegenerative disease caused by an increase in TREK-1 activity relative to a person without the neurodegenerative disease. In embodiments of the method, the cell is associated with a disease associated with an increase in TREK-1 activity relative to a person without the disease. In embodiments of the method, the cell is associated with a disease associated with a TREK-1 mutation. In embodiments, the method includes increasing the activity of TREK-2. In embodiments, the method includes decreasing the activity of TREK-2. In embodiments of the method, the cell is in a patient. In embodiments of the method, the cell is isolated from a patient. In embodiments of the method, the cell is in cell culture. In embodiments of the method, the cell is a neuron. In embodiments of the method, the cell is a brain cell. In embodiments of the method, the cell is associated with a disease caused by a decrease in TREK-2 activity relative to a person without the disease. In embodiments of the method, the cell is associated with a neurological disease caused by a decrease in TREK-2 activity relative to a person without the neurological disease. In embodiments of the method, the cell is associated with a neurodegenerative disease caused by a decrease in TREK-2 activity relative to a person without the neurodegenerative disease. In embodiments of the method, the cell is associated with a disease associated with a decrease in TREK-2 activity relative to a person without the disease. In embodiments of the method, the cell is associated with a disease caused by an increase in TREK-2 activity relative to a person without the disease. In embodiments of the method, the cell is associated with a neurodegenerative disease caused by an increase in TREK-2 activity relative to a person without the neurodegenerative disease. In embodiments of the method, the cell is associated with a disease associated with an increase in TREK-2 activity relative to a person without the disease. In embodiments of the method, the cell is associated with a disease associated with a TREK-2 mutation. In embodiments, the method includes increasing the activity of TRAAK. In embodiments, the method includes decreasing the activity of TRAAK. In embodiments of the method, the cell is in a patient. In embodiments of the method, the cell is isolated from a patient. In embodiments of the method, the cell is in cell culture. In embodiments of the method, the cell is a neuron. In embodiments of the method, the cell is a brain cell. In embodiments of the method, the cell is associated with a disease caused by a decrease in TRAAK activity relative to a person without the disease. In embodiments of the method, the cell is associated with a neurological disease caused by a decrease in TRAAK activity relative to a person without the neurological disease. In embodiments of the method, the cell is associated with a neurodegenerative disease caused by a decrease in TRAAK activity relative to a person without the neurodegenerative disease. In embodiments of the method, the cell is associated with a disease associated with a decrease in TRAAK activity relative to a person without the disease. In embodiments of the method, the cell is associated with a disease caused by an increase in TRAAK activity relative to a person without the disease. In embodiments of the method, the cell is associated with a neurodegenerative disease caused by an increase in TRAAK activity relative to a person without the neurodegenerative disease. In embodiments of the method, the cell is associated with a disease associated with an increase in TRAAK activity relative to a person without the disease. In embodiments of the method, the cell is associated with a disease associated with a TRAAK mutation. In embodiments of the method, the cell is associated with a neurodegenerative disease that is selected from the group consisting of Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, stroke, ischemic injury, or decompression sickness. In embodiments of the method, the cell is associated with a neurological disease. In embodiments of the method, the cell is associated with pain perception. In embodiments of the method, the cell is associated with pain. In embodiments of the method, the cell is associated with stroke. In embodiments of the method, the cell is associated with ischemic injury. In embodiments of the method, the cell is associated with migraine. In embodiments of the method, the cell is associated with neurological function. In embodiments of the method, the cell is associated with a neurological disease. In embodiments of the method, the cell is a neurological cell. In embodiments of the method, the cell is associated with ischemia. In embodiments of the method, the cell is associated with brain ischemia. In embodiments of the method, the cell is associated with decompression sickness. In embodiments of the method, the cell is associated with anesthesia. In embodiments of the method, the cell is associated with depression. In embodiments of the method, the cell is associated with a mood disorder. In embodiments, the compound is in a pharmaceutical composition including a pharmaceutically acceptable excipient. In embodiments, the compound is in a pharmaceutically acceptable salt. In embodiments of the method, the compound is co-administered with a second agent (e.g. therapeutic agent). In embodiments of the method, the second agent is administered in a therapeutically effective amount.

In embodiments of the method, the compound is a compound described herein, including embodiments (e.g. compound of formula I, II, III, IV, V, or VI), for example in the Compounds section below, methods of treatment section above, figures, tables, or Examples section below.

C. Compounds

Compounds useful in the methods disclosed herein are described above and below. Thus, the compounds described herein, including those set forth below in this Compounds section, are useful in the methods provided here, including all embodiments thereof. In addition to the compounds disclosed above, in a third aspect is provided a compound, or a pharmaceutically acceptable salt thereof, having the formula:

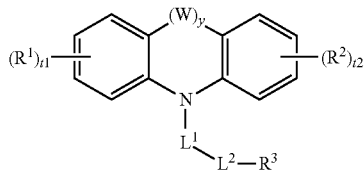
(I)

wherein $R^1$, $R^2$, $R^3$, $L^1$, $L^2$, W, y, t1, t2, are as described herein, including embodiments and in the methods sections above. $L^1$ may be a substituted or unsubstituted $C_1$-$C_{10}$ alkylene, substituted or unsubstituted 2 to 10 membered heteroalkylene, or substituted or unsubstituted $C_3$-$C_6$ cycloalkylene. $L^2$ may be a bond, —O—, —S—, —NH—, —C(O)—, —C(O)NH—, —NHC(O)—, —S(O)—, or —S(O)$_2$—. $R^1$, $R^2$, $R^4$, and $R^5$ may independently be hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

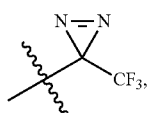

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, —CCH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^4$ and $R^5$ may optionally be joined to form a substituted or unsubstituted cycloalkyl or substituted or unsubstituted heterocycloalkyl. $R^3$ may be hydrogen, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$)C=(O)R$^9$, —NR$^7$C(O)—OR$^9$, —NR$^7$OR$^9$, —OCX$_3$, —OCHX$_2$, —OPO(OH)$_2$, —PO(OH)$_2$, —SO$_3$H, —SO$_4$H, —C(O) NR$^7$S(O)$_2$R$^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$, may independently be hydrogen, oxo, halogen, —C(O)CH$_3$, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)CH$_3$, —NHC=(O)NH$_2$, —NHSO$_2$H, —NHC=(O)H, —NHC(O)—OH, —NHOH, —OCF$_3$, —OCHF$_2$, —N$_3$,

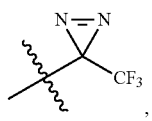

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. The symbol W may be —O—, —S—, —S(O)—, —S(O)$_2$—, or —C(R$^4$)(R$^5$)—. The symbol y may be 0 or 1. The symbols t1 and t2 may independently be 1 to 4.

In embodiments, the compound has the formula:

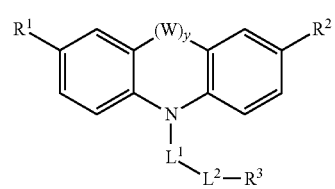
(II)

In embodiments, the compound has the formula:

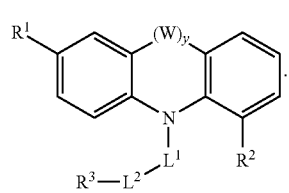
(IIa)

In embodiments, $L^1$ is an unsubstituted $C_1$-$C_{10}$ alkylene. In embodiments, $L^1$ is an unsubstituted $C_1$-$C_8$ alkylene. In embodiments, $L^1$ is an unsubstituted $C_1$-$C_6$ alkylene. In embodiments, $L^1$ is an unsubstituted $C_1$-$C_4$ alkylene. In embodiments, $L^1$ is an unsubstituted saturated $C_1$-$C_{10}$ alkylene. In embodiments, $L^1$ is an unsubstituted $C_1$-$C_{10}$ alkenylene. In embodiments, $L^1$ is an unsubstituted polyunsaturated $C_1$-$C_{10}$ alkenylene. In embodiments, $L^1$ is an unsubstituted $C_3$-$C_6$ cycloalkylene. In embodiments, $L^1$ is an unsubstituted $C_4$-$C_6$ cycloalkylene. In embodiments, $L^1$ is an unsubstituted $C_5$-$C_6$ cycloalkylene. In embodiments, $L^1$ is an unsubstituted $C_3$-$C_5$ cycloalkylene. In embodiments, $L^1$ is an unsubstituted $C_3$-$C_4$ cycloalkylene. In embodiments, $L^1$ is an unsubstituted cyclobutylene. In embodiments, $L^1$ is an unsubstituted 2 to 10 membered heteroalkylene. In embodiments, L¹ is an unsubstituted 2 to 8 membered heteroalkylene. In embodiments, L¹ is an unsubstituted 2 to 6 membered heteroalkylene. In embodiments, L¹ is an unsubstituted 2 to 4 membered heteroalkylene. In embodiments, L¹ is a substituted $C_1$-$C_{10}$ alkylene. In embodiments, L¹ is a substituted $C_1$-$C_8$ alkylene. In embodiments, L¹ is a substituted $C_1$-$C_6$ alkylene. In embodiments, L¹ is a substituted $C_1$-$C_4$ alkylene. In embodiments, L¹ is a substituted saturated $C_1$-$C_{10}$ alkylene. In embodiments, L¹ is a substituted $C_1$-$C_{10}$ alkenylene. In embodiments, L¹ is a substituted polyunsaturated $C_1$-$C_{10}$ alkenylene. In embodiments, L¹ is a substituted $C_3$-$C_6$ cycloalkylene. In embodiments, L¹ is a substituted $C_4$-$C_6$ cycloalkylene. In embodiments, L¹ is a substituted $C_5$-$C_6$ cycloalkylene. In embodiments, L¹ is a substituted $C_3$-$C_5$ cycloalkylene. In embodiments, L¹ is a substituted $C_3$-$C_4$ cycloalkylene. In embodiments, L¹ is a substituted cyclobutylene. In embodiments, L¹ is a substituted 2 to 10 membered heteroalkylene. In embodiments, L¹ is a substituted 2 to 8 membered heteroalkylene. In embodiments, L¹ is a substituted 2 to 6 membered heteroalkylene. In embodiments, L¹ is a substituted 2 to 4 membered heteroalkylene. In embodiments, L¹ is substituted with oxo. In embodiments, L¹ is substituted with —OH. In embodiments, L¹ is an unsubstituted $C_1$-$C_3$ alkylene. In embodiments, L¹ is an unsubstituted $C_1$-$C_2$ alkylene. In embodiments, L¹ is an unsubstituted $C_2$-$C_3$ alkylene. In embodiments, L¹ is an unsubstituted methylene. In embodiments, L¹ is an unsubstituted ethylene. In embodiments, L¹ is an unsubstituted propylene. In embodiments, L¹ is an unsubstituted n-propylene. In embodiments, L¹ is an unsubstituted butylene. In embodiments, L¹ is a substituted $C_1$-$C_3$ alkylene. In embodiments, L¹ is a substituted $C_1$-$C_2$ alkylene. In embodiments, L¹ is a substituted $C_2$-$C_3$ alkylene. In embodiments, L¹ is a substituted methylene. In embodiments, L¹ is a substituted ethylene. In embodiments, L¹ is a substituted propylene. In embodiments, L¹ is a substituted n-propylene. In embodiments, L¹ is a substituted butylene. In embodiments, L¹ is substituted with —CH₂CH₂COOH. In embodiments, L¹ is ethylene substituted with —CH₂CH₂COOH.

In embodiments, L² is a bond. In embodiments, L² is —O—. In embodiments, L² is —S—. In embodiments, L² is —NH—. In embodiments, L² is —C(O)—. In embodiments, L² is —S(O)—. In embodiments, L² is —S(O)₂—. In embodiments, L² is —C(O)NH—. In embodiments, L² is —NHC(O)—.

In embodiments, R¹ is hydrogen, halogen, substituted or unsubstituted $C_1$-$C_3$ alkyl, or —N₃. In embodiments, R¹ is hydrogen, halogen, —CH₂OH, or —N₃. In embodiments, R¹ is halogen. In embodiments, R¹ is —Br. In embodiments, R¹ is —Cl. In embodiments, R² is hydrogen, halogen, substituted or unsubstituted $C_1$-$C_3$ alkyl, or —N₃. In embodiments, R² is hydrogen, halogen, —CH₂OH, or —N₃. In embodiments, R² is halogen. In embodiments, R² is —Br. In embodiments, R² is —Cl.

In embodiments, R¹ is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCH₃, —OCF₃, —OCHF₂, —N₃,

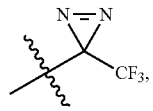 [SMILES: *C1(C(F)(F)F)N=N1]

—C(CH₃)₃, —OCH₂CCH, —NHCH₂CCH, —NHCH₃, —N(CH₃)₂, —NHS(O)CH₃, —C(O)CH₃, —CH₃, —CH₂CCH, —NHC(O)CH₃, —CCH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R¹ is independently halogen. In embodiments, R¹ is —F. In embodiments, R¹ is —Cl. In embodiments, R¹ is —Br. In embodiments, R¹ is —I. In embodiments, R¹ is —CF₃. In embodiments, R¹ is independently substituted or unsubstituted alkyl. In embodiments, R¹ is independently substituted or unsubstituted $C_1$-$C_{10}$ alkyl. In embodiments, R¹ is independently substituted or unsubstituted $C_1$-$C_8$ alkyl. In embodiments, R¹ is independently substituted or unsubstituted $C_1$-$C_6$ alkyl. In embodiments, R¹ is independently substituted or unsubstituted $C_1$-$C_4$ alkyl. In embodiments, R¹ is independently substituted or unsubstituted $C_1$-$C_3$ alkyl. In embodiments, R¹ is independently unsubstituted alkyl. In embodiments, R¹ is independently unsubstituted $C_1$-$C_{10}$ alkyl. In embodiments, R¹ is independently unsubstituted $C_1$-$C_8$ alkyl. In embodiments, R¹ is independently unsubstituted $C_1$-$C_6$ alkyl. In embodiments, R¹ is independently unsubstituted $C_1$-$C_4$ alkyl. In embodiments, R¹ is independently unsubstituted $C_1$-$C_3$ alkyl. In embodiments, R¹ is unsubstituted methyl. In embodiments, R¹ is unsubstituted ethyl. In embodiments, R¹ is unsubstituted propyl. In embodiments, R¹ is unsubstituted butyl. In embodiments, R¹ is unsubstituted isopropyl. In embodiments, R¹ is unsubstituted tert-butyl. In embodiments, R¹ is

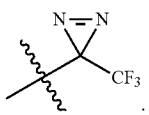

In embodiments, R¹ is —N₃. In embodiments, R¹ is —OCH₂CCH. In embodiments, R¹ is —CCH.

In embodiments, R² is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCH₃, —OCF₃, —OCHF₂, —N₃,

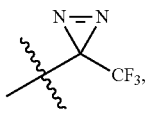

—C(CH₃)₃, —OCH₂CCH, —NHCH₂CCH, —NHCH₃, —N(CH₃)₂, —NHS(O)CH₃, —C(O)CH₃, —CH₃, —CH₂CCH, —NHC(O)CH₃, —CCH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R² is independently halogen. In embodiments, R² is —F. In embodiments, R² is —Cl. In embodiments, R² is —Br. In embodiments, R² is —I. In embodiments, R² is —CF₃. In embodiments, R² is independently substituted or unsubstituted alkyl. In embodiments, R² is independently substituted or unsubstituted $C_1$-$C_{10}$ alkyl. In embodiments, R² is independently substituted or unsubstituted $C_1$-$C_8$ alkyl. In embodiments, $R^2$ is independently substituted or unsubstituted $C_1$-$C_6$ alkyl. In embodiments, $R^2$ is independently substituted or unsubstituted $C_1$-$C_4$ alkyl. In embodiments, $R^2$ is independently substituted or unsubstituted $C_1$-$C_3$ alkyl. In embodiments, $R^2$ is independently unsubstituted alkyl. In embodiments, $R^2$ is independently unsubstituted $C_1$-$C_{10}$ alkyl. In embodiments, $R^2$ is independently unsubstituted $C_1$-$C_8$ alkyl. In embodiments, $R^2$ is independently unsubstituted $C_1$-$C_6$ alkyl. In embodiments, $R^2$ is independently unsubstituted $C_1$-$C_4$ alkyl. In embodiments, $R^2$ is independently unsubstituted $C_1$-$C_3$ alkyl. In embodiments, $R^2$ is unsubstituted methyl. In embodiments, $R^2$ is unsubstituted ethyl. In embodiments, $R^2$ is unsubstituted propyl. In embodiments, $R^2$ is unsubstituted butyl. In embodiments, $R^2$ is unsubstituted isopropyl. In embodiments, $R^2$ is unsubstituted tert-butyl. In embodiments, $R^2$ is

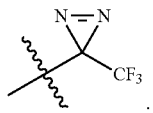 [SMILES: *C1(C(F)(F)F)N=N1]

In embodiments, $R^2$ is —$N_3$. In embodiments, $R^2$ is —$OCH_2CCH$. In embodiments, at least one of $R^1$ or $R^2$ is not hydrogen. In embodiments, $R^2$ is —CCH.

In embodiments, $R^3$ is —C(O)O$R^9$, —C(O)N$R^7R^8$, —SO$_2R^{10}$, —OPO(OH)$_2$, —PO(OH)$_2$, —SO$_3$H, —SO$_4$H, substituted or unsubstituted sulfonate, substituted or unsubstituted phosphate, substituted or unsubstituted $C_1$-$C_{10}$ alkyl, substituted or unsubstituted 2 to 10 membered heteroalkyl, substituted or unsubstituted cycloalkyl, substituted or unsubstituted heterocycloalkyl, or substituted or unsubstituted heteroaryl. In embodiments, $R^3$ is —C(O)O$R^9$, —C(O)N$R^7R^8$, —SO$_2R^{10}$, —OPO(OH)$_2$, —PO(OH)$_2$, —SO$_3$H, —SO$_4$H, substituted or unsubstituted $C_1$-$C_{10}$ alkyl, substituted or unsubstituted 2 to 10 membered heteroalkyl, substituted or unsubstituted $C_3$-$C_8$ cycloalkyl, substituted or unsubstituted heterocycloalkyl, or substituted or unsubstituted heteroaryl. In embodiments, $R^3$ is —C(O)OH. In embodiments, $R^3$ is —C(O)NH$_2$. In embodiments, $R^3$ is —SO$_2R^{10}$. In embodiments, $R^3$ is —SO$_2$CH$_3$. In embodiments, $R^3$ is —SO$_2$Ph. In embodiments, $R^3$ is —SO$_2$Ph-$R^{20}$. In embodiments, $R^3$ is —SO$_2$PhCCH. In embodiments, $R^3$ is substituted or unsubstituted $C_1$-$C_{10}$ alkyl. In embodiments, $R^3$ is substituted or unsubstituted $C_1$-$C_8$ alkyl. In embodiments, $R^3$ is substituted or unsubstituted $C_1$-$C_6$ alkyl. In embodiments, $R^3$ is substituted or unsubstituted $C_1$-$C_4$ alkyl. In embodiments, $R^3$ is substituted or unsubstituted $C_1$-$C_3$ alkyl. In embodiments, $R^3$ is unsubstituted $C_1$-$C_{10}$ alkyl. In embodiments, $R^3$ is unsubstituted $C_1$-$C_8$ alkyl. In embodiments, $R^3$ is unsubstituted $C_1$-$C_6$ alkyl. In embodiments, $R^3$ is unsubstituted $C_1$-$C_4$ alkyl. In embodiments, $R^3$ is unsubstituted $C_1$-$C_3$ alkyl. In embodiments, $R^3$ is substituted or unsubstituted $C_3$-$C_7$ cycloalkyl. In embodiments, $R^3$ is substituted or unsubstituted $C_3$-$C_6$ cycloalkyl. In embodiments, $R^3$ is substituted or unsubstituted $C_3$-$C_5$ cycloalkyl. In embodiments, $R^3$ is substituted or unsubstituted $C_3$-$C_4$ cycloalkyl. In embodiments, $R^3$ is substituted or unsubstituted $C_4$-$C_6$ cycloalkyl. In embodiments, $R^3$ is unsubstituted $C_3$-$C_8$ cycloalkyl. In embodiments, $R^3$ is unsubstituted $C_3$-$C_6$ cycloalkyl. In embodiments, $R^3$ is unsubstituted $C_3$-$C_5$ cycloalkyl. In embodiments, $R^3$ is unsubstituted $C_3$-$C_4$ cycloalkyl. In embodiments, $R^3$ is —OPO(OH)$_2$. In embodiments, $R^3$ is —PO(OH)$_2$. In embodiments, $R^3$ is —SO$_3$H. In embodiments, $R^3$ is —SO$_4$H. In embodiments, $R^3$ is substituted or unsubstituted 3 to 8 membered heterocycloalkyl. In embodiments, $R^3$ is substituted or unsubstituted 3 to 6 membered heterocycloalkyl. In embodiments, $R^3$ is substituted or unsubstituted 3 to 5 membered heterocycloalkyl. In embodiments, $R^3$ is unsubstituted 3 to 8 membered heterocycloalkyl. In embodiments, $R^3$ is unsubstituted 3 to 6 membered heterocycloalkyl. In embodiments, $R^3$ is unsubstituted 3 to 5 membered heterocycloalkyl. In embodiments, $R^3$ is substituted or unsubstituted 2 to 10 membered heteroalkyl. In embodiments, $R^3$ is substituted or unsubstituted 2 to 8 membered heteroalkyl. In embodiments, $R^3$ is substituted or unsubstituted 2 to 6 membered heteroalkyl. In embodiments, $R^3$ is substituted or unsubstituted 2 to 4 membered heteroalkyl. In embodiments, $R^3$ is unsubstituted 2 to 8 membered heteroalkyl. In embodiments, $R^3$ is unsubstituted 2 to 6 membered heteroalkyl. In embodiments, $R^3$ is unsubstituted 2 to 4 membered heteroalkyl. In embodiments, $R^3$ is substituted 2 to 10 membered heteroalkyl. In embodiments, $R^3$ is substituted 2 to 8 membered heteroalkyl. In embodiments, $R^3$ is substituted 2 to 6 membered heteroalkyl. In embodiments, $R^3$ is substituted 2 to 4 membered heteroalkyl. In embodiments, $R^3$ is substituted or unsubstituted 5 to 10 membered heteroaryl. In embodiments, $R^3$ is substituted or unsubstituted 5 to 9 membered heteroaryl. In embodiments, $R^3$ is substituted or unsubstituted 5 to 6 membered heteroaryl. In embodiments, $R^3$ is substituted or unsubstituted 5 membered heteroaryl. In embodiments, $R^3$ is substituted or unsubstituted 6 membered heteroaryl. In embodiments, $R^3$ is unsubstituted 5 to 10 membered heteroaryl. In embodiments, $R^3$ is unsubstituted 5 to 9 membered heteroaryl. In embodiments, $R^3$ is unsubstituted 5 to 6 membered heteroaryl. In embodiments, $R^3$ is unsubstituted 5 membered heteroaryl. In embodiments, $R^3$ is unsubstituted 6 membered heteroaryl. In embodiments, $R^3$ is substituted or unsubstituted tetrazolyl. In embodiments, $R^3$ is unsubstituted tetrazolyl. In embodiments, $R^3$ is substituted tetrazolyl. In embodiments, $R^3$ is unsubstituted phosphate. In embodiments, $R^3$ is unsubstituted sulfonate. In embodiments, $R^3$ is unsubstituted phosphonate. In embodiments, $R^3$ is unsubstituted sulfate. In embodiments, $R^3$ is substituted or unsubstituted triazolyl. In embodiments, $R^3$ is substituted or unsubstituted imidazolyl. In embodiments, $R^3$ is substituted or unsubstituted pyrazolyl. In embodiments, $R^3$ is substituted or unsubstituted oxazolyl. In embodiments, $R^3$ is substituted or unsubstituted isoxazolyl. In embodiments, $R^3$ is substituted or unsubstituted thiazolyl. In embodiments, $R^3$ is substituted or unsubstituted triazinyl. In embodiments, $R^3$ is substituted or unsubstituted pyridazinyl. In embodiments, $R^3$ is substituted or unsubstituted pyrimidinyl. In embodiments, $R^3$ is substituted or unsubstituted pyridinyl. In embodiments, $R^3$ is substituted or unsubstituted furanyl. In embodiments, $R^3$ is substituted or unsubstituted pyrrolyl. In embodiments, $R^3$ is substituted or unsubstituted thienyl. In embodiments, $R^3$ is substituted or unsubstituted isoxazolyl. In embodiments, $R^3$ is substituted or unsubstituted 1,2,5-oxadiazolyl. In embodiments, $R^3$ is substituted or unsubstituted 1,3,4-oxadiazolyl. In embodiments, $R^3$ is substituted or unsubstituted 1H-1,2,4-triazolyl. In embodiments, $R^3$ is substituted or unsubstituted isothiazolyl. In embodiments, $R^3$ is substituted or unsubstituted 1,2,5-thiadiazolyl. In embodiments, $R^3$ is substituted or unsubstituted 4,5-dihydro-1H-tetrazolyl. In embodiments, $R^3$ is substituted or unsubstituted 2H-tetrazolyl. In embodiments, $R^3$ is substituted or unsubstituted 1,2,4-oxadiazolidinyl. In embodiments, $R^3$ is substituted or unsubstituted 4,5-dihydro-1,2,4-oxadiazolyl. In embodiments, $R^3$ is substituted or unsubstituted 4,5- dihydro-1H-1,2,4-triazolyl. In embodiments, $R^3$ is substituted or unsubstituted 4H-1,2,4-triazolyl. In embodiments, $R^3$ is substituted or unsubstituted 1H-pyrazolyl. In embodiments, $R^3$ is substituted or unsubstituted 1H-1,2,3-triazolyl. In embodiments, $R^3$ is substituted or unsubstituted 1H-imidazolyl. In embodiments, $R^3$ is substituted or unsubstituted 1,2,5-thiadiazolidinyl. In embodiments, $R^3$ is substituted or unsubstituted 1,2,5-thiadiazolidinyl 1,1-dioxide. In embodiments, $R^3$ is substituted or unsubstituted 1,2,4-thiadiazolidinyl. In embodiments, $R^3$ is substituted or unsubstituted 1,2,4-thiadiazolidinyl 1,1-dioxide. In embodiments, $R^3$ is substituted or unsubstituted thiazolidinyl. In embodiments, $R^3$ is substituted or unsubstituted oxazolidinyl. In embodiments, $R^3$ is substituted or unsubstituted pyrrolidinyl. In embodiments, $R^3$ is substituted or unsubstituted 2,5-dihydrofuranyl. In embodiments, $R^3$ is substituted or unsubstituted cyclobutenyl.

In embodiments, $R^3$ is substituted or unsubstituted

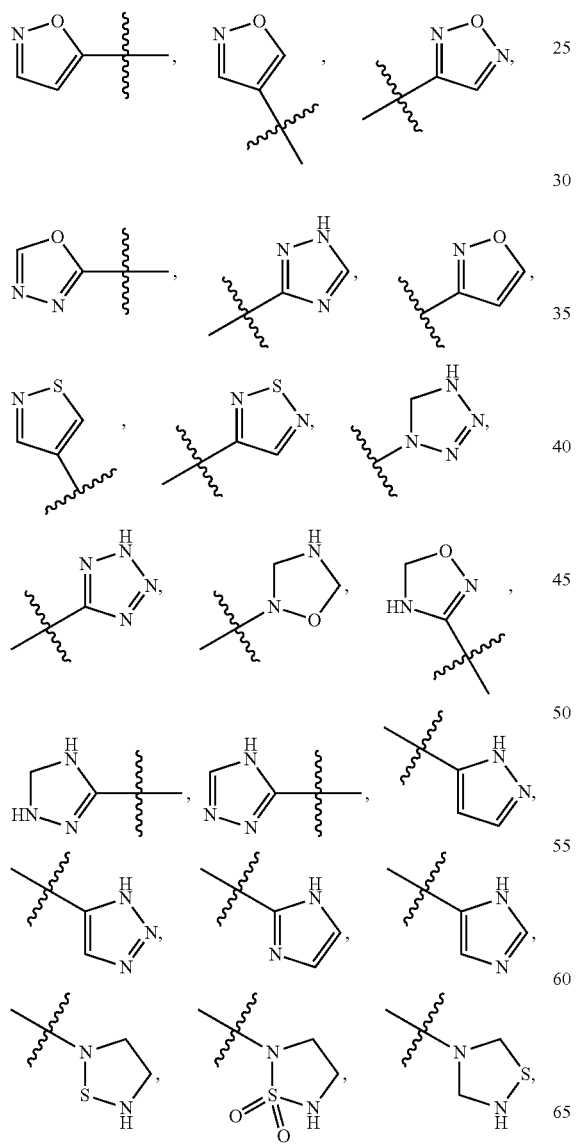

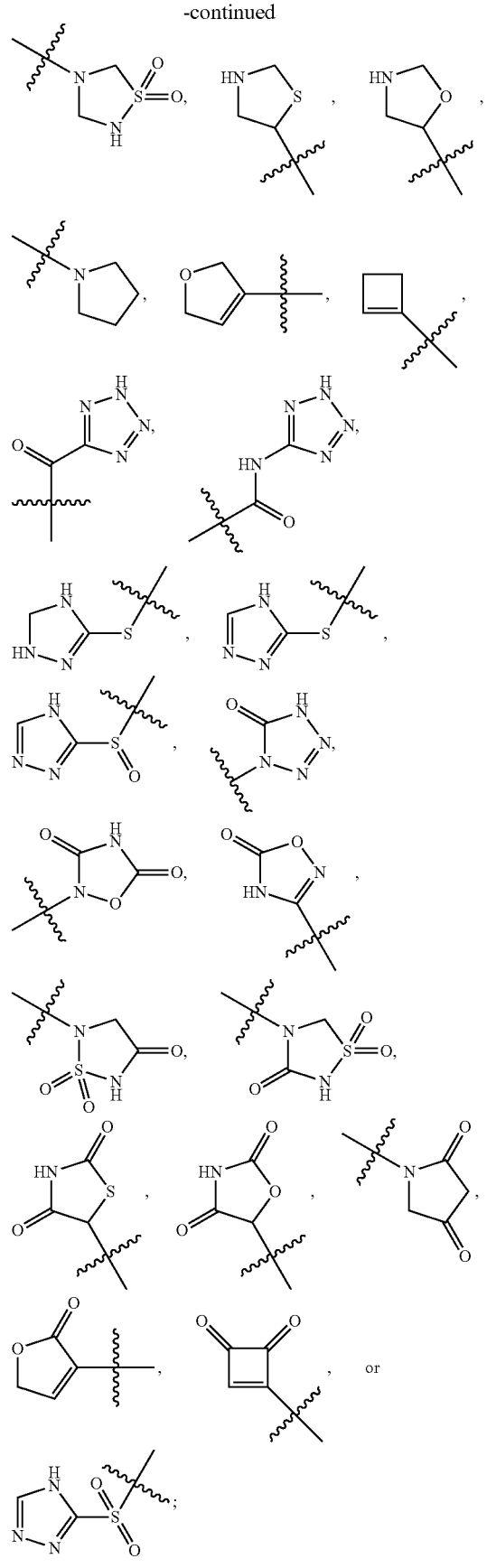

wherein a substituted R³ may optionally have one or more substituents in place of one or more of the ring hydrogens in the structures immediately above.

In embodiments, R³ is substituted or unsubstituted

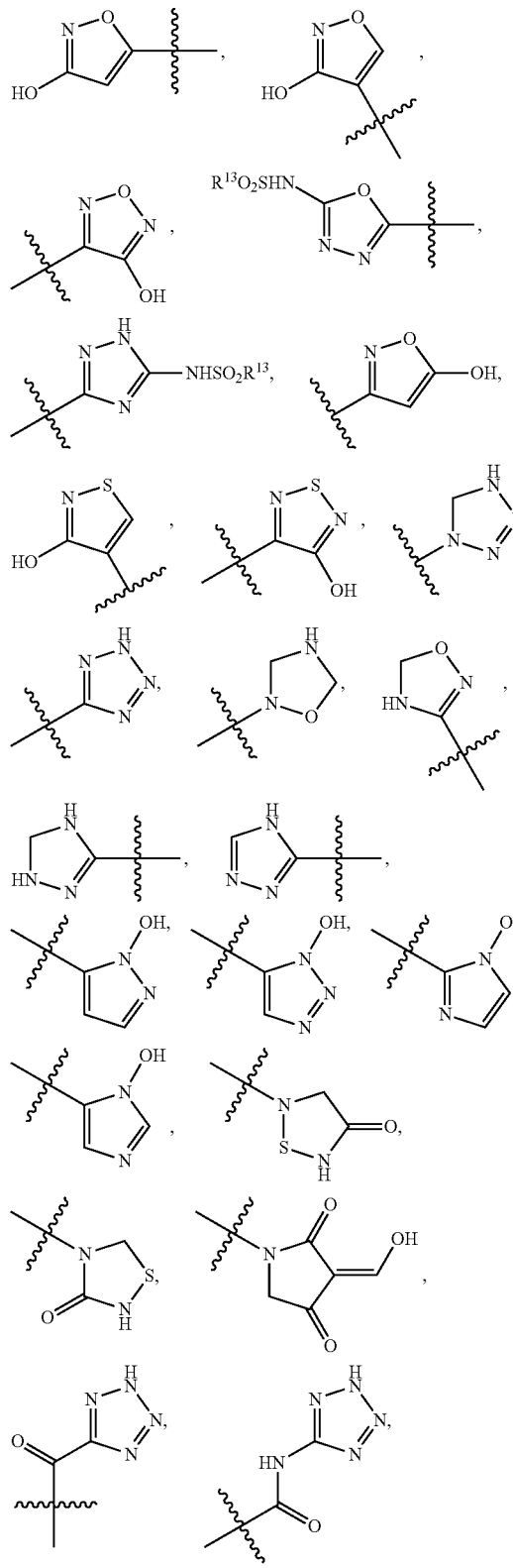

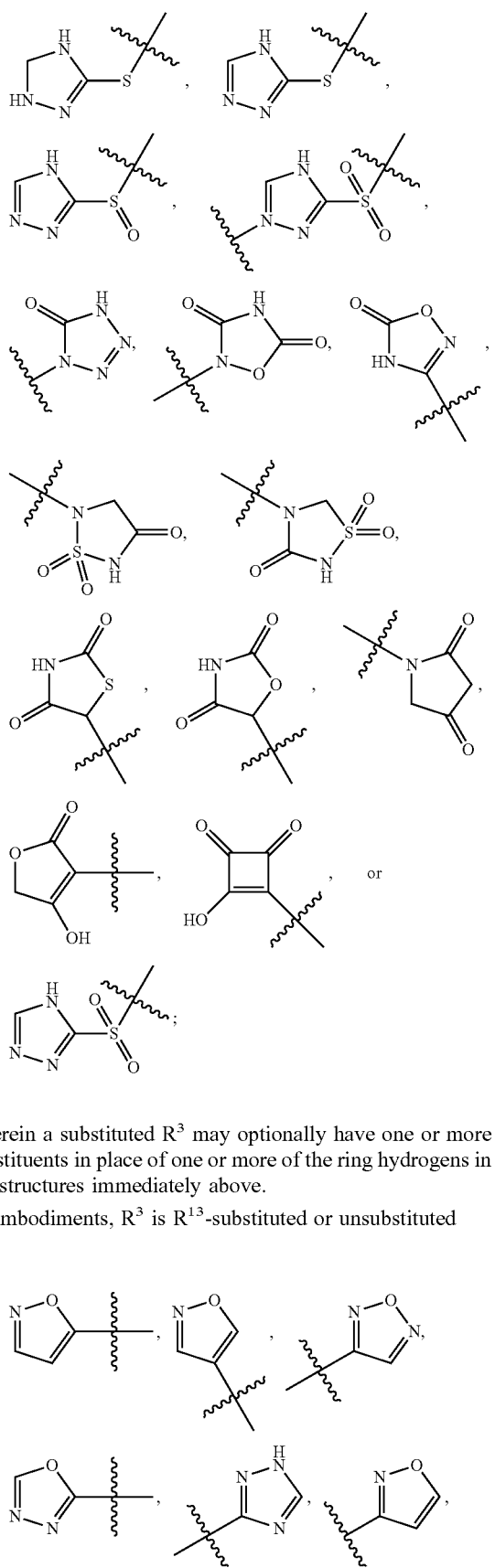

wherein a substituted R³ may optionally have one or more substituents in place of one or more of the ring hydrogens in the structures immediately above.

In embodiments, R³ is R¹³-substituted or unsubstituted

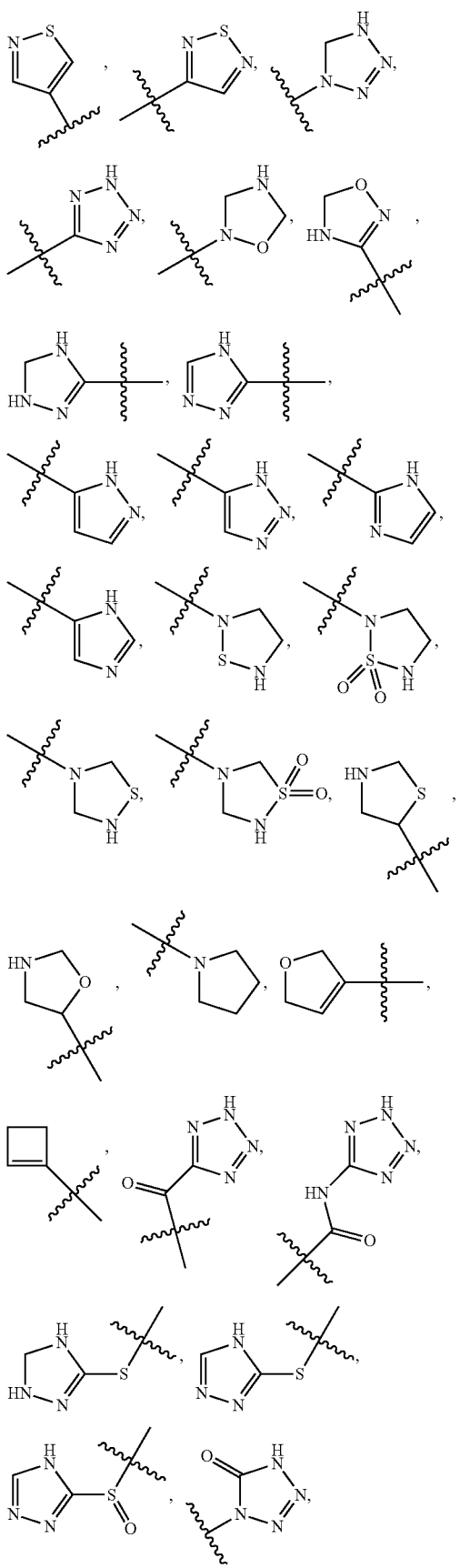
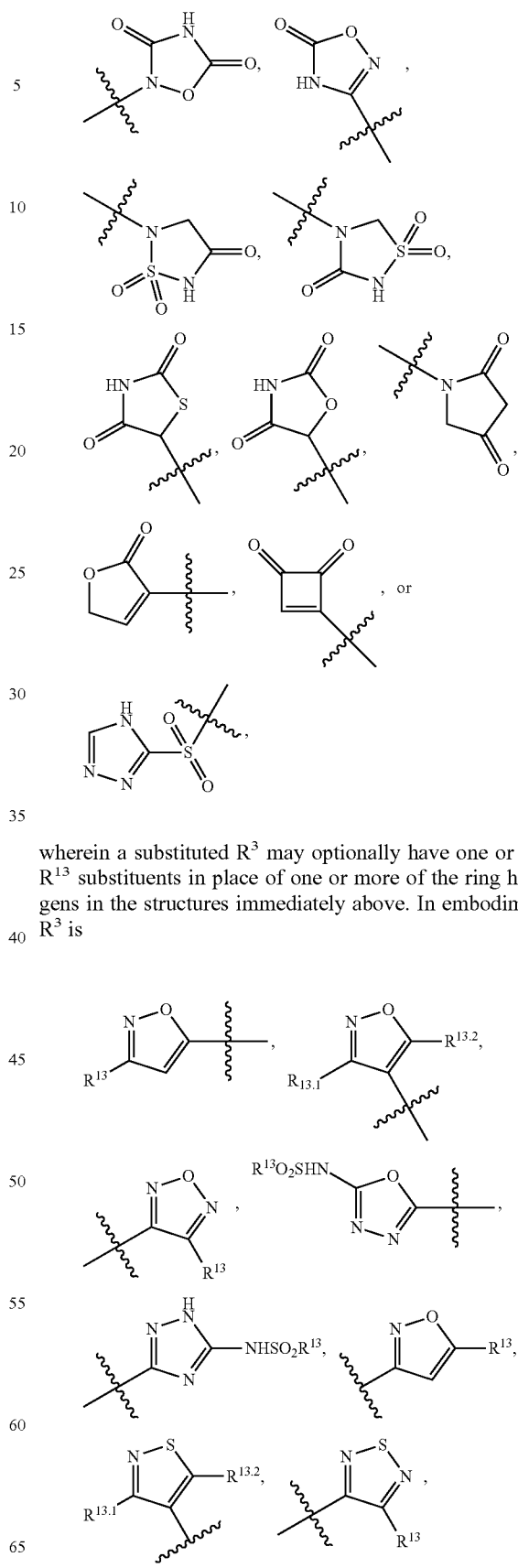
wherein a substituted $R^3$ may optionally have one or more $R^{13}$ substituents in place of one or more of the ring hydrogens in the structures immediately above. In embodiments, $R^3$ is

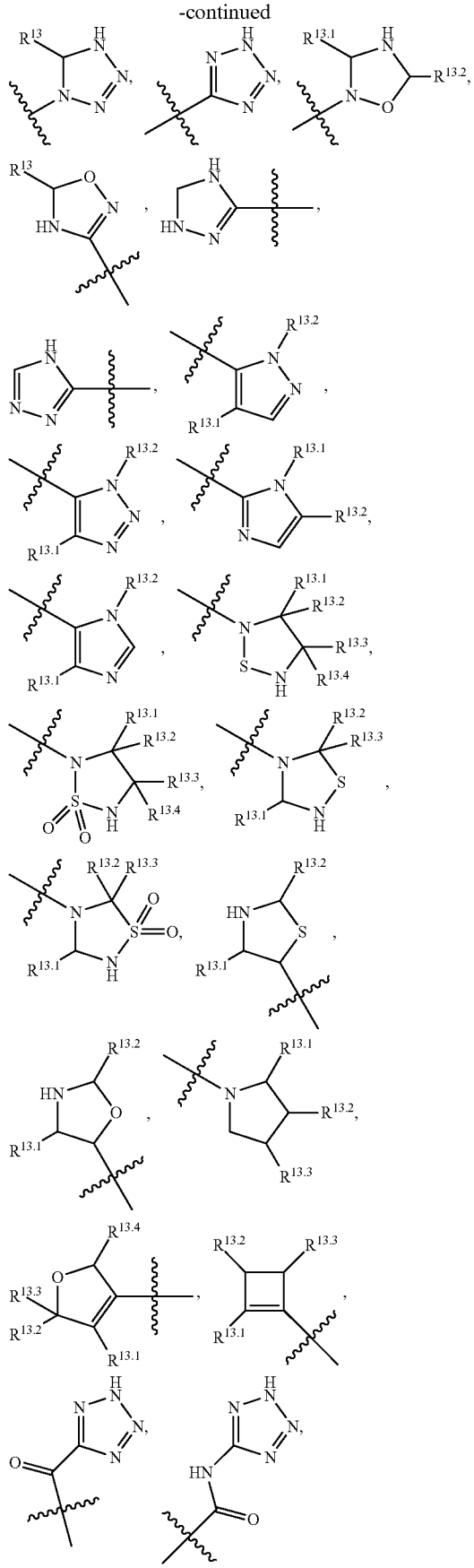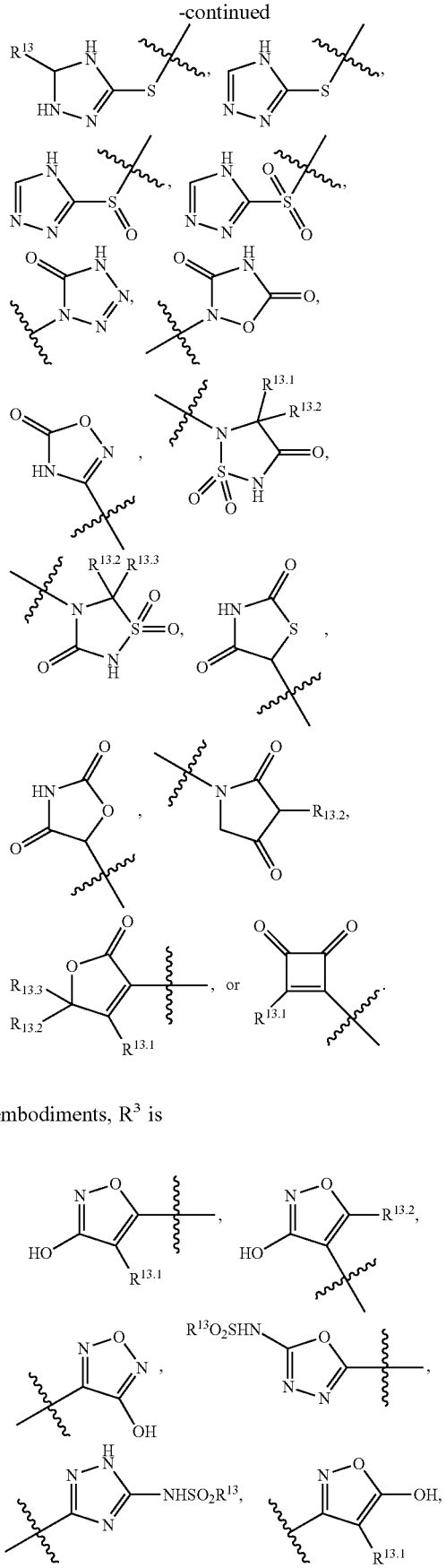
In embodiments, $R^3$ is
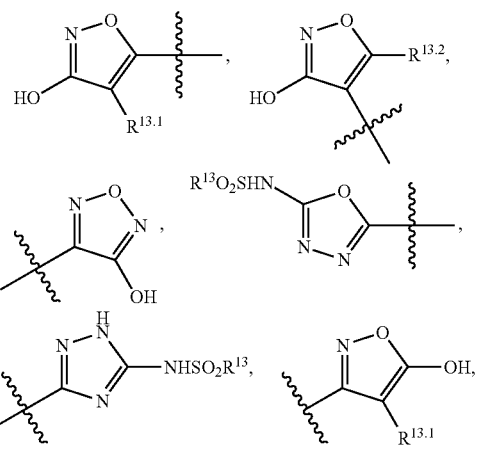

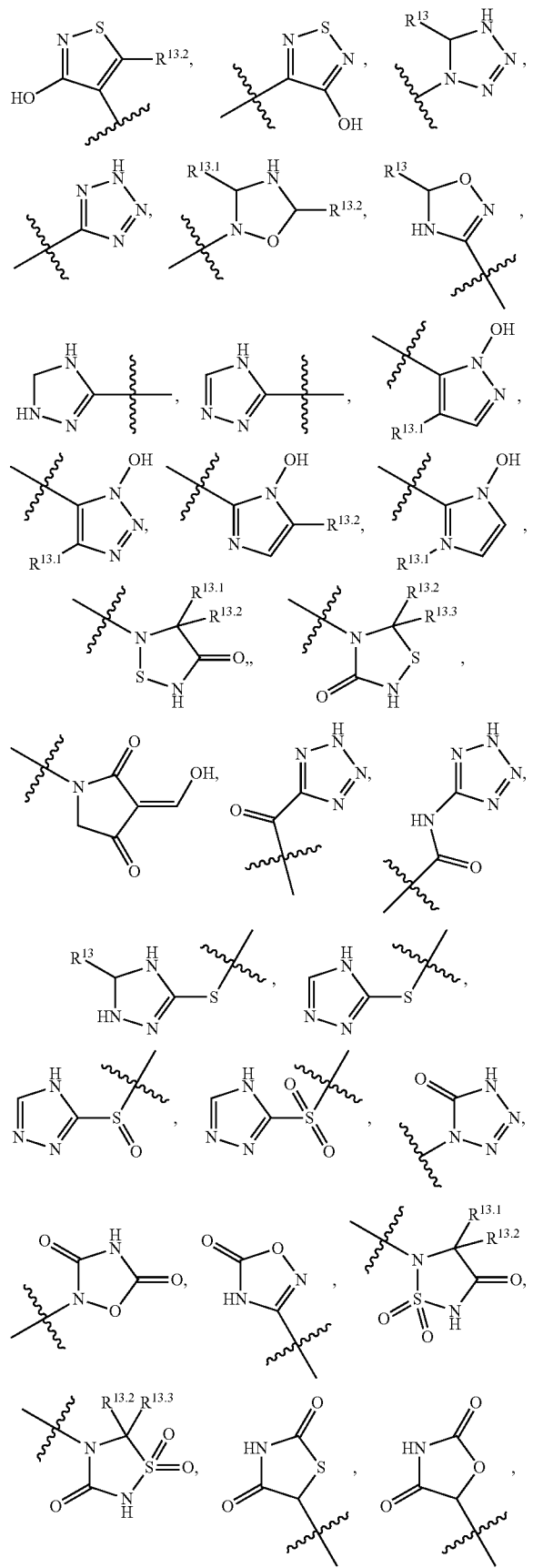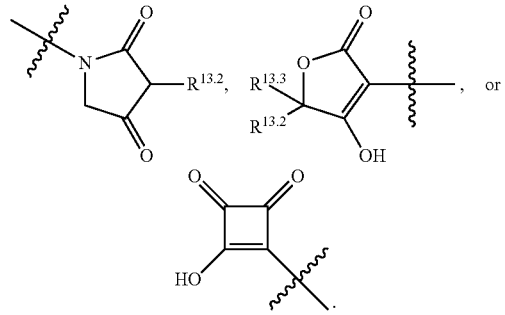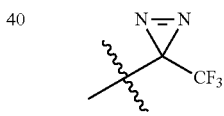

It will be understood that an $R^{13}$ substituent may be an oxo in accordance with the normal rules of valency. Thus, where two $R^{13}$ groups are attached to a common carbon, one $R^{13}$ group will be absent where the other $R^{13}$ group is an oxo. Thus, where an $R^{13}$ group and a hydrogen are attached to a common carbon, the hydrogen will be absent where the $R^{13}$ group is an oxo. In embodiments, $R^3$ is —$S(O)_2CH_3$, —$S(O)_2NHC(O)CH_3$, or —$S(O)_2OH$. In embodiments, $R^3$ is —$C(O)NR^7S(O)_2R^{10}$.

In embodiments, $R^4$ is substituted or unsubstituted alkyl or substituted or unsubstituted heteroalkyl. In embodiments, $R^4$ is substituted or unsubstituted $C_1$-$C_8$ alkyl. In embodiments, $R^4$ is substituted or unsubstituted $C_1$-$C_6$ alkyl. In embodiments, $R^4$ is substituted or unsubstituted $C_1$-$C_4$ alkyl. In embodiments, $R^4$ is substituted or unsubstituted $C_1$-$C_3$ alkyl. In embodiments, $R^4$ is unsubstituted $C_1$-$C_8$ alkyl. In embodiments, $R^4$ is unsubstituted $C_1$-$C_6$ alkyl. In embodiments, $R^4$ is unsubstituted $C_1$-$C_4$ alkyl. In embodiments, $R^4$ is unsubstituted $C_1$-$C_3$ alkyl. In embodiments, $R^4$ is unsubstituted methyl. In embodiments, $R^4$ is unsubstituted ethyl. In embodiments, $R^4$ is unsubstituted propyl. In embodiments, $R^4$ is unsubstituted isopropyl. In embodiments, $R^4$ is In embodiments, $R^4$ is —$N_3$. In embodiments, $R^4$ is —$OCH_2CCH$. In embodiments, $R^4$ is —$CF_3$. In embodiments, $R^4$ is —$NHC(O)CH_3$. In embodiments, $R^4$ is —$OH$. In embodiments, $R^4$ is —$OCH_3$. In embodiments, $R^4$ is —$NHCH_3$. In embodiments, $R^4$ is —$NHC(S)CH_3$. In embodiments, $R^4$ is —$N(CH_3)_2$. In embodiments, $R^4$ is —$C(CH_3)_3$, —$OCH_2CCH$, —$NHCH_2CCH$, —$NHCH_3$, —$N(CH_3)_2$, —$NHS(O)CH_3$, —$C(O)CH_3$, —$CH_3$, —$CH_2CCH$, or —$NHC(O)CH_3$.

In embodiments, $R^5$ is substituted or unsubstituted alkyl or substituted or unsubstituted heteroalkyl. In embodiments, $R^5$ is substituted or unsubstituted $C_1$-$C_8$ alkyl. In embodiments, $R^5$ is substituted or unsubstituted $C_1$-$C_6$ alkyl. In embodiments, $R^5$ is substituted or unsubstituted $C_1$-$C_4$ alkyl. In embodiments, $R^5$ is substituted or unsubstituted $C_1$-$C_3$ alkyl. In embodiments, $R^5$ is unsubstituted $C_1$-$C_8$ alkyl. In embodiments, $R^5$ is unsubstituted $C_1$-$C_6$ alkyl. In embodiments, $R^5$ is unsubstituted $C_1$-$C_4$ alkyl. In embodiments, $R^5$ is unsubstituted $C_1$-$C_3$ alkyl. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted isopropyl. In embodiments, $R^5$ is

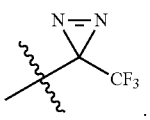

In embodiments, $R^5$ is $-N_3$. In embodiments, $R^5$ is $-OCH_2CCH$. In embodiments, $R^5$ is $-CF_3$. In embodiments, $R^5$ is $-NHC(O)CH_3$. In embodiments, $R^5$ is $-OH$. In embodiments, $R^5$ is $-OCH_3$. In embodiments, $R^5$ is $-NHCH_3$. In embodiments, $R^5$ is $-NHC(S)CH_3$. In embodiments, $R^5$ is $-N(CH_3)_2$. In embodiments, $R^5$ is $-C(CH_3)_3$, $-OCH_2CCH$, $-NHCH_2CCH$, $-NHCH_3$, $-N(CH_3)_2$, $-NHS(O)CH_3$, $-C(O)CH_3$, $-CH_3$, $-CH_2CCH$, or $-NHC(O)CH_3$.

In embodiments, $R^4$ and $R^5$ are joined to form a substituted or unsubstituted cycloalkyl, substituted or unsubstituted heterocycloalkyl, substituted or unsubstituted aryl, or substituted or unsubstituted heteroaryl. In embodiments, $R^4$ and $R^5$ are joined to form a substituted or unsubstituted cycloalkyl or substituted or unsubstituted heterocycloalkyl. In embodiments, $R^4$ and $R^5$ are joined to form a substituted or unsubstituted cycloalkyl. In embodiments, $R^4$ and $R^5$ are joined to form a substituted or unsubstituted $C_3$-$C_8$ cycloalkyl. In embodiments, $R^4$ and $R^5$ are joined to form a substituted or unsubstituted $C_3$-$C_6$ cycloalkyl. In embodiments, $R^4$ and $R^5$ are joined to form a substituted or unsubstituted $C_3$-$C_5$ cycloalkyl. In embodiments, $R^4$ and $R^5$ are joined to form an unsubstituted cycloalkyl. In embodiments, $R^4$ and $R^5$ are joined to form an unsubstituted $C_3$-$C_8$ cycloalkyl. In embodiments, $R^4$ and $R^5$ are joined to form an unsubstituted $C_3$-$C_6$ cycloalkyl. In embodiments, $R^4$ and $R^5$ are joined to form an unsubstituted $C_3$-$C_5$ cycloalkyl. In embodiments, $R^4$ and $R^5$ are joined to form an unsubstituted $C_4$ cycloalkyl. In embodiments, $R^4$ and $R^5$ are joined to form a substituted $C_4$ cycloalkyl. In embodiments, $R^4$ and $R^5$ are joined to form an unsubstituted $C_5$ cycloalkyl. In embodiments, $R^4$ and $R^5$ are joined to form a substituted $C_5$ cycloalkyl. In embodiments, $R^4$ and $R^5$ are joined to form an unsubstituted $C_6$ cycloalkyl. In embodiments, $R^4$ and $R^5$ are joined to form a substituted $C_6$ cycloalkyl. In embodiments, $R^4$ and $R^5$ are joined to form an unsubstituted $C_7$ cycloalkyl. In embodiments, $R^4$ and $R^5$ are joined to form a substituted $C_7$ cycloalkyl. In embodiments, $R^4$ and $R^5$ are joined to form an unsubstituted $C_8$ cycloalkyl. In embodiments, $R^4$ and $R^5$ are joined to form a substituted $C_8$ cycloalkyl. In embodiments, $R^4$ and $R^5$ are joined to form an unsubstituted cyclopropyl. In embodiments, $R^4$ and $R^5$ are joined to form an unsubstituted cyclobutyl. In embodiments, $R^4$ and $R^5$ are joined to form an unsubstituted cyclopentyl. In embodiments, $R^4$ and $R^5$ are joined to form an unsubstituted cyclohexyl. In embodiments, $R^4$ and $R^5$ are joined to form a substituted cyclopropyl. In embodiments, $R^4$ and $R^5$ are joined to form a substituted cyclobutyl. In embodiments, $R^4$ and $R^5$ are joined to form a substituted cyclopentyl. In embodiments, $R^4$ and $R^5$ are joined to form a substituted cyclohexyl. In embodiments, $R^4$ and $R^5$ are joined to form a substituted cycloheptyl. In embodiments, $R^4$ and $R^5$ are joined to form a substituted cycloheptyl. In embodiments, $R^4$ and $R^5$ are joined to form an unsubstituted cycloheptyl. In embodiments, $R^4$ and $R^5$ are joined to form a substituted cyclooctyl. In embodiments, $R^4$ and $R^5$ are joined to form an unsubstituted cyclooctyl. In embodiments, $R^4$ and $R^5$ are joined to form a substituted or unsubstituted heterocycloalkyl. In embodiments, $R^4$ and $R^5$ are joined to form a substituted or unsubstituted 3 to 10 membered heterocycloalkyl. In embodiments, $R^4$ and $R^5$ are joined to form a substituted or unsubstituted 3 to 8 membered heterocycloalkyl. In embodiments, $R^4$ and $R^5$ are joined to form a substituted or unsubstituted 3 to 6 membered heterocycloalkyl. In embodiments, $R^4$ and $R^5$ are joined to form a substituted or unsubstituted 3 to 5 membered heterocycloalkyl. In embodiments, $R^4$ and $R^5$ are joined to form a substituted or unsubstituted 3 to 4 membered heterocycloalkyl. In embodiments, $R^4$ and $R^5$ are joined to form a substituted or unsubstituted piperidinyl. In embodiments, $R^4$ and $R^5$ are joined to form an N-substituted piperidinyl. In embodiments, $R^4$ and $R^5$ are joined to form a piperidinyl substituted with $-CH_3$, $-CH_2CCH$, $-C(O)CH_3$, $-NHC(O)CH_3$, unsubstituted alkyl, or unsubstituted heteroalkyl. In embodiments, $R^4$ and $R^5$ are joined to form a substituted or unsubstituted tetrahydropyranyl.

In embodiments, $R^7$, $R^8$, $R^9$, and $R^{10}$, are independently hydrogen, oxo, halogen, $-C(O)CH_3$, $-CF_3$, $-CCl_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)CH_3$, $-NHC=(O)NH_2$, $-NHSO_2H$, $-NHC=(O)H$, $-NHC(O)-OH$, $-NHOH$, $-OCF_3$, $-OCHF_2$, $-N_3$,

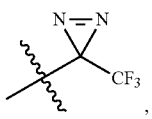

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl.

In embodiments, $R^7$, $R^8$, $R^9$, and $R^{10}$, are independently hydrogen. In embodiments, $R^7$, $R^8$, $R^9$, and $R^{10}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$, $R^8$, $R^9$, and $R^{10}$, are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$, $R^8$, $R^9$, and $R^{10}$, are independently unsubstituted alkyl, unsubstituted heteroalkyl, unsubstituted cycloalkyl, unsubstituted heterocycloalkyl, unsubstituted aryl, or unsubstituted heteroaryl.

In embodiments, the symbol W is $-O-$. In embodiments, the symbol W is $-S-$. In embodiments, the symbol W is $-C(R^4)(R^5)-$. In embodiments, the symbol W is $-S(O)-$. In embodiments, the symbol W is $-S(O)_2-$. In embodiments, the symbol y is 0. In embodiments, the symbol y is 1. In embodiments, the symbols m and v are independently 1. In embodiments, the symbols m and v are independently 2. In embodiments, the symbol n is independently 0. In embodiments, the symbol n is independently 1. In embodiments, the symbol n is independently 2. In embodiments, the symbol n is independently 3. In embodiments, the symbol n is independently 4. In embodiments, the symbol t1 is independently 0. In embodiments, the symbol t1 is independently 1. In embodiments, the symbol t1 is independently 2. In embodiments, the symbol t1 is independently 3. In embodiments, the symbol t1 is independently 4. In embodiments, the symbol t2 is independently 0. In embodiments, the symbol t2 is independently 1. In embodiments, the symbol t2 is independently 2. In embodiments, the symbol t2 is independently 3. In embodiments, the symbol t2 is independently 4. In embodiments, the symbol X is independently —Cl. In embodiments, the symbol X is independently —Br. In embodiments, the symbol X is independently —I. In embodiments, the symbol X is independently —F.

In embodiments, the compound is not a compound having the formula:

(II)

wherein y is 0, $R^1$ and $R^2$ are independently halide, $L^1$-$L^2$ is unsubstituted ethylene, and $R^3$ is —COOH. In embodiments, the compound is not a compound of formula (II) wherein y is 0, $R^1$ and $R^2$ are independently hydrogen, $L^1$-$L^2$ is unsubstituted ethylene, and $R^3$ is —COOH. In embodiments, the compound is not a compound of formula (II) wherein y is 0, $R^1$ and $R^2$ are independently hydrogen or halide, $L^1$-$L^2$ is unsubstituted ethylene, and $R^3$ is —COOH. In embodiments, the compound is not a compound of formula (II) wherein y is 0, $R^1$ and $R^2$ are independently hydrogen or halide, $L^1$-$L^2$ is unsubstituted ethylene, and $R^3$ is —COOH or —CN. In embodiments, the compound is not a compound of formula (II) wherein y is 0, $R^1$ and $R^2$ are independently hydrogen or halide, $L^1$-$L^2$ is unsubstituted ethylene, and $R^3$ is —CN. In embodiments, the compound is not a compound of formula (II) wherein y is 0, $R^1$ and $R^2$ are independently hydrogen or halide, $L^1$-$L^2$ is unsubstituted ethylene, and $R^3$ is —COOH or —CN or —C(O)NHNH$_2$. In embodiments, the compound is not a compound of formula (II) wherein y is 0, $R^1$ and $R^2$ are independently hydrogen or halide, $L^1$-$L^2$ is unsubstituted ethylene, and $R^3$ is C(O)NHNH$_2$. In embodiments, the compound is not a compound of formula (II) wherein y is 0, $R^1$ and $R^2$ are independently hydrogen or halide, $L^1$-$L^2$ is unsubstituted C$_1$-C$_4$ alkylene, and $R^3$ is —COOH or —CN or —C(O)NHNH$_2$. In embodiments, the compound is not a compound of formula (II) wherein y is 0, $R^1$ and $R^2$ are independently hydrogen or halide, $L^1$-$L^2$ is C$_1$-C$_4$ alkylene substituted with —OH, and $R^3$ is —OH or —COOH or —CN or —C(O)NHNH$_2$. In embodiments, the compound is not a compound of formula (II) wherein y is 0, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$.

In embodiments, the compound is not a compound of formula (I) wherein y is 0, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$. In embodiments, the compound is not a compound of formula (I) wherein t1 and t2 are 1, y is 1, W is —S—, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$. In embodiments, the compound is not a compound of formula (I) wherein t1 and t2 are 1, y is 1, W is —S— or —O—, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$. In embodiments, the compound is not a compound of formula (I) wherein t1 and t2 are 1, y is 0 or 1, W is —S— or —O—, $R^1$ and $R^2$ are independently hydrogen or halide, $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (I) wherein t1 and t2 are 1, $R^1$ and $R^2$ are independently hydrogen or halide, $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (I) wherein t1 and t2 are 1, $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (I) wherein $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (I) wherein $R^3$ is —OH or —COOH or —CN or —C(O)NHNH$_2$. In embodiments, the compound is not a compound of formula (II) wherein y is 0, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$. In embodiments, the compound is not a compound of formula (II) wherein t1 and t2 are 1, y is 1, W is —S—, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$. In embodiments, the compound is not a compound of formula (II) wherein t1 and t2 are 1, y is 1, W is —S— or —O—, $R^1$ and $R^2$ are independently hydrogen or halide, $L^1$-$L^2$ is —OH substituted or unsubstituted C$_1$-C$_4$ alkylene, and $R^3$ is —OH or —COOH or —CN or —C(O)NHNH$_2$. In embodiments, the compound is not a compound of formula (II) wherein t1 and t2 are 1, y is 0 or 1, W is —S— or —O—, $R^1$ and $R^2$ are independently hydrogen or halide, $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (II) wherein t1 and t2 are 1, $R^1$ and $R^2$ are independently hydrogen or halide, $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (II) wherein t1 and t2 are 1, $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (II) wherein $L^1$-$L^2$ is substituted or unsubstituted C$_1$-C$_4$ alkylene, and $R^3$ is —OH or —COOH or —CN or —C(O)NHNH$_2$. In embodiments, the compound is not a compound of formula (II) wherein $R^3$ is —OH or —COOH or —CN or —C(O)NHNH$_2$.

In embodiments, the compound is a compound selected from the group consisting of -continued
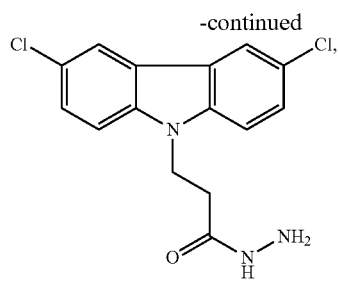
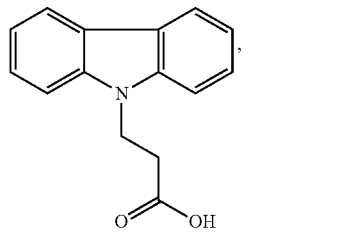
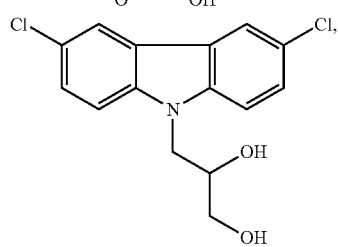
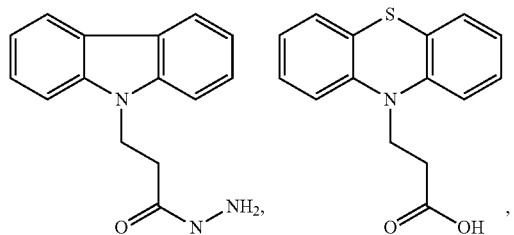
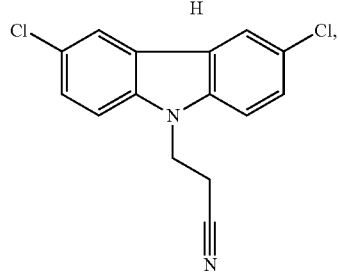
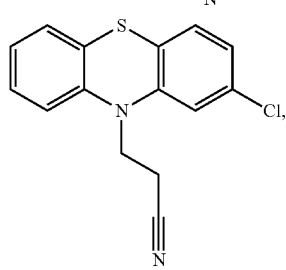
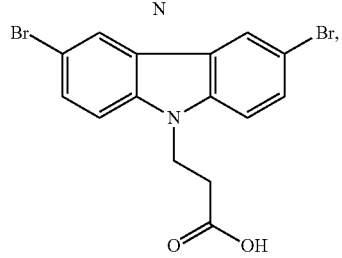
-continued
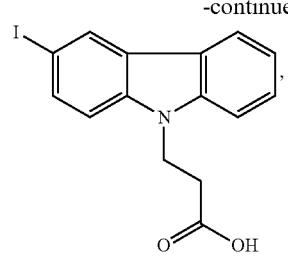
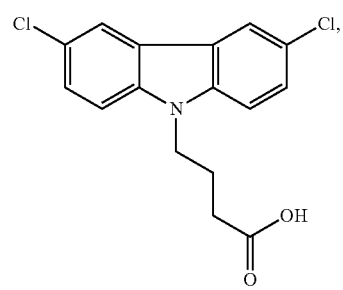
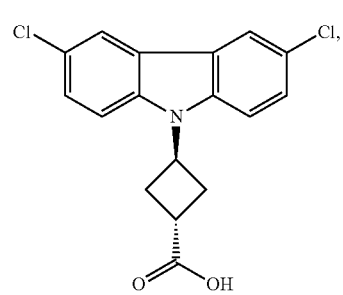
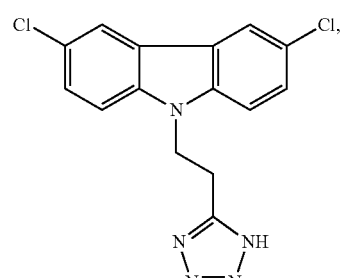
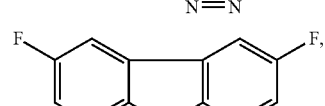
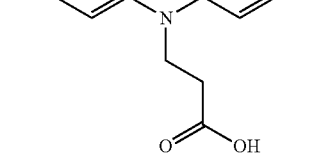
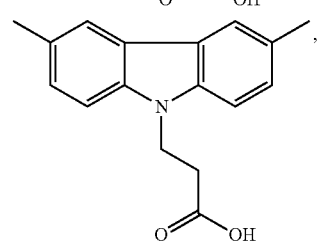

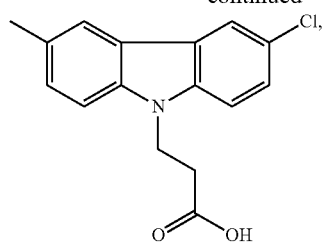
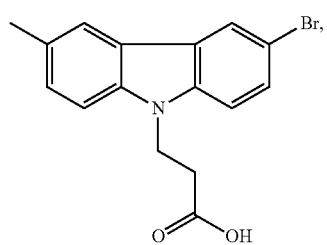
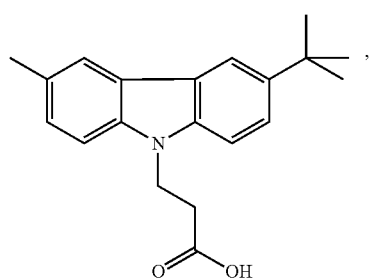
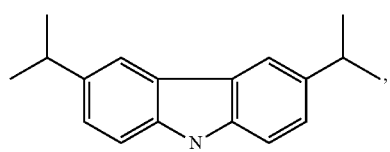
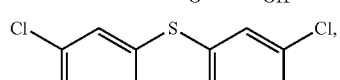
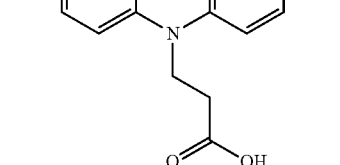
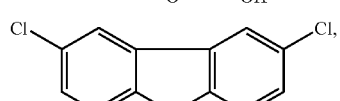
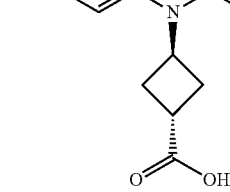
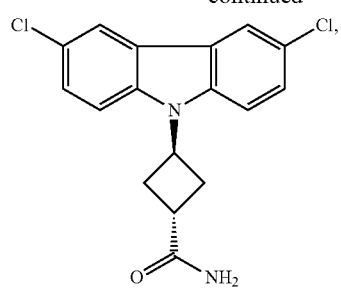
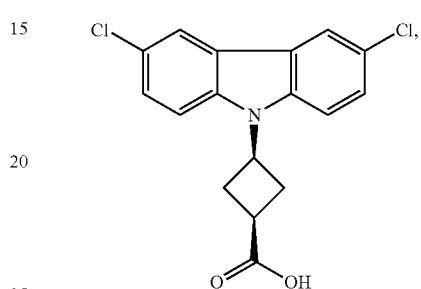
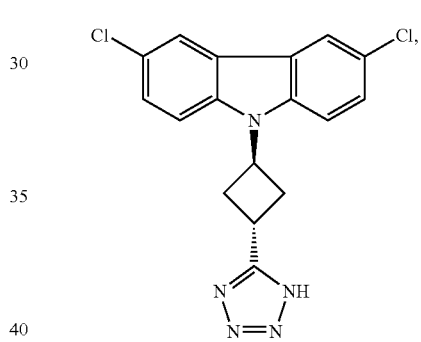
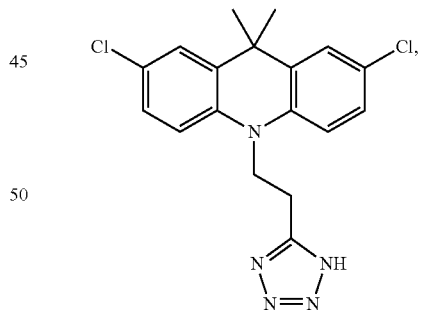
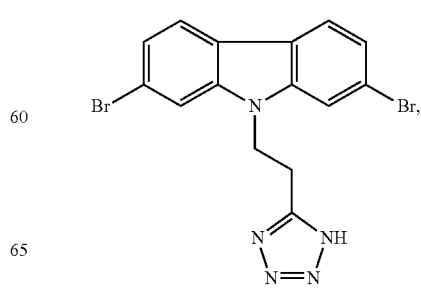

67
-continued
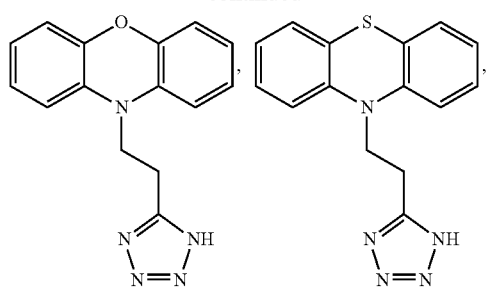
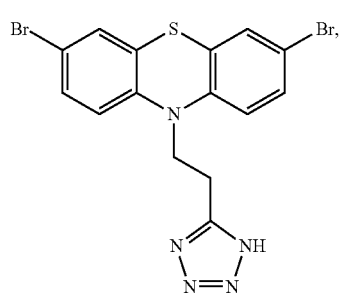
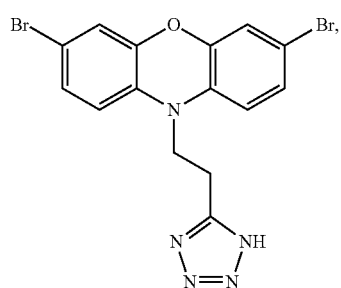
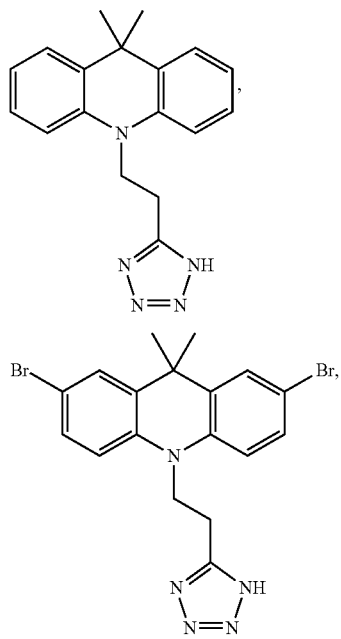
68
-continued
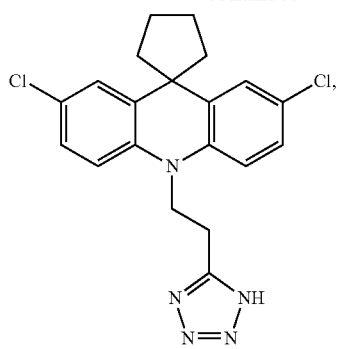
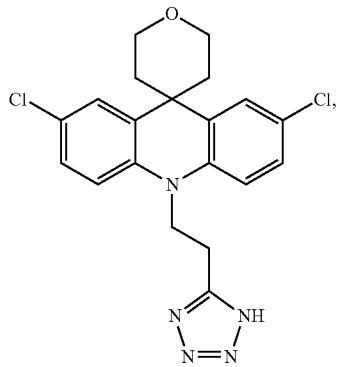
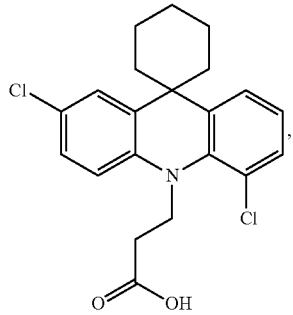
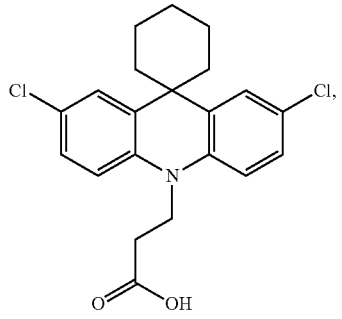
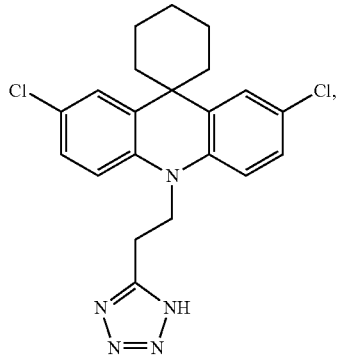

69
-continued
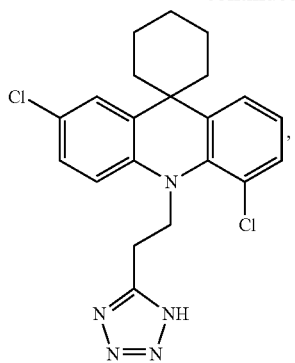
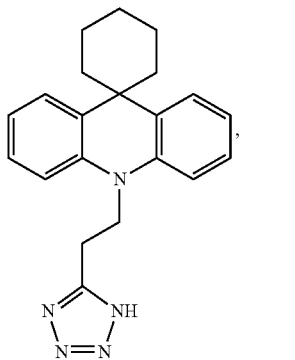
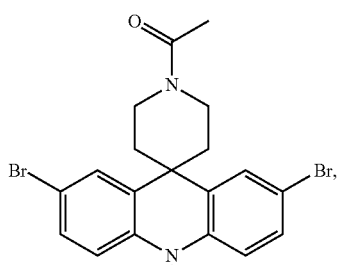
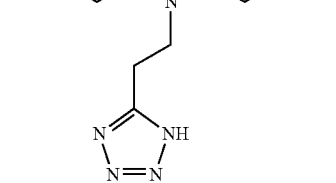
70
-continued
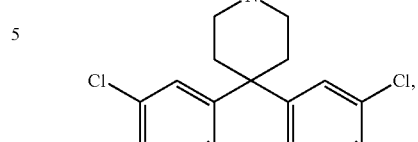
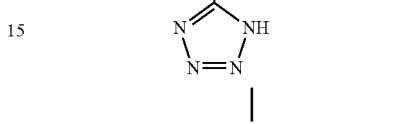
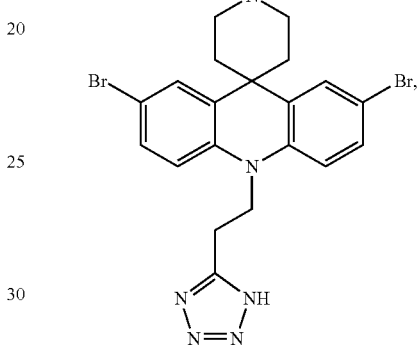
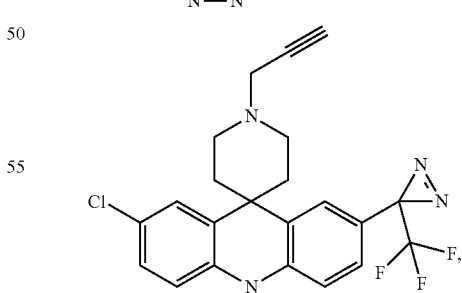

71
-continued
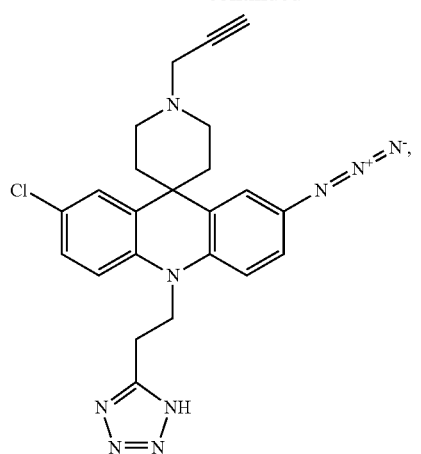
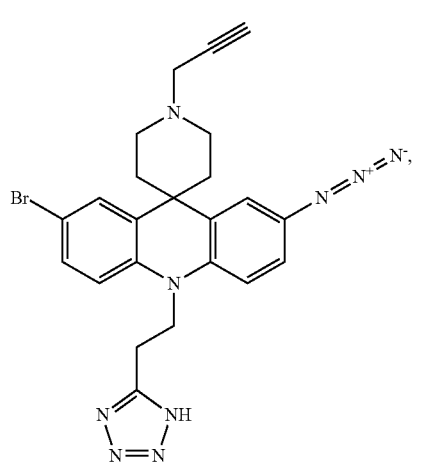
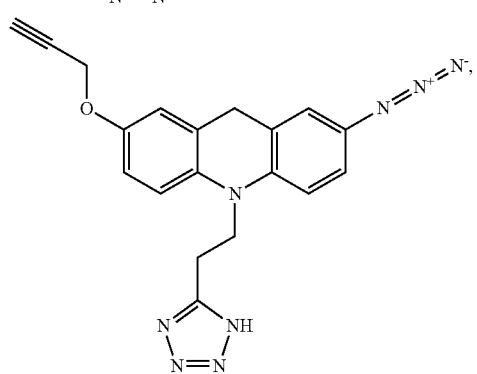
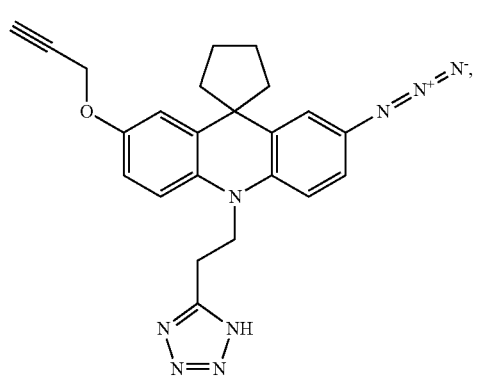
72
-continued
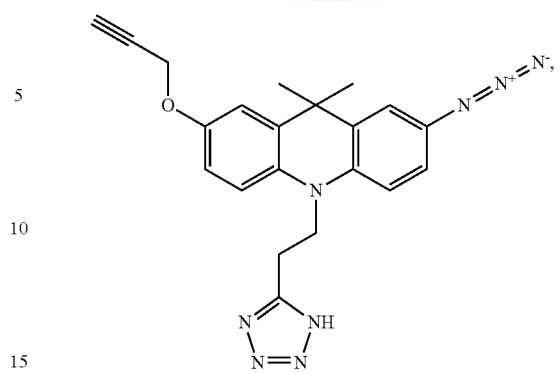
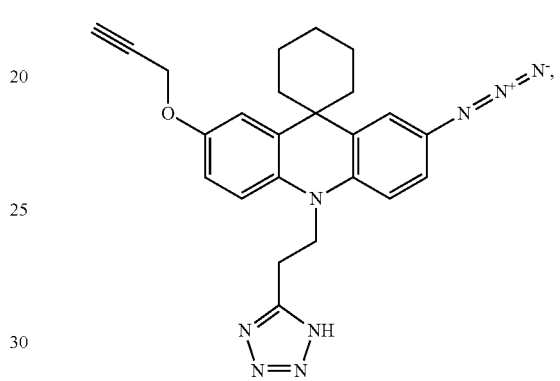
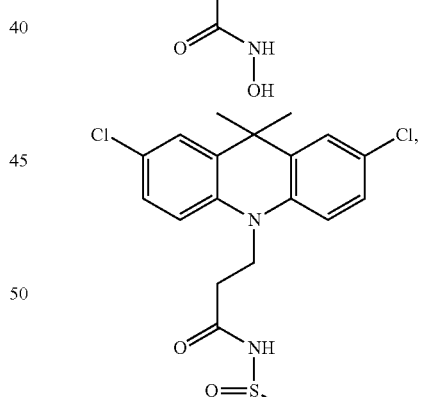
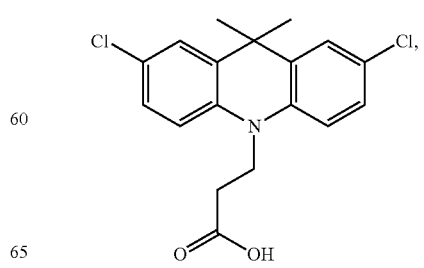

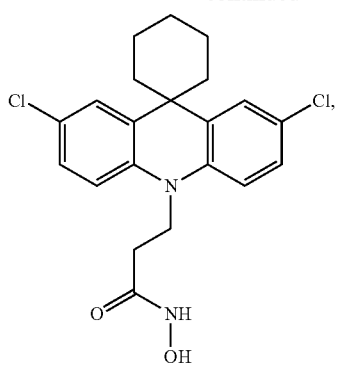
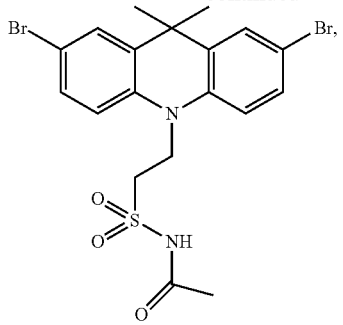

75
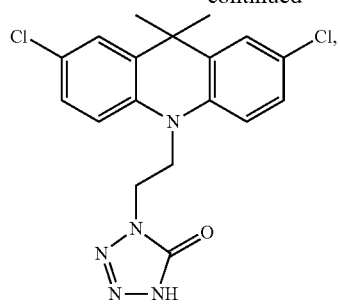
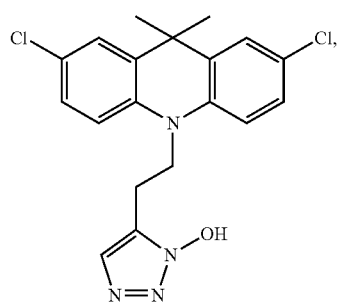
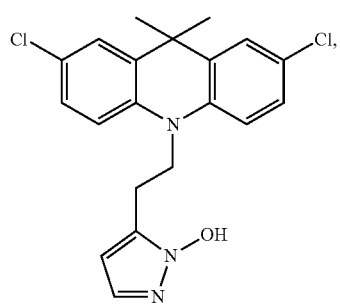
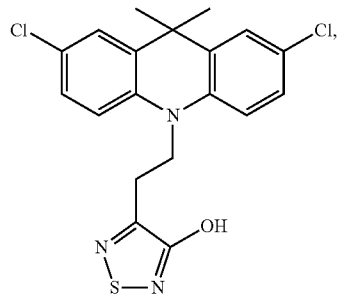
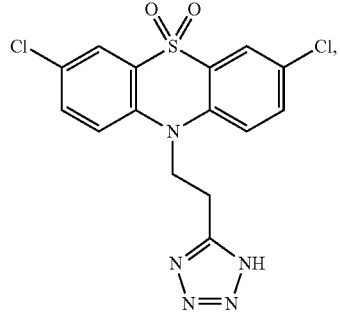
76
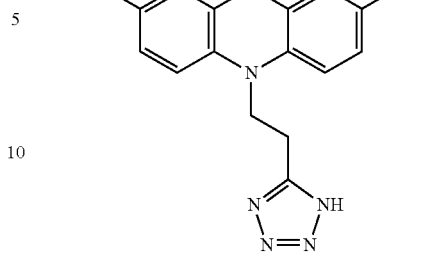
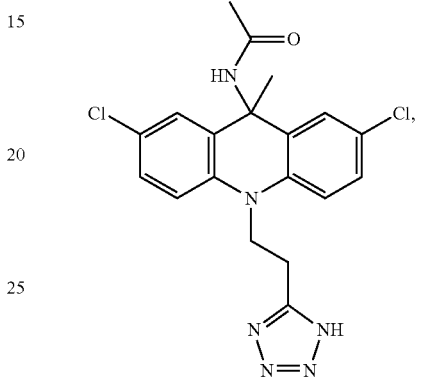
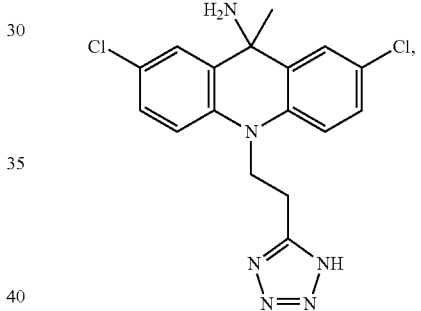
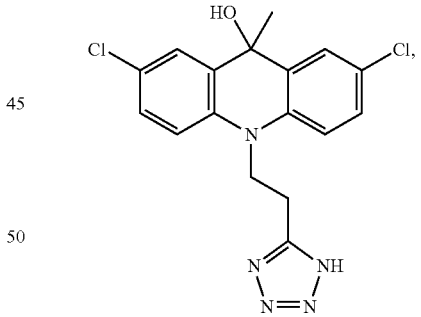
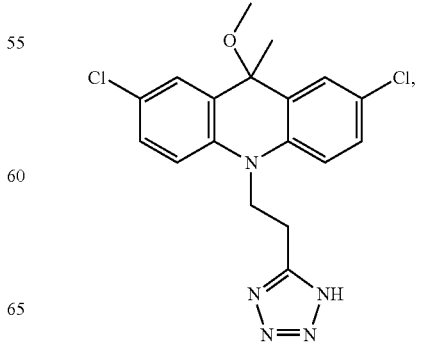

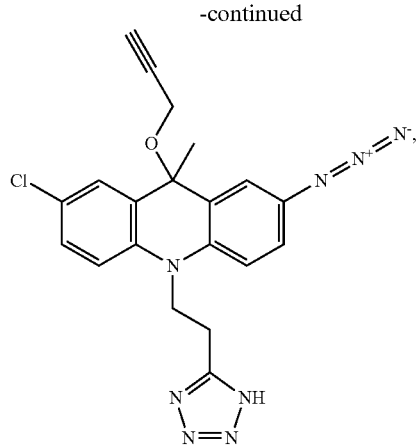
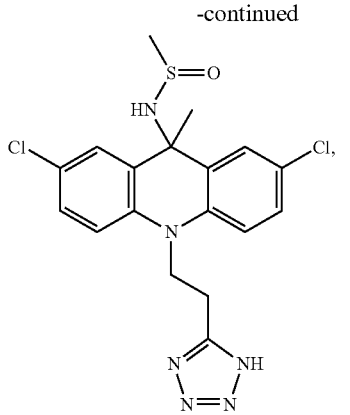
In embodiments, the compound is a compound selected from the group consisting of
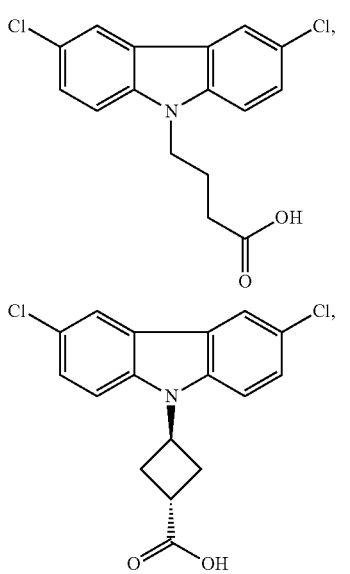

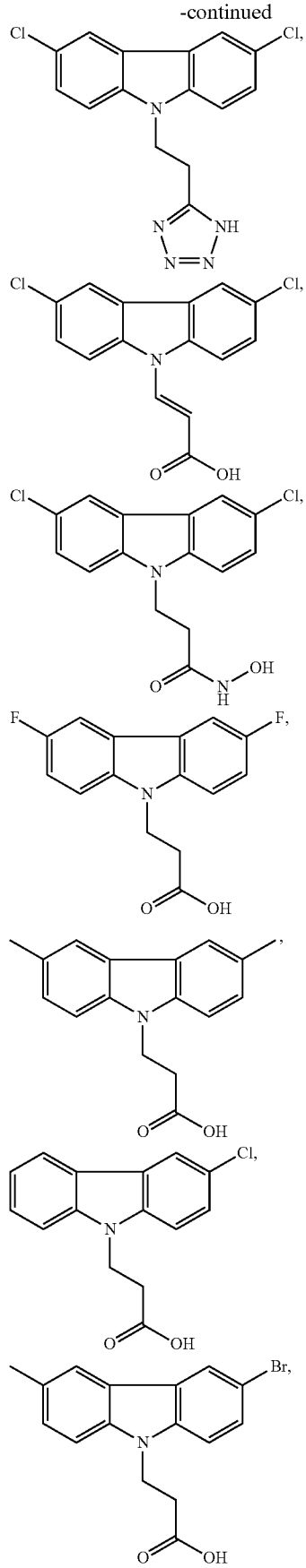
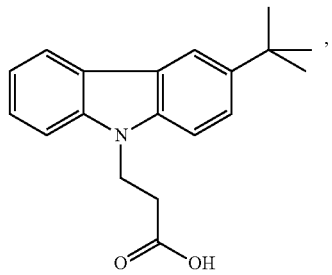
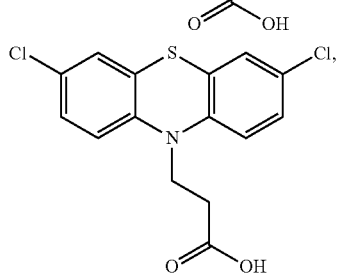
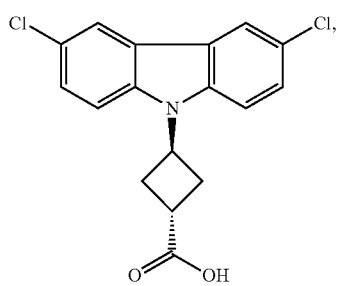
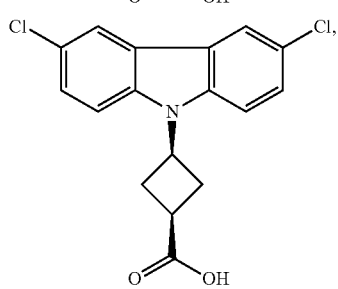
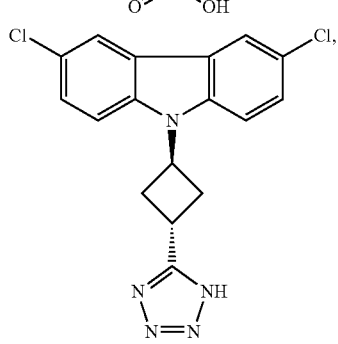

81
-continued
82
-continued
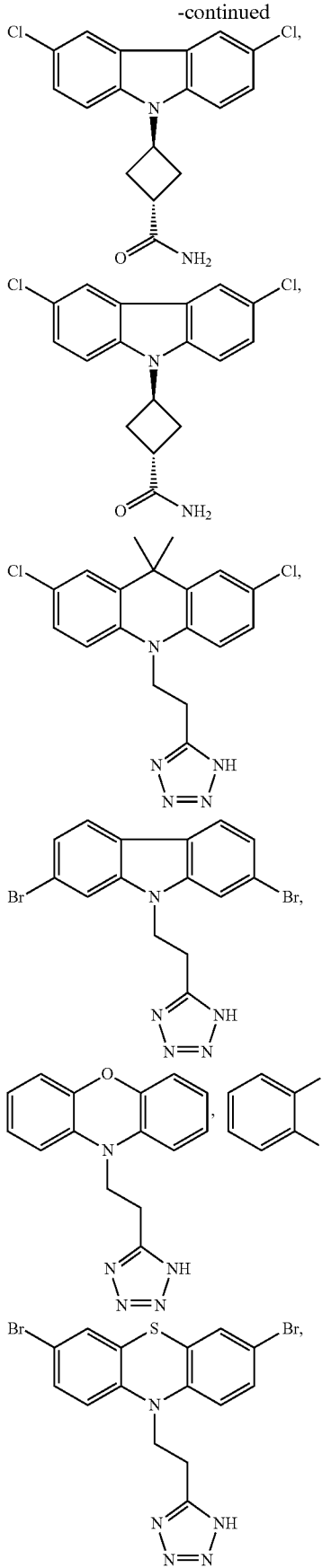
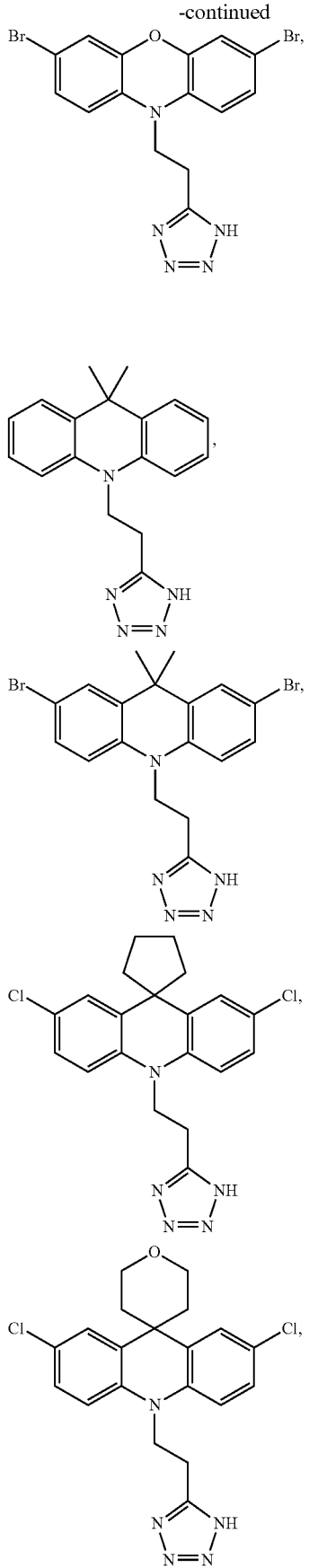

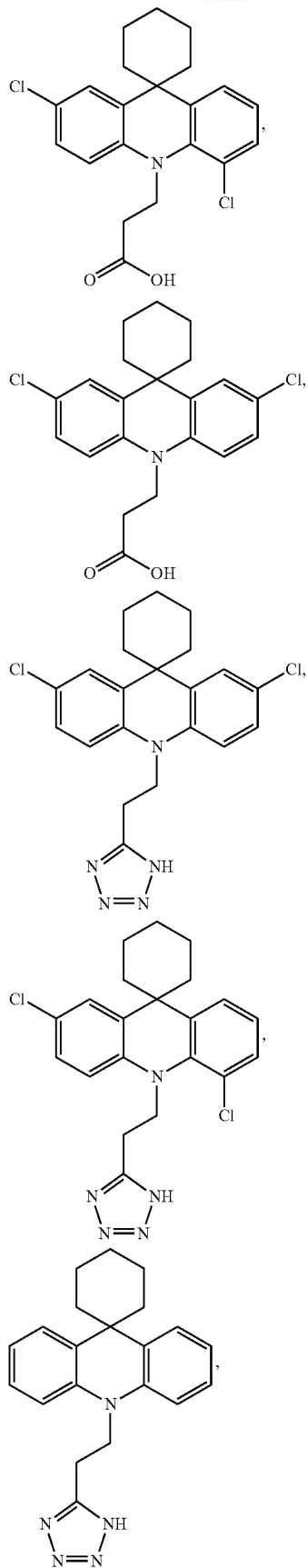
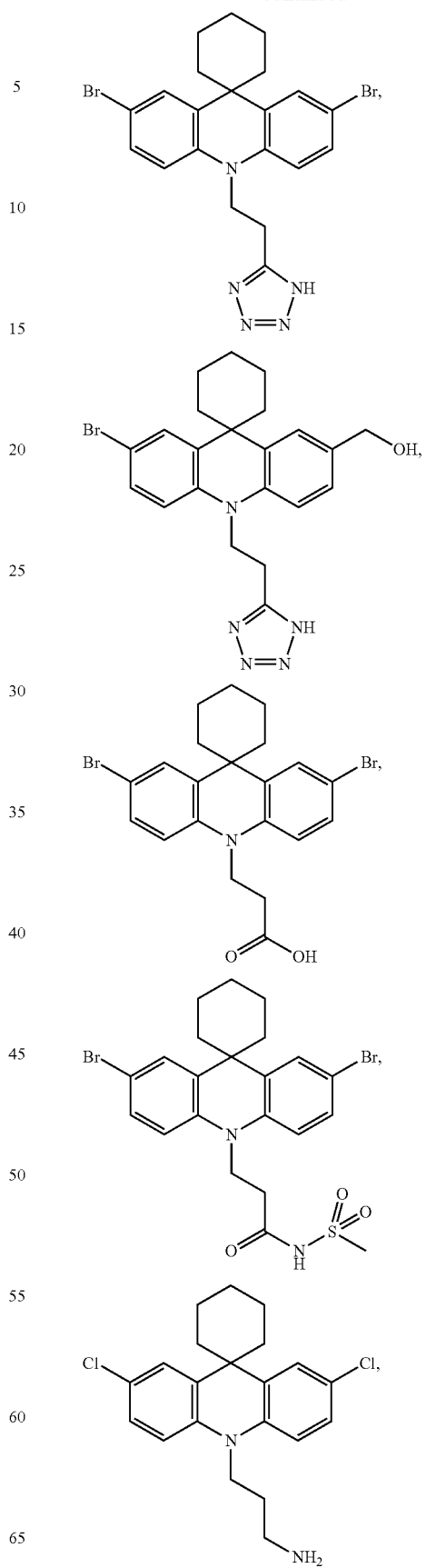

-continued
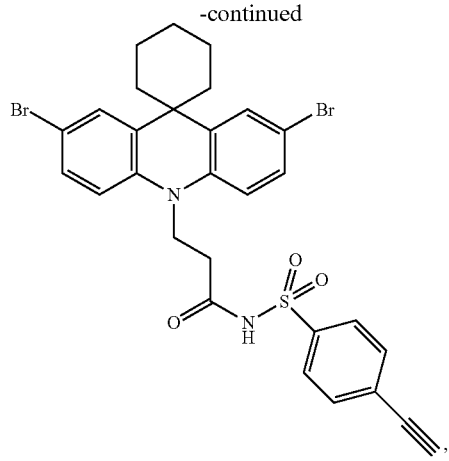
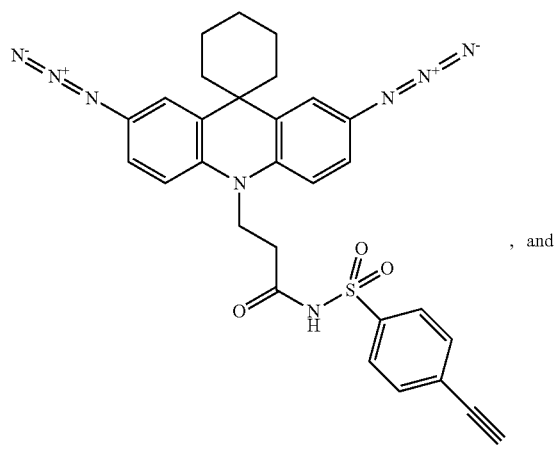
, and
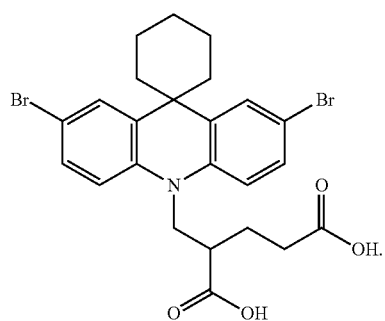
In embodiments, the compound is
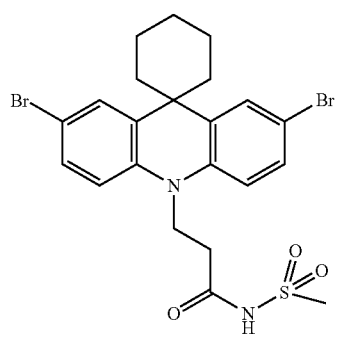
.
In embodiments, the compound is
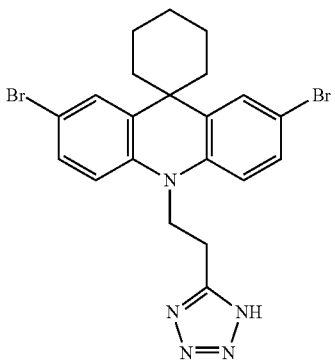
.
In embodiments, the compound is
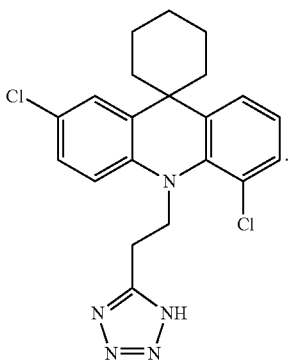 [SMILES: Clc1ccc2c(c1)C1(CCCCC1)c1cccc(Cl)c1N2CCc1nnn[nH]1 ; "."]
.
In embodiments, the compound is
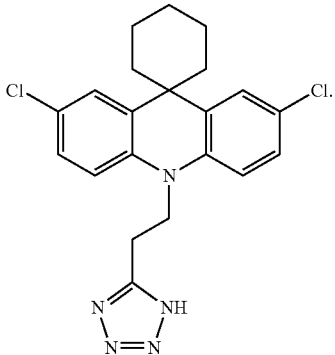 [SMILES: Clc1ccc2c(c1)C1(CCCCC1)c1cc(Cl)ccc1N2CCc1nnn[nH]1]
.
In embodiments, the compound is
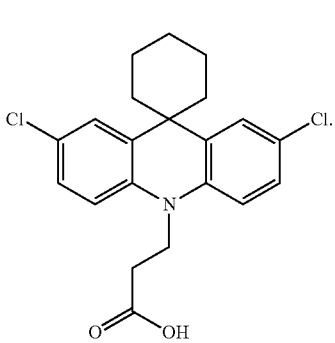 [SMILES: O=C(O)CCN1c2ccc(Cl)cc2C2(CCCCC2)c2cc(Cl)ccc21]

In embodiments, the compound is
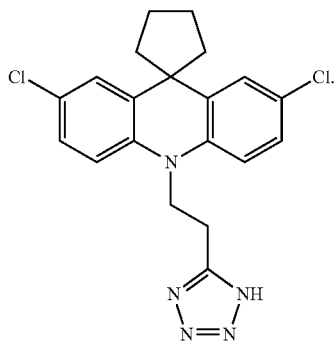 [SMILES: Clc1ccc2c(c1)C1(CCCC1)c1cc(Cl)ccc1N2CCc1nnn[nH]1]
In embodiments, the compound is
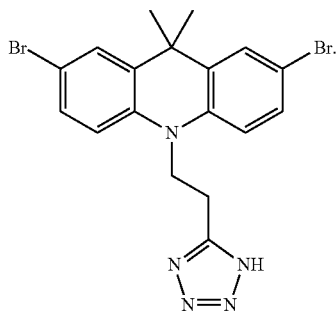 [SMILES: CC1(C)c2cc(Br)ccc2N(CCc2nnn[nH]2)c2ccc(Br)cc21]
In embodiments, the compound is
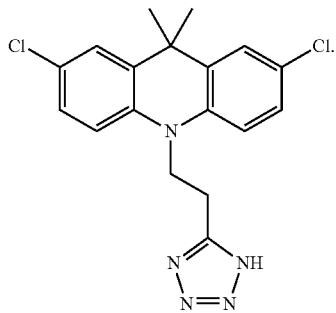 [SMILES: CC1(C)c2cc(Cl)ccc2N(CCc2nnn[nH]2)c2ccc(Cl)cc21]
In embodiments, the compound is not a compound selected from the group consisting
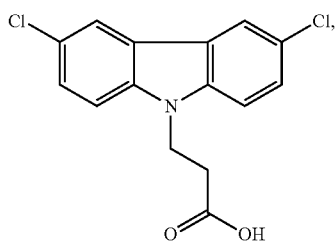
-continued
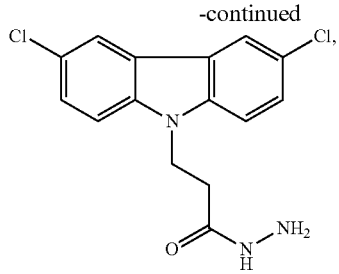
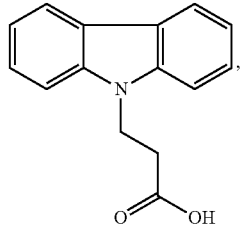
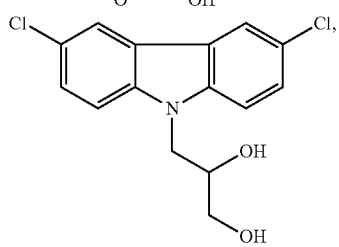
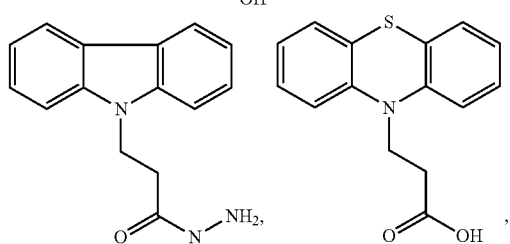
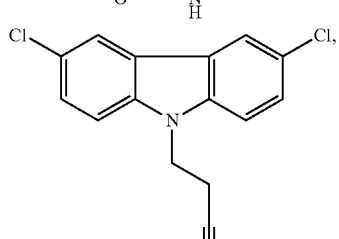
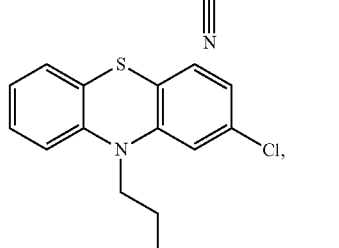
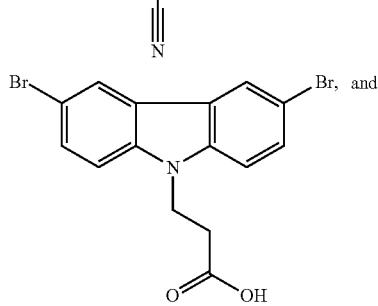

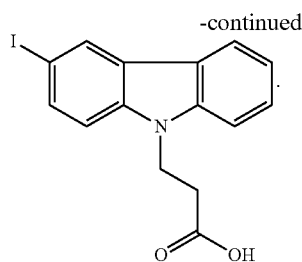

In embodiments, the compound is a TREK-1 agonist. In embodiments, the compound is a TREK-1 antagonist. In embodiments, the compound is selective for binding TREK-1 over other potassium channels. In embodiments, the compound is about 2-fold, 3-fold, 4-fold, 5-fold, 6-fold, 7-fold, 8-fold, 9-fold, 10-fold, 100-fold selective for binding TREK-1 over other potassium channels. In embodiments, the compound is 2-fold, 3-fold, 4-fold, 5-fold, 6-fold, 7-fold, 8-fold, 9-fold, 10-fold, 100-fold selective for binding TREK-1 over other potassium channels. In embodiments, the compound is selective for binding to TREK-1, TREK-2, and TRAAK over other potassium channels. In embodiments, the compound binds the C-type gate of TREK-1. In embodiments, the compound binds the C-type selectivity filter based gate located on the extracellular side of the membrane of the potassium channel (e.g. TREK-1). In embodiments, the compound binds the extracellular portion of TREK-1. In embodiments, the compound does not bind the intracellular C terminal domain of TREK-1. In embodiments, the compound is an analgesic. In embodiments, the compound is an anesthetic. In embodiments, the compound is a neuroprotectant. In embodiments, the compound is a mood modifier. In embodiments, the compound is an antidepressant. In embodiments, the compound treats decompression sickness. In embodiments, the compound increases TREK-1 activity. In embodiments, the compound decreases TREK-1 activity. In embodiments, the compound increases TREK-1 activity relative to the absence of the compound. In embodiments, the compound increases TREK-1 activity about 2-fold, 3-fold, 4-fold, 5-fold, 6-fold, 7-fold, 8-fold, 9-fold, 10-fold, 11-fold, 12-fold, 15-fold, 20-fold, 30-fold, 40-fold, 50-fold, or 100-fold compared to the activity in the absence of the compound. In embodiments, the compound increases TREK-1 activity 2-fold, 3-fold, 4-fold, 5-fold, 6-fold, 7-fold, 8-fold, 9-fold, 10-fold, 11-fold, 12-fold, 15-fold, 20-fold, 30-fold, 40-fold, 50-fold, or 100-fold compared to the activity in the absence of the compound. In embodiments, the compound is a TREK-2 agonist. In embodiments, the compound is a TREK-2 antagonist. In embodiments, the compound is selective for binding TREK-2 over other potassium channels. In embodiments, the compound is about 2-fold, 3-fold, 4-fold, 5-fold, 6-fold, 7-fold, 8-fold, 9-fold, 10-fold, 100-fold selective for binding TREK-2 over other potassium channels. In embodiments, the compound is 2-fold, 3-fold, 4-fold, 5-fold, 6-fold, 7-fold, 8-fold, 9-fold, 10-fold, 100-fold selective for binding TREK-2 over other potassium channels. In embodiments, the compound binds the C-type gate of TREK-2. In embodiments, the compound binds the C-type selectivity filter based gate located on the extracellular side of the membrane of the potassium channel (e.g. TREK-2). In embodiments, the compound binds the extracellular portion of TREK-2. In embodiments, the compound does not bind the intracellular C terminal domain of TREK-2. In embodiments, the compound increases TREK-2 activity. In embodiments, the compound decreases TREK-2 activity. In embodiments, the compound increases TREK-2 activity relative to the absence of the compound. In embodiments, the compound increases TREK-2 activity about 2-fold, 3-fold, 4-fold, 5-fold, 6-fold, 7-fold, 8-fold, 9-fold, 10-fold, 11-fold, 12-fold, 15-fold, 20-fold, 30-fold, 40-fold, 50-fold, or 100-fold compared to the activity in the absence of the compound. In embodiments, the compound increases TREK-2 activity 2-fold, 3-fold, 4-fold, 5-fold, 6-fold, 7-fold, 8-fold, 9-fold, 10-fold, 11-fold, 12-fold, 15-fold, 20-fold, 30-fold, 40-fold, 50-fold, or 100-fold compared to the activity in the absence of the compound. In embodiments, the compound is a TRAAK agonist. In embodiments, the compound is a TRAAK antagonist. In embodiments, the compound is selective for binding TRAAK over other potassium channels. In embodiments, the compound is about 2-fold, 3-fold, 4-fold, 5-fold, 6-fold, 7-fold, 8-fold, 9-fold, 10-fold, 100-fold selective for binding TRAAK over other potassium channels. In embodiments, the compound is 2-fold, 3-fold, 4-fold, 5-fold, 6-fold, 7-fold, 8-fold, 9-fold, 10-fold, 100-fold selective for binding TRAAK over other potassium channels. In embodiments, the compound binds the C-type gate of TRAAK. In embodiments, the compound binds the C-type selectivity filter based gate located on the extracellular side of the membrane of the potassium channel (e.g. TRAAK). In embodiments, the compound binds the extracellular portion of TRAAK. In embodiments, the compound does not bind the intracellular C terminal domain of TRAAK. In embodiments, the compound increases TRAAK activity. In embodiments, the compound decreases TRAAK activity. In embodiments, the compound increases TRAAK activity relative to the absence of the compound. In embodiments, the compound increases TRAAK activity about 2-fold, 3-fold, 4-fold, 5-fold, 6-fold, 7-fold, 8-fold, 9-fold, 10-fold, 11-fold, 12-fold, 15-fold, 20-fold, 30-fold, 40-fold, 50-fold, or 100-fold compared to the activity in the absence of the compound. In embodiments, the compound increases TRAAK activity 2-fold, 3-fold, 4-fold, 5-fold, 6-fold, 7-fold, 8-fold, 9-fold, 10-fold, 11-fold, 12-fold, 15-fold, 20-fold, 30-fold, 40-fold, 50-fold, or 100-fold compared to the activity in the absence of the compound.

In embodiments, the compound is ML67-33. In embodiments, the compound is ML67-137. In embodiments, the compound is ML67-148. In embodiments, the compound is ML67-145. In embodiments, the compound is ML67-143. In embodiments, the compound is ML67-142. In embodiments, the compound is ML67-141. In embodiments, the compound is ML67-138.

In embodiments, $R^1$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

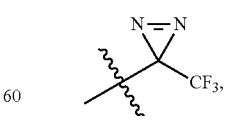

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, —CCH, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

In embodiments, $R^2$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

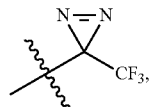

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, —CCH, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

In embodiments, $R^3$ is independently hydrogen, oxo, halogen, —$CF_3$, —CN, —OH, —$NH_2$, —COOH, —$CONH_2$, —$NO_2$, —SH, —$SO_2Cl$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

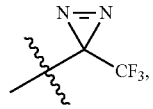

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, —OPO(OH)$_2$, —PO(OH)$_2$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

In embodiments, $R^4$ is independently hydrogen, oxo, halogen, —$CF_3$, —CN, —OH, —$NH_2$, —COOH, —$CONH_2$, —$NO_2$, —SH, —$SO_2Cl$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

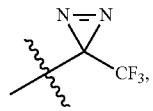

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl. In embodiments, $R^4$ and $R^5$ may optionally be joined to form a $R^{14}$-substituted or unsubstituted cycloalkyl or $R^{14}$-substituted or unsubstituted heterocycloalkyl.

In embodiments, $R^5$ is independently hydrogen, oxo, halogen, —$CF_3$, —CN, —OH, —$NH_2$, —COOH, —$CONH_2$, —$NO_2$, —SH, —$SO_2Cl$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

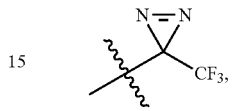

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl. In embodiments, $R^4$ and $R^5$ may optionally be joined to form a $R^{15}$-substituted or unsubstituted cycloalkyl or $R^{15}$-substituted or unsubstituted heterocycloalkyl.

In embodiments, $R^6$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

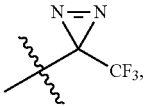

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

In embodiments, $R^7$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

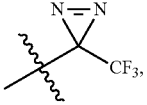

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl. In embodiments, where $R^7$ and $R^8$ are bonded to the same nitrogen atom, they may optionally be joined to form a $R^{17}$-substituted or unsubstituted heterocycloalkyl or $R^{17}$-substituted or unsubstituted heteroaryl.

In embodiments, $R^8$ is independently hydrogen, oxo, halogen, —$CF_3$, —CN, —OH, —$NH_2$, —COOH, —$CONH_2$, —$NO_2$, —SH, —$SO_2Cl$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

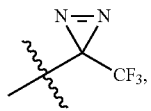

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. In embodiments, where $R^7$ and $R^8$ are bonded to the same nitrogen atom, they may optionally be joined to form a $R^{18}$-substituted or unsubstituted heterocycloalkyl or $R^{18}$-substituted or unsubstituted heteroaryl.

In embodiments, $R^9$ is independently hydrogen, oxo, halogen, —$CF_3$, —CN, —OH, —$NH_2$, —COOH, —$CONH_2$, —$NO_2$, —SH, —$SO_2Cl$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

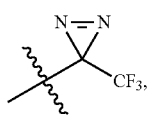

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In embodiments, $R^{19}$ is independently hydrogen, oxo, halogen, —$CF_3$, —CN, —OH, —$NH_2$, —COOH, —$CONH_2$, —$NO_2$, —SH, —$SO_2Cl$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, —$N_3$,

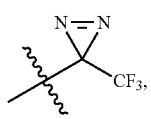 [SMILES: *C1(C(F)(F)F)N=N1]

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, $R^{20}$-substituted or unsubstituted alkyl, $R^N$-substituted or unsubstituted heteroalkyl, $R^{20}$-substituted or unsubstituted cycloalkyl, $R^N$-substituted or unsubstituted heterocycloalkyl, $R^{20}$-substituted or unsubstituted aryl, or $R^N$-substituted or unsubstituted heteroaryl.

In embodiments, $L^1$ is independently a bond, $R^{21}$-substituted or unsubstituted alkylene, $R^{21}$-substituted or unsubstituted heteroalkylene, $R^{21}$-substituted or unsubstituted cycloalkylene, $R^{21}$-substituted or unsubstituted heterocycloalkylene, $R^{21}$-substituted or unsubstituted arylene, or $R^{21}$-substituted or unsubstituted heteroarylene.

Each $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$N_3$

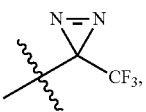

—$CCl_3$, —$OCH_2CCH$, —NHC(O)$CH_3$, —$OCH_3$, —$NHCH_3$, —NHC(S)$CH_3$, —N($CH_3$)$_2$, —$CH_3$, —$CH_2CCH$, —C(O)$CH_3$, —C(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, a compound as described herein may include multiple instances of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and/or $R^{21}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{8.1}$, $R^{8.2}$, $R^{8.3}$, $R^{8.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, $R^{14.4}$, $R^{15.1}$, $R^{15.2}$, $R^{15.3}$, $R^{15.4}$, $R^{16.1}$, $R^{16.2}$, $R^{16.3}$, $R^{16.4}$, $R^{17.1}$, $R^{17.2}$, $R^{17.3}$, $R^{17.4}$, $R^{18.1}$, $R^{18.2}$, $R^{18.3}$, $R^{18.4}$, $R^{19.1}$, $R^{19.2}$, $R^{19.3}$, $R^{19.4}$, $R^{20.1}$, $R^{20.2}$, $R^{20.3}$, $R^{20.4}$, $R^{21.1}$, $R^{21.2}$, $R^{21.3}$, and/or $R^{21.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{3.2}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^8$ is assumed by $R^{8.1}$, $R^{8.2}$, $R^{8.3}$, and/or $R^{8.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or $R^{10.4}$, the definition of $R^{11}$ is assumed by $R^{11.1}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$, the definition of $R^{15}$ is assumed by $R^{15.1}$, $R^{15.2}$, $R^{15.3}$, and/or $R^{15.4}$, the definition of $R^{16}$ is assumed by $R^{16.1}$, $R^{16.2}$, $R^{16.3}$, and/or $R^{16.4}$, the definition of $R^{17}$ is assumed by $R^{17.1}$, $R^{17.2}$, $R^{17.3}$, and/or $R^{17.4}$, the definition of $R^{18}$ is assumed by $R^{18.1}$, $R^{18.2}$, $R^{18.3}$, and/or $R^{18.4}$, the definition of $R^{19}$ is assumed by $R^{19.1}$, $R^{19.2}$, $R^{19.3}$, and/or $R^{19.4}$, the definition of $R^{20}$ is assumed by $R^{20.1}$, $R^{20.2}$, $R^{20.3}$, and/or $R^{20.4}$, the definition of $R^{21}$ is assumed by $R^{21.1}$, $R^{21.2}$, $R^{21.3}$, and/or $R^{21.4}$. The variables used within a definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and/or $R^{21}$, and/or other variables that appear at multiple instances and are different may similarly be appropriately labeled to distinguish each group for greater clarity.

In embodiments, $R^{13}$ is independently oxo. In embodiments, $R^{13}$ is independently —CN. In embodiments, $R^{13}$ is independently —OH. In embodiments, $R^{13}$ is independently —NH$_2$. In embodiments, $R^{13}$ is independently —COOH. In embodiments, $R^{13}$ is independently —CONH$_2$. In embodiments, $R^{13}$ is independently —NO$_2$. In embodiments, $R^{13}$ is independently —SH. In embodiments, $R^{13}$ is independently —SO$_2$Cl. In embodiments, $R^{13}$ is independently —SO$_3$H. In embodiments, $R^{13}$ is independently —SO$_4$H. In embodiments, $R^{13}$ is independently —SO$_2$NH$_2$. In embodiments, $R^{13}$ is independently —NHNH$_2$. In embodiments, $R^{13}$ is independently —ONH$_2$. In embodiments, $R^{13}$ is independently —NHC=(O)NHNH$_2$. In embodiments, $R^{13}$ is independently —NHC=(O)NH$_2$. In embodiments, $R^{13}$ is independently —NHSO$_2$H. In embodiments, $R^{13}$ is independently —NHC=(O)H. In embodiments, $R^{13}$ is independently —NHC(O)—OH. In embodiments, $R^{13}$ is independently —NHOH. In embodiments, $R^{13}$ is independently —OCF$_3$. In embodiments, $R^{13}$ is independently —OCHF$_2$. In embodiments, $R^{13}$ is independently —N$_3$. In embodiments, $R^{13}$ is independently

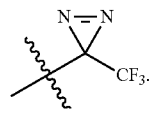

In embodiments, $R^{13}$ is independently —CCl$_3$. In embodiments, $R^{13}$ is independently —OCH$_2$CCH. In embodiments, $R^{13}$ is independently —NHC(O)CH$_3$. In embodiments, $R^{13}$ is independently —OCH$_3$. In embodiments, $R^{13}$ is independently —NHCH$_3$. In embodiments, $R^{13}$ is independently —NHC(S)CH$_3$. In embodiments, $R^{13}$ is independently —N(CH$_3$)$_2$. In embodiments, $R^{13}$ is independently —CH$_2$CCH. In embodiments, $R^{13}$ is independently —C(O)CH$_3$. In embodiments, $R^{13}$ is independently —C(O)NHNH$_2$. In embodiments, $R^{13}$ is independently halogen. In embodiments, $R^{13}$ is independently —F. In embodiments, $R^{13}$ is independently —Cl. In embodiments, $R^{13}$ is independently —Br. In embodiments, $R^{13}$ is independently —I. In embodiments, $R^{13}$ is independently —CF$_3$. In embodiments, $R^{13}$ is independently substituted or unsubstituted alkyl. In embodiments, $R^{13}$ is independently substituted or unsubstituted $C_1$-$C_{10}$ alkyl. In embodiments, $R^{13}$ is independently substituted or unsubstituted $C_1$-$C_8$ alkyl. In embodiments, $R^{13}$ is independently substituted or unsubstituted $C_1$-$C_6$ alkyl. In embodiments, $R^{13}$ is independently substituted or unsubstituted $C_1$-$C_4$ alkyl. In embodiments, $R^{13}$ is independently substituted or unsubstituted $C_1$-$C_3$ alkyl. In embodiments, $R^{13}$ is independently unsubstituted alkyl. In embodiments, $R^{13}$ is independently unsubstituted $C_1$-$C_{10}$ alkyl. In embodiments, $R^{13}$ is independently unsubstituted $C_1$-$C_8$ alkyl. In embodiments, $R^{13}$ is independently unsubstituted $C_1$-$C_6$ alkyl. In embodiments, $R^{13}$ is independently unsubstituted $C_1$-$C_4$ alkyl. In embodiments, $R^{13}$ is independently unsubstituted $C_1$-$C_3$ alkyl. In embodiments, $R^{13}$ is independently unsubstituted methyl. In embodiments, $R^{13}$ is independently unsubstituted ethyl. In embodiments, $R^{13}$ is independently unsubstituted propyl. In embodiments, $R^{13}$ is independently unsubstituted butyl. In embodiments, $R^{13}$ is independently unsubstituted isopropyl. In embodiments, $R^{13}$ is independently unsubstituted tert-butyl. In embodiments, $R^{13}$ is independently —N$_3$. In embodiments, $R^{13}$ is independently —OCH$_2$CCH. In embodiments, $R^{13}$ is independently —CCH. In embodiments, $R^{13}$ is independently unsubstituted 2 to 8 membered heteroalkyl. In embodiments, $R^{13}$ is independently unsubstituted 2 to 6 membered heteroalkyl. In embodiments, $R^{13}$ is independently unsubstituted 2 to 4 membered heteroalkyl. In embodiments, $R^{13}$ is independently unsubstituted 3 to 8 membered heterocycloalkyl. In embodiments, $R^{13}$ is independently unsubstituted 3 to 6 membered heterocycloalkyl. In embodiments, $R^{13}$ is independently unsubstituted 3 to 4 membered heterocycloalkyl. In embodiments, $R^{13}$ is independently unsubstituted 5 to 10 membered heteroaryl. In embodiments, $R^{13}$ is independently unsubstituted 5 to 9 membered heteroaryl. In embodiments, $R^{13}$ is independently unsubstituted $C_1$-$C_8$ alkyl. In embodiments, $R^{13}$ is independently unsubstituted $C_1$-$C_6$ alkyl. In embodiments, $R^{13}$ is independently unsubstituted $C_1$-$C_4$ alkyl. In embodiments, $R^{13}$ is independently unsubstituted $C_3$-$C_8$ cycloalkyl. In embodiments, $R^{13}$ is independently unsubstituted $C_3$-$C_6$ cycloalkyl. In embodiments, $R^{13}$ is independently unsubstituted $C_3$-$C_4$ cycloalkyl. In embodiments, $R^{13}$ is independently unsubstituted $C_6$-$C_{10}$ aryl. In embodiments, $R^{13}$ is independently substituted 2 to 8 membered heteroalkyl. In embodiments, $R^{13}$ is independently substituted 2 to 6 membered heteroalkyl. In embodiments, $R^{13}$ is independently substituted 2 to 4 membered heteroalkyl. In embodiments, $R^{13}$ is independently substituted 3 to 8 membered heterocycloalkyl. In embodiments, $R^{13}$ is independently substituted 3 to 6 membered heterocycloalkyl. In embodiments, $R^{13}$ is independently substituted 3 to 4 membered heterocycloalkyl. In embodiments, $R^{13}$ is independently substituted 5 to 10 membered heteroaryl. In embodiments, $R^{13}$ is independently substituted 5 to 9 membered heteroaryl. In embodiments, $R^{13}$ is independently substituted $C_1$-$C_8$ alkyl. In embodiments, $R^{13}$ is independently substituted $C_1$-$C_6$ alkyl. In embodiments, $R^{13}$ is independently substituted $C_1$-$C_4$ alkyl. In embodiments, $R^{13}$ is independently substituted $C_3$-$C_8$ cycloalkyl. In embodiments, $R^{13}$ is independently substituted $C_3$-$C_6$ cycloalkyl. In embodiments, $R^{13}$ is independently substituted $C_3$-$C_4$ cycloalkyl. In embodiments, $R^{13}$ is independently substituted $C_6$-$C_{10}$ aryl.

In some embodiments, the compound is a compound described herein. In some embodiments, the compound is a compound described in the Examples, an example, a table, the figures, a figure, included herein. In embodiments, the compound is a compound described in the method sections herein above.

In a fourth aspect is provided a compound, or pharmaceutically acceptable salt thereof, having the formula:

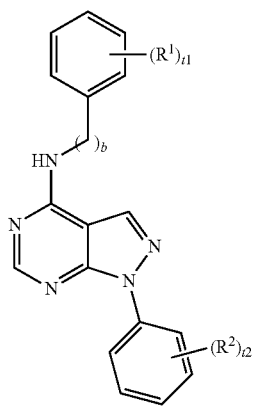
(III)

wherein $R^1$ and $R^2$ are independently halogen, —$CF_3$, —$CCl_3$, —CN, —OH, —$NH_2$, —COOH, —$CONH_2$, —$NO_2$, —SH, —$OCF_3$, —$OCHF_2$, —CCH, —$S(O)_2NH_2$, unsubstituted $C_1$-$C_5$ alkyl, or unsubstituted 2 to 5 membered heteroalkyl; the symbol b is an integer from 1 to 5, in embodiments an integer from 1 to 2, in embodiments 2; the symbol t1 is an integer from 0 to 5; and the symbol t2 is an integer from 0 to 5.

In embodiments, $R^1$ and $R^2$ are hydrogen. In embodiments, t1 is 0. In embodiments, t1 is 1. In embodiments, t1 is 2. In embodiments, t1 is 3. In embodiments, t1 is 4. In embodiments, t1 is 5. In embodiments, t2 is 0. In embodiments, t2 is 1. In embodiments, t2 is 2. In embodiments, t2 is 3. In embodiments, t2 is 4. In embodiments, t2 is 5. In embodiments, $R^2$ is unsubstituted $C_1$-$C_5$ alkyl. In embodiments, $R^2$ is unsubstituted methyl. In embodiments, $R^1$ is unsubstituted $C_1$-$C_5$ alkyl. In embodiments, $R^1$ is unsubstituted methyl. In embodiments, $R^2$ is halogen. In embodiments, $R^1$ is halogen. In embodiments, $R^2$ is —Cl. In embodiments, $R^1$ is —Cl. In embodiments, $R^1$ is —S$(O)_2NH_2$. In embodiments, $R^2$ is —$S(O)_2NH_2$. In embodiments, the compound is an antagonist of a K2P channel. In embodiments, the compound is an antagonist of TREK-1. In embodiments, the compound is an antagonist of TREK-2. In embodiments, the compound is an antagonist of TRAAK. In embodiments, the compound is

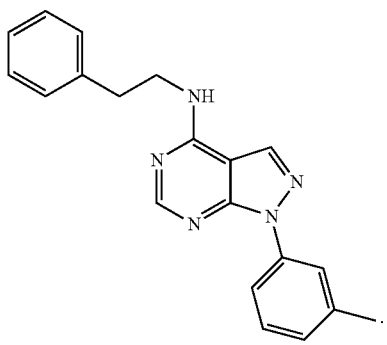 [SMILES: Cc1cccc(-n2ncc3c(NCCc4ccccc4)ncnc32)c1]

In embodiments, the compound is

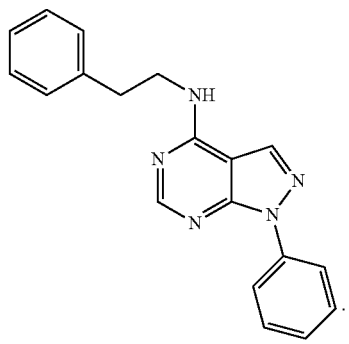

In embodiments, the compound is

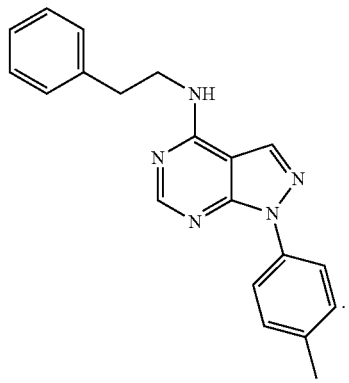 [SMILES: Cc1ccc(-n2ncc3c(NCCc4ccccc4)ncnc32)cc1]

In embodiments, the compound is

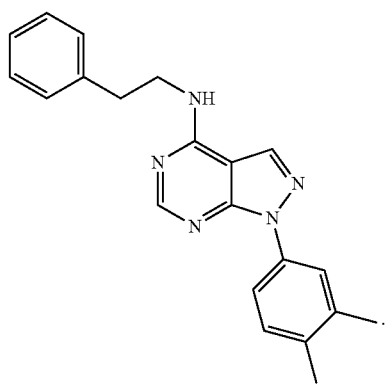 [SMILES: Cc1ccc(-n2ncc3c(NCCc4ccccc4)ncnc32)cc1C]

In embodiments, the compound is
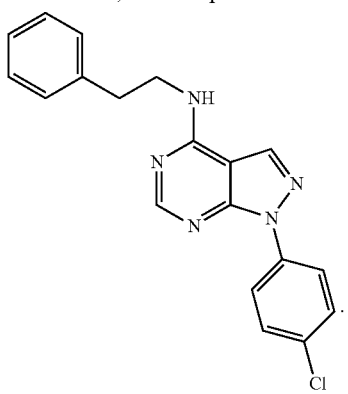
In embodiments, the compound is not
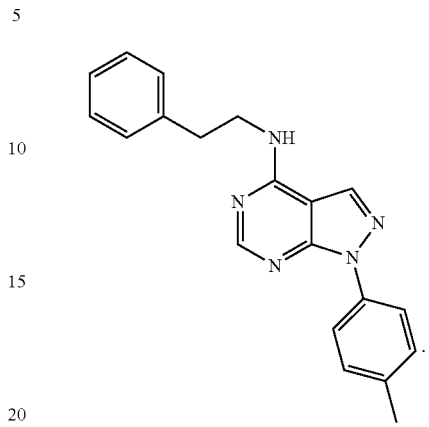
In embodiments, the compound is
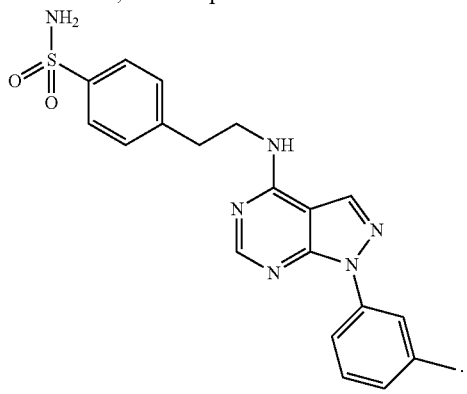
In embodiments, the compound is not
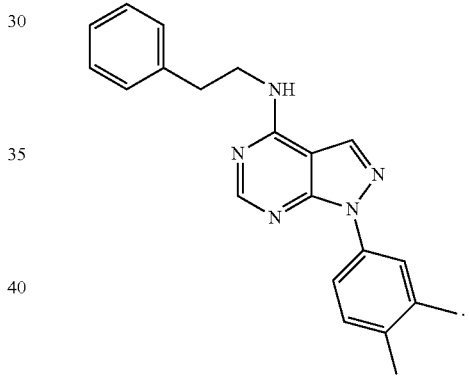
In embodiments, the compound is not
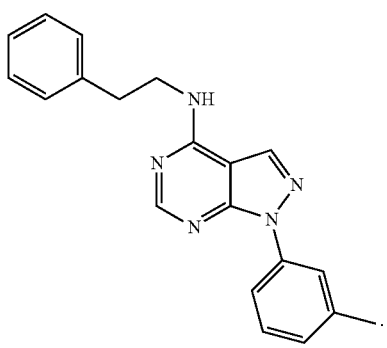 [SMILES: Cc1cccc(-n2ncc3c(NCCc4ccccc4)ncnc32)c1]
In embodiments, the compound is not
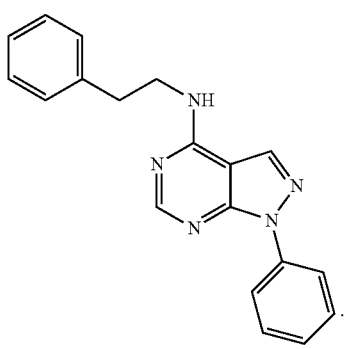 [SMILES: c1ccc(CCNc2ncnc3c2cnn3-c2ccccc2)cc1]
In embodiments, the compound is not
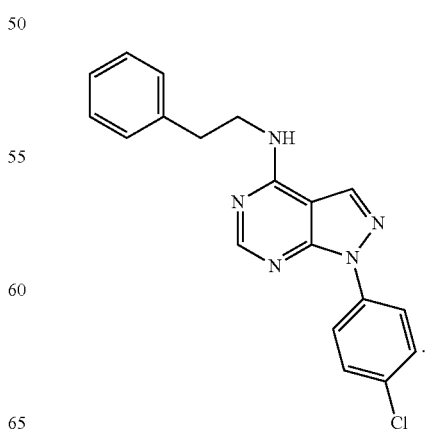

In embodiments, the compound is not

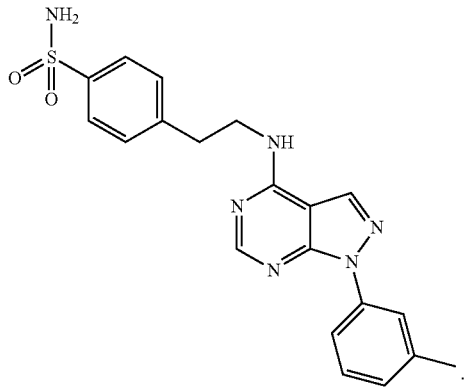 [SMILES: Cc1cccc(-n2ncc3c(NCCc4ccc(S(N)(=O)=O)cc4)ncnc32)c1]

In a fifth aspect is provided a compound, or pharmaceutically acceptable salt thereof, having the formula:

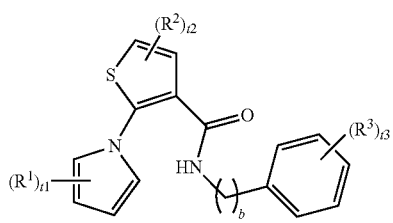

(IV)

wherein R¹, R², and R³ are independently halogen, —CF₃, —CCl₃, —CN, —OH, —NH₂, —COOH, —CONH₂, —NO₂, —SH, —OCF₃, —OCHF₂, —CCH, unsubstituted C₁-C₅ alkyl, or unsubstituted 2 to 5 membered heteroalkyl; the symbol b is an integer from 1 to 5, in embodiments an integer from 1 to 2, in embodiments 1; the symbol t1 is an integer from 0 to 4; the symbol t2 is an integer from 0 to 2; and the symbol t3 is an integer from 0 to 5.

In a sixth aspect is provided a compound, or pharmaceutically acceptable salt thereof, having the formula:

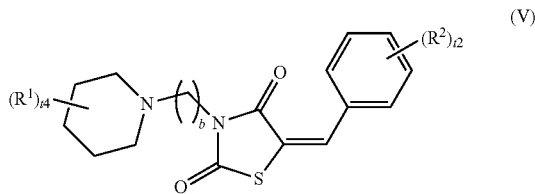

(V)

wherein R¹ and R² are independently halogen, —CF₃, —CCl₃, —CN, —OH, —NH₂, —COOH, —CONH₂, —NO₂, —SH, —OCF₃, —OCHF₂, —CCH, unsubstituted C₁-C₅ alkyl, or unsubstituted 2 to 5 membered heteroalkyl; the symbol b is an integer from 1 to 5, in embodiments an integer from 1 to 2, in embodiments 2; the symbol t4 is an integer from 0 to 10; and the symbol t2 is an integer from 0 to 5.

In a seventh aspect is provided a compound, or pharmaceutically acceptable salt thereof, having the formula:

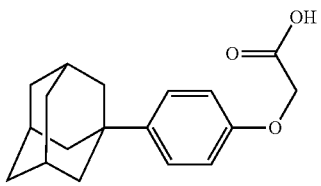

(VI)

D. Pharmaceutical Compositions

In an eighth aspect is provided a pharmaceutical composition including a pharmaceutically acceptable excipient and a compound, or pharmaceutically acceptable salt thereof, as described herein, including embodiments (e.g. compound of formula I, II, III, IV, V, or VI, or any embodiment thereof), including compounds described for use in a method herein or in the Compounds section above or in an example, table, figure, or claim.

In embodiments of the pharmaceutical compositions, the pharmaceutical composition includes a compound, or pharmaceutically acceptable salt thereof, as described herein (e.g. compound of formula I, II, III, IV, V, or VI, or any embodiment thereof) in a therapeutically effective amount. In embodiments of the pharmaceutical compositions, the pharmaceutical composition includes a second agent (e.g. therapeutic agent). In embodiments of the pharmaceutical compositions, the pharmaceutical composition includes a second agent in a therapeutically effective amount. In embodiments of the pharmaceutical compositions, the second agent is an agent for treating a neurological disease, pain, migraine, depression, a mood disorder, ischemic injury, stroke, neurodegeneration (e.g. due to disease, ischemic injury, stroke, or traumatic brain injury), or decompression sickness. In embodiments of the pharmaceutical compositions, the second agent is an analgesic. In embodiments of the pharmaceutical compositions, the second agent is an anesthetic. In embodiments of the pharmaceutical compositions, the second agent is an agent for treating a neurological disease (e.g. neurodegenerative disease). In embodiments of the pharmaceutical compositions, the second agent is an agent for treating ischemia. In embodiments of the pharmaceutical compositions, the second agent is an agent for treating a mood disorder. In embodiments of the pharmaceutical compositions, the second agent is an agent for treating a migraine. In embodiments of the pharmaceutical compositions, the second agent is an agent for treating a stroke. In embodiments of the pharmaceutical compositions, the second agent is an agent for treating depression. In embodiments of the pharmaceutical compositions, the second agent is an agent for treating pain.

$K_{2P}$ channels are the most diverse potassium channel class {Goldstein, 2005; Yu, 2005} and have important roles in the function of both excitable and non-excitable cells {Enyedi, 2010; Lesage, 2011}. The fact that this potassium channel family responds poorly to classic potassium channel blockers {Lotshaw, 2007} and remains largely pharmacologically orphaned {Es-Salah-Lamoureux, 2010; Lotshaw, 2007} limits the ability to probe its function. Additionally, because $K_{2P}$s produce voltage-independent leak current, they present difficult targets for modulator discovery by conventional electrophysiological screening techniques. Our studies demonstrate that a yeast-based screening platform that is built upon solution measurements of rescue of potassium uptake by a functional $K_{2P}$ channel can be used to identify both inhibitors and activators of $K_{2P}$s. This assay provides a substantial advantage in terms of scalability and quantification over solid-based media assays that have used previously {Zaks-Makhina, 2004; Zaks-Makhina, 2009}.

We identified a set of novel $K_{2P}2.1$ (TREK-1) inhibitors and activators in a single screening campaign covering 105,863 compounds. As all of the identified compounds inhibited $K_{2P}2.1$ (TREK-1)-dependent yeast growth, the identification of molecules that proved to be activators in electrophysiological experiments was unexpected. Examination of the potassium-dependency showed that unlike the potassium transporter Trk1p, $K_{2P}2.1$ (TREK-1) conferred a bell-shaped dependence on growth rescue as a function of potassium (FIG. 1a), an effect not seen previously in solid media assays {Bagriantsev, 2011}. Prior identification of gain-of-function mutants of the yeast channel YKC1 (TOK1), has established that hyperactive potassium channel activity can negatively impact yeast growth {Loukin, 1997}. Although the exact mechanism by which $K_{2P}2.1$ (TREK-1) hyper-activation causes growth inhibition remains unclear, the prior observations with YKC1 (TOK1) provide an hypothesis for why our high-throughput screen identified both inhibitors and activators of $K_{2P}2.1$ (TREK-1) in a single screening campaign. As identification of both inhibitors and activators of $K_{2P}2.1$ (TREK-1) is desirable for both physiological studies and as possible leads for a variety of therapeutic applications {Goonetilleke, 2012; Bayliss, 2008; Es-Salah-Lamoureux, 2010}, this unexpected benefit substantially expands the potential of this assay for the further screening of diverse chemical libraries.

The two inhibitors and three activators that we identified all produced fast, reversible changes in $K_{2P}2.1$ (TREK-1) function that occurred within seconds of compound application and removal when assayed using electrophysiology (FIGS. 9a-b and 10a-c). This notable as the timescale of the yeast assay used to discover the compounds, which is hours, could favor the identification of slow-acting compounds that have indirect effects on channel function by affecting factors such as channel biogenesis, assembly, or trafficking. While such compounds could be identified in this sort of screen, the identification of diverse compounds that appear to act directly and immediately on the channel underscores the potential of this assay as a discovery platform for fast-acting $K_{2P}$ channel modulators.

Figure 3:
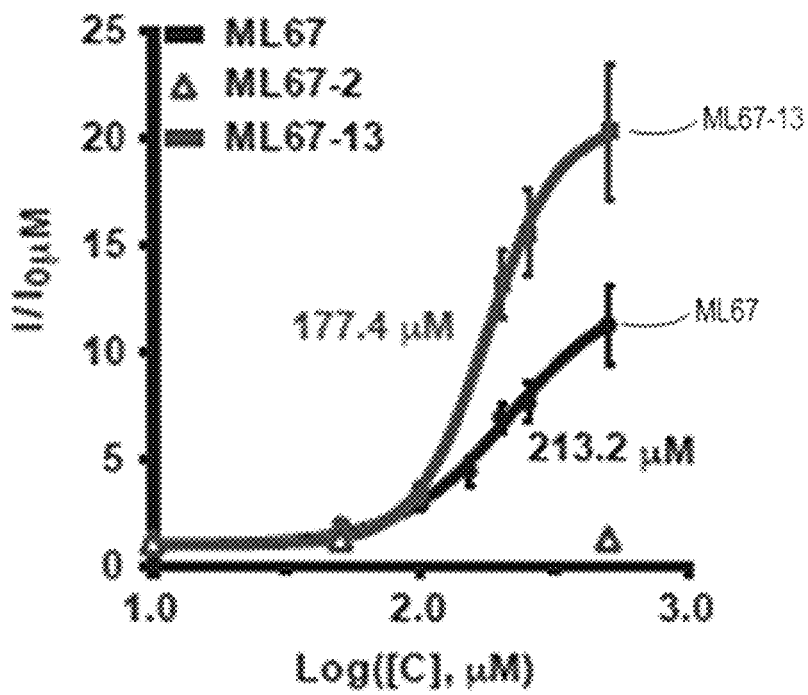
FIG. 3 SAR studies of ML67 improve potency effects of changes to the a, halogen positions, b, linker region, and c, acidic group of ML67 and their effects on $K_{2P}2.1$ (TREK-1) measured by two-electrode voltage clamp in Xenopus oocytes; currents were elicited by a voltage ramp from −150 to 50 mV, from a holding potential of −80 mV, in 2 mM $[K^+]_o$ pH 7.4; data (mean±s.e., n≥6, N≥2) was taken at 0 mV, normalized to basal activity and fitted to the Hill equation; mean $IC_{50}$ values are indicated next to the curves and were as follows: ML67-13, 177.4±1.08 µM; ML67-17, 162.2±1.24 µM; ML67-29, 250.6±2 µM; ML67-18, $EC_{50}$ 124.8±1.21 µM; ML67-33, 36.3±1.04 µM; c:t indicates cis:trans ratios for ML67-17 and ML67-29; error bars show s.e. n≥6 and N≥2 for all except ML67-2 and ML67-15 where n=4 and N=2.
Figure 3:
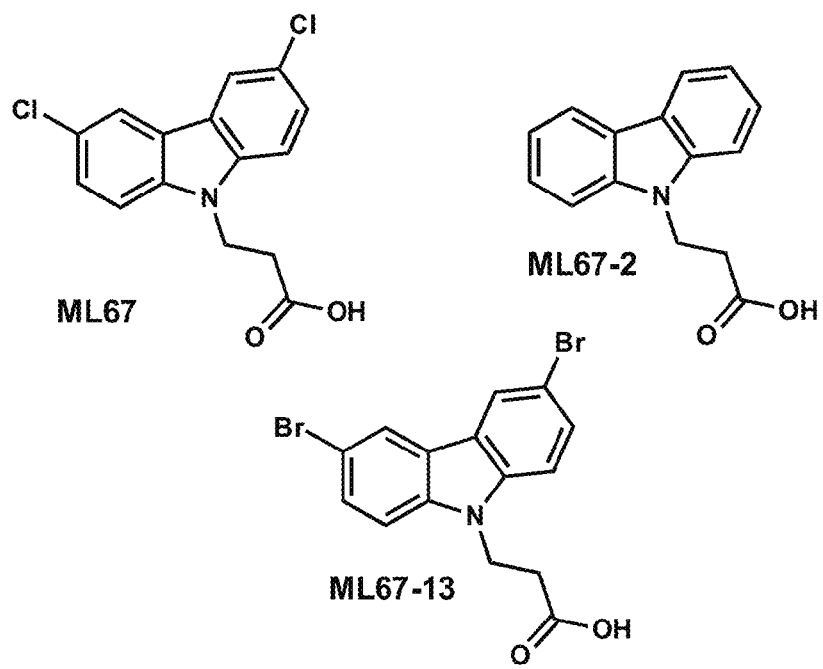
Figure 3:
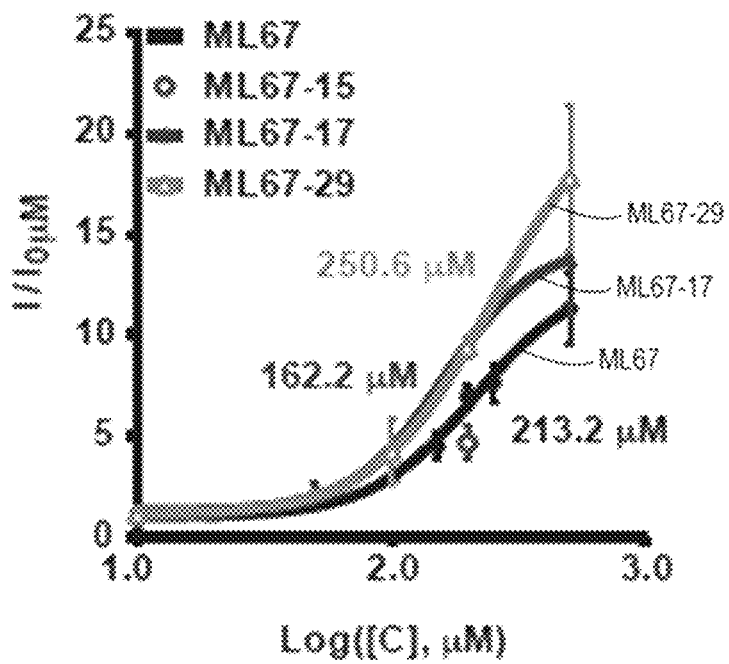
Figure 3:
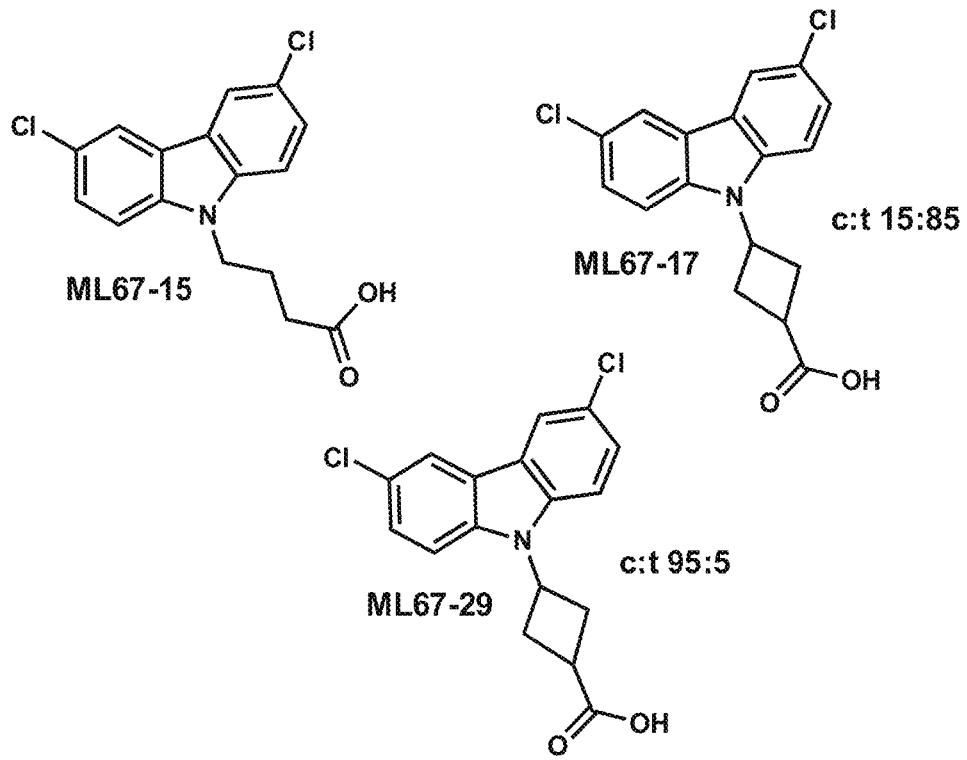
Figure 3:
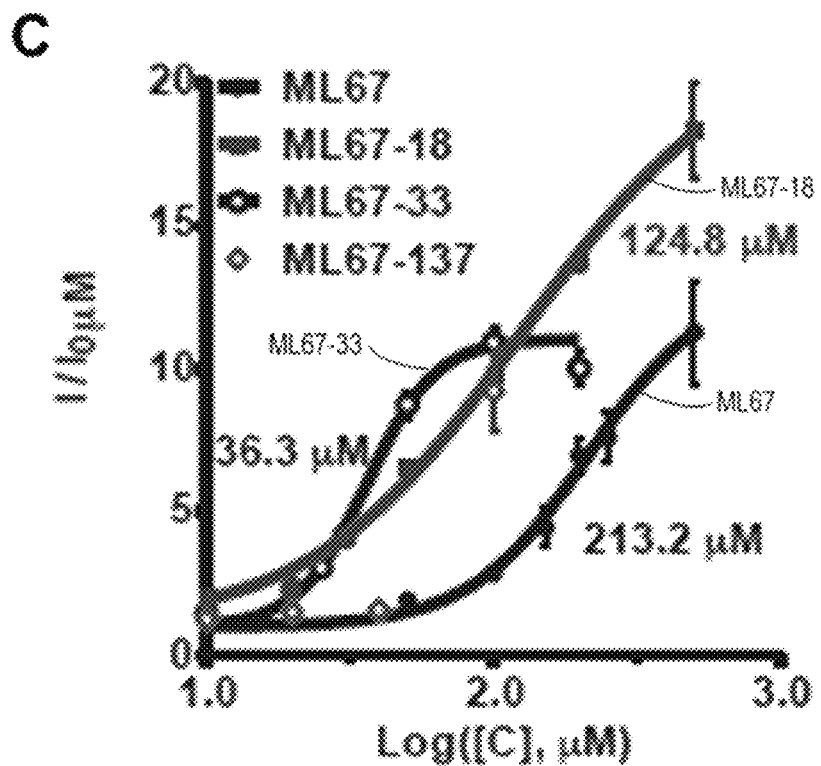
Figure 3:
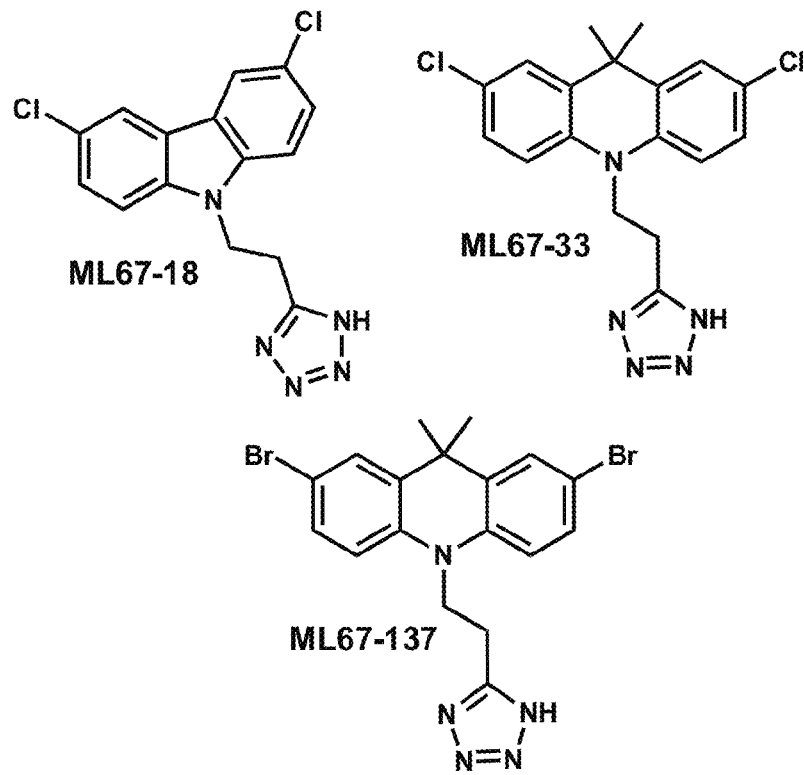

By using a combination of biophysical characterization and chemical synthesis, we were able to improve an initial lead channel opener, ML67 (FIG. 3, Table 1), to create an acridine-based derivative that reversibly activated $K_{2P}2.1$ (TREK-1) (FIG. 4a-d) with an $EC_{50}$ in the low-micromolar range (Table 1). We found that that ML67-33 activates $K_{2P}2.1$ (TREK-1) in excised membrane patches (FIG. 5a-d). This result demonstrates that ML67-33 does not act by interfering with channel trafficking or via a mechanism that involves cytosolic proteins and suggests that the compound acts directly on the channel.

Figure 5:
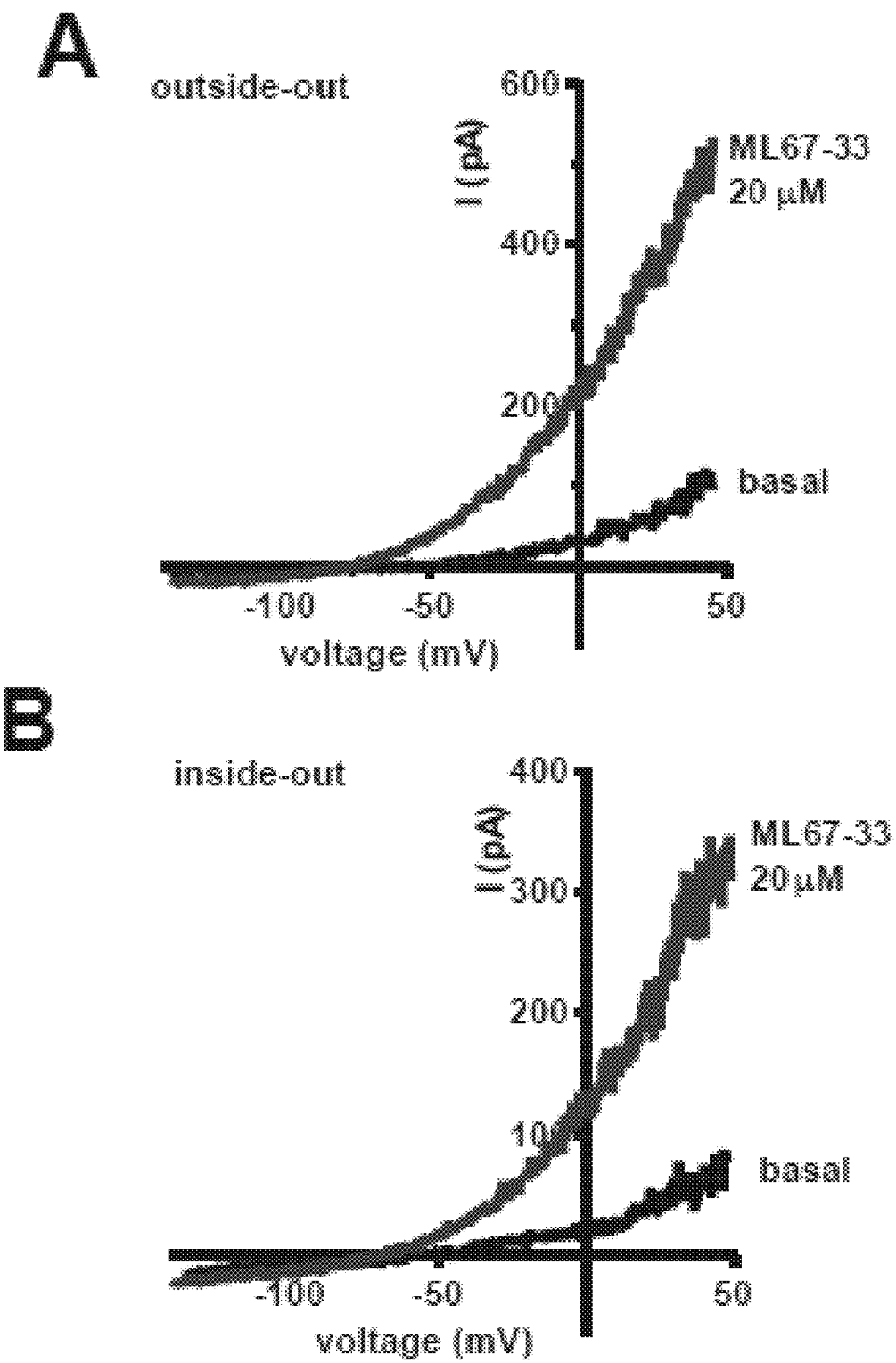
Figure 5:
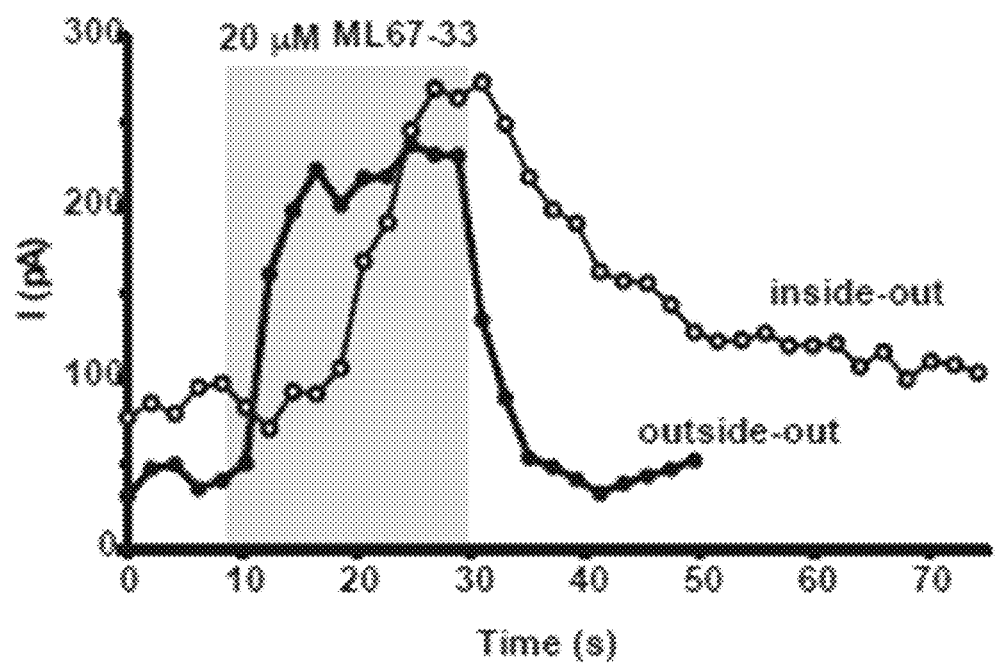
Figure 5:
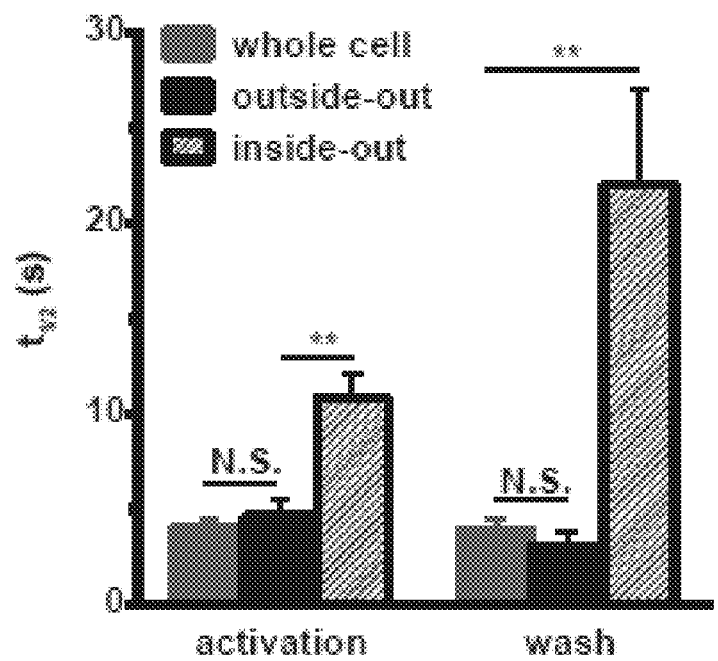

Diverse gating signals that include protons, temperature, mechanical force, and phosphorylation control $K_{2P}2.1$ (TREK-1) function by acting on a C-type selectivity filter based gate located on the extracellular side of the membrane {Piechotta, 2011; Rapedius, 2012; Bagriantsev, 2011; Cohen, 2008; Bagriantsev, 2012}. Many of these gating cues are sensed by an intracellular cytoplasmic domain, Ct, {Honore, 2002: Maingret, 2000; Bagriantsev, 2012: Chemin', 2005; Segal-Hayoun, 2010} that is coupled to the C-type gate via the M4 transmembrane segment and the P1 pore helix {Bagriantsev, 2012}. We found that a variety of manipulations that stabilize C-type gate, such as high concentrations of extracellular potassium {Cohen, 2008}, and mutations in M4, W275S {Bagriantsev, 2011}, and P1, G137I {Bagriantsev, 2012}, reduced or eliminated the activating effects of ML67-33 (FIG. 6c-f). In contrast, decoupling Ct from the C-type gate failed to significantly affect channel sensitivity to ML67-33 (FIG. 6O. This result eliminates this region as the target of ML67-33 action and is striking as in addition to sensing physiological inputs, Ct is thought to be central to $K_{2P}2.1$ (TREK-1) activation by chloroform and arachidonic acid {Patel, 1998} and inhibition by the antidepressant fluoxetine (Prozac) {Sandoz, 2011}. Further, we found that ML67-33 acts quickly and reversibly when applied to channels in whole cells and outside-out patches but displays slower on and off rates when applied to channels in the inside-out patch configuration (FIG. 5c, d). Taken together, these observations strongly support the idea that ML67-33 acts directly on the extracellular C-type gate and indicate that ML67-33 directly target the core machinery that controls channel gating responses.

In addition to its effects on $K_{2P}2.1$ (TREK-1), ML67-33 activates the other two, closely related temperature and mechanosensitive $K_{2P}$ channels, $K_{2P}10.1$ (TREK-2) and $K_{2P}4.1$ (TRAAK) with an $EC_{50}$ in the low-micromolar range (FIG. 7a-g, Table 1). In contrast, it was relatively ineffective against more distantly related members of the $K_{2P}$ family $K_{2P}3.1$ (TASK-1), $K_{2P}9.1$ (TASK-3), $K_{2P}5.1$ (TASK-2), $K_{2P}18.1$ (TRESK), and against the voltage-gated channel Kv7.2 (KCNQ2) (FIG. 7a-g, FIG. 12). The C-type, selectivity filter-based gating mechanism is known to function in channels that respond to ML67-33, $K_{2P}2.1$ (TREK-1) {Bagriantsev, 2011; Cohen, 2008; Piechotta, 2011} and $K_{2P}10.1$ (TREK-2) {Bagriantsev, 2011}, as well as those that were resistant to the compound, $K_{2P}3.1$ (TASK-1) {Lopes, 2000; Lopes, 2001; Yuill, 2007} and $K_{2P}5.1$ (TASK-2) {Niemeyer, 2010}. Thus, these data demonstrate that the presence of a C-type gate is necessary but not sufficient for activation by ML67-33. Further, the good selectivity profile of the compound, suggests that key targets of ML67-33 must lie in elements that are common to the $K_{2P}2.1$ (TREK-1) subfamily.

A number of compounds have been shown previously to modulate $K_{2P}2.1$ (TREK-1) activity {Lotshaw, 2007}. Many are well known drugs with broad molecular specificity or metabolites involved in multiple pathways. These compounds include local {Nayak, 2009; Punke, 2003; Takahira, 2005} and general {Patel, 1999; Patel, 1998; Gruss, 2004} anesthetics, antidepressants {Patel, 1998; Kennard, 2005}, neuroprotectants {Ji, 2011; Duprat, 2000; Cadaveira-Mosquera, 2011}, phospholipids {Chemin, 2005; Chemin, 2007; Lopes, 2005}, protons {Cohen, 2008; Honore, 2002; Sandoz, 2009} and heavy metal ions {Gruss, 2004}. Most of these $K_{2P}2.1$ (TREK-1) modulators act at concentrations>100 μM and have limited effects on current amplitude {Lotshaw, 2007}, showing current enhancements of less than 2-fold {truss, 2004; Patel, 1999; Takahira, 2005; Tertyshnikova, 2005}. The largest activation effects have been demonstrated for chloroform (5.5-fold activation at 1.6 mM) {Patel, 1998} and arachidonic acid (3-12 fold at 10-20 μM) {Patel, 1998; Takahira, 2005}, a polyunsaturated fatty acid with multiple biological functions. ML67-33 acts at a lower concentration (9.7-36.3 μM) and has a larger stimulatory effect ($E_{max}$ ~11 fold) than most previously reported activators. Although the ML67-33 activation effects match that of the most effective but unspecific activator, arachidonic acid[10,55], ML67-33 stimulation of $K_{2P}2.1$ (TREK-1) does not require Ct (FIG. 6a), a channel element that is central to the action of chloroform[5,10], arachidonic acid[5,10] and other gating inputs[9,24,45-47]. Instead, our data indicate that the potent activation caused by ML67-33 involves direct action on the C-type gate that forms the core gating apparatus of the channel[24-26,48]. These properties, together with the fact that ML67-33 acts within seconds suggests that ML67-33 has a novel mechanism of action and focuses attention on the C-type gate for future structure-based development of $K_{2P}$ modulators.

E. Additional Embodiments

1p. A method of treating a disease in a patient in need of such treatment, said method comprising administering a therapeutically effective amount of a compound to said patient, wherein said disease is selected from the group consisting of a neurological disease, pain, migraine, ischemic injury, brain ischemia, stroke, a neurodegenerative disease, a mood disorder, depression, and decompression sickness; and wherein said compound has the formula:

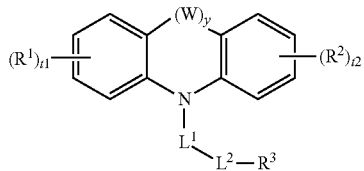

(I)

wherein $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ is a bond, —O—, —S—, —NH—, —C(O)—, —C(O)NH—, —NHC(O)—, —S(O)—, or —S(O)$_2$—; $R^1$, $R^2$, $R^4$, and $R^5$ are independently hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

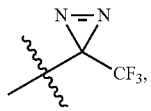

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_3$, —CH$_2$C CH, —NHC(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^4$ and $R^5$ may optionally be joined to form a substituted or unsubstituted cycloalkyl or substituted or unsubstituted heterocycloalkyl; $R^3$ is hydrogen, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$) C=(O)R$^9$, —NR$^7$C(O)—OR$^9$, —NR$^7$OR$^9$, —OCX$_3$, —OCHX$_2$, —OPO(OH)$_2$, —PO (OH)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, oxo, halogen, —C(O)CH$_3$, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)CH$_3$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl; W is —O—, —S—, —S(O)—, —S(O)$_2$—, or —C(R$^4$)(R$^5$)—; y is 0 or 1; m and v are independently 1 or 2; n is independently 0 to 4; t1 and t2 are independently 1 to 4; X is independently —Cl, —Br, —I, or —F.

2p. The method of embodiment 1p, wherein the disease is pain.

3p. The method of embodiment 1p, wherein the disease is a neurodegenerative disease.

4p. The method of embodiment 1p, wherein the disease is a mood disorder.

5p. The method of embodiment 1p, wherein the disease is depression.

6p. A method of increasing the level of activity of TREK-1 in a cell comprising contacting the cell with an effective amount of a compound, wherein the compound has the formula:

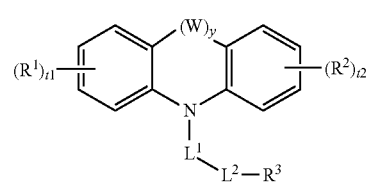

(I)

herein $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ is a bond, —O—, —S—, —NH—, —C(O)—, —C(O)NH—, —NHC(O)—, —S(O)—, or —S(O)$_2$—; $R^1$, $R^2$, $R^4$, and $R^5$ are independently hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

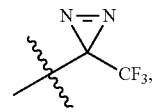

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^4$ and $R^5$ may optionally be joined to form a substituted or unsubstituted cycloalkyl or substituted or unsubstituted heterocycloalkyl; $R^3$ is hydrogen, halogen, —$CX_3$, —CN, —$SO_2Cl$, —$SO_nR^{10}$, —$SO_vNR^7R^8$, —$NHNH_2$, —$ONR^7R^8$, —NHC=(O)$NHNH_2$, —NHC=(O)$NR^7R^8$, —N(O)$_m$, —$NR^7R^8$, —C(O)$R^9$, —C(O)$OR^9$, —C(O)$NR^7R^8$, —$OR^{10}$, —$NR^7SO_2R^{10}$, —N($R^7$)C=(O)$R^9$, —$NR^7C(O)$—$OR^9$, —$NR^7OR^9$, —$OCX_3$, —$OCHX_2$, —OPO(OH)$_2$, —PO(OH)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$, are independently hydrogen, oxo, halogen, —C(O)$CH_3$, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$CH_3$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl; W is —O—, —S—, —S(O)—, —S(O)$_2$—, or —C($R^4$)($R^5$)—; y is 0 or 1; m and v are independently 1 or 2; n is 0 to 4; t1 and t2 are independently an integer from 0 to 4; X is independently —Cl, —Br, —I, or —F 7p. The method of any one of embodiments 1p to 6p, wherein the compound has the formula:

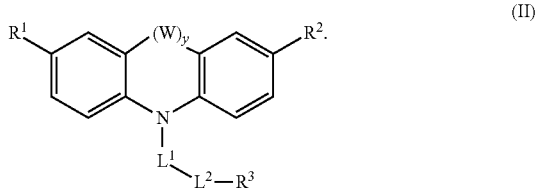

(II)

8p. The method of any one of embodiments 1p to 7p, wherein W is —C($R^4$)($R^5$)—.

9p. The method of any one of embodiments 1p to 8p, wherein y is 0.

10p. The method of any one of embodiments 1p to 9p, wherein $R^1$ is halogen.

11p. The method of any one of embodiments 1p to 10p, wherein $R^2$ is halogen.

12p. The method of any one of embodiments 1p to 11p, wherein at least one of $R^1$ or $R^2$ is not hydrogen.

13p. The method of any one of embodiments 1p to 12p, wherein $R^3$ is —C(O)$OR^9$, —C(O)$NR^7R^8$, substituted or unsubstituted sulfonate, substituted or unsubstituted phosphate, substituted or unsubstituted $C_1$-$C_{10}$ alkyl, substituted or unsubstituted 2 to 10 membered heteroalkyl, substituted or unsubstituted cycloalkyl, substituted or unsubstituted heterocycloalkyl, or substituted or unsubstituted heteroaryl.

14p. The method of any one of embodiments 1p to 13p, wherein $R^3$ is substituted or unsubstituted heteroaryl.

15p. The method of any one of embodiments 1p to 13p, wherein $R^3$ is substituted or unsubstituted sulfonate, phosphate, or tetrazolyl.

16p. The method of any one of embodiments 1p to 13p, wherein $R^3$ is —COOH.

17p. A compound having the formula:

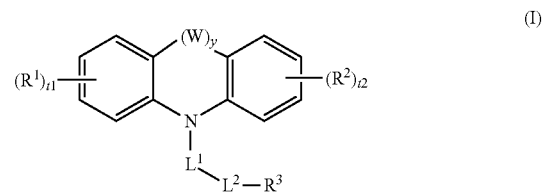

(I)

wherein $L^1$ is an unsubstituted $C_1$-$C_{10}$ alkylene or unsubstituted $C_3$-$C_6$ cycloalkylene; $L^2$ is a bond, —O—, —S—, —NH—, —C(O)—, —C(O)NH—, —NHC(O)—, —S(O)—, or —S(O)$_2$—; $R^1$, $R^2$, $R^4$, and $R^5$ are independently hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCH_3$, —$OCF_3$, —$OCHF_2$, —$N_3$,

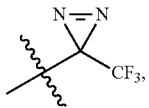

—C($CH_3$)$_3$, —$OCH_2CCH$, —$NHCH_2CCH$, —$NHCH_3$, —N($CH_3$)$_2$, —NHS(O)$CH_3$, —C(O)$CH_3$, —$CH_3$, —$CH_2CCH$, —NHC(O)$CH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^4$ and $R^5$ may optionally be joined to form a substituted or unsubstituted cycloalkyl or substituted or unsubstituted heterocycloalkyl; $R^3$ is —C(O)$OR^9$, —C(O)$NR^7R^8$, —$SO_2R^{10}$, —OPO(OH)$_2$, —PO(OH)$_2$, —$SO_3H$, —$SO_4H$, substituted or unsubstituted sulfonate, substituted or unsubstituted phosphate, substituted or unsubstituted $C_1$-$C_{10}$ alkyl, substituted or unsubstituted 2 to 10 membered heteroalkyl, substituted or unsubstituted cycloalkyl, substituted or unsubstituted heterocycloalkyl, or substituted or unsubstituted heteroaryl; $R^7$, $R^8$, $R^9$, and $R^{10}$, are independently hydrogen, oxo, halogen, —C(O)$CH_3$, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$CH_3$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl; W is —O—, —S—, —S(O)—, —S(O)$_2$—, or —C($R^4$)($R^5$)—; y is 0 or 1; t1 and t2 are independently an integer from 1 to 4; or a pharmaceutically acceptable salt thereof 18p. The compound of embodiment 17p, having the formula:

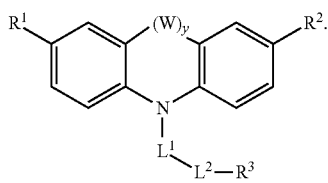

(II)

19p. The compound, or a pharmaceutically acceptable salt thereof, of any one of embodiments 17p or 18p, wherein W is —C(R$^4$)(R$^5$)—.

20p. The compound, or a pharmaceutically acceptable salt thereof, of any one of embodiments 17p to 19p, wherein y is 0.

21p. The compound, or a pharmaceutically acceptable salt thereof, of any one of embodiments 17p to 20p, wherein R$^1$ is halogen.

22p. The compound, or a pharmaceutically acceptable salt thereof, of any one of embodiments 17p to 21p, wherein R$^2$ is halogen.

23p. The compound, or a pharmaceutically acceptable salt thereof, of any one of embodiments 17p to 22p, wherein R$^3$ is substituted or unsubstituted heteroaryl.

24p. The compound, or a pharmaceutically acceptable salt thereof, of any one of embodiments 17p to 22p, wherein R$^3$ is substituted or unsubstituted sulfonate, phosphate, or tetrazolyl.

25p. The compound, or a pharmaceutically acceptable salt thereof, of any one of embodiments 17p to 22p, wherein R$^3$ is —COOH.

26p. A pharmaceutical composition comprising a pharmaceutically acceptable excipient and a compound, or a pharmaceutically acceptable salt thereof, of any one of embodiments 17p to 25p.

1. A method of treating a disease in a patient in need of such treatment, said method comprising administering a therapeutically effective amount of a compound to said patient, wherein said disease is selected from the group consisting of a neurological disease, pain, migraine, ischemic injury, brain ischemia, stroke, a neurodegenerative disease, a mood disorder, depression, and decompression sickness; and wherein said compound has the formula:

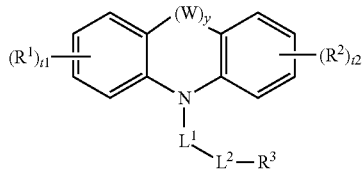

(I)

wherein L$^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; L$^2$ is a bond, —O—, —S—, —NH—, —C(O)—, —C(O)NH—, —NHC(O)—, —S(O)—, or —S(O)$_2$—; W is —O—, —S—, —S(O)—, —S(O)$_2$—, or —C(R$^4$)(R$^5$)—; R$^1$, R$^2$, R$^4$, and R$^5$ are independently hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$,

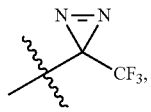

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^4$ and R$^5$ may optionally be joined to form a substituted or unsubstituted cycloalkyl or substituted or unsubstituted heterocycloalkyl; R$^3$ is hydrogen, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$)C=(O)R$^9$, —NR$^7$C(O)OR$^9$, —NR$^7$OR$^9$, —OCX$_3$, —OCHX$_2$, —O PO(OH)$_2$, —PO(OH)$_2$, —C(O)NR$^7$S(O)$_2$R$^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$, R$^8$, R$^9$, and R$^{10}$, are independently hydrogen, oxo, halogen, —C(O)CH$_3$, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)CH$_3$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^7$ and R$^8$ are bonded to the same nitrogen atom, they may optionally be joined to form a substituted or unsubstituted heterocycloalkyl or substituted or unsubstituted heteroaryl; y is 0 or 1; m and v are independently 1 or 2; n is independently 0 to 4; t1 and t2 are independently 1 to 4; X is independently —Cl, —Br, —I, or —F.

2. The method of embodiment 1, wherein the disease is pain.

3. The method of embodiment 1, wherein the disease is a neurodegenerative disease.

4. The method of embodiment 1, wherein the disease is a mood disorder.

5. The method of embodiment 1, wherein the disease is depression.

6. A method of increasing the level of activity of TREK-1 in a cell comprising contacting the cell with an effective amount of a compound, wherein the compound has the formula:

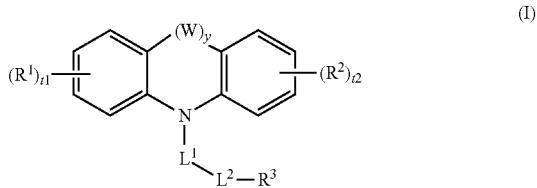

(I)

wherein L¹ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; L² is a bond, —O—, —S—, —NH—, —C(O)—, —C(O)NH—, —NHC(O)—, —S(O)—, or —S(O)₂—; W is —O—, —S—, —S(O)—, —S(O)₂—, or —C(R⁴)(R⁵)—; R¹, R², R⁴, and R⁵ are independently hydrogen, halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —OCH₃, —OCF₃, —OCHF₂, —N₃,

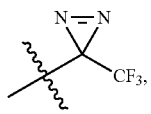 [SMILES: *C1(C(F)(F)F)N=N1]

—C(CH₃)₃, —OCH₂CCH, —NHCH₂CCH, —NHCH₃, —N(CH₃)₂, —NHS(O)CH₃, —C(O)CH₃, —CH₃, —CH₂CH, —NHC(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁴ and R⁵ may optionally be joined to form a substituted or unsubstituted cycloalkyl or substituted or unsubstituted heterocycloalkyl; R³ is hydrogen, halogen, —CX₃, —CN, —SO₂Cl, —SO_nR¹⁰, —SO_vNR⁷R⁸, —NHNH₂, —ONR⁷R⁸, —NHC=(O)NHNH₂, —NHC=(O)NR⁷R⁸, —N(O)_m, —NR⁷R⁸, —C(O)R⁹, C(O)OR⁹, —C(O)NR⁷R⁸, —OR¹⁰, —NR⁷SO₂R¹⁰, —N(R⁷) C=(O)R⁹, —NR⁷C(O)OR⁹, —NR⁷OR⁹, —OCX₃, —OCHX₂, —OPO(OH)₂, —PO(OH)₂, —C(O)NR⁷S(O)₂R¹⁰, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁷, R⁸, R⁹, and R¹⁰, are independently hydrogen, oxo, halogen, —C(O)CH₃, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)CH₃, —NHC=(O) NH₂, —NHSO₂H, —NHC=(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl; y is 0 or 1; m and v are independently 1 or 2; n is independently 0 to 4; t1 and t2 are independently 1 to 4; X is independently —Cl, —Br, —I, or —F.

7. The method of any one of embodiments 1 to 6, wherein L¹ is an unsubstituted C₁-C₁₀ alkylene or unsubstituted C₃-C₆ cycloalkylene.

8. The method of any one of embodiments 1 to 6, wherein L¹ is an unsubstituted C₁-C₄ alkylene.

9. The method of any one of embodiments 1 to 6, wherein L¹ is an unsubstituted C₂-C₃ alkylene.

10. The method of any one of embodiments 1 to 6, wherein L¹ is an unsubstituted ethylene.

11. The method of any one of embodiments 1 to 10, wherein L² is a bond.

12. The method of any one of embodiments 1 to 10, wherein L² is —C(O)NH—.

13. The method of any one of embodiments 1 to 12, wherein the compound has the formula:

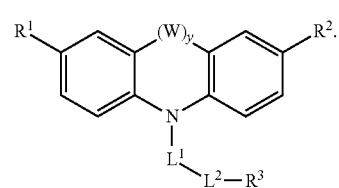

(II)

14. The method of any one of embodiments 1 to 12, wherein the compound has the formula:

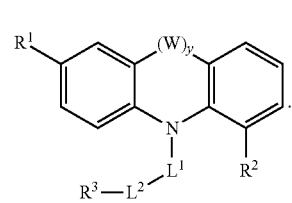

(IIa)

15. The method of any one of embodiments 1 to 14, wherein W is —C(R⁴)(R⁵)—.

16. The method of any one of embodiments 1 to 15, wherein R⁴ and R⁵ are unsubstituted C₁-C₂ alkyl.

17. The method of any one of embodiments 1 to 15, wherein R⁴ and R⁵ are unsubstituted methyl.

18. The method of any one of embodiments 1 to 15, wherein R⁴ and R⁵ are joined to form a substituted or unsubstituted cycloalkyl or substituted or unsubstituted heterocycloalkyl.

19. The method of any one of embodiments 1 to 15, wherein R⁴ and R⁵ are joined to form an unsubstituted cycloalkyl.

20. The method of any one of embodiments 1 to 15, wherein R⁴ and R⁵ are joined to form an unsubstituted C₄-C₈ cycloalkyl.

21. The method of any one of embodiments 1 to 15, wherein R⁴ and R⁵ are joined to form an unsubstituted C₅-C₆ cycloalkyl.

22. The method of any one of embodiments 1 to 15, wherein R⁴ and R⁵ are joined to form an unsubstituted C₆ cycloalkyl.

23. The method of any one of embodiments 1 to 15, wherein R⁴ and R⁵ are joined to form an unsubstituted cyclohexyl.

24. The method of any one of embodiments 1 to 23, wherein y is 1.

25. The method of any one of embodiments 1 to 23, wherein y is 0.

26. The method of any one of embodiments 1 to 25, wherein R¹ is independently hydrogen, halogen, substituted or unsubstituted C₁-C₃ alkyl, or —N₃.

27. The method of any one of embodiments 1 to 25, wherein R¹ is independently hydrogen, halogen, —CH₂OH, or —N₃.

28. The method of any one of embodiments 1 to 25, wherein R¹ is halogen.

29. The method of any one of embodiments 1 to 25, wherein R¹ is —Br.

30. The method of any one of embodiments 1 to 25, wherein $R^1$ is —Cl.

31. The method of any one of embodiments 1 to 30, wherein $R^2$ is independently hydrogen, halogen, substituted or unsubstituted $C_1$-$C_3$ alkyl, or —$N_3$.

32. The method of any one of embodiments 1 to 30, wherein $R^2$ is independently hydrogen, halogen, —$CH_2OH$, or —$N_3$.

33. The method of any one of embodiments 1 to 30, wherein $R^2$ is halogen.

34. The method of any one of embodiments 1 to 30, wherein $R^2$ is —Br.

35. The method of any one of embodiments 1 to 30, wherein $R^2$ is —Cl.

36. The method of any one of embodiments 1 to 35, wherein $R^3$ is substituted or unsubstituted heteroaryl.

37. The method of any one of embodiments 1 to 35, wherein $R^3$ is substituted or unsubstituted sulfonate, substituted or unsubstituted phosphate, or substituted or unsubstituted tetrazolyl.

38. The method of any one of embodiments 1 to 35, wherein $R^3$ is unsubstituted tetrazolyl.

39. The method of any one of embodiments 1 to 35, wherein $R^3$ is —COOH.

40. The method of any one of embodiments 1 to 35, wherein $R^3$ is —$S(O)_2CH_3$ or —$S(O)_2PhCCH$.

41. A method of any one of embodiments 1 to 40, wherein the compound is not a compound selected from the group consisting

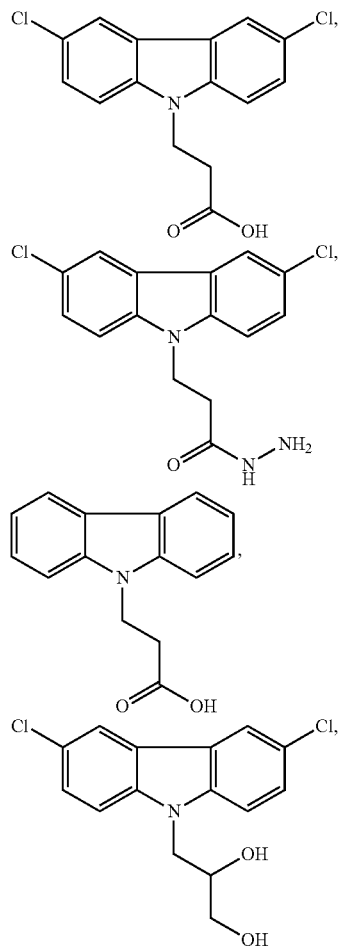

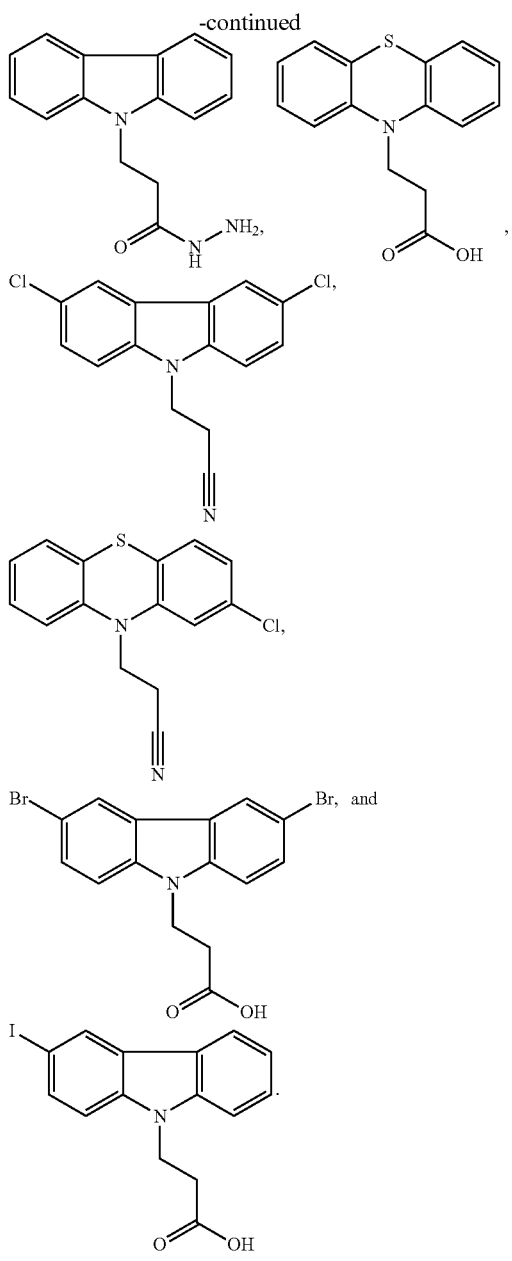

42. A compound having the formula:

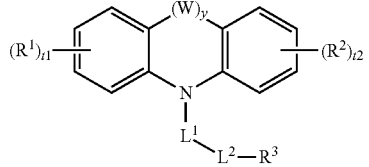

(I)

wherein $L^1$ is a substituted or unsubstituted $C_1$-$C_{10}$ alkylene or substituted or unsubstituted $C_3$-$C_6$ cycloalkylene; $L^2$ is a bond, —O—, —S—, —NH—, —C(O)—, —C(O)NH—, —NHC(O)—, —S(O)—, or —$S(O)_2$—; W is —O—, —S—, —S(O)—, —$S(O)_2$—, or —$C(R^4)(R^5)$—; $R^1$, $R^2$, $R^4$, and $R^5$ are independently hydrogen, halogen, —$CF_3$, —$CCl_3$, —CN, —OH, —$NH_2$, —COOH, —$CONH_2$, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCH₃, —OCF₃, —OCHF₂, —N₃,

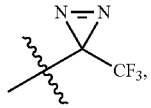 [SMILES: *C1(C(F)(F)F)N=N1]

—C(CH₃)₃, —OCH₂CCH, —NHCH₂CCH, —NHCH₃, —N(CH₃)₂, —NHS(O)CH₃, —C(O)CH₃, —CH₃, —CH₂CCH, —NHC(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁴ and R⁵ may optionally be joined to form a substituted or unsubstituted cycloalkyl or substituted or unsubstituted heterocycloalkyl; R³ is —C(O)OR⁹, —C(O)NR⁷R⁸, —SO₂R¹⁰, —OPO(OH)₂, —PO(OH)₂, —SO₃H, —SO₄H, substituted or unsubstituted sulfonate, substituted or unsubstituted phosphate, substituted or unsubstituted C₁-C₁₀ alkyl, substituted or unsubstituted 2 to 10 membered heteroalkyl, substituted or unsubstituted cycloalkyl, substituted or unsubstituted heterocycloalkyl, or substituted or unsubstituted heteroaryl; R⁷, R⁸, R⁹, and R¹⁰, are independently hydrogen, oxo, halogen, —C(O)CH₃, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)CH₃, —NHC=(O)NH₂, —NHSO₂H, —NHC=(O)H, —NHC(O)—OH, —NHOH, —OCF₃, —OCHF₂, —C(O)NR⁷S(O)₂R¹⁰, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl; y is 0 or 1; t1 and t2 are independently an integer from 1 to 4; or a pharmaceutically acceptable salt thereof 43. The compound of embodiment 42, wherein L¹ is an unsubstituted C₁-C₁₀ alkylene or unsubstituted C₃-C₆ cycloalkylene.

44. The compound of embodiment 42, wherein L¹ is an unsubstituted C₁-C₄ alkylene.

45. The compound of embodiment 42, wherein L¹ is an unsubstituted C₂-C₃ alkylene.

46. The compound of embodiment 42, wherein L¹ is an unsubstituted ethylene.

47. The compound of any one of embodiments 42 to 46, wherein L² is a bond.

48. The compound of any one of embodiments 42 to 46, wherein L² is —C(O)NH—.

49. The compound of any one of embodiments 42 to 48, wherein the compound has the formula

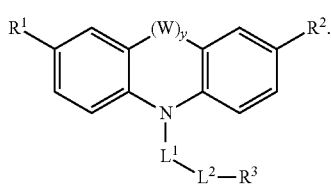

(II)

50. The compound of any one of embodiments 42 to 48, wherein the compound has the formula:

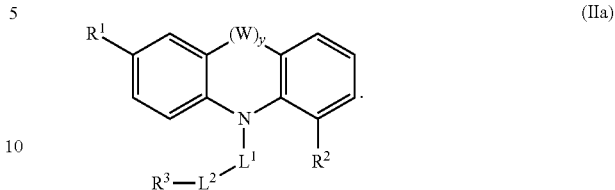

(IIa)

51. The compound of any one of embodiments 42 to 50, wherein W is —C(R⁴)(R⁵)—.

52. The compound of any one of embodiments 42 to 51, wherein R⁴ and R⁵ are unsubstituted C₁-C₂ alkyl.

53. The compound of any one of embodiments 42 to 51, wherein R⁴ and R⁵ are unsubstituted methyl.

54. The compound of any one of embodiments 42 to 51, wherein R⁴ and R⁵ are joined to form a substituted or unsubstituted cycloalkyl or substituted or unsubstituted heterocycloalkyl.

55. The compound of any one of embodiments 42 to 51, wherein R⁴ and R⁵ are joined to form an unsubstituted cycloalkyl.

56. The compound of any one of embodiments 42 to 51, wherein R⁴ and R⁵ are joined to form an unsubstituted C₄-C₈ cycloalkyl.

57. The compound of any one of embodiments 42 to 51, wherein R⁴ and R⁵ are joined to form an unsubstituted C₅-C₆ cycloalkyl.

58. The compound of any one of embodiments 42 to 51, wherein R⁴ and R⁵ are joined to form an unsubstituted C₆ cycloalkyl.

59. The compound of any one of embodiments 42 to 51, wherein R⁴ and R⁵ are joined to form an unsubstituted cyclohexyl.

60. The compound of any one of embodiments 42 to 59, wherein y is 1.

61. The compound of any one of embodiments 42 to 59, wherein y is 0.

62. The compound of any one of embodiments 42 to 61, wherein R¹ is independently hydrogen, halogen, substituted or unsubstituted C₁-C₃ alkyl, or —N₃.

63. The compound of any one of embodiments 42 to 61, wherein R¹ is independently hydrogen, halogen, —CH₂OH, or —N₃.

64. The compound of any one of embodiments 42 to 61, wherein R¹ is halogen.

65. The compound of any one of embodiments 42 to 61, wherein R¹ is —Br.

66. The compound of any one of embodiments 42 to 61, wherein R¹ is —Cl.

67. The compound of any one of embodiments 42 to 66, wherein R² is independently hydrogen, halogen, substituted or unsubstituted C₁-C₃ alkyl, or —N₃.

68. The compound of any one of embodiments 42 to 66, wherein R² is independently hydrogen, halogen, —CH₂OH, or —N₃.

69. The compound of any one of embodiments 42 to 66, wherein R² is halogen.

70. The compound of any one of embodiments 42 to 66, wherein R² is —Br.

71. The compound of any one of embodiments 42 to 66, wherein R² is —Cl.

72. The compound of any one of embodiments 42 to 71, wherein R³ is substituted or unsubstituted heteroaryl.

73. The compound of any one of embodiments 42 to 71, wherein R³ is substituted or unsubstituted sulfonate, substituted or unsubstituted phosphate, or substituted or unsubstituted tetrazolyl.

74. The compound of any one of embodiments 42 to 71, wherein R³ is unsubstituted tetrazolyl.

75. The compound of any one of embodiments 42 to 71, wherein R³ is —COOH.

76. The compound of any one of embodiments 42 to 71, wherein R³ is —S(O)₂CH₃ or —S(O)₂PhCCH.

77. A compound of any one of embodiments 42 to 76, wherein the compound is not a compound selected from the group consisting

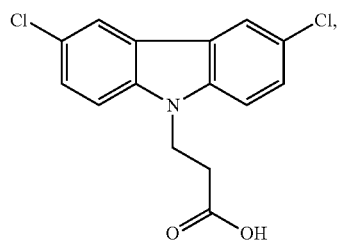
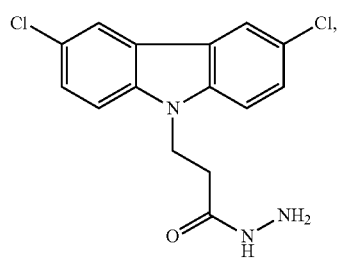
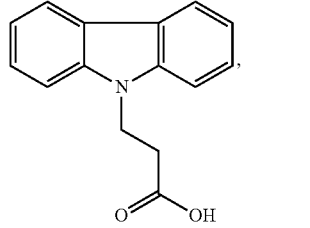
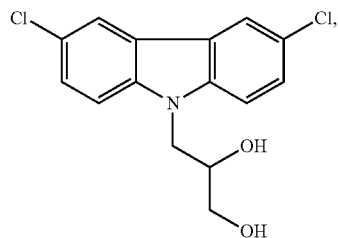
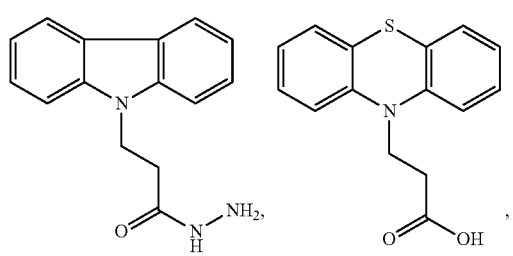
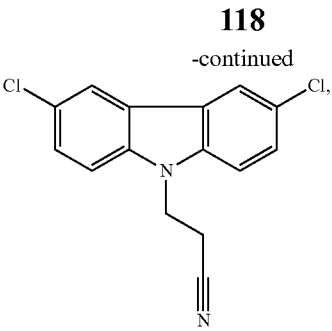
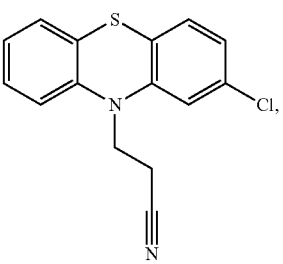
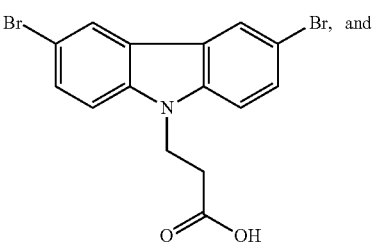
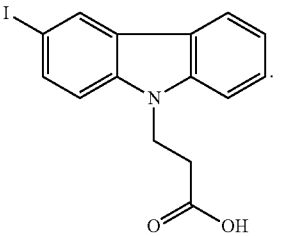

78. A pharmaceutical composition comprising a pharmaceutically acceptable excipient and a compound, or a pharmaceutically acceptable salt thereof, of any one of embodiments 42 to 77.

79. A pharmaceutical composition of embodiment 78, wherein the compound is not a compound selected from the group consisting

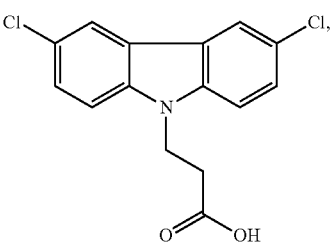

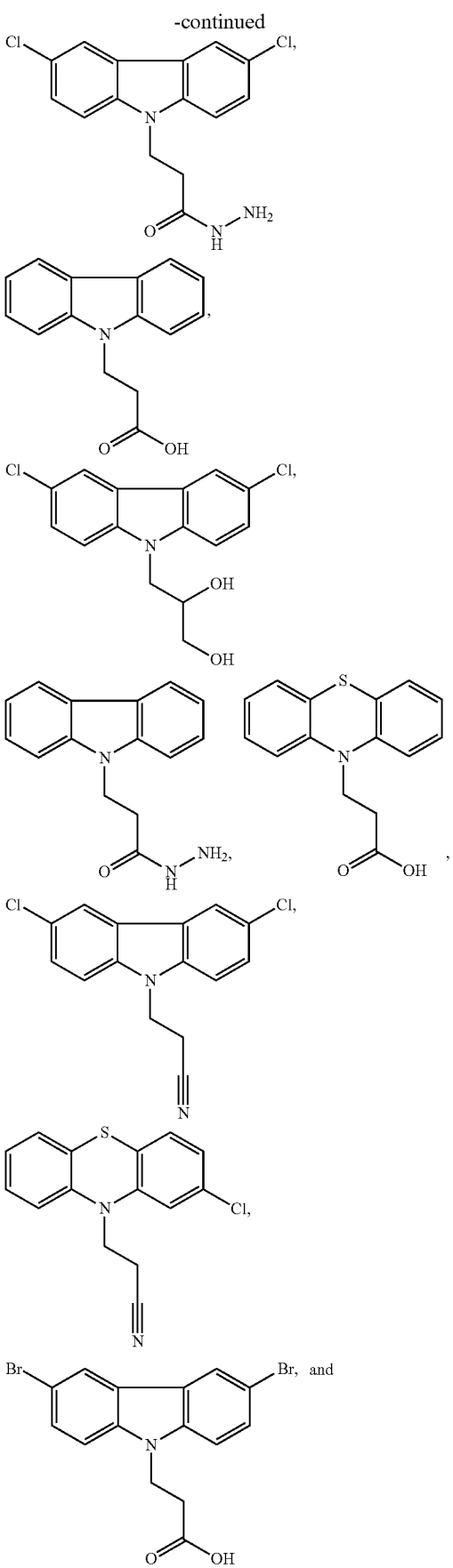

80. A method of treating a disease associated with a reduced level of activity of a K2P channel (e.g. TREK-1, TREK-2, or TRAAK) relative to a control in a patient in need of such treatment, said method comprising administering a therapeutically effective amount of a compound of one of embodiments 42 to 77 to said patient.

81. A method of treating a disease associated with a reduced level of activity of TREK-1 relative to a control in a patient in need of such treatment, said method comprising administering a therapeutically effective amount of a compound of one of embodiments 42 to 77 to said patient.

82. A method of treating a disease associated with a reduced level of activity of TREK-2 relative to a control in a patient in need of such treatment, said method comprising administering a therapeutically effective amount of a compound of one of embodiments 42 to 77 to said patient.

83. A method of treating a disease associated with a reduced level of activity of TRAAK relative to a control in a patient in need of such treatment, said method comprising administering a therapeutically effective amount of a compound of one of embodiments 42 to 77 to said patient.

F. Examples

1. High-throughput Yeast Screen Identifies $K_{2P}2.1$ (Trek-1) Activators And Inhibitors Here, we report the development of a high-throughput yeast-based screening assay to detect small molecule modulators of the polymodal $K_{2P}$, $K_{2P}2.1$ (KCNK2, TREK-1) {Fink, 1996; Honore, 2007; Noel, 2011}. This channel is regulated by heat {Maingret, 2000}, mechanical force {Patel, 1998}, general anesthetics {Patel, 1998; Patel, 1999}, and a number of G-protein coupled receptors {Noel, 2011}. Its activity is involved in pain {Alloui, 2006; Noel, 2009}, general anesthetic responses {Heurteaux, 2004}, neuroprotection from ischemia {Heurteaux, 2004}, and depression {Heurteaux, 2006}. Although $K_{2P}2.1$ (TREK-1) function is affected by a variety of pharmacologic agents such as both volatile halogenated {Solt, 2007; Patel, 1998; Patel, 1999 Lesage, 2000; Lotshaw, 2007; Harinath, 2004}), and gasesous general anesthetics {Solt, 2007; Gruss, 2004}, the neuroprotective agent riluzole {Duprat, 2000}, and antidepressant fluoxetine (Prozac) {Kennard, 2005; Sandoz, 2011}, these compounds have other molecular targets {Franks, 2004; Solt, 2007}. Hence, we set out to identify and develop small molecules that could be used to specifically control $K_{2P}2.1$ (TREK-1) activity. Such molecules should serve as tools to dissect the unconventional gating apparatus that controls $K_{2P}2.1$ (TREK-1) function {Bagriantsev, 2012; Bagriantsev, 2011; Piechotta, 2011}, and may also provide lead compounds for the development of novel anesthetics, neuroprotectants, and drugs against mood disorders.

Using a yeast-based screen, coupled with electrophysiological analysis, we discovered both inhibitors and activators of $K_{2P}2.1$ (TREK-1) in a single screening campaign. These compounds comprise different chemical classes, and reversibly affect $K_{2P}2.1$ (TREK-1) activity. Beginning with a carbazole-based scaffold, we were able to develop a $K_{2P}2.1$ (TREK-1) activator, ML67-33, that rapidly and reversibly affects the $K_{2P}2.1$ (TREK-1) extracellular C-type gate. This acridine-based compound also activates two heat- and mechano-sensitive $K_{2P}$ channels that are most closely related to $K_{2P}2.1$ (TREK-1), $K_{2P}10.1$ (TREK-2) and $K_{2P}4.1$ (TRAAK), but has no effects on more distantly related $K_{2P}$s. Thus, ML67-33 represents a novel non-metabolic $K_{2P}$ activator that has specificity within the $K_{2P}$ family. The new $K_{2P}$ modulators presented here, should facilitate both mechanistic and physiological tests of $K_{2P}$ activity. Further, the yeast-based assay should enable the discovery of other $K_{2P}$ small molecule modulators.

We set out to address the dearth of $K_{2P}$ pharmacology by developing a high-throughput screen (HTS) for small molecule modulators of $K_{2P}$ channels. Prior studies have established that growth of the potassium-uptake-deficient yeast strain SGY1528 {Ko, 1991} could be rescued in solid-media based assays by ectopic expression of a variety of potassium channels {Tang, 1995; Minor, 1999; Minor, 2009; Chatelain, 2009}, including, $K_{2P}2.1$ (TREK-1) {Bagriantsev, 2011}. Although this platform has been used to screen small libraries of <10,000 compounds against the inward rectifier Kir2.1 {Zaks-Makhina, 2004; Zaks-Makhina, 2009} and has proven advantageous for studying interactions of potassium channels with known blockers {Chatelain, 2005; Chatelain, 2009}, the solid media format limits the ease of test compound delivery and scalability for large test compounds libraries. Hence, we focused on developing a means to monitor rescue of growth under limiting potassium concentrations by heterologously expressed potassium channels, such as $K_{2P}2.1$ (TREK-1), in a liquid media format that would be compatible for an HTS assay and that would facilitate the screening of large libraries of compounds.

To this end, we measured the signal generated by the vital dye resazurin (Alamar Blue), which live cells convert to a fluorescent form {Nakayama, 1997}, to quantify the abundance of living SGY1528 grown in liquid culture in 386-well plates for 24 hours in media containing a range of potassium concentrations (FIG. 1a-d). Cells expressing the yeast potassium transporter Trk1p {Gaber, 1988} exhibited similar levels of resazurin fluorescence signals when cultured in media containing a wide range of potassium concentrations, 0-50 mM KCl, indicative of robust growth (fluorescence intensity range: 116±3.2-110±3.3, arbitrary units, AU, mean±s.e.; p=0.18, t-test, FIG. 1a). In contrast, yeast bearing a plasmid for a non-functional channel {Minor, 1999} showed little growth in limited potassium conditions, 0-2 mM KCl (30±0.1-32±0.2 AU), and only propagated in the presence of 50 mM KCl (87±1.5 AU, FIG. 1a). Resazurin fluorescence signals from cells expressing $K_{2P}2.1$ (TREK-1) under conditions in which potassium was limited, 0-2 mM KCl (67±0.5 vs. 30±0.1 AU, respectively, p<0.001, t-test, FIG. 1a) were significantly larger than the negative control. Interestingly, in 50 mM potassium media, which is non-limiting, the $K_{2P}2.1$ (TREK-1)-expressing cells exhibited reduced growth compared to media having lower potassium concentrations, 1.2 or 2 mM KCl (84±1.2 AU, p<0.001 vs. 1.2 or 2 mM KCl, t-test) and that was comparable to the negative control (FIG. 1a). This effect was not observed in the Trk1p-expressing culture (FIG. 1a) and is reminiscent of prior studies of yeast channels in which activation of a heterologously expressed channel inhibited growth {Loukin, 1997}. Together, these experiments show that $K_{2P}2.1$ (TREK-1) supports viability of the SGY1528 yeast in liquid media under potassium-limiting conditions, a result that is in line with prior studies using solid media {Bagriantsev, 2011}. Importantly, this liquid based, 384-well format was suited to automated plate reader analysis and hence, we next sought to define conditions that would be suitable for a HTS screen for regulators of $K_{2P}2.1$ (TREK-1) activity.

Resazurin assessment of the effects of the carrier for test compounds, 1% dimethyl sulfoxide (DMSO), and a control for growth inhibition, 0.1% sodium dodecyl sulfate, SDS, on $K_{2P}2.1$ (TREK-1)-expressing yeast grown in potassium-limited conditions in which the channel is required for growth, 2 mM KCl liquid media, established two important assay properties. First, DMSO did not inhibit growth, whereas SDS was lethal. Second, the two controls yielded a favorable Z' value {Zhang, 1999}, Z'=0.76 (FIG. 1b), a widely used metric for determining the degree of separation between negative and positive controls in HTS assays. As robust HTS assays should have Z'>0.5 {Zhang, 1999}, and these controls passed that metric, we proceeded with a larger screening campaign to find possible $K_{2P}2.1$ (TREK-1) modulators.

We then used a 384 well format and the resazurin assay to screen a library of 105,863 small molecules at 10 µM each for their ability to inhibit growth of the $K_{2P}2.1$ (TREK-1)-expressing SGY1528 yeast (FIG. 1b and FIG. 8). Each plate included lanes for 1% DMSO and 0.1% SDS, which served as the 0% and 100% growth inhibition controls used to calculate the degree of compound-induced growth inhibition (FIG. 8). We then chose 320 compounds that inhibited growth in the range of 44-92% (HTS score) from the initial screen for further evaluation. To distinguish compounds that were generally toxic from those that caused $K_{2P}2.1$ (TREK-1)-specific growth inhibition, we tested each of the 320 compounds in a dose-response screen over a range of 0.4-50 µM against yeast expressing either $K_{2P}2.1$ (TREK-1) or Trk1p (FIGS. 1c and d). These tests identified 81 compounds in which there was at least a 2-fold difference in the apparent $IC_{50}$ required to inhibit the growth of yeast expressing $K_{2P}2.1$ (TREK-1)-versus those expressing Trk1, e.g. compounds ML45 and ML67 (FIGS. 1c and d). Sixty-one $K_{2P}2.1$ (TREK-1)-specific compounds were tested in electrophysiological analysis.

Figure 9:
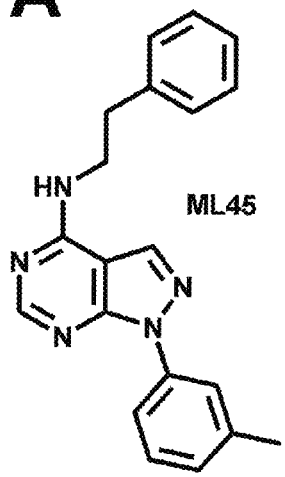
FIG. 9 Exemplar $K_{2P}2.1$ (TREK-1) inhibitors a, ML45 and b, ML58 identified in the high-throughput yeast screen. Panels show from left to right: chemical structure; HTS score, percent of growth inhibition for the indicated compound in the high-throughput screen; SMILES and chemical names; and activity. Activity plots show the effect of the compounds at the indicated concentrations against $K_{2P}2.1$ (TREK-1) measured by two-electrode voltage clamp in *Xenopus* oocytes in 90 mM $[K^+]_o$ pH 7.4. Currents were elicited by a ramp from −100 to 50 mV from a 0 mV holding potential. Values shown were taken at +40 mV.
Figure 9:
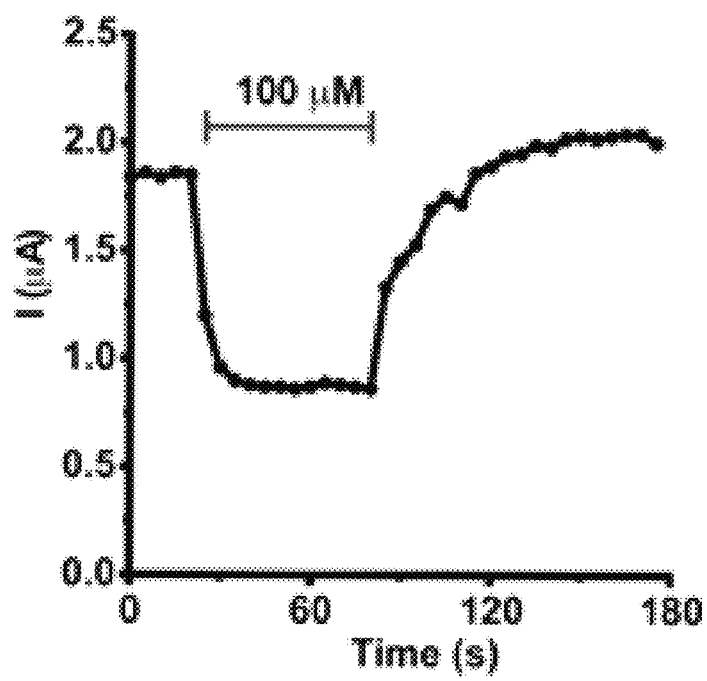
Figure 9:
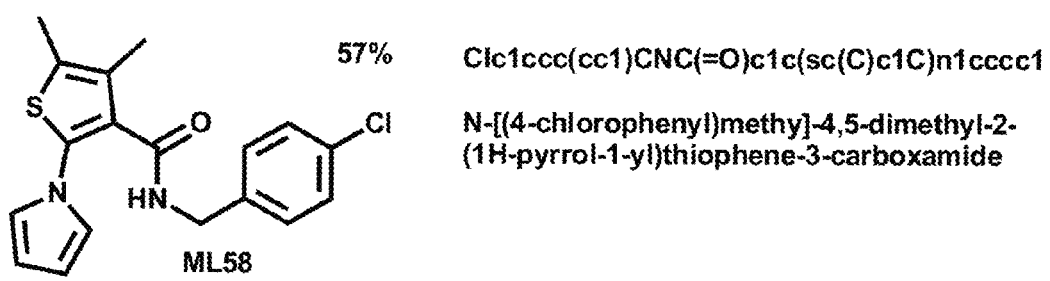
Figure 9:
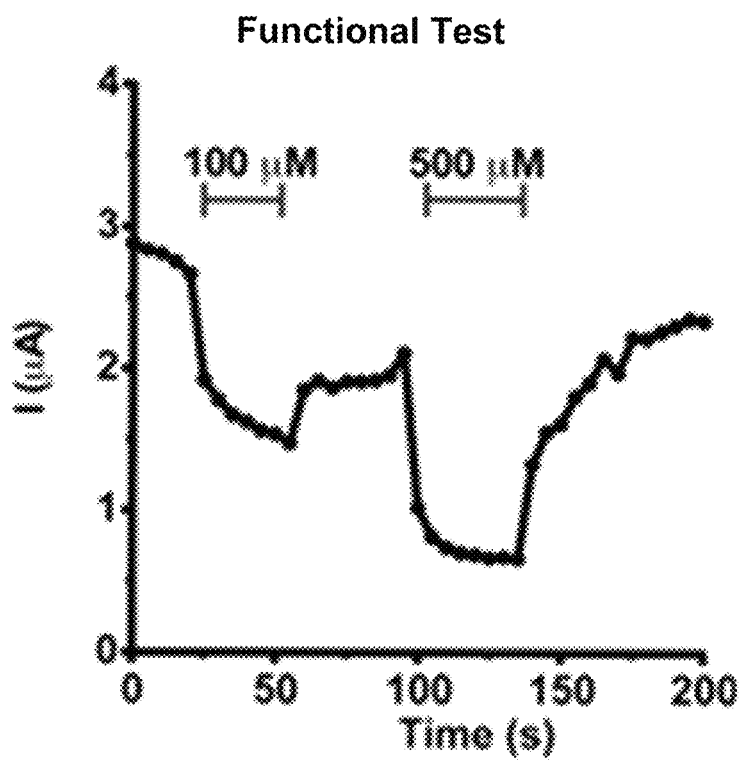
Figure 10:
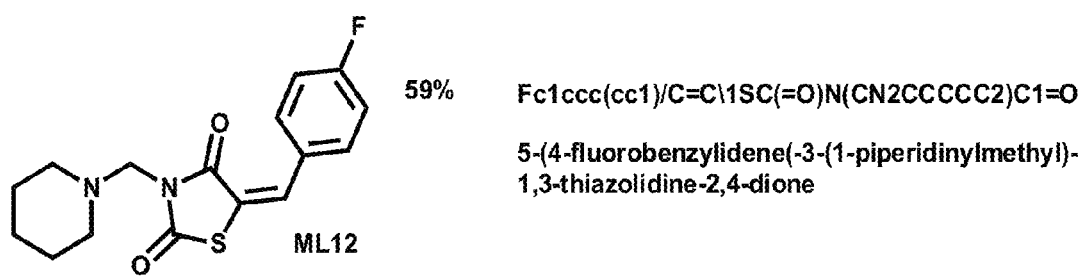
FIG. 10 Exemplar $K_{2P}2.1$ (TREK-1) activators a, ML12, b, ML42, and c, ML67 identified in the high-throughput yeast screen. Panels show from left to right: chemical structure; HTS score, percent of growth inhibition for the indicated compound in the high-throughput screen; SMILES and chemical names; and activity. Activity plots show the effect of the compounds at the indicated concentrations against $K_{2P}2.1$ (TREK-1) measured by two-electrode voltage clamp in *Xenopus* oocytes in 90 mM $[K^+]_o$ pH 7.4. Currents were elicited by a ramp from −100 to 50 mV from a 0 mV holding potential. Values shown were taken at +40 mV.
Figure 10:
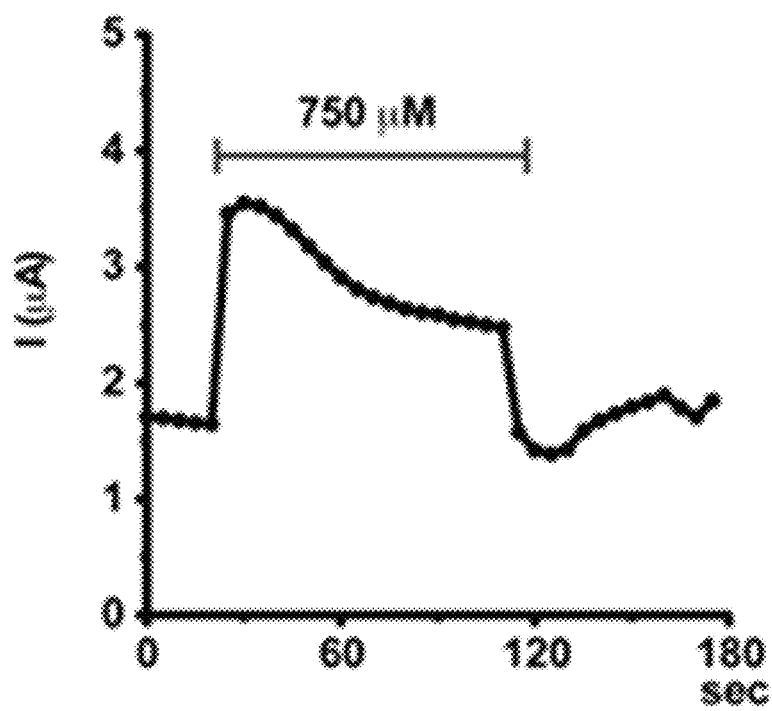
Figure 10:
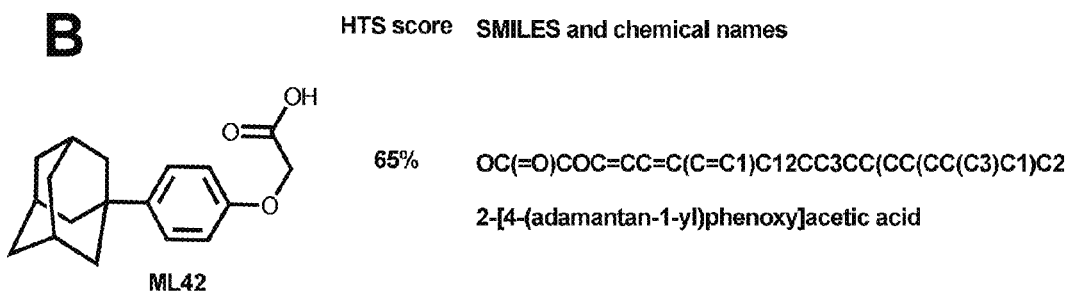
Figure 10:
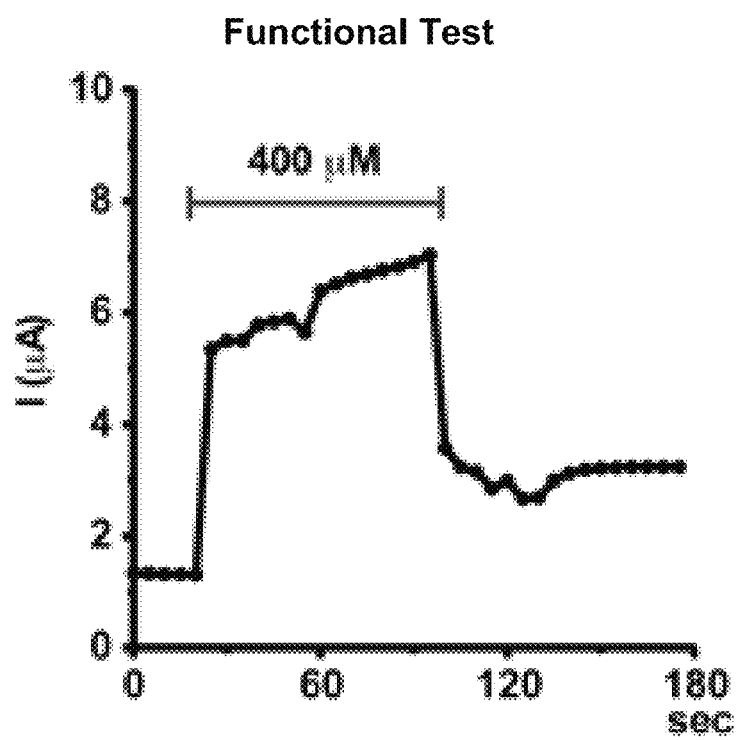
Figure 10:
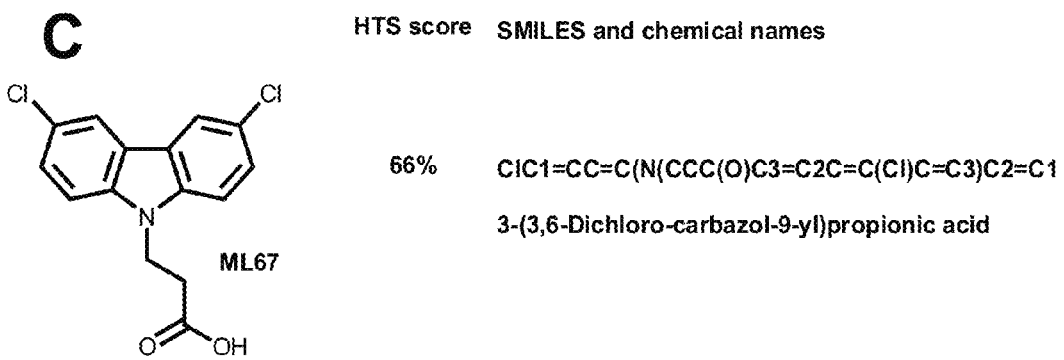
Figure 10:
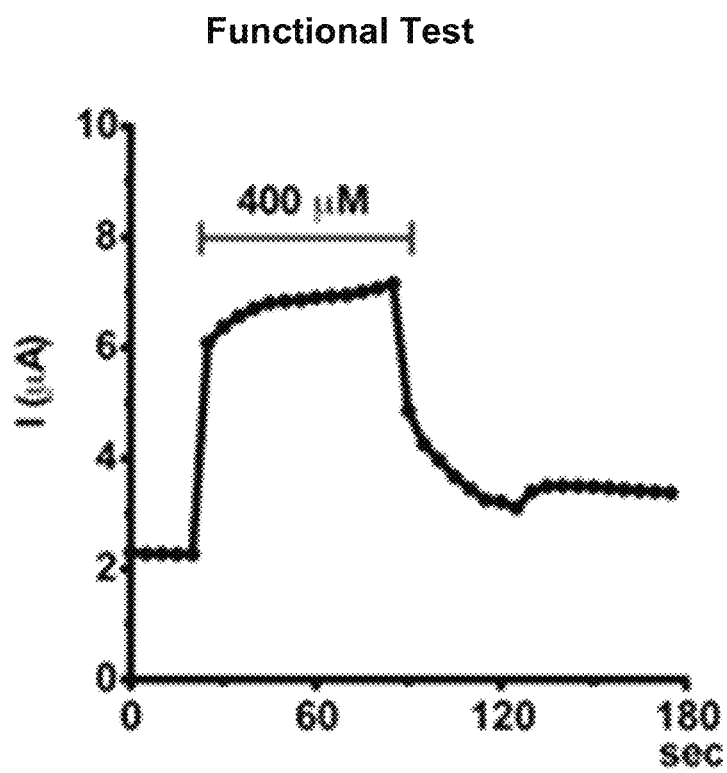

Twenty-five compounds were tested for activity against $K_{2P}2.1$ (TREK-1) expressed in *Xenopus* oocytes by two-electrode voltage clamp. Electrophysiological characterization identified five compounds that affected $K_{2P}2.1$ (TREK-1) function. Two acted as inhibitors: a pyrimidine based compound (ML45) and a thiophene based compound (ML58) (FIG. 9a-b). Three activated the channel: a thiazolidine (ML12), an amantadine derivative (ML42), and a carbazole (ML67) (FIG. 10a-c). Dose-response studies showed that that ML45 reversibly inhibited $K_{2P}2.1$ (TREK-1) by ~70% at the highest concentration tested ($IC_{50}$ ~21 µM, FIG. 2a, c, and e). In contrast, ML67 reversibly activated $K_{2P}2.1$ (TREK-1), increasing currents by up to ~11 fold ($EC_{50}$ 213.0±1.2 µM, FIG. 2b, d, and e, and Table 1). Because $K_{2P}2.1$ (TREK-1) activators could provide a path to novel anesthetics, analgesics, and neuroprotectants {Es-Salah-Lamoureux, 2010} and because there were a number of derivatives readily available, we chose to focus further studies on the $K_{2P}2.1$ (TREK-1) activating compound ML67.

Figure 2:
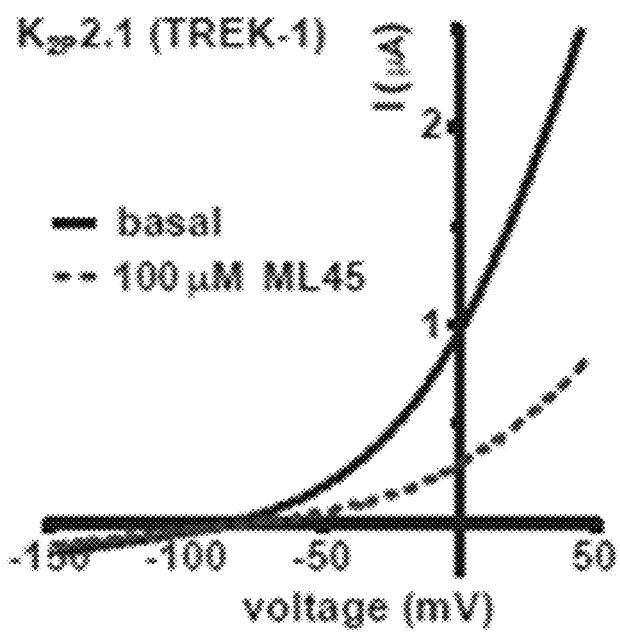
FIG. 2 ML45 and ML67 reversibly modulate $K_{2P}$ activity a, and b, two-electrode voltage clamp exemplar I-V curves showing the effect of application of 100 μM a, ML45 or b, ML67 to Xenopus oocytes expressing $K_{2P}2.1$ (TREK-1) measured in a solution contain 2 mM $[K^+]_o$ pH 7.4; currents were elicited by a voltage ramp from −150 to 50 mV, from a holding potential of −80 mV; c, and d, exemplar $K_{2P}2.1$ (TREK-1) responses to the addition of 100 μM c, ML45 or d, ML67 measured at 20 mV and 0 mV for ML45 and ML67, respectively; e, dose-response relations for ML45 and ML67 on $K_{2P}2.1$ (TREK-1); data was normalized to basal channel activity and fitted to the Hill equation; f, dose-response curves measured by two-electrode voltage clamp in Xenopus oocytes for the effect of ML67 against $K_{2P}2.1$ (TREK-1), black; $K_{2P}10.1$ (TREK-2), red; $K_{2P}3.1$ (TASK-1), green; and Kv7.2 (KCNQ2), blue; error bars show s.e., n≥6, N≥2, where n and N is the number of oocytes or independent oocyte batches, respectively.
Figure 2:
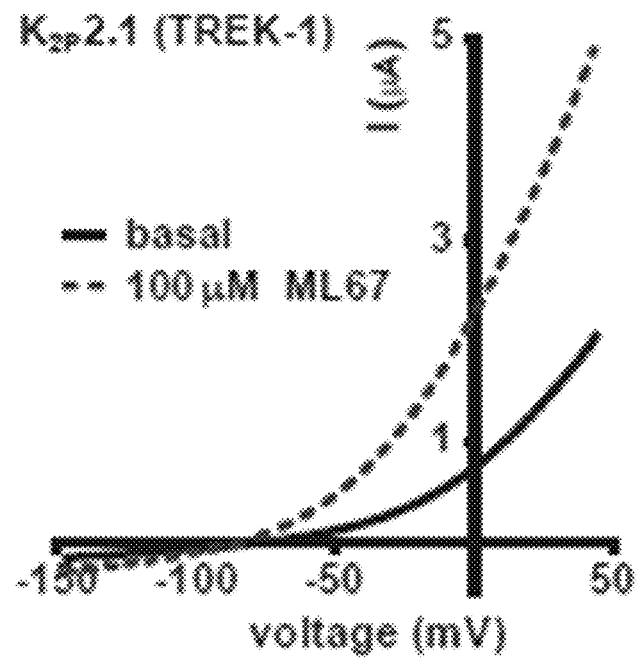
Figure 2:
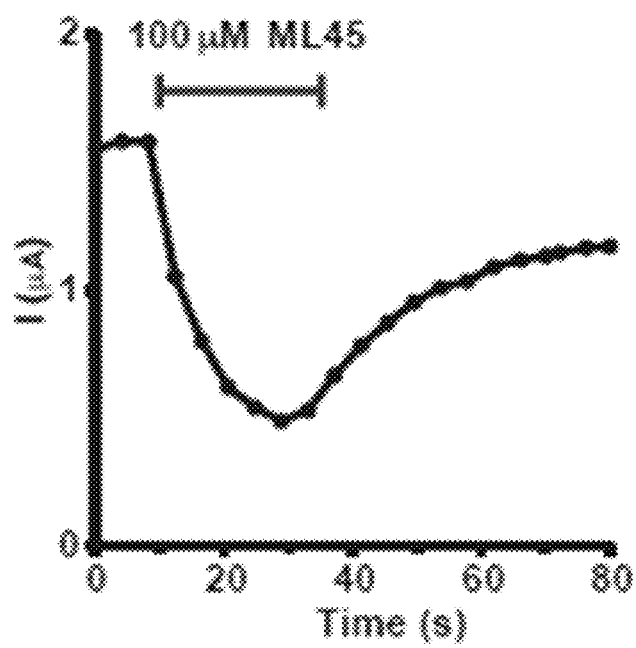
Figure 2:
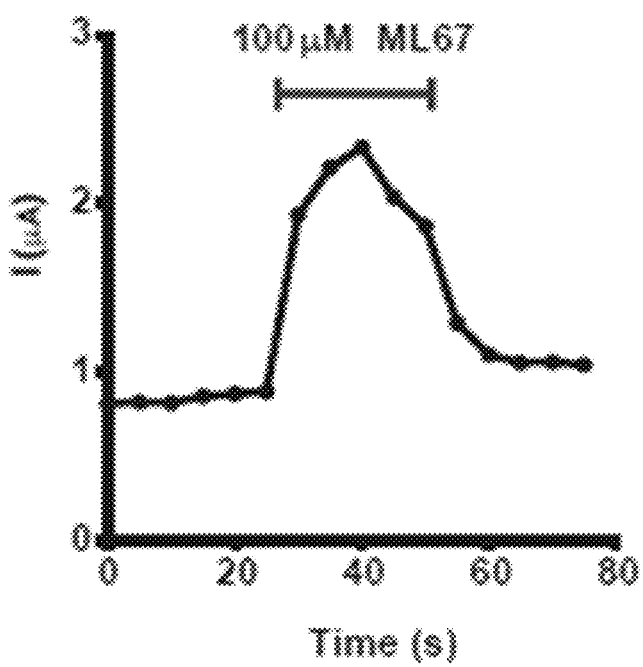
Figure 2:
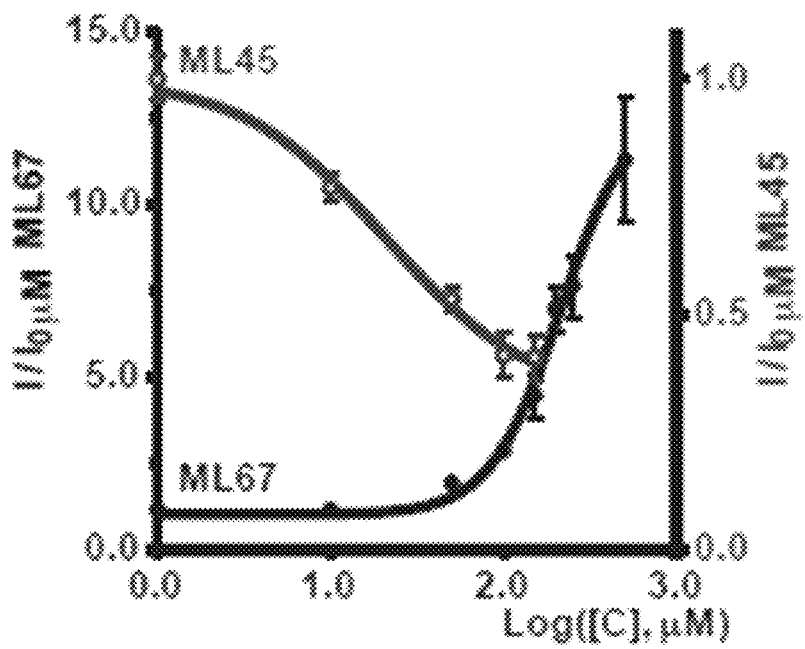
Figure 2:
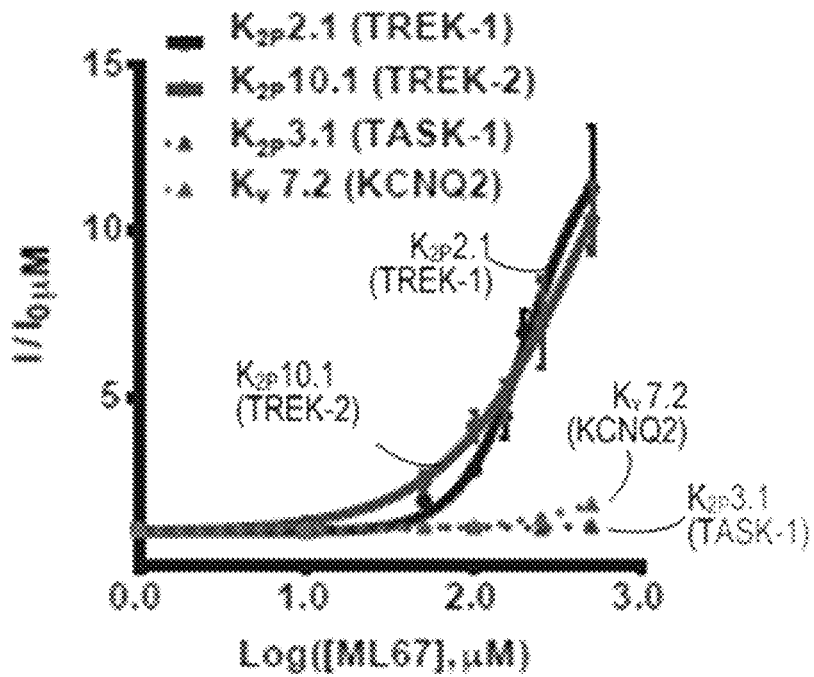

We first addressed whether ML67 was a selective or general potassium channel opener. Two electrode voltage clamp studies showed that ML67 activated $K_{2P}10.1$ (TREK-2) ($EC_{50}$>250 µM), the closest $K_{2P}2.1$ (TREK-1) homolog (FIG. 11), but not the more distantly related $K_{2P}3.1$ (TASK- 1) (FIG. 2f). Further, ML67 had no effect on the voltage-gated channel Kv7.2 (KCNQ2) (FIG. 20, a representative of a channel class for which small molecule openers have been previously described {Xiong, 2008; Xiong, 2007; Xiong, 2008}. Having established that ML67 had some selectivity among diverse potassium channels, we sought to characterize which features of the compound were important for channel activation in order to understand the basic structure-activity relationships (SAR) and improve upon its properties.

Murine $K_{2P}$ channels were cloned into pGEMHE/pMO {Bagriantsev, 2011}, IRES-GFP (Invitrogen), or pYES2-MET25 (high copy 2µ, URA3) {Minor, 1999} for expression in oocytes, HEK-293T cells, and yeast, respectively, using standard molecular biology procedures, and verified by DNA sequencing.

The Saccharomyces cerevisiae strain SGY1528 (W303, MATα, ade2-1, canl-100, his3-11,15, leu2-3,112, trp1-1, ura3-1, trkl::HIS3, trk2::TRP1) was transformed using the lithium-chloride method and cultivated at 30° C. using standard techniques {Sherman, 2002} in synthetic liquid media without uracil (Ura, for plasmid selection) and methionine (Met, to drive $K_{2P}$2.1 (TREK-1) expression from the MET25 promoter of the pYES2-MET25 vector). The synthetic media, estimated to contain ~5 µM potassium {Rodriguez-Navarro, 1984} and designated as '0 mM KCl', was additionally supplemented with up to 50 mM KCl. YPAD, non-selective medium: 10 g/L yeast extract, 20 g/L dextrose, 20 g/L peptone, 24 mg/L adenine hemisulfate, 100 mM KCl. Plasmid-selective -Ura/-Met synthetic medium: 1.5 g/L -Ura/-Met dropout powder, 6.7 g/L yeast nitrogen base (without amino acids), 20 g/L dextrose, 100 mM KCl, pH 6.5 (adjusted with 1M Tris base). -Ura/-Met test medium: 2.1 g arginine (free base), 1.5 g/L dropout powder -Ura/-Met, 10 g/L dextrose, 1× trace minerals and vitamins (see 1000× stock recipes below), 1 mM $MgSO_4$, 0.1 mM $CaCl_2$, 0-50 mM KCl, pH 6.0 with adjusted with phosphoric acid. -Ura/-Met dropout powder: 6.0 g glutamic acid, 2.5 g adenine hemisulfate, 1.2 g arginine, 6.0 g aspartic acid, 1.8 g lysine, 3.0 g phenylalanine, 22.5 g serine, 12.0 g threonine, 2.4 g tryptophane, 1.8 g tyrosine, 9.0 g valine, 1.2 g histidine, 3.4 g leucine. 1000× Vitamin 1000× stock solution: 2 mg/L biotin, 400 mg/L D-panthothenic acid, 400 mg/L pyridoxine, 400 mg/L thiamin, 2 g/L inositol. Trace mineral 1000× stock solution: 500 mg/L boric acid, 40 mg/L $CuSO_4$, 100 mg/L KI, 500 mg/L $FeCl_3$, 400 mg/L $MnSO_4$, 900 mg/L molybdic acid, 400 mg/L $ZnSO_4$, 10 ml concentrated HCl.

Library compounds were assembled at the Small Molecule Discovery Center from commercial sources. Individual compounds were purchased or synthesized.

The SGY1528 strain was transformed with $K_{2P}$2.1 (TREK-1) or Trk1p plasmid and grown on the plasmid-selective -Ura/-Met synthetic medium. For each plasmid, a single colony was grown in -Ura/-Met synthetic medium with 100 mM KCl to saturation, diluted with the same media to optical density at 600 nm ($OD_{600}$)=0.3, and grown until $OD_{600}$ reached 0.8. Cells were pelleted, washed with water, and resuspended in -Ura/-Met test medium supplemented with 2 mM KCl to $OD_{600}$ 0.3. Using an automated dispenser, the cultures were aliquoted into 384-square-well plates (30 µl per well) containing, per well: 3 µl 10% DMSO (0% growth inhibition control), or 3 µl 1% SDS (100% growth inhibition control), or 3 µl of a 100 µM library compound in 10% DMSO. Following 24 hour incubation 30° C. at constant shaking, 5 µl of the vital dye resazurin (Alamar Blue, Invitrogen) was dispensed into each well, and the plates were incubated for 3 hours in the same conditions to allow the dye penetrate into the cells. The amount of fluorescent resazurin reduced in the cytosol of living cells was quantified using an automated plate reader at 560 nm excitation/590 nm emission settings.

Two-electrode voltage clamp recordings were performed from defolliculated stage V-VI Xenopus oocytes 24-48 hours after injection with 0.015-6.0 ng cRNA, using microelectrodes (0.3-3.0 MΩ) filled with 3M KCl. Data was acquired using the GeneClamp 500B (MDS Analytical Technologies) amplifier controlled by the pClamp software (Molecular Devices), and digitized at 1 kHz using Digidata 1332A (MDS Analytical Technologies). Recording solutions (mM): 2K (96 NaCl, 2 KCl, 1.8 $CaCl_2$, 2 $MgCl_2$), 90K (90 KCl, 8 NaCl, 1.8 $CaCl_2$, 2 $MgCl_2$), were buffered 5 mM HEPES pH 7.4. For $K_{2P}$ recordings, currents we elicited by a 1 second long ramp from −150 to +50 mV from a holding potential of −80 mV (2K), or −100 to +50 mV from a holding potential of 0 mV (90K). For KCNQ2 recordings, currents were elicited by a step protocol from −120 to 60 mV, in 20 mV increments, from a holding potential of −80 mV. Patch-clamp recordings from HEK-293T cells were performed using microelectrodes (2-3 MΩ) filled with 1M KCl. Data was acquired using the Axopatch 200B amplifier controlled by pClamp software, and digitized at 1 kHz using Digidata 1332A. Recording solutions (mM): intracellular (145 KCl, 5 EGTA, 3 $MgCl_2$,) extracellular (150 NaCl, 5 KCl, 3 $MgCl_2$, 1 $CaCl_2$) were buffered with 5 mM HEPES pH 7.2 and 7.4, respectively. Currents were elicited by a 1 second long ramp from −150 to +50 mV from a holding potential of −80 mV. Data were fitted with a modified Hill's equation: $I=I_{min}+(I_{max}-I_{min})/(1+10^{((Log\ EC_{50}-Log\ [C])*H)})$, where $I_{max}$ and $I_{min}$ are maximal and minimal current values, respectively, $EC_{50}$ is a half-maximal effective concentration of the compound, and H is the Hill coefficient.

Results are presented as mean±s.d. or s.e.m. of at least two independent experiments. Statistical analyses were made using the two-tailed Student's t-test, with significance set at p≤0.05.

2. Chemical Modifications Improve Potency of ML67 Against $K_{2P}$2.1 (TREK-1)

Investigation of the importance of the halide groups attached to the central carbazole ring of ML67 showed that these moieties were important for activity. Removal of the halides from the at 3- and 6-positions of the carbazole ring (ML67-2) reduced activity (FIG. 3a, Table 1), whereas exchange of bromine for chlorine (ML67-13) slightly increased potency and had a dramatic effect on maximum response ($EC_{50}$ 177.4±1.1 µM, $E_{max}$~20 fold) (FIG. 3a, Table 1). Thus, these halogenated positions are important for ML67 function.

Tests for the importance of the alkyl chain connecting carbazole showed that increasing the length of the alkyl chain by a single carbon linker did not significantly improve potency in the context of this compound (ML67-15, FIG. 3b). Similarly, rigidification of the alkyl chain by incorporation of a cyclobutane group (ML67-17 and ML67-29, cis:trans stereoisomer ratio 15:85 and 95:5, respectively) had limited impact in this chemical context: $EC_{50}$ 162.2±1.24 and 250.6±2 µM for ML67-17 and ML67-29, respectively (FIG. 3b, Table 1). Substitution of the carboxylic acid with its bioisostere tetrazol improved potency almost two fold (ML67-18, $EC_{50}$ 124.8±1.21, $E_{max}$ ~18 fold, FIG. 3c, Table 1). Hence, we decided to maintain both the halogen positions and the tetrazol embodied in ML67-18 and turned to examine whether we could modify the core carbazole ring scaffold to improve activity in this context.

Substitution of the carbazole ring of ML67-18 with dimethyl dihydro acridine resulted in a fivefold potency improvement, but did not affect efficacy (ML67-33, $EC_{50}$ 36.3±1.1 µM, $E_{max}$ 11.1±0.4 fold, FIG. 3c, Table 1). Further modification of ML67-33 by bromine substitutions of the chlorines in the acridine ring, did not significantly improve activity in this compound (ML67-137, FIG. 3c, Table 1). As the ML67 derivative ML67-33 (2,7-Dichloro-9,9-dimethyl-10-[2-(1H-tetrazol-5-yl)-ethyl]-9,10-dihydro-acridine) was the most potent of the all tested compounds at that time and had favorable solubility properties, we pursued a series of experiments designed to test its mechanism of action.

3. ML67-33 Activates the $K_{2P}2.1$ (TREK-1) C-type Gate

Figure 4:
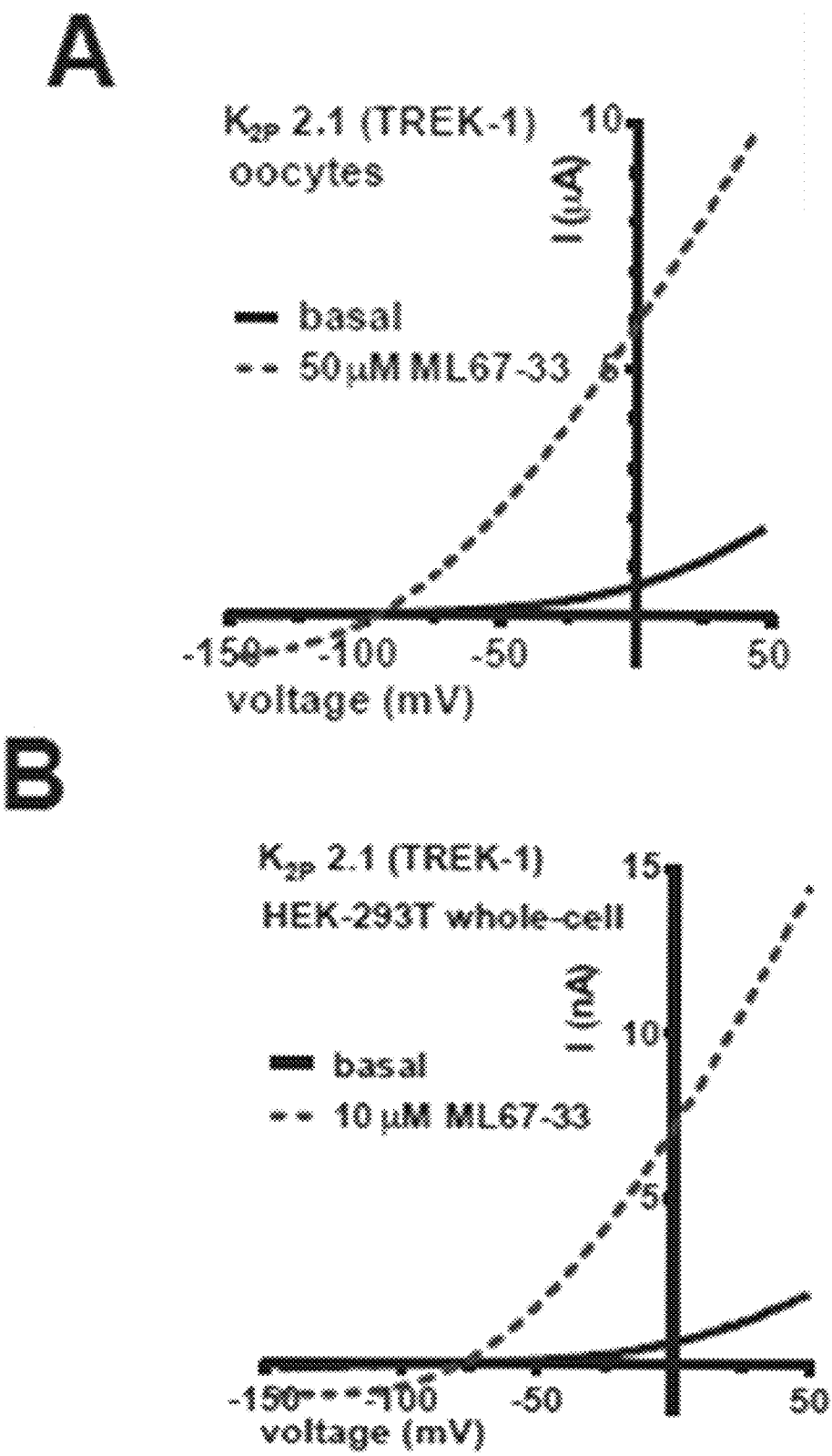
FIG. 4 ML67-33 reversibly activates $K_{2P}2.1$ (TREK-1) independent of expression system a, and b, exemplar I-V curves showing the effect of ML67-33 on $K_{2P}2.1$ (TREK-1) activity measured in a, *Xenopus* oocytes by two-electrode voltage clamp or b, HEK-293T cells by whole cell patch clamp. In both the external solution contained 2 mM $[K^+]_o$, pH 7.4; currents were elicited by a voltage ramp from −150 to 50 mV, from a holding potential of −80 mV (oocytes) or −40 mV (HEK-293T); c, quantification of the effect of ML67-33 on the indicated channels; data (mean±s.e., n≥6, N≥2) was normalized to basal channel activity and fitted to the Hill equation; $EC_{50}$ 36.3±1.0 µM, 9.7±1.2 µM and $E_{max}$ at 100 µM 11.1±0.4, 11.4±1.1 for oocytes and HEK cells, respectively; d, exemplar reversible activation of $K_{2P}2.1$ (TREK-1) by ML67-33 measured at 0 mV in HEK-293T cells FIG. 5 ML67-33 activates $K_{2P}2.1$ (TREK-1) in excised membrane patches a, and b, exemplar I-V curves showing the effect of ML67-33 on $K_{2P}2.1$ (TREK-1) in a, outside-out and b, inside-out excised patches from HEK-293T cells; currents were elicited by a voltage ramp from −100 to 50 mV from a holding potential of −40 mV. c, Exemplar channel responses to ML67-33 measured at 0 mV in the indicated configurations. Grey region indicates presence of 20 µM ML67-33. d, Times of half-maximal activation following ML67-33 application and recovery from activation (wash) following ML67-33 removal, measured in HEK-293T cells at 0 mV. Error bars: mean±s.e. n≥6, N≥2. '**' indicates p≤0.01 and 'N.S.' indicates not significant (p≥0.05) as determined by t-test analysis.
Figure 4:
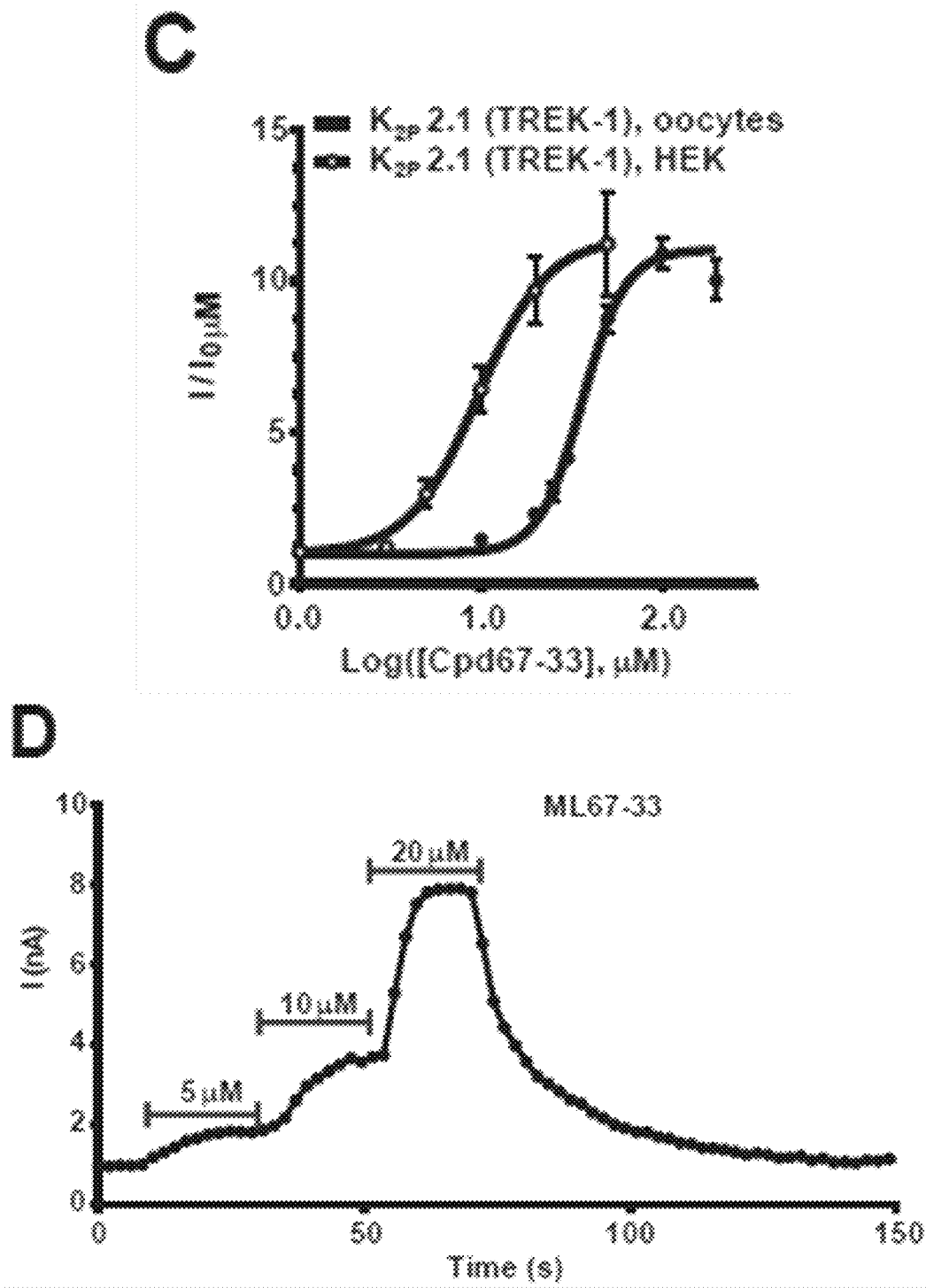

To understand the mechanism of action of ML67-33, we examined how it affected $K_{2P}2.1$ (TREK-1) expressed in two widely-used experimental systems, *Xenopus* oocytes and mammalian cells. Comparison of the effects of ML67-33 on $K_{2P}2.1$ (TREK-1) expressed in *Xenopus* oocytes (FIG. 4a) and mammalian HEK-293T cells (FIG. 4b) showed similar potencies and efficacies ($EC_{50}$ 36.3±1.1 µM and 9.7±1.2 µM and $E_{max}$ 11.1±0.4 and 11.4±1.1 for oocytes and HEK cells, respectively, FIG. 4c Table 1) and demonstrated that the compound acts independent of cellular context (FIG. 4a-c). Further, the effects of ML-67-33 were fast, occurring within seconds (half-maximal activation time, 4.1±0.5 s, mean±s.e., n=7, N=2) and were reversible upon washout (FIG. 4d). Application of ML67-33 to excised membrane patched from HEK cells expressing $K_{2P}2.1$ (TREK-1) showed that ML67-33 activated $K_{2P}2.1$ (TREK-1) in both the outside-out (FIG. 5a) and inside-out (FIG. 5b) configurations. The effectiveness of ML67-33 in both contexts strongly suggests that ML67-33 acts directly on the channel and does not require soluble cytosolic factors. The times of half-maximal activation and return to baseline following compound washout ($t_{1/2act}$ and $t_{1/2wash}$, respectively) in the outside-out configuration were indistinguishable from the same parameters measured in the whole-cell configuration ($t_{1/2act}$:$t_{1/2wash}$, mean±s.e. 4.1±0.5 s:3.9±0.5 s and 4.6±0.9 s:3.1±0.7 s for whole-cell and outside-out, respectively, FIGS. 5c and d). In stark contrast, both $t_{1/2}$ values slowed substantially when the compound was applied to the inside-out configuration. Notably, there was a larger effect on washout from inside-out patches ($I_{1/2act}$: $t_{1/2wash}$, 10.8±1.3 s:22.0±5.1 s, FIGS. 5c and d). Taken together, these data indicate that although ML67-33 appears to be membrane permeable, its site of action on $K_{2P}2.1$ (TREK-1) is more readily accessible from the extracellular side of the plasma membrane.

Figure 6:
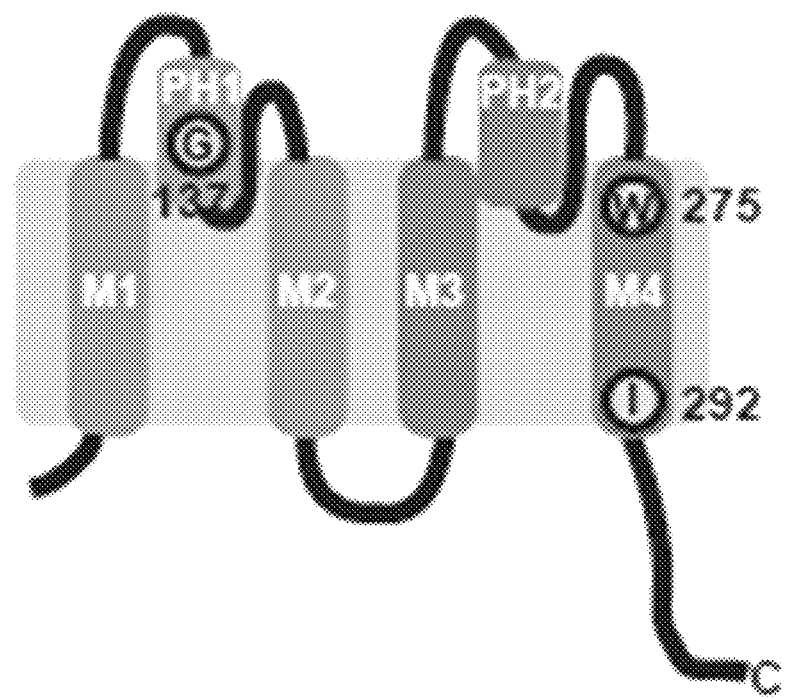
FIG. 6 ML67-33 activates $K_{2P}2.1$ (TREK-1) through the extracellular C-type gate. a, Cartoon diagram of a single $K_{2P}2.1$ (TREK-1) subunit. Positions of the key residues, transmembrane segments (M1-M4), and pore helices (PH1 and PH2) are indicated; first and second pore-forming regions are colored light gray and dark gray, respectively. b-d, Exemplar I-V curves showing the effect of C-type gate stabilization on ML67-33 responses. b, effect of C-type gate stabilization by 90 mM $[K^+]_o$. c, and d, Effect of C-type gate stabilization by the mutations G137I and d, W275S. e, Response of $K_{2P}2.1$ (TREK-1)-3G in which Ct is uncoupled from the pore by a triple glycine mutation. I-V curves were measured by two-electrode voltage clamp of *Xenopus* oocytes in b, 90 mM $[K^+]_o$. or c-e, 2 mM $[K^+]_o$. Currents were elicited by a voltage ramp from −100 to 50 mV from a holding potential of 0 mV (90 mM $[K^+]_o$) or from −150 to 50 mV, from a holding potential of −80 mV (2 mM $[K^+]_o$). f, Dose responses of the indicated channels to ML67-33. Data (were measured at 20 mV (90 mM $[K^+]_o$) or 0 mV (2 mM $[K^+]_o$), normalized to basal channel activity, and fitted to the Hill equation. Error bars indicate s.e., n≥6, N≥2.
Figure 6:
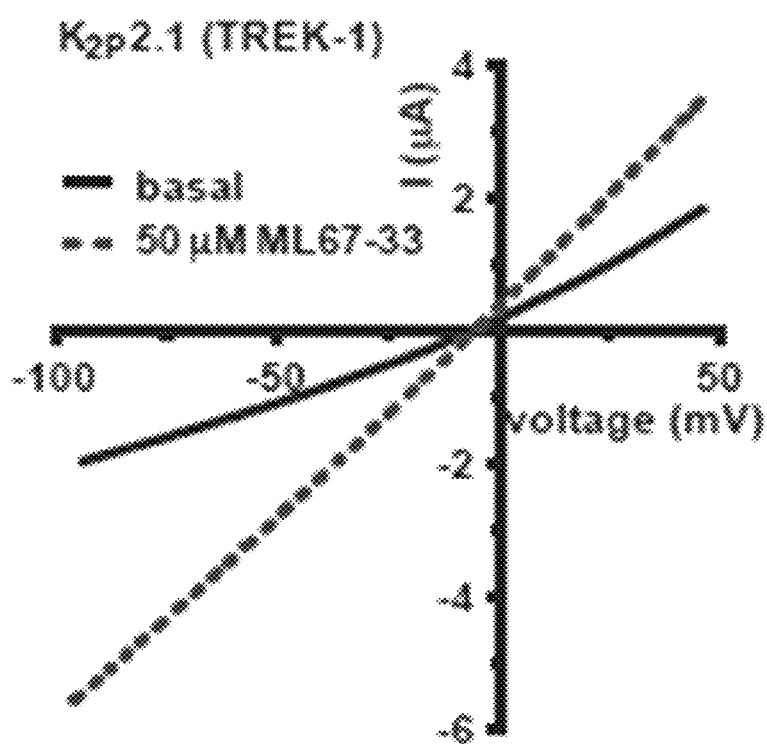
Figure 6:
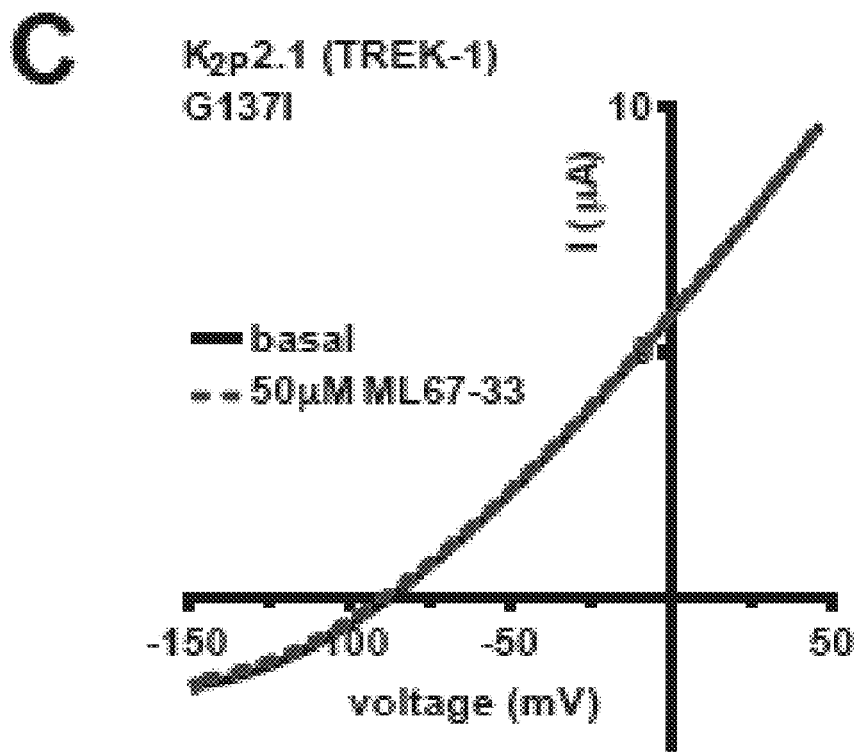
Figure 6:
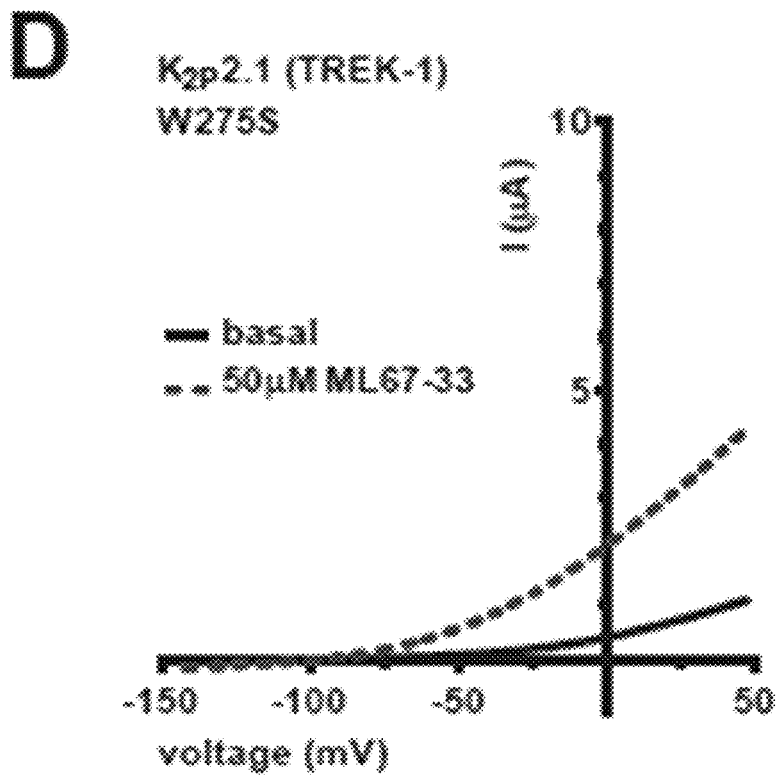
Figure 6:
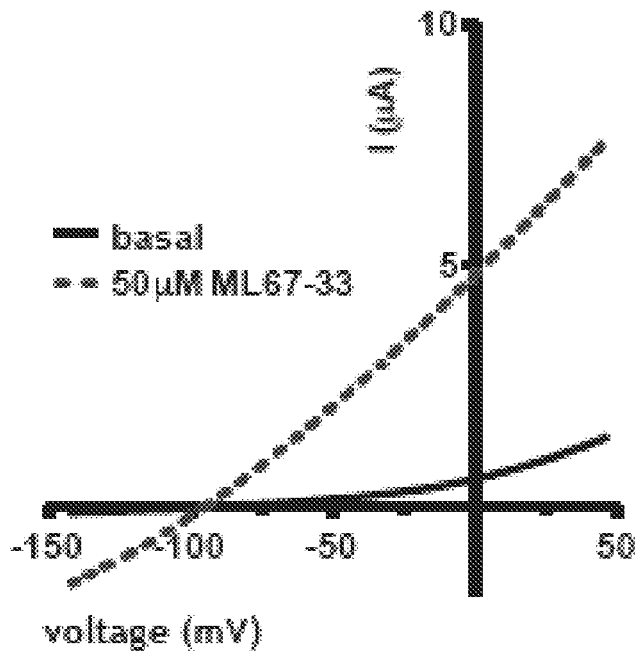
Figure 6:
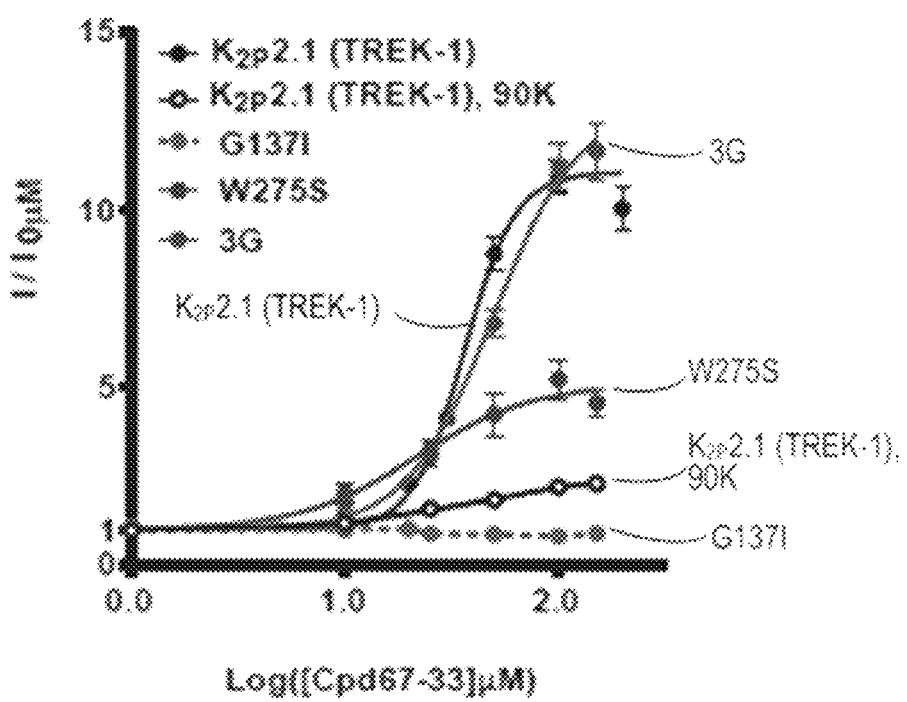

A selectivity filter-based C-type-like gate mediates $K_{2P}2.1$ (TREK-1) activation from a diverse inputs that include basic extracellular pH {Cohen, 2008}, intracellular acidosis {Piechotta, 2011}, temperature {Bagriantsev, 2011}, mechanical force Bagriantsev, 20111, and phosphorylation of the intracellular C-terminal domain, Ct {Bagriantsev, 2012}. This C-type gate can be stabilized in an active conformation by a variety of manipulations including high concentrations of extracellular potassium, $[K^+]_o$ {Bagriantsev, 2012; Bagriantsev, 2011; Cohen, 2008; Piechotta, 2011}, a G137I mutation in pore helix P1 {Bagriantsev, 2012} (FIG. 6a), or a W275S mutation in transmembrane helix M4 {Bagriantsev, 2011} (FIG. 6a). We tested how each of these C-type gate stabilizations affected the response to ML67-33. The data show that all reduced the response of $K_{2P}2.1$ (TREK-1) to ML67-33 (FIG. 6b-d and f). Indeed, the change causing the most potent stabilization of the C-type gate, G137I {Bagriantsev, 2012}, made the channels completely resistant to ML67-33 activation. In contrast, use of a triple glycine mutation, $K_{2P}2.1$-3G {Bagriantsev, 2012} (FIG. 6a) that uncouples the pore from Ct, which acts as a sensor for temperature {Maingret, 2000; Bagriantsev, 2011; Bagriantsev, 2012} and mechanical force {Patel, 1998; Bagriantsev, 2011}, resulted in channels that could be readily activated by ML67-33. In this case, both the ML67-33 potency and efficacy was similar to wild-type channels ($EC_{50}$ 49.4±0.1 µM, $E_{max}$12.9±1.0, FIGS. 6e and f). The observation that activation of the C-type gate renders the channels resistant to ML67-33 whereas loss of coupling to Ct does not, indicates that ML67-33 acts directly on the C-type gate. Ct is central to $K_{2P}2.1$ (TREK-1) activation by the two most effective activators previously reported chloroform[5,10] and arachidonic acid[5,10] and is also crucial for channel inhibition by fluoxetine (Prozac)[22]. The lack of involvement of Ct in ML67-33 activation evidence for its direct action on the C-type gate indicates that ML67-33 activates the channel by a novel mechanism.

4. ML67-33 Activates Heat- and Mechano-sensitive $K_{2P}$ Channels

Figure 7:
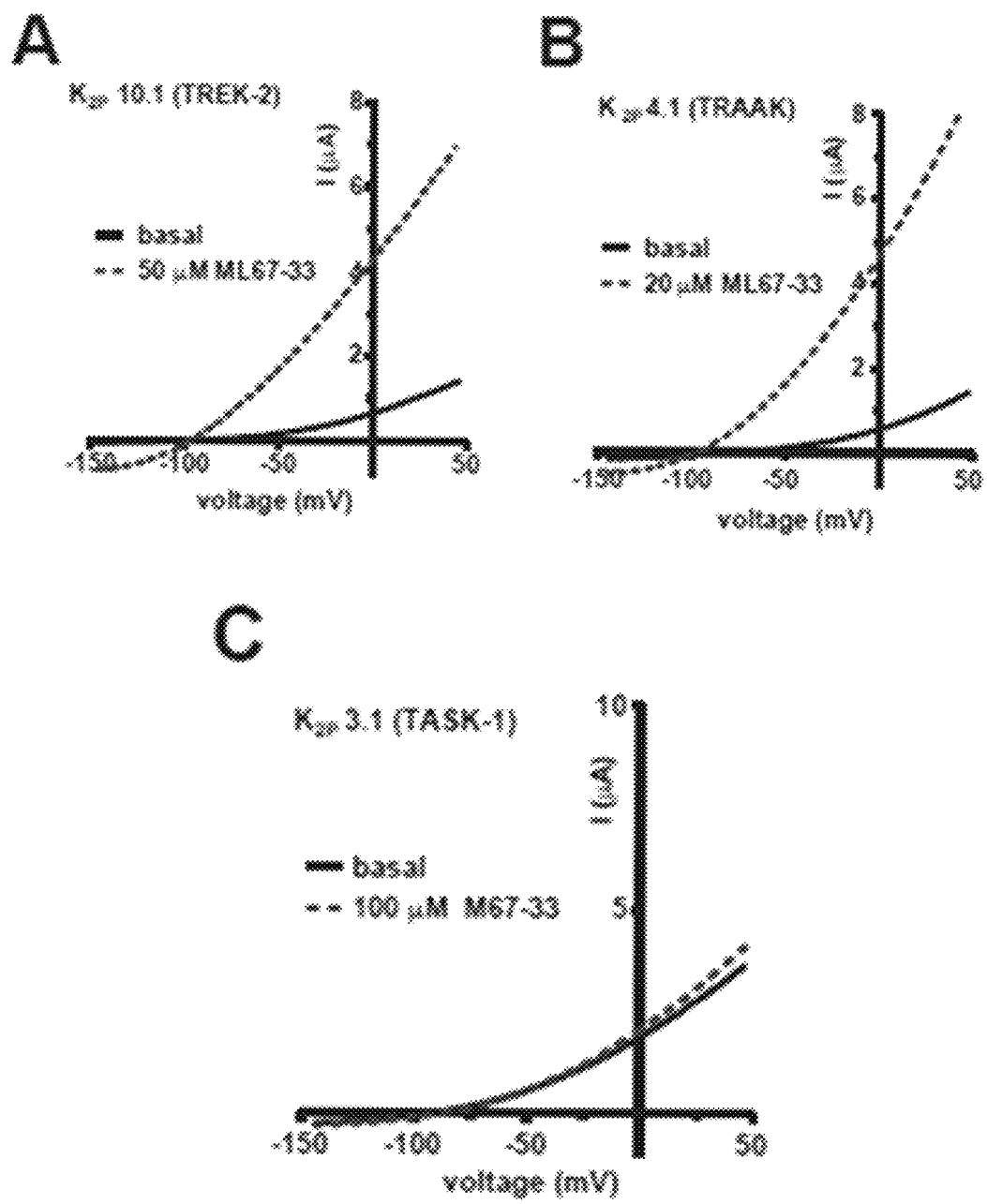
FIG. 7 ML67-33 is a selective activator of heat- and mechanosensitive $K_{2P}$ channels. a-f, Exemplar I-V curves showing the effect of ML67-33 on a, $K_{2P}10.1$ (TREK-2), b, $K_{2P}4.1$ (TRAAK), c, $K_{2P}3.1$ (TASK-1), d, $K_{2P}9.1$ (TASK-3), e, $K_{2P}5.1$ (TASK-2), and f, $K_{2P}18.1$ (TRESK) measured in *Xenopus* oocytes in 2 mM $[K^+]_o$ pH 7.4. Currents were elicited by a voltage ramp from −150 to 50 mV, from a holding potential of −80 mV. g, Quantification of the effect of ML67-33 on the indicated channels. Data (mean±s.e., n≥6, N≥2) was normalized to basal channel activity and fitted to the Hill equation. $EC_{50}$ values are: $K_{2P}2.1$ (TREK-1) 36.3±1.0 µM, $K_{2P}10.1$ (TREK-2) 30.2±1.4 µM, and $K_{2P}4.1$ (TRAAK) 27.3±1.2 µM. $E_{max}$ values at 100 µM are: $K_{2P}2.1$ (TREK-1) 11.1±0.4, $K_{2P}10.1$ (TREK-2) 11.4±1.8, $K_{2P}4.1$ (TRAAK) 14.7±1.1, $K_{2P}9.1$ (TASK-3), 2.0±0.1; $K_{2P}5.1$ (TASK-2), 1.7±0.3; $K_{2P}3.1$ (TASK-1), 1.1±0.0; $K_{2P}18.1$ (TRESK), 0.9±0.1. Error bars indicate s.e., n≥6, N≥2.
Figure 7:
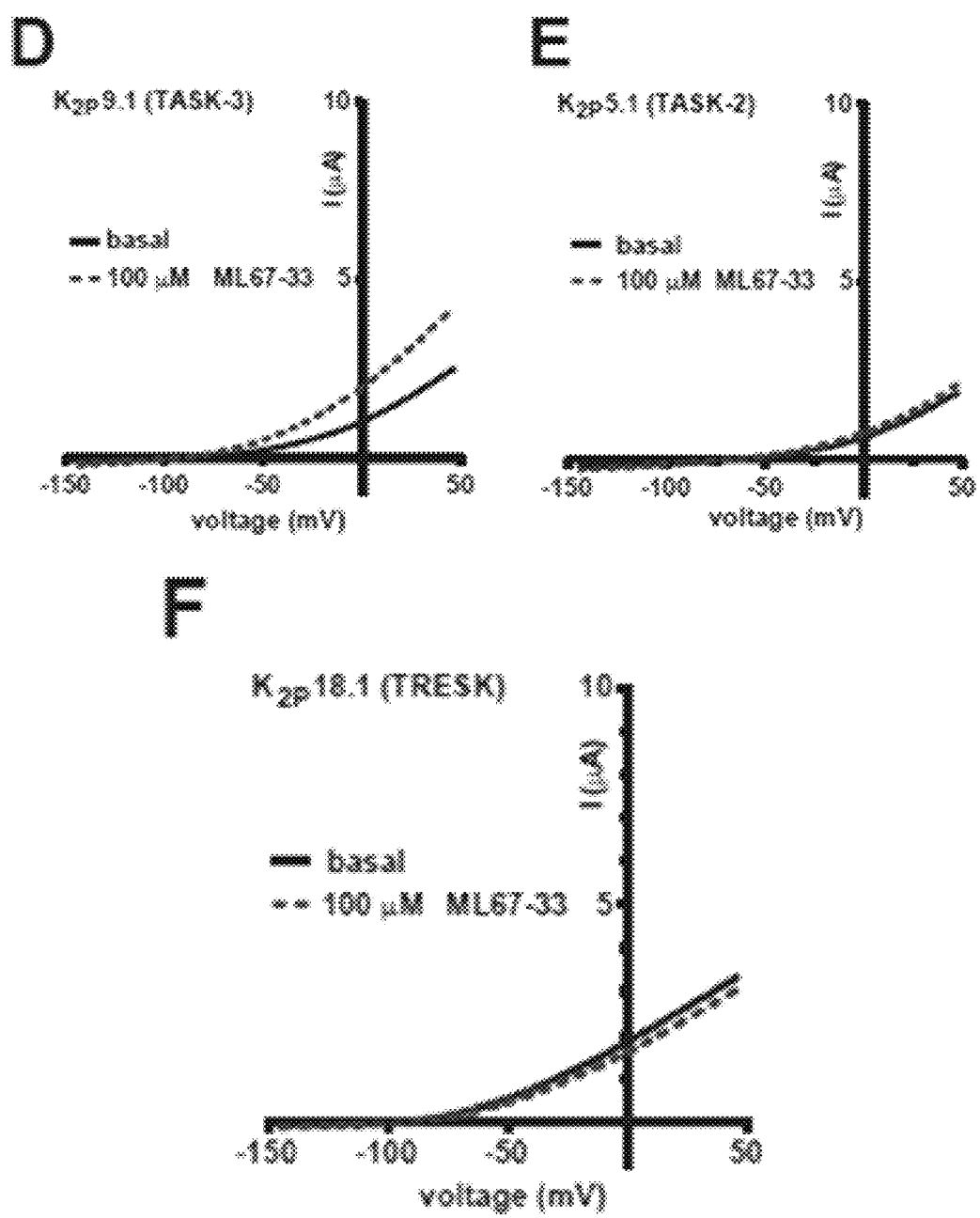
Figure 7:
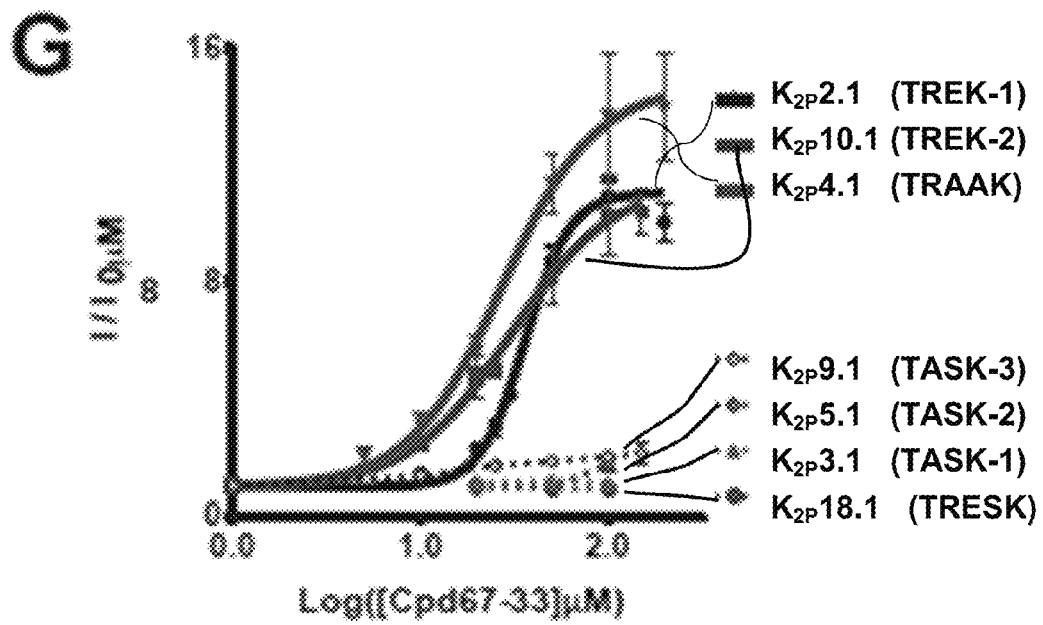
Figure 11:
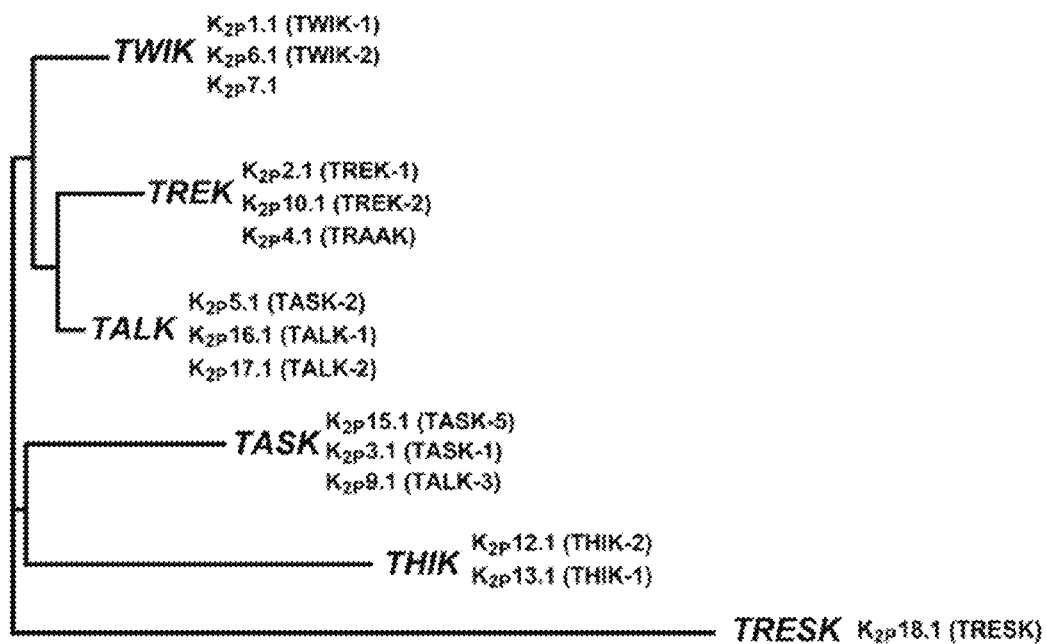
FIG. 11 Dendrogram of $K_{2P}$ channels based on {Enyedi, 2010} and {Lesage, 2011}
Figure 12:
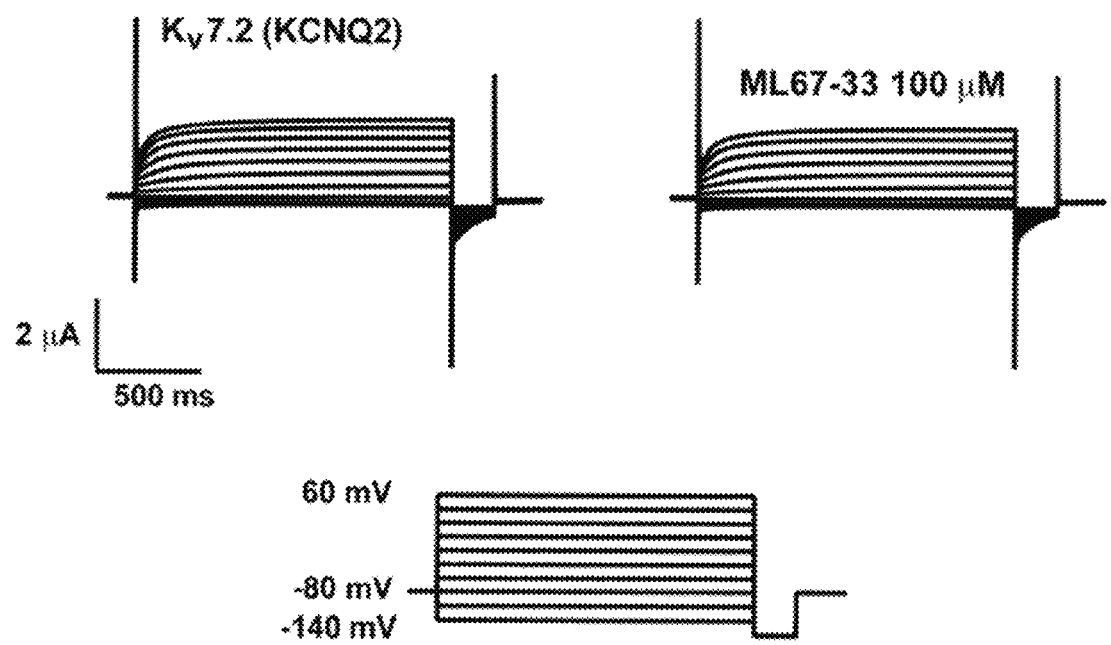
FIG. 12 Exemplar I-V curves showing the effect of 100 µM ML67-33 Kv7.2 (KCNQ2) measured by two-electrode voltage clamp in *Xenopus* oocytes in 2 mM $[K^+]_o$ pH 7.4. Currents were elicited by a step protocol from −120 to 60 mV, in 20 mV increments, from a holding potential of −80 mV.
Figure 13:
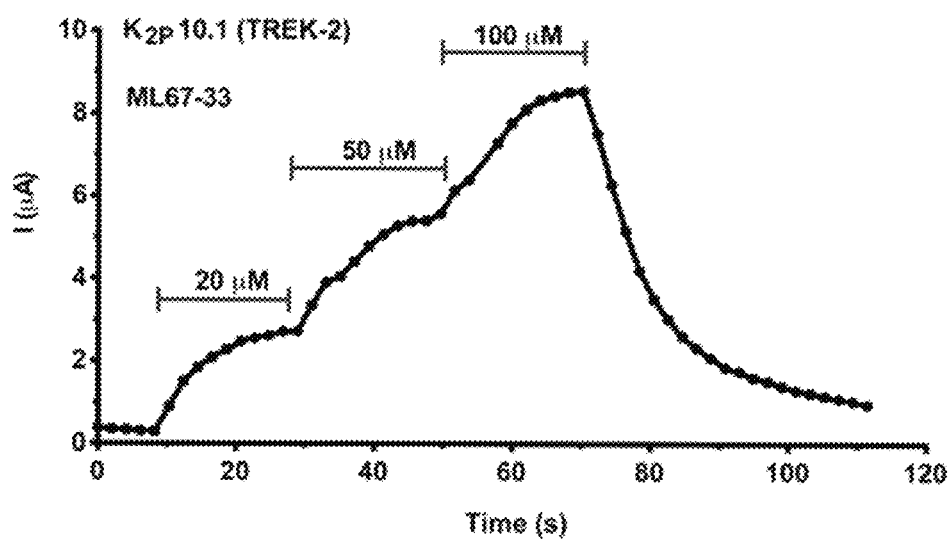
FIG. 13 Exemplar responses (at 0 mV) of a, $K_{2P}10.1$ (TREK-2) and b $K_{2P}4.1$ (TRAAK) to the indicated concentration of ML67-33 measured by two-electrode voltage clamp in *Xenopus* oocytes in 2 mM $[K^+]_o$ pH 7.4. Currents were elicited by a voltage ramp from −150 to 50 mV, from a holding potential of −80 mV.
Figure 13:
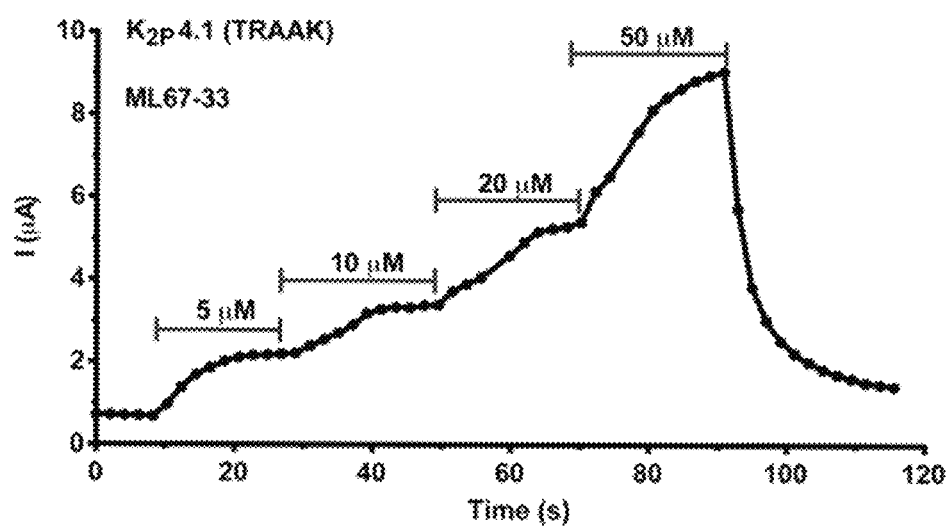
Figure 14:
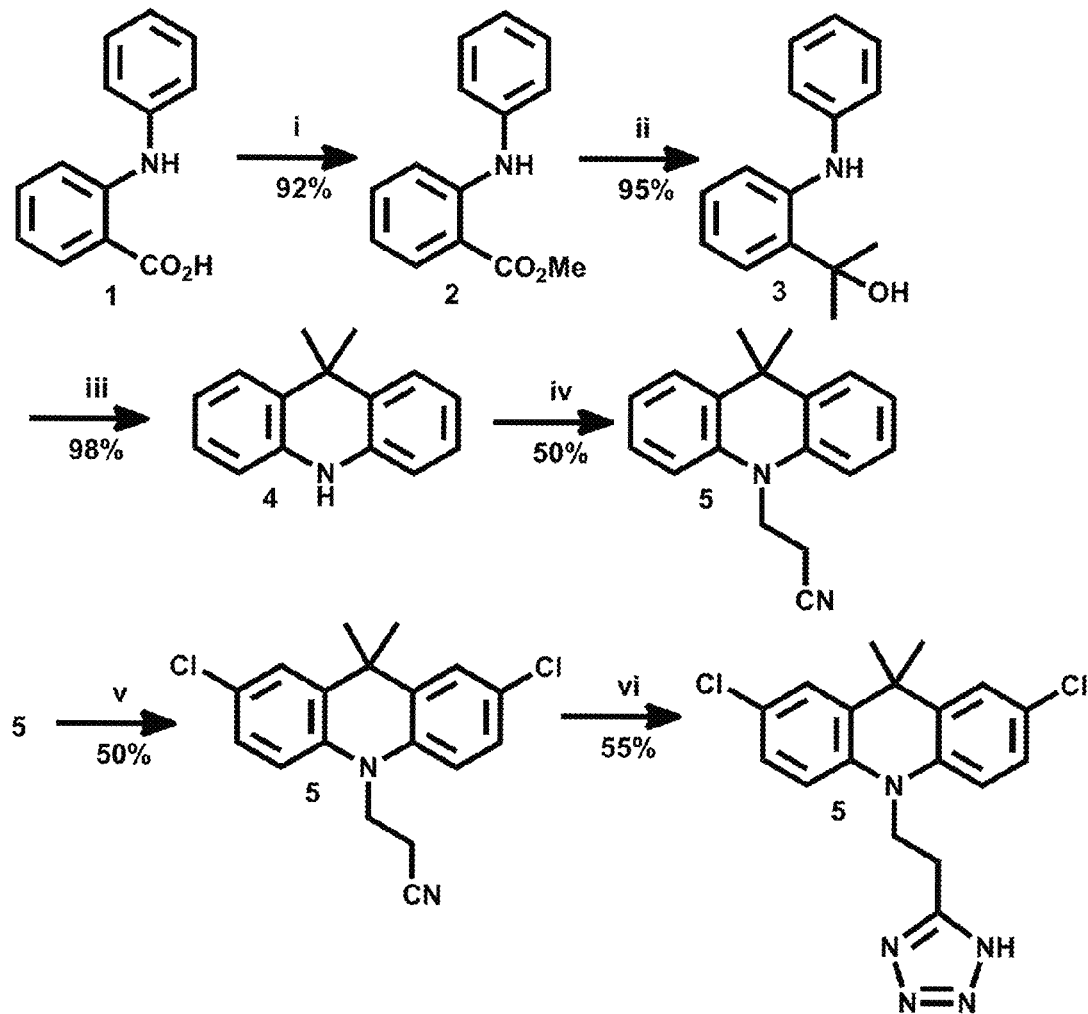
FIG. 14 Synthesis of compound ML67-33.

There are six $K_{2P}$ subgroups {Noel, 2011} (FIG. 11). To examine the specificity of ML67-33 within the $K_{2P}$ family, we used heterologous expression in *Xenopus* oocytes to test its effects on the two $K_{2P}$s that are most closely related to $K_{2P}2.1$ (TREK-1), $K_{2P}10.1$ (TREK-2) and $K_{2P}4.1$ (TRAAK), and on $K_{2P}$s that represent subgroups distant from $K_{2P}2.1$ (TREK-1), (TASK group, $K_{2P}3.1$ (TASK-1) and $K_{2P}9.1$ (TASK-3); TALK group, $K_{2P}5.1$ (TASK-2); and $K_{2P}18.1$ (TRESK)). ML67-33 showed substantial effects on the temperature- and mechano-sensitive channels $K_{2P}10.1$ (TREK-2) (FIG. 7a, FIG. 13a) ($EC_{50}$ 30.2±1.4, $E_{max}$ 11.4±1.8 fold, Table 1) and $K_{2P}4.1$ (TRAAK) (FIG. 7b, FIG. 13b) ($EC_{50}$ 27.3±1.18 µM, $E_{max}$ 14.7±1.12 fold, Table 1). In stark contrast, ML67-33 showed little or no functional effects against representative channels from the TASK group, $K_{2P}3.1$ (TASK-1) (FIGS. 7c and g, Table 1) and $K_{2P}9.1$ (TASK-3) (FIGS. 7d and g, Table 1); TALK group, $K_{2P}5.1$ (TASK-2) (FIGS. 7e and g, Table 1); and $K_{2P}18.1$ (TRESK) (FIGS. 7f and g, Table 1) even when applied at 100 µM, a concentration at which $K_{2P}2.1$ (TREK-1) shows a maximal response. Similar to the parent compound ML67 (FIG. 2f), 100 µM ML67-33 showed no effect on the voltage-gated channel Kv7.2 (KCNQ2) (FIG. 12). Together, these data establish that ML67-33 is a selective activator of channels from the $K_{2P}2.1$ (TREK-1) subfamily.

Figure 15:
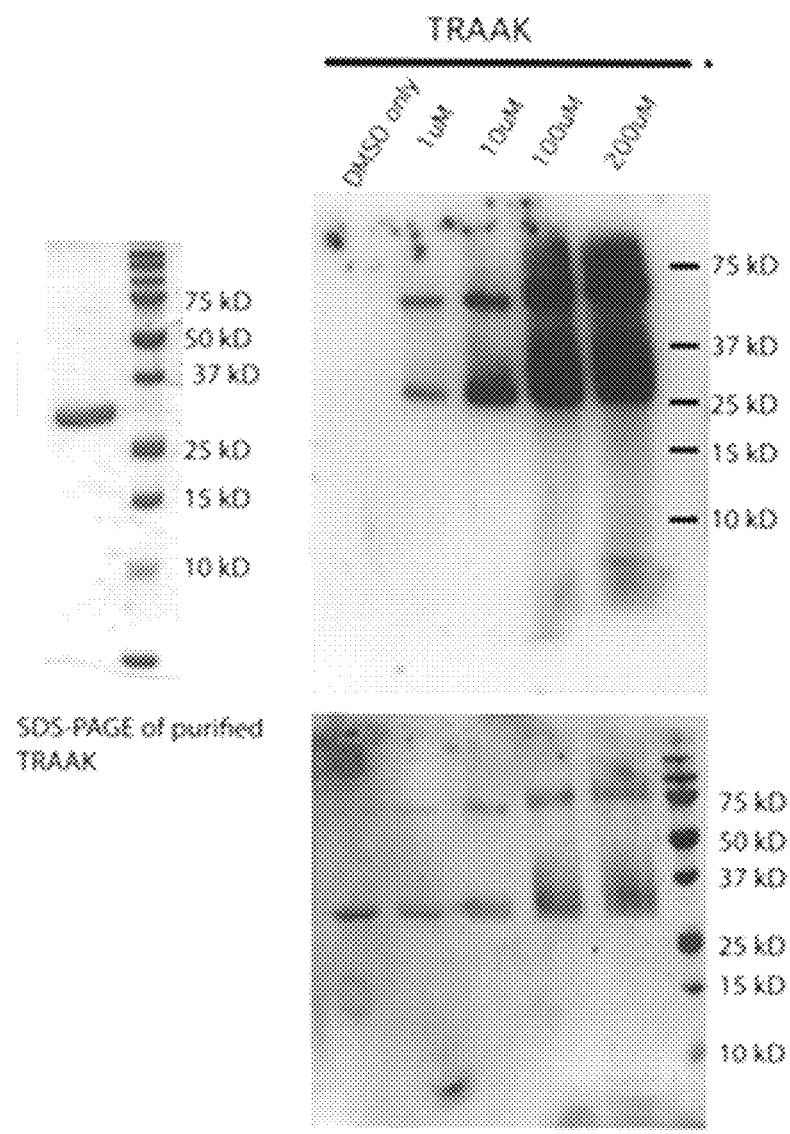
FIG. 15 Crosslinking and labeling of TRAAK channel with ML67-151; crosslinking of ML67-151 to purified TRAAK channels (3 µM) following exposure to 254 nm UV light for 30 seconds; left is SDS-PAGE of purified TRAAK, top middle is streptavidin-HRP detection following addition of clickable biotin; bottom middle is Ponceau S staining
Figure 15:
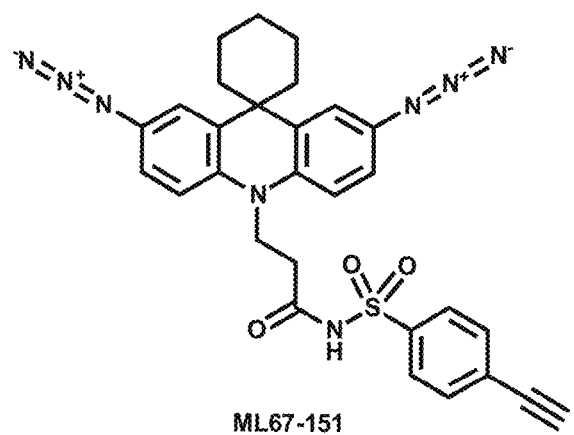

ML67-151 is capable of crosslinking and labeling TRAAK channel (FIG. 15). Crosslinking of ML67-151 to purified TRAAK channels (3 µM) following exposure to 254 nm UV light for 30 seconds is shown in the top middle blot of FIG. 15, including streptavidin-HRP detection following addition of clickable biotin. Crosslinking with ML67-151 shows that the compounds as described herein are capable of contacting TRAAK channel and may specifically contact and bind to related proteins (e.g. TREK-1, $K_{2P}$ channels).

5. Selected Synthetic Methods

Synthesis of ML67-15

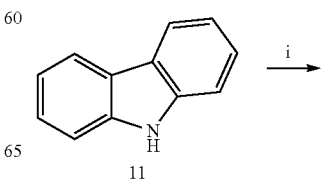

11

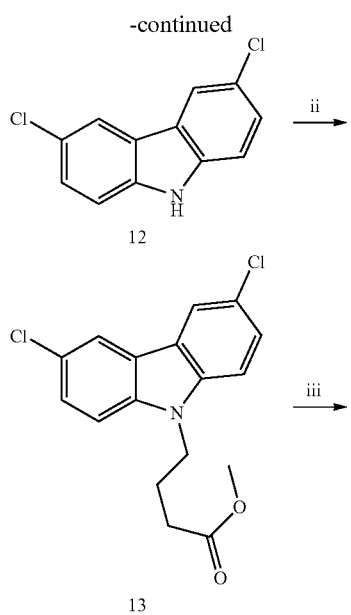

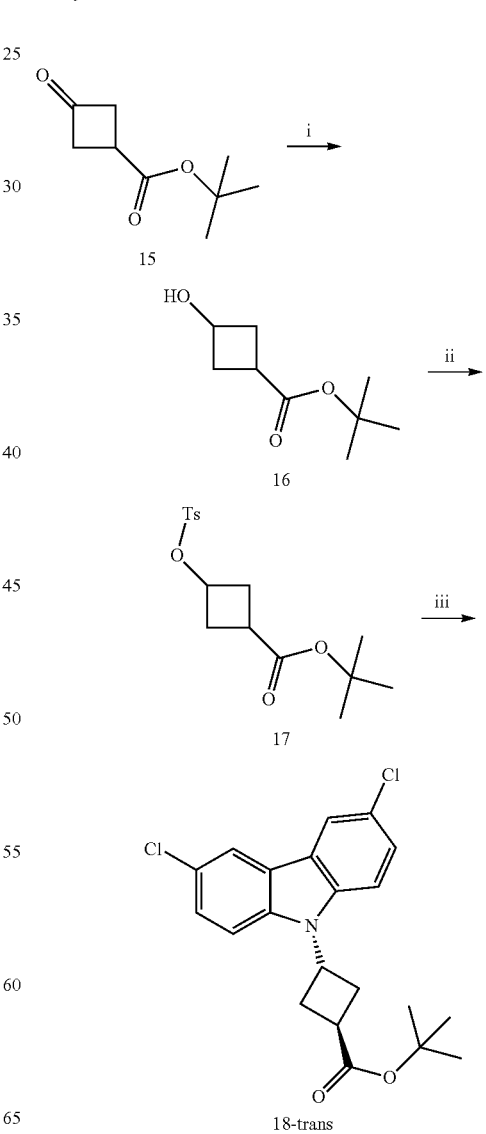

i) SO₂Cl₂, CH₂Cl₂; ii) methyl 4-bromobutanoate, NaH, DMF; iii) LiOH, MeOH, THF.

3,6-dichlorocarbazole (12). A round bottom flask was charged with 9H-carbazole (11, 20.0 g, 119.6 mmol) and dichloromethane (200 mL) and the mixture was stirred at 0° C. Sulfuryl chloride (9.69 mL, 119.6 mmol) was slowly added at that temperature. The dark reaction mixture was stirred at 0° C. for 2 h and then diluted with CH₂Cl₂ and aq. NaHCO₃. The organic layer was separated and washed with aq. NaHSO₃, brine, and dried (Na₂SO₄). The solution was then filtered and concentrated to afford the crude product as a thick oil. This was recrystallized from hexanes/ethyl acetate to afford 3,6-dichlorocarbazole (12) as a white solid (15.2 g, 54%). $^1$H NMR (300 MHz, DMSO-d6): δ 11.56 (s, 1H), 8.27 (d, J=1.8 HZ, 2H), 7.50 (d, J=8.7 Hz, 2H), 7.39 (d, J=8.7 Hz, 2H).

Methyl 4-(3,6-dichloro-9H-carbazol-9-yl)butanoate (13). A round bottom flask was charged with 3,6-dichlorocarbazole (12, 175 mg, 0.74 mmole), sodium hydride (27 mg, 1.11 mmol) and DMF (5 mL) under nitrogen. The reaction mixture was stirred at 60° C. for 30 minutes and methyl-4-bromobutyrate (83 uL, 0.74 mmol) was added and the reaction stirred at 60° C. over night. The reaction was cooled to room temperature and diluted with ethyl acetate and washed with water and brine. The organic solvents were removed under reduced pressure and the residue purified by flash chromatography over silica gel (0-30% ethyl acetate/hexanes) to afford methyl 4-(3,6-dichloro-9H-carbazol-9-yl)butanoate (13) as white solid (0.13 g, 52%). $^1$H NMR (300 MHz, DMSO-d6): δ 7.97 (d, J=1.8 Hz, 2H), 7.43 (d, J=2.1 Hz, 1H), 7.41 (d, J=2.1 Hz, 1H), 7.35 (s, 1H), 7.31 (S, 1H), 4.34 (t, J=7.2 Hz, 2H), 3.67 (s, 3H), 2.33 (t, J=7.2 Hz, 2H), 2.20-2.14 (m, 2H). LCMS m/z 337.2 (MH+).

4-(3,6-Dichloro-9H-carbozol-9-yl)butanoic acid (ML67-15). A round bottom flask was charged with methyl 4-(3,6-dichloro-9H-carbazol-9-yl)butanoate (13, 130 mg, 0.39 mmol), methanol (3 ml), THF (3 mL) and 1M lithium hydroxide (1.16 ml, 1.16 mmol) and the reaction stirred for 2 hours. The organic solvents were removed under reduced pressure and the aqueous residue was acidified with 3N HCl. The precipitate formed was collected by filtration and dried. The white solid obtained was purified by flash chromatography over silica gel (0-5% MeOH/CH₂Cl₂) to afford 4-(3,6-dichloro-9H-carbozol-9-yl)butanoic acid (ML67-15) as white solid (97 mg, 77%). 1H NMR (300 MHz, DMSO-d6): δ 8.32 (d, J=2.1 Hz, 2H), 7.67 (s, 1H), 7.64 (s, 1H), 7.50 (d, J=2.1 Hz, 1H), 7.47 (d, J=2.1 Hz, 1H), 4.39 (t, J=7.5 Hz, 2H), 2.25 (t, J=7.2 Hz, 2H), 1.96-1.91 (m, 2H); LCMS m/z 321.9 (M-1).

Synthesis of ML67-17 and ML67-29

-continued

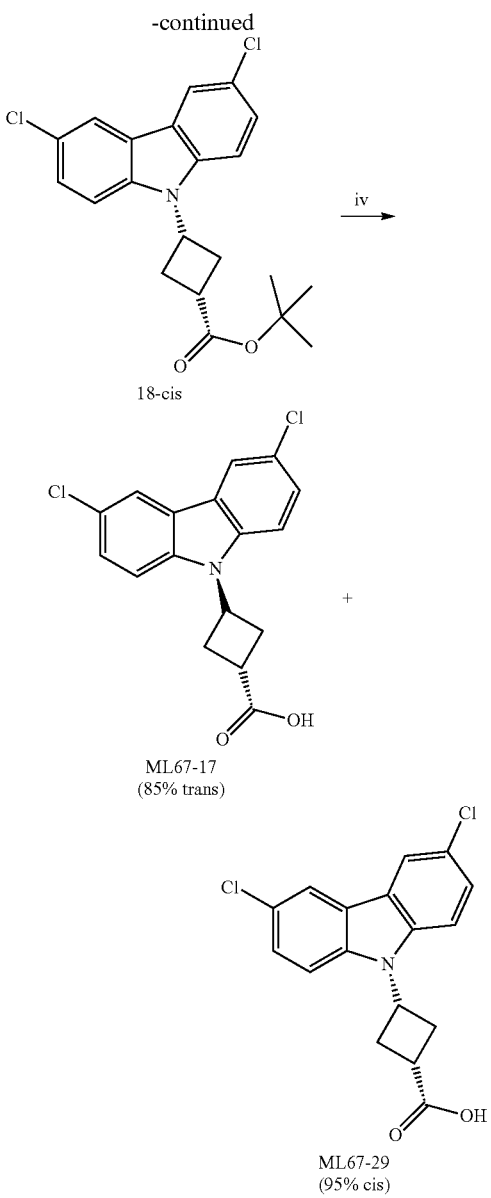

i) NaBH₄, THF, MeOH; ii) TsCl, pyridine, CH₂Cl₂; iii) 12, NaH, DMF; iv) LiOH, MeOH, THF.

tert-butyl 3-(tosyloxy)cyclobutanecarboxylate (17). A mixture of tert-butyl 3-oxocyclobutanecarboxylate (15, 1.50 g, 8.8 mmol) in THF:MeOH (3:1, 16 mL) was added dropwise to a stirring slurry of sodium borohydride (0.167 g, 4.4 mmol) in THF (8 mL) in round bottom flask cooled in an ice bath. The mixture was stirred at 0-5° C. for two hours. Water was added dropwise (10 mL) followed by aq. Na₂CO₃, and the mixture was extracted with ethyl acetate. The combined organic layers were washed with brine and dried over sodium sulfate. After filtration, the organic layer was concentrated to give the crude tert-butyl 3-hydroxycyclobutanecarboxylate (16) as a white semi-solid (2.3 g, 100%), which was used in the next step without purification. p-Toluenesulphonyl chloride (4.201 g, 0.022 moles) was added to a stirring solution of crude tert-butyl 3-hydroxycyclobutanecarboxylate (16, 2.30 g, 8.8 mmol) in dry pyridine (10 mL) and CH₂Cl₂ (20 mL) at 0° C. The mixture was allowed to warm to room temperature and stirred under nitrogen overnight. The solvent was then removed under reduced pressure and the residue was partitioned between ethyl ether (100 mL) and 0.5 N aq. HCl (20 mL). The organic layer was separated and washed with saturated NaHCO₃ and brine, and dried (Na₂SO₄). After filtration, the solvent was removed under reduced pressure and the residue purified by silica gel flash chromatography (0-50% EtOAc-hexane) to afford tert-butyl 3-(tosyloxy)cyclobutanecarboxylate (17) as a colorless oil that slowly solidified at room temperature (2.6 g, 90% yield over 2 steps). ¹H NMR (300 MHz, CDCl₃): δ 7.79 (d, 2H, J=8.4 Hz), 7.35 (d, 2H, J=8.1 Hz), 4.72 (m, 1H), 2.60-2.30 (m, 8H), 1.44 (s, 9H).

cis and trans-tert-butyl 3-(3,6-dichloro-9H-carbazol-9-yl)cyclobutanecarboxylate (18). To a stirred solution of 3,6-dichlorocarbazole (12, 694 mg, 2.94 mmol) in dry DMF (15 mL) under nitrogen was added 60% sodium hydride in mineral oil (127 mg, 3.19 mmol). The reaction mixture was stirred at room temperature for 20 min and then at 60° C. for 30 minutes, and then cooled to rt. Solid tert-butyl 3-(tosyloxy)cyclobutanecarboxylate (17, 800 mg, 2.45 mmol) was added and the reaction mixture was stirred at 60° C. overnight. The reaction mixture was then cooled to room temperature and quenched with water and extracted with ethyl acetate. The organic layer was separated and washed with brine, dried (Na₂SO₄), filtered, and concentrated. The crude residue was purified over silica gel (0-20% ethyl acetate/hexane) to afford cis-18 as a light yellow syrup which solidified on standing (220 mg), and then trans-18 as colorless syrup which solidified on standing (580 mg). cis-18: ¹H NMR (300 MHz, CDCl₃): δ 7.99 (d, 2H, J=1.8 Hz), 7.47 (AB, 2H, J=8.7 Hz), 7.41 (AB d, 2H, J=8.7, 1.8 Hz), 5.45 (m, 1H), 3.35-3.15 (m, 3H), 3.00-2.80 (m, 2H), 1.57 (s, 9H). trans-18: ¹H NMR (300 MHz, CDCl₃): δ 7.99 (d, 2H, J=2.1 Hz), 7.66 (d, 2H, J=9.0 Hz), 7.43 (dd, 2H, J=8.7, 2.1 Hz), 5.08 (m, 1H), 3.40-3.20 (m, 2H), 3.02 (5 peaks, 1H, J=8.7 Hz), 2.90-2.75 (m, 2H), 1.56 (s, 9H).

cis-3-(3,6-dichloro-9H-carbazol-9-yl)cyclobutanecarboxylic acid (ML67-29). A mixture of cis-tert-butyl 3-(3,6-dichloro-9H-carbazol-9-yl)cyclobutanecarboxylate (cis-18, 90 mg, 0.23 mmol) and lithium hydroxide monohydrate (47 mg, 1.15 mmol) in THF-MeOH (1:1, 10 mL) was stirred at room temperature overnight. The reaction mixture was then concentrated and the residue treated with water, adjusted to pH ~3 with 2N aq. HCl, and extracted with ethyl acetate. The organic layer was washed with brine, dried (Na₂SO₄), filtered, and concentrated. The crude residue was recrystallized from EtOAc/hexane to afford cis-3-(3,6-dichloro-9H-carbazol-9-yl)cyclobutanecarboxylic acid as a white solid that was further purified by preparative HPLC (C18 column, 40-80% ACN-water with 0.1% HCO₂H) to afford the title compound (55 mg, 69% yield; 95% cis). ¹H NMR (300 MHz, DMSO-d6): δ 12.45 (br s, 1H), 8.33 (d, 2H, J=2.1 Hz), 7.76 (d, 2H, J=8.7 Hz), 7.45 (dd, 2H, J=8.7, 2.1 Hz), 5.47 (m, 1H), 3.40-3.00 (m, 3H), 2.81 (m, 2H). LCMS m/z 332.0 (M-1).

trans-3-(3,6-dichloro-9H-carbazol-9-yl)cyclobutanecarboxylic acid (ML67-17). A mixture of trans-tert-butyl 3-(3,6-dichloro-9H-carbazol-9-yl)cyclobutanecarboxylate (trans-18, 320 mg, 0.82 mmol) and lithium hydroxide monohydrate (336 mg, 8.2 mmol) in THF-MeOH (1:1, 10 mL) was stirred at room temperature overnight and then concentrated. The residue was treated with water and adjusted to pH ~3 with 2N aq. HCl. The solids that precipitated out of this solution were collected by filtration, washed with water, and dried in air to afford the title compound (275 mg, >95% yield; 85% trans). ¹H NMR (300 MHz, DMSO-d6): δ 8.33 (d, 2H, J=2.1 Hz), 7.87 (d, 2H, J=9.0 Hz), 7.47 (dd, 2H, J=9.0, 2.1 Hz), 5.32 (m, 1H), 3.15-2.90 (m, 3H), 2.85-2.65 (m, 2H); LCMS m/z 331.8 (M-1).

Synthesis of ML67-18

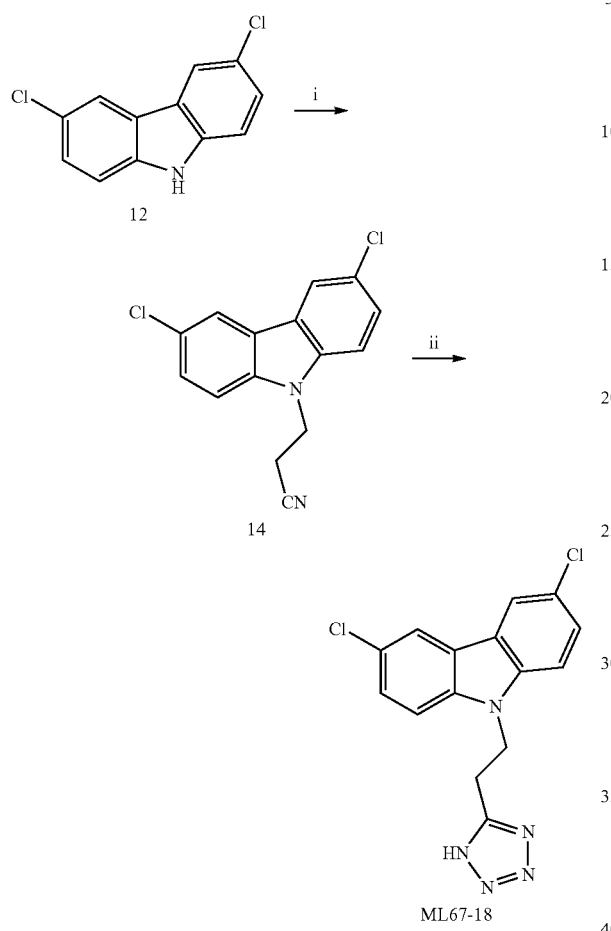

i) BrCH₂CH₂CN, NaH, DMF; ii) NaN₃, NH₄Cl, DMF.

3-(3,6-dichloro-9H-carbazol-9-yl)propanenitrile (14). A round bottom flask was charged with 3,6-dichlorocarbazole (12, 175 mg, 0.74 mmol), sodium hydride (27 mg, 1.11 mmol) and DMF (5 mL) under nitrogen. The reaction mixture was stirred at 60° C. for 30 minutes and 3-bromopropionitrile (62 uL, 0.74 mmol) was added and the reaction mixture stirred at 60° C. overnight. The reaction mixture was then cooled to room temperature, diluted with ethyl acetate, and washed with water and brine. The organic solvents were removed under reduced pressure and the residue purified by flash chromatography over silica gel (0-30% ethyl acetate-hexanes) to give 3-(3,6-dichloro-9H-carbazol-9-yl)propanenitrile (14) as white solid (140 mg, 65%). ¹H NMR (300 MHz, CDCl₃) δ 8.00 (dd, J=2.1 &0.6 MHz, 2H), 7.49 (d, J=2.1 Hz, 1H), 7.46 (d, J=1.8 Hz, 1H), 7.35 (s, 1H), 7.33 (s, 1H), 4.63 (t, J=6.9 Hz, 2H), 2.86 (t, J=6.9 Hz, 2H).

9-(2-(1H-tetrazol-5-yl)ethyl-3,6-dichloro-9H-carbazole (ML67-18). A mixture of 3-(3,6-dichloro-9H-carbazol-9-yl)propanenitrile (14, 140 mg, 0.48 mmol), sodium azide (94 mg, 1.45 mmol) and ammonium chloride (104 mg, 1.94 mmol) in DMF (5 mL) was stirred at 120° C. for 6 h, after which time LCMS analysis indicated complete reaction. The reaction mixture was diluted with EtOAc (50 mL), washed with brine, dried over Na₂SO₄, filtered, and concentrated. The crude residue was purified by flash chromatography over silica gel (0-10% MeOH/CH₂Cl₂) to afford 9-(2-(1H-tetrazol-5-yl)ethyl-3,6-dichloro-9H-carbazole (ML67-18) as a beige solid (165 mg, 93%). ¹H NMR (300 MHz, CDCl₃) δ 8.23 (d, 1H, J=1.5 Hz), 8.13 (d, 1H, J=1.8 Hz), 7.25 (t, 2H, J=8.1 Hz), 7.05 (t, 1H, J=7.5 Hz), 6.83 (d, 2H, J=7.8 Hz), 3.35 (s, 3H), 3.13 (t, 4H, J=7.2 Hz), 1.31-1.20 (m, 4H), 1.13-0.99 (m, 4H), 0.80 (t, 6H, J=7.2 Hz); LCMS m/z 444.2 (MH+).

Synthesis of ML67-33

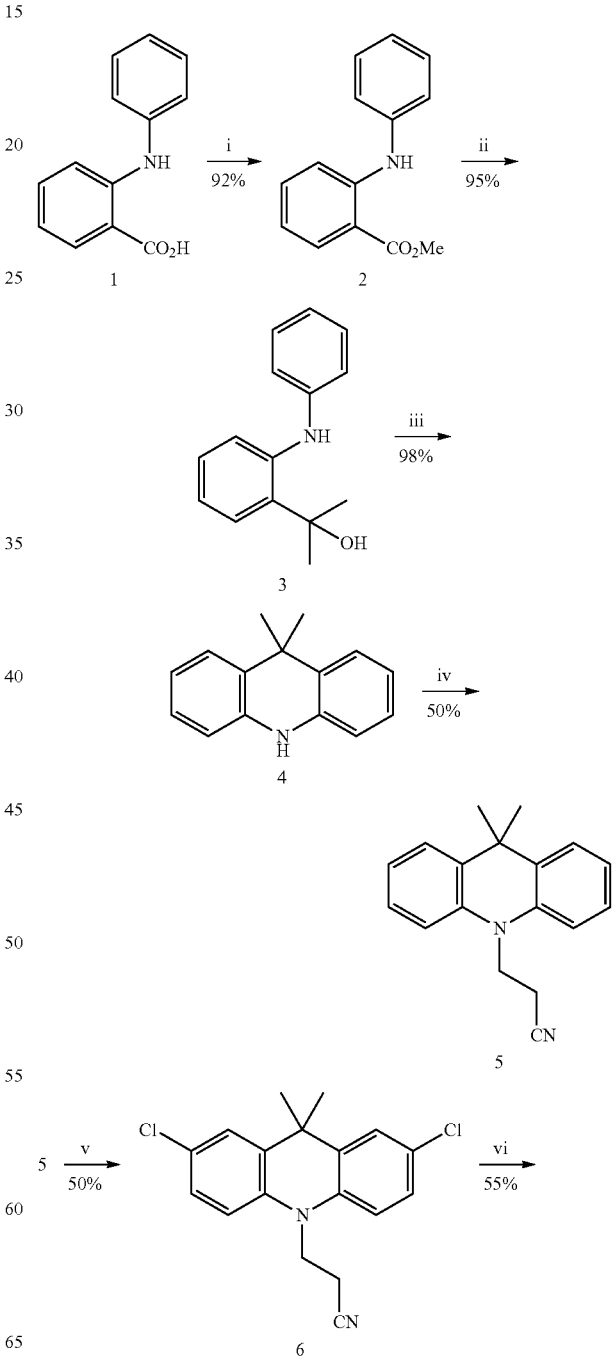

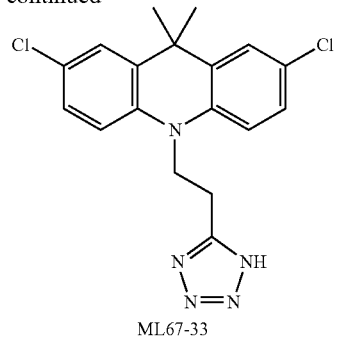

ML67-33 i) Me₂SO₄, K₂CO₃, acetone; ii) 3M MeLi, DEM; iii) 85% H₃PO₄; iv) acrylonitrile, triton-B; v) SO₂Cl₂, DCM; vi) NaN₃, NH₄Cl, DMF.

Methyl 2-(phenylamino)benzoate (2)³. Commercially available N-phenyl anthranilic acid (1) (2.0 g, 10 mmol) in acetone (30 mL) was refluxed with dimethyl sulphate (2.0 gr, 1.55 mL, 15 mmol) and potassium carbonate (1.38 g, 10 mmol) for 2 hrs. The progress of the reaction was monitored by TLC and when reaction was judged complete, the reaction mixture was allowed to cool to room temperature and poured into crushed ice. The aqueous layer was extracted with $CH_2Cl_2$ (2×30 mL), dried over anhydrous $MgSO_4$, filtered and concentrated under reduced pressure. The residue was purified by silica gel column chromatography with gradient elution (10 to 40% EtOAc-hexane) to afford the title compound as light yellow oil (2.1 g, 92% yield). ¹H NMR (300 MHz, DMSO-d₆): δ 9.29 (s, 1H), 7.88 (d, 1H, J=7.8 Hz), 7.45-7.30 (m, 3H), 7.28-7.18 (m, 3H), 7.07 (t, 1H, J=7.5 Hz), 6.80 (t, 1H, J=7.5 Hz), 3.85 (s, 3H). LCMS (ESI) m/z 228 (MH+).

2-(2-(phenylamino)phenyl)propan-2-ol (3). To a stirred solution of methyl 2-(phenylamino)benzoate (2, 1.0 g, 4.40 mmol) in dry THF (10 mL) at −78° C. was added a 3.0M solution of methyllithium in diethoxymethane (4.40 ml, 13.2 mmol) over a period of 30 min. The mixture was stirred at −78° C. for 30 min and then returned to room temperature and stirred for an additional 1 hour. The reaction mixture was then poured into crushed ice and extracted with EtOAc. The organic layer was dried over anhydrous $Na_2SO_4$, and concentrated under reduced pressure. The residue was purified by silica gel column chromatography with gradient elution (10-30% EtOAc-hexane) to afford the title compound as thick yellow oil (0.95 g, 95% yield). ¹H NMR (300 MHz, DMSO-d₆): δ 8.46 (s, 1H), 7.30-7.10 (m, 5H), 6.97 (d, 2H, J=7.8 Hz), 6.88-6.76 (m, 2H), 5.76 (s, 1H), 1.52 (s, 6H). LCMS (ESI) m/z 228 (MH+).

9,9-dimethyl-10H-acridine (4). A mixture of 2-(2-(phenylamino)phenyl)propan-2-ol (3, 1.0 g, 4.5 moles) in 85.0% phosphoric acid (15 ml) was stirred at 35° C. for 2 h until judged complete by TLC. The reaction mixture was then poured onto crushed ice and the precipitate was filtered, washed with water, and dried to afford the title compound (0.90 g, 98% yield) as a white powder. ¹H NMR (300 MHz, CDCl₃) δ 7.39 (d, 2H, J=8.1 Hz), 7.11 (t, 2H, J=7.2 Hz), 6.92 (t, 2H, J=7.2 Hz), 6.71 (d, 2H, J=7.8 Hz), 6.15 (br s, 1H), 1.61 (s, 6H); LCMS (ESI) m/z 210 (MH+).

3-(9,9-dimethylacridin-10-yl)propanenitrile (5). To a stirred solution of 9,9-dimethyl-10H-acridine (4, 0.30 g, 1.0 mmol) in acrylonitrile (8 mL) was added benzyltrimethylammonium hydroxide solution (Triton-B, 50 uL) dropwise at room temperature. A vigorous exothermic reaction occurs, after which the reaction mixture was stirred for another hour and then dissolved in EtOAc (50 mL) and filtered through a pad of silica gel, washing with more EtOAc. The filtrate was evaporated and the crude product purified by silica gel column chromatography with gradient elution (0-20% EtOAc-hexane) to afford the title compound as off white crystals (0.27 g, 73% yield). ¹H NMR (300 MHz, CDCl₃) δ 1.60 (s, 6 H) 2.84-3.02 (m, 2 H) 4.32-4.48 (m, 2 H) 6.95 (d, J=8.29 Hz, 2 H) 7.03-7.17 (m, 2 H) 7.24-7.39 (m, 2 H) 7.50 (dd, J=7.72, 1.51 Hz, 2 H). LCMS (ESI) m/z 263 (MH+).

3-(2,7-dichloro-9,9-dimethylacridin-10-yl)propanenitrile (6). To a stirred solution of 3-(9,9-dimethylacridin-10-yl)propanenitrile (5, 2.0 g, 7.62 mmol) in $CH_2Cl_2$ (30 mL) at 0° C. was added a solution of sulfuryl chloride (1.13 g, 0.68 mL, 8.4 mmol) in $CH_2Cl_2$ (5 mL) dropwise. The reaction mixture was stirred until starting material was consumed as judged by TLC, and then an additional 1.1 equivalents of sulfuryl chloride (1.13 g, 0.68 mL, 8.4 mmol) in $CH_2Cl_2$ (5 mL) was added dropwise. The dark solution was stirred until the monochloro adduct had been consumed, as judged by TLC. Aqueous $NaHCO_3$ was added to the reaction mixture carefully until the solution was pH ~8, and the organic layer was then separated, dried over anhydrous $MgSO_4$, filtered, and evaporated under reduced pressure. The crude residue was adsorbed to silica gel and purified by silica gel column chromatography with gradient elution (0 to 40% EtOAc-hexane) to afford the title compound as a light brown oil (1.5 g, 60% yield). ¹H NMR (300 MHz, DMSO-d6) δ ppm 1.51 (s, 6 H) 2.97 (t, J=6.50 Hz, 2 H) 4.35 (t, J=6.69 Hz, 2 H) 7.20 (d, J=8.85 Hz, 2 H) 7.29 (dd, J=8.76, 2.35 Hz, 2 H) 7.45 (d, J=2.26 Hz, 2 H). LCMS (ESI) m/z 332 (MH+).

9,9-dimethyl-10-[2-(1 H-1,2,3,4-tetrazol-5-yl)ethyl]acridine (ML67-33). A sealed tube was charged with 3-(9,9-dimethylacridin-10-yl)propanenitrile (5, 0.1 g, 0.46 mmol), 1.2 equivalents of sodium azide (30 mg, 0.46 mmole), ammonium chloride (25 mg, 0.46 mmol) and DMF (5 mL). The tube was sealed under nitrogen and stirred at 120° C. overnight. After cooling, the reaction was diluted with water (20 mL) and adjusted to pH ~5 with aqueous 1N HCl. The aqueous solution was then extracted with EtOAc and the organic layer was washed with brine, dried over anhydrous $Na_2SO_4$, filtered and concentrated under reduced pressure. The crude residue was purified by silica gel column chromatography with gradient elution (0 to 5% MeOH—$CH_2Cl_2$) to afford the title compound as an off white solid (40 mg, 35% yield). ¹H NMR (300 MHz, CDCl₃) δ ppm 1.48 (s, 6 H) 3.49-3.60 (m, 2 H) 4.42-4.54 (m, 2 H) 6.93-7.03 (m, 2 H) 7.07 (d, J=8.10 Hz, 2 H) 7.15-7.25 (m, 2 H) 7.42 (dd, J=7.72, 1.51 Hz, 2 H). LCMS (ESI) m/z 306 (MH+).

Synthesis of ML67-137

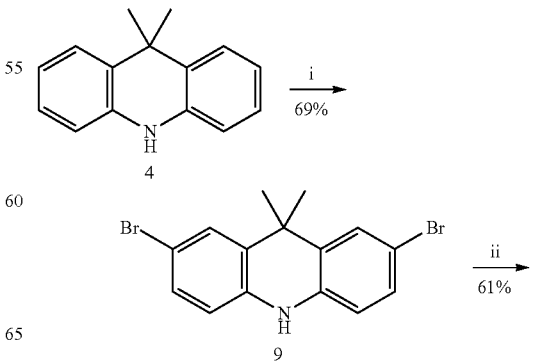

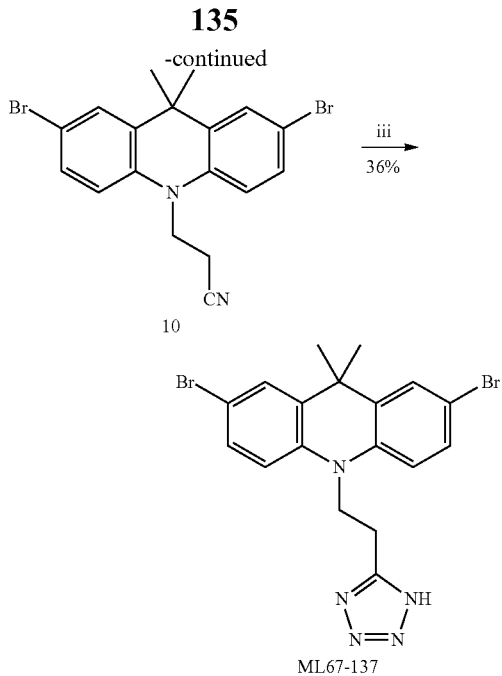

i) Trimethylphenylammonium tribromide (PTT), THF; ii) acrylonitrile, Triton-B; iii) NaN₃, NH₄Cl, DMF.

2,7-dibromo-9,9-dimethyl-10H-acridine (9). To a stirred solution of 9,9-dimethyl-10H-acridine (4, 0.50 g, 2.4 mmol) in dry THF (10 mL), was added trimethylphenylammonium tribromide (PTT) (1.8 g, 4.8 mmol) in one portion. The reaction mixture was stirred overnight at room temperature. After the reaction was judged complete (TLC), the reaction mixture was poured in water (30 mL) and extracted with EtOAc (2×30 mL). The combined organic layers were dried over anhydrous MgSO₄, filtered and evaporated under reduced pressure. The crude product was purified by silica gel column chromatography with gradient elution (0 to 30% EtOAc-hexane) to afford the title compound as a light brown oil (0.6 g, 69% yield). ¹H NMR (300 MHz, DMSO-d6) δ 1.47 (s, 6 H) 6.74 (d, J=8.48 Hz, 2 H) 7.22 (dd, J=8.48, 2.26 Hz, 2 H) 7.46 (d, J=2.07 Hz, 2 H) 9.18 (s, 1 H). LCMS (ESI) m/z 368 (MH+).

3-(2,7-dibromo-9,9-dimethylacridin-10-yl)propanenitrile (10). To a stirred solution of 2,7-dibromo-9,9-dimethyl-10H-acridine (9, 0.20 g, 0.54 mmol) in acrylonitrile (5 mL) was added benzyltrimethylammonium hydroxide solution (50 uL) at room temperature. After the initial vigorous exothermic reaction subsided, the reaction mixture was stirred at room temperature for 1 hour. The thick reaction mixture was then diluted with EtOAc (50 mL) and the mixture filtered through a pad of silica gel and washed with more EtOAc. The filtrate was evaporated and the crude product purified by silica gel column chromatography with gradient elution (0-20% EtOAc-hexane) to afford the title compound as a light brown foam (139 mg, 61% yield). ¹H NMR (300 MHz, CDCl₃) δ 1.55 (s, 6 H) 2.82-2.94 (m, 2 H) 4.33 (t, J=7.35 Hz, 2 H) 6.80 (d, J=8.67 Hz, 2 H) 7.38 (dd, J=8.67, 2.26 Hz, 2 H) 7.54 (d, J=2.26 Hz, 2 H). LCMS (ESI) m/z 421 (MH+).

2,7-dibromo-9,9-dimethyl-10-[2-(1H-1,2,3,4-tetrazol-5-yl)ethyl]acridine (ML67-137). A sealed tube was charged with 3-(2,7-dibromo-9,9-dimethylacridin-10-yl)propanenitrile (10, 0.1 g, 0.24 mmol), sodium azide (31 mg, 0.48 mmol), ammonium chloride (26 mg, 0.48 mmol) and DMF (5 mL). The tube was sealed under nitrogen and stirred at 120° C. overnight. After cooling, the reaction mixture was diluted with water (20 mL) and adjusted to pH-5 with 1N aq. HCl, and extracted with EtOAc. The organic layer was washed with brine, dried over anhydrous Na₂SO₄ and concentrated. The residue was purified by silica gel column chromatography with gradient elution (0 to 5% MeOH—CH₂Cl₂) to afford the title compound as a light brown foam (40 mg, 36% yield). ¹H NMR (300 MHz, DMSO-d6) δ 1.34 (s, 6 H) 3.32 (t, J=7.16 Hz, 2 H) 4.40 (t, J=7.25 Hz, 2 H) 7.15 (d, J=8.85 Hz, 2 H) 7.39 (dd, J=8.67, 1.88 Hz, 2 H) 7.50 (d, J=2.07 Hz, 2 H). LCMS (ESI) m/z 464 (MH+).

REFERENCES

Enyedi, P. & Czirjak, G. Molecular background of leak K+ currents: two-pore domain potassium channels. Physiol Rev 90, 559-605 (2010). Lesage, F. & Barhanin, J. Molecular physiology of pH-sensitive background K(2P) channels. Physiology (Bethesda) 26, 424-37 (2011). Es-Salah-Lamoureux, Z., Steele, D. F. & Fedida, D. Research into the therapeutic roles of two-pore-domain potassium channels. Trends Pharmacol Sci 31, 587-95 (2010). Mathie, A. & Veale, E. L. Therapeutic potential of neuronal two-pore domain potassium-channel modulators. Curr Opin Investig Drugs 8, 555-62 (2007). Bayliss, D. A. & Barrett, P. Q. Emerging roles for two-pore-domain potassium channels and their potential therapeutic impact. Trends Pharmacol Sci 29, 566-75 (2008). Lotshaw, D. P. Biophysical, pharmacological, and functional characteristics of cloned and native mammalian two-pore domain K+ channels. Cell Biochem Biophys 47, 209-56 (2007). Fink, M. et al. Cloning, functional expression and brain localization of a novel unconventional outward rectifier K+ channel. Embo J 15, 6854-62 (1996). Honore, E. The neuronal background K2P channels: focus on TREK1. Nat Rev Neurosci 8, 251-61 (2007). Noel, J., Sandoz, G. & Lesage, F. Molecular regulations governing TREK and TRAAK channel functions. Channels (Austin) 5, 402-9 (2011). Maingret, F. et al. TREK-1 is a heat-activated background K(+) channel. Embo J 19, 2483-91 (2000). Patel, A. J. et al. A mammalian two pore domain mechanogated S-like K+ channel. Embo J 17, 4283-90 (1998). Patel, A. J. et al Inhalational anesthetics activate two-pore-domain background K+ channels. Nat Neurosci 2, 422-6 (1999). Alloui, A. et al. TREK-1, a K+ channel involved in polymodal pain perception. Embo J 25, 2368-76 (2006). Noel, J. et al. The mechano-activated K+ channels TRAAK and TREK-1 control both warm and cold perception. Embo J 28, 1308-18 (2009). Heurteaux, C. et al. TREK-1, a K+ channel involved in neuroprotection and general anesthesia. Embo J 23, 2684-95 (2004). Heurteaux, C. et al. Deletion of the background potassium channel TREK-1 results in a depression-resistant phenotype. Nat Neurosci 9, 1134-41 (2006). Solt, K. & Forman, S. A. Correlating the clinical actions and molecular mechanisms of general anesthetics. Curr Opin Anaesthesiol 20, 300-6 (2007). Lesage, F., Terrenoire, C., Romey, G. & Lazdunski, M. Human TREK2, a 2P domain mechano-sensitive K+ channel with multiple regulations by polyunsaturated fatty acids, lysophospholipids, and Gs, Gi, and Gq protein-coupled receptors. J Biol Chem 275, 28398-405 (2000). Harinath, S. & Sikdar, S. K. Trichloroethanol enhances the activity of recombinant human TREK-1 and TRAAK channels. Neuropharmacology 46, 750-60 (2004). Gruss, M. et al. Two-pore-domain K+ channels are a novel target for the anesthetic gases xenon, nitrous oxide, and cyclopropane. Mol Pharmacol 65, 443-52 (2004). Duprat, F. et al. The neuroprotective agent riluzole activates the two P domain K(+) channels TREK-1 and TRAAK. Mol Pharmacol 57, 906-12 (2000). Kennard, L. E. et al Inhibition of the human two-pore domain potassium channel, TREK-1, by fluoxetine and its metabolite norfluoxetine. Br J Pharmacol 144, 821-9 (2005). Sandoz, G., Bell, S. C. & Isacoff, E. Y. Optical probing of a dynamic membrane interaction that regulates the TREK1 channel. Proc Natl Acad Sci USA 108, 2605-10 (2011). Franks, N. P. & Honore, E. The TREK K2P channels and their role in general anaesthesia and neuroprotection. Trends Pharmacol Sci 25, 601-8 (2004). Bagriantsev, S. N., Clark, K. A. & Minor, D. L., Jr. Metabolic and thermal stimuli control K(2P)2.1 (TREK-1) through modular sensory and gating domains. EMBO J 31, 3297-308 (2012). Bagriantsev, S. N., Peyronnet, R., Clark, K. A., Honore, E. & Minor, D. L., Jr. Multiple modalities converge on a common gate to control K2P channel function. EMBO J 30, 3594-606 (2011). Piechotta, P. L. et al. The pore structure and gating mechanism of K2P channels. EMBO J 30, 3607-19 (2011). Ko, C. H. & Gaber, R. F. TRK1 and TRK2 encode structurally related K+ transporters. Mol. Cell. Biol. 11, 4266-4273 (1991). Tang, W. et al. Functional expression of a vertebrate inwardly rectifying K+ channel in yeast. Mol. Biol. Cell 6, 1231-1240 (1995). Minor, D. L., Jr., Masseling, S. J., Jan, Y. N. & Jan, L. Y. Transmembrane structure of an inwardly rectifying potassium channel. Cell 96, 879-891 (1999). Minor, D. L., Jr. Searching for interesting channels: pairing selection and molecular evolution methods to study ion channel structure and function. Mol Biosyst 5, 802-10 (2009). Chatelain, F. C. et al. Selection of inhibitor-resistant viral potassium channels identifies a selectivity filter site that affects barium and amantadine block. PloS ONE 4, e7496 (2009). Zaks-Makhina, E., Kim, Y., Aizenman, E. & Levitan, E. S. Novel neuroprotective K+ channel inhibitor identified by high-throughput screening in yeast. Mol Pharmacol 65, 214-9 (2004). Zaks-Makhina, E., Li, H., Grishin, A., Salvador-Recatala, V. & Levitan, E. S. Specific and slow inhibition of the kir2.1 K+ channel by gambogic acid. J Biol Chem 284, 15432-8 (2009). Chatelain, F. C. et al. The pore helix dipole has a minor role in inward rectifier channel function. Neuron 47, 833-43 (2005). Nakayama, G. R., Caton, M. C., Nova, M. P. & Parandoosh, Z. Assessment of the Alamar Blue assay for cellular growth and viability in vitro. J Immunol Methods 204, 205-8 (1997). Gaber, R. F., Styles, C. A. & Fink, G. R. TRK1 encodes a plasma membrane protein required for high-affinity potassium transport in Saccharomyces cerevisiae. Mol Cell Biol 8, 2848-59 (1988). Loukin, S. H. et al. Random mutagenesis reveals a region important for gating of the yeast K+ channel Ykc1. Embo J 16, 4817-25 (1997). Zhang, J. H., Chung, T. D. & Oldenburg, K. R. A Simple Statistical Parameter for Use in Evaluation and Validation of High Throughput Screening Assays. J Biomol Screen 4, 67-73 (1999). Xiong, Q., Gao, Z., Wang, W. & Li, M. Activation of Kv7 (KCNQ) voltage-gated potassium channels by synthetic compounds. Trends Pharmacol Sci 29, 99-107 (2008). Xiong, Q., Sun, H. & Li, M. Zinc pyrithione-mediated activation of voltage-gated KCNQ potassium channels rescues epileptogenic mutants. Nat Chem Biol 3, 287-96 (2007). Xiong, Q., Sun, H., Zhang, Y., Nan, F. & Li, M. Combinatorial augmentation of voltage-gated KCNQ potassium channels by chemical openers. Proc Natl Acad Sci USA 105, 3128-33 (2008). Cohen, A., Ben-Abu, Y., Hen, S. & Zilberberg, N. A novel mechanism for human K2P2.1 channel gating. Facilitation of C-type gating by protonation of extracellular histidine residues. J Biol Chem 283, 19448-55 (2008). Goldstein, S. A. et al. International Union of Pharmacology. LV. Nomenclature and molecular relationships of two-P potassium channels. Pharmacol Rev 57, 527-40 (2005). Yu, F. H., Yarov-Yarovoy, V., Gutman, G. A. & Catterall, W. A. Overview of molecular relationships in the voltage-gated ion channel superfamily. Pharmacol Rev 57, 387-95 (2005). Goonetilleke, L. & Quayle, J. TREK-1 K(+) channels in the cardiovascular system: their significance and potential as a therapeutic target. Cardiovasc Ther 30, e23-9 (2012). Rapedius, M. et al. State-independent intracellular access of quaternary ammonium blockers to the pore of TREK-1. Channels (Austin) 6, 473-8 (2012). Honore, E., Maingret, F., Lazdunski, M. & Patel, A. J. An intracellular proton sensor commands lipid- and mechano-gating of the K(+) channel TREK-1. Embo J 21, 2968-76 (2002). Segal-Hayoun, Y., Cohen, A. & Zilberberg, N. Molecular mechanisms underlying membrane-potential-mediated regulation of neuronal K2P2.1 channels. Mol Cell Neurosci 43, 117-26 (2010). Lopes, C. M., Gallagher, P. G., Buck, M. E., Butler, M. H. & Goldstein, S. A. Proton block and voltage gating are potassium-dependent in the cardiac leak channel Kcnk3 J Biol Chem 275, 16969-78 (2000). Lopes, C. M., Zilberberg, N. & Goldstein, S. A. Block of Kcnk3 by protons. Evidence that 2-P-domain potassium channel subunits function as homodimers. J Biol Chem 276, 24449-52 (2001). Yuill, K. H., Stansfeld, P. J., Ashmole, I., Sutcliffe, M. J. & Stanfield, P. R. The selectivity, voltage-dependence and acid sensitivity of the tandem pore potassium channel TASK-1: contributions of the pore domains. Pflugers Arch 455, 333-48 (2007). Niemeyer, M. I., Cid, L. P., Pena-Munzenmayer, G. & Sepulveda, F. V. Separate Gating Mechanisms Mediate the Regulation of K2P Potassium Channel TASK-2 by Intra- and Extracellular pH. J Biol Chem 285, 16467-75 (2010). Nayak, T. K., Harinath, S., Nama, S., Somasundaram, K. & Sikdar, S K Inhibition of human two-pore domain K+ channel TREK1 by local anesthetic lidocaine: negative cooperativity and half-of-sites saturation kinetics. Mol Pharmacol 76, 903-17 (2009). Punke, M. A., Licher, T., Pongs, O. & Friederich, P Inhibition of human TREK-1 channels by bupivacaine. Anesth Analg 96, 1665-73, table of contents (2003). Takahira, M., Sakurai, M., Sakurada, N. & Sugiyama, K. Fenamates and diltiazem modulate lipid-sensitive mechano-gated 2P domain K(+) channels. Pflugers Arch 451, 474-8 (2005). Ji, X. C., Zhao, W. H., Cao, D. X., Shi, Q. Q. & Wang, X. L. Novel neuroprotectant chiral 3-n-butylphthalide inhibits tandem-pore-domain potassium channel TREK-1. Acta Pharmacol Sin 32, 182-7 (2011). Cadaveira-Mosquera, A., Ribeiro, S. J., Reboreda, A., Perez, M. & Lamas, J. A. Activation of TREK currents by the neuroprotective agent riluzole in mouse sympathetic neurons. J Neurosci 31, 1375-85 (2011). Chemin, J. et al. A phospholipid sensor controls mechanogating of the K+ channel TREK-1. EMBO J 24, 44-53 (2005). Chemin, J. et al. Up- and down-regulation of the mechano-gated K(2P) channel TREK-1 by PIP (2) and other membrane phospholipids. Pflugers Arch 455, 97-103 (2007). Lopes, C. M. et al. PIP2 hydrolysis underlies agonist-induced inhibition and regulates voltage gating of two-pore domain K+ channels. J Physiol 564, 117-29 (2005). Sandoz, G., Douguet, D., Chatelain, F., Lazdunski, M. & Lesage, F. Extracellular acidification exerts opposite actions on TREK1 and TREK2 potassium channels via a single conserved histidine residue. Proc Natl Acad Sci USA 106, 14628-33 (2009). Tertyshnikova, S. et al. BL-1249 [(5,6,7,8-tetrahydro-naphthalen-1-yl)-[2-(1H-tetrazol-5-yl)-phenyl]-amine]: a putative potassium channel opener with bladder-relaxant properties. J Pharmacol Exp Ther 313, 250-9 (2005). Sherman, F. Getting started with yeast. Methods Enzymol 350, 3-41 (2002). Rodriguez-Navarro, A. & Ramos, J. Dual system for potassium transport in *Saccharomyces cerevisiae*. J Bacteriol 159, 940-5 (1984).

TABLE 1

Effects of activator compounds on $K_{2P}$ channels and mutants

| Channel | Compound | $EC_{50}$ (μM) | $E_{max}$ (fold) |
|---|---|---|---|
| $K_{2P}2.1$ (TREK-1) | ML67 | 213.0 ± 1.2 | ~11 |
| | ML67-2 | N.D. | 1.3 ± 0.1 at 500 μM |
| | ML67-13 | 177.4 ± 1.1 | ~20 |
| | ML67-15 | N.D. | 4.7 ± 0.9 at 200 μM |
| | ML67-17 | 162.2 ± 1.2 | ~14 |
| | ML67-18 | 124.8 ± 1.2 | ~18 |
| | ML67-29 | 250.6 ± 2.0 | ~18 |
| | ML67-33 | 36.3 ± 1.0 | 11.1 ± 0.4 |
| | | 9.7 ± 1.2* | 11.4 ± 1.1 |
| | ML67-137 | >40 | 9.2 ± 1.4** |
| $K_{2P}2.1$ (TREK-1) G137I | ML67-33 | N.D. | 0.9 ± 0.1 at 150 μM |
| $K_{2P}2.1$ (TREK-1) W275S | ML67-33 | 21.8 ± 1.3 | 5.1 ± 0.6 |
| $K_{2P}2.1$ (TREK-1)-3G | ML67-33 | 49.4 ± 1.1 | 12.9 ± 1.0 |
| $K_{2P}10.1$ (TREK-2) | ML67 | ~250 | 10.1 ± 1.1 at 500 μM |
| | ML67-33 | 30.2 ± 1.4 | 11.4 ± 1.8 |
| $K_{2P}4.1$ (TRAAK) | ML67-33 | 27.3 ± 1.2 | 14.7 ± 1.1** |
| $K_{2P}9.1$ (TASK-3) | ML67-33 | N.D. | 2.1 ± 0.4 at 150 μM |
| $K_{2P}5.1$ (TASK-2) | ML67-33 | N.D. | 1.7 ± 0.3** |
| $K_{2P}3.1$ (TASK-1) | ML67 | N.D. | 1.2 ± 0.0 at 500 μM |
| | ML67-33 | N.D. | 1.1 ± 0.1** |
| $K_{2P}18.1$ (TRESK) | ML67-33 | N.D. | 0.9 ± 0.1** |
| Kv7.2 (KCNQ2) | ML67 | N.D. | 1.8 ± 0.0 at 500 μM |

TABLE 2

| name | name | IUPAC | Smiles |
|---|---|---|---|
| | ML-67 | 3-(3,6-dichlorocarbazol-9-yl)propanoic acid | C3=C2C(=CC=C3C1)N(C1=C2C=C(C=C1)C1)CCC(=O)O |
| | ML67-1 | 3-(3,6-dichlorocarbazol-9-yl)propanehydrazide | C3=C2C(=CC=C3C1)N(C1=C2C=C(C=C1)C1)CCC(=O)NN |
| | ML67-2 | 3-carbazol-9-ylpropanoic acid | C3=C2C(=CC=C3)N(C1=C2C=CC=C1)CCC(=O)O |
| | ML67-3 | 3-(3,6-dichlorocarbazol-9-yl)propane-1,2-diol | C3=C2C(=CC=C3C1)N(C1=C2C=C(C=C1)C1)CC(CO)O |
| | ML67-4 and ML67-11 | 3-carbazol-9-ylpropanehydrazide | C3=C2C(=CC=C3)N(C1=C2C=CC=C1)CCC(NN)=O |
| | ML67-5 | 3-phenothiazin-10-ylpropanoic acid | C3=C2C(=CC=C3)N(C1=C(C=CC=C1)S2)CCC(O)=O |
| | ML67-8 | 3-[3-(imidazol-1-ylmethyl)-2-methylindol-1-yl]propanoic acid | C3=C2C(=CC=C3)N(C(=C2CN1C=NC=C1)C)CCC(=O)O |
| | ML67-12 | 3-(2-chlorophenothiazin-10-yl)propanenitrile | C3=C2C(=CC=C3)N(C1=C(C=CC(=C1)C1)S2)CCC#N |
| | ML67-13 | 3-(3,6-dibromocarbazol-9-yl)propanoic acid | C3=C2C(=CC=C3Br)N(C1=C2C=C(C=C1)Br)CCC(=O)O |
| | ML67-14 | 3-(3-iodocarbazol-9-yl)propanoic acid | C3=C2C(=CC=C3I)N(C1=C2C=CC=C1)CCC(=O)O |
| | ML67-15 | 4-(3,6-dichlorocarbazol-9-yl)butanoic acid | C3=C2C(=CC=C3C1)N(C1=C2C=C(C=C1)C1)CCCC(=O)O |
| | ML67-16 | methyl 3-(6,7-dimethoxyspiro[1,3-dihydroisoquinoline-4,1'-cyclopentane]-2-yl)propanoate | C3=C2C(=CC(=C3OC)OC)CN(CC12CCCC1)CCC(=O)OC |
| | ML67-17; ML67-28; ML-67-31 | 3-(3,6-dichlorocarbazol-9-yl)cyclobutane-1-carboxylic acid | C4=C3C(=CC=C4C1)[N@](C1=C3C=C(C=C1)C1)[C@@H]2C[C@@H](C(=O)O)C2 |
| | ML67-18 | 3,6-dichloro-9-[2-(1H-tetrazol-5-yl)ethyl]carbazole | C4=C3C(=CC=C4C1)N(C1=C3C=C(C=C1)C1)CCC2=NN=NN2 |
| | ML67-20 | 3-(3,6-difluorocarbazol-9-yl)propanoic acid | C3=C2C(=CC=C3F)N(C1=C2C=C(C=C1)F)CCC(=O)O |
| | ML67-21 | 3-(3,6-dimethylcarbazol-9-yl)propanoic acid | C3=C2C(=CC=C3C)N(C1=C2C=C(C=C1)C)CCC(=O)O |
| | ML67-22 | 3-(3-chloro-6-methylcarbazol-9-yl)propanoic acid | C3=C2C(=CC=C3C)N(C1=C2C=C(C=C1)C1)CCC(=O)O |
| | ML67-23 | 3-(3-bromo-6-methylcarbazol-9-yl)propanoic acid | C3=C2C(=CC=C3C)N(C1=C2C=C(C=C1)Br)CCC(=O)O |
| | ML67-24 | 3-(3-tert-butylcarbazol-9-yl)propanoic acid | C3=C2C(=CC=C3)N(C1=C2C=C(C=C1)C(C)(C)C)CCC(=O)O |
| | ML67-25 | 3-[3,6-di(propan-2-yl)carbazol-9-yl]propanoic acid | C3=C2C(=CC=C3C(C)C)N(C1=C2C=C(C=C1)C(C)C)CCC(=O)O |
| | ML67-26 | 3-(3,7-dichlorophenothiazin-10-yl)propanoic acid | C3=C2C(=CC=C3C1)N(C1=C(C=C(C=C1)C1)S2)CCC(=O)O |
| | ML67-17; ML-67-28; ML67-31 | 3-(3,6-dichlorocarbazol-9-yl)cyclobutane-1-carboxylic acid | C4=C3C(=CC=C4C1)[N@](C1=C3C=C(C=C1)C1)[C@@H]2C[C@@H](C(=O)O)C2 |

TABLE 2-continued

| name | name | IUPAC | Smiles |
|---|---|---|---|
| | ML67-29 | 3-(3,6-dichlorocarbazol-9-yl)cyclobutane-1-carboxylic acid | C4=C3C(=CC=C4C1)[N@](C1=C3C=C(C=C1)C1)[C@@H]2C[C@H](C(=O)O)C2 |
| | ML67-30 | 3,6-dichloro-9-[3-(1H-tetrazol-5-yl)cyclobutyl]carbazole | C5=C4C(=CC=C5C1)[N@](C1=C4C=C(C=C1)C1)[C@@H]3C[C@@H](C2=NN=NN2)C3 |
| 757254 | ML67-33 | 2,7-dichloro-9,9-dimethyl-10-[2-(1H-tetrazol-5-yl)ethyl]acridine | C4=C3C(=CC=C4C1)N(C1=C(C=C(C=C1)C1)C3(C)C)CCC2=NN=NN2 |
| 757083 | ML67-34 | 2,7-dibromo-9-[2-(1H-tetrazol-5-yl)ethyl]carbazole | C4=C3C(=CC=C4)Br)N(C1=C3C=CC(=C1)Br)CCC2=NN=NN2 |
| 757084 | ML67-35 | 10-[2-(1H-tetrazol-5-yl)ethyl]phenoxazine | C4=C3C(=CC=C4)N(C1=C(C=CC=C1)O3)CCC2=NN=NN2 |
| 757085 | ML67-36 | 10-[2-(1H-tetrazol-5-yl)ethyl]phenothiazine | C4=C3C(=CC=C4)N(C1=C(C=CC=C1)S3)CCC2=NN=NN2 |
| 757134 | ML67-37 | 3,7-dibromo-10-[2-(1H-tetrazol-5-yl)ethyl]phenothiazine | C4=C3C(=CC=C4Br)N(C1=C(C=C(C=C1)Br)S3)CCC2=NN=NN2 |
| 757135 | ML67-38 | 3,7-dibromo-10-[2-(1H-tetrazol-5-yl)ethyl]phenoxazine | C4=C3C(=CC=C4Br)N(C1=C(C=C(C=C1)Br)O3)CCC2=NN=NN2 |
| 757136 | ML67-39 | 9,9-dimethyl-10-[2-(1H-tetrazol-5-yl)ethyl]acridine | C4=C3C(=CC=C4)N(C1=C(C=C(C=C1)C3(C)C)CCC2=NN=NN2 |
| 757137 | ML67-137 | 2,7-dibromo-9,9-dimethyl-10-[2-(1H-tetrazol-5-yl)ethyl]acridine | C4=C3C(=CC=C4Br)N(C1=C(C=C(C=C1)Br)C3(C)C)CCC2=NN=NN2 |
| 83508 | | 2,7-dichloro-10-[2-(1H-tetrazol-5-yl)ethyl]spiro[acridine-9,1'-cyclopentane] | C5=C4C(=CC=C5C1)N(C2=C(C=C(C=C2)C1)C14CCCC1)CCC3=NN=NN3 |
| 835115 | | 2,7-dichloro-10-[2-(1H-tetrazol-5-yl)ethyl]spiro[acridine-9,4'-oxane] | C5=C4C(=CC=C5C1)N(C2=C(C=C(C=C2)C1)C14CCOCC1)CCC3=NN=NN3 |
| 915114 | | 3-(2,5-dichlorospiro[acridine-9,1'-cyclohexane]-10-yl)propanoic acid | C4=C3C(=CC=C4C1)N(C2=C(C13CCCCC1)C=CC=C2C1)CCC(=O)O |
| 915120 | | 3-(2,7-dichlorospiro[acridine-9,1'-cyclohexane]-10-yl)propanoic acid | C4=C3C(=CC=C4C1)N(C2=C(C13CCCCC1)C=C(C=C2)C1)CCC(=O)O |
| 910074 | | 2,7-dichloro-10-[2-(1H-tetrazol-5-yl)ethyl]spiro[acridine-9,1'-cyclohexane] | C5=C4C(=CC=C5C1)N(C2=C(C14CCCCC1)C=C(C=C2)C1)CCC3=NN=NN3 |
| 914581 | | 2,5-dichloro-10-[2-(1H-tetrazol-5-yl)ethyl]spiro[acridine-9,1'-cyclohexane] | C5=C4C(=CC=C5C1)N(C2=C(C14CCCCC1)C=CC=C2C1)CCC3=NN=NN3 |
| 910075 | | 10-[2-(1H-tetrazol-5-yl)ethyl]spiro[acridine-9,1'-cyclohexane] | C5=C4C(=CC=C5)N(C2=C(C14CCCCC1)C=CC=C2)CCC3=NN=NN3 |
| | | 1-[2,7-dibromo-10-[2-(1H-tetrazol-5-yl)ethyl]spiro[acridine-9,4'-piperidine]-1'-yl]ethanone | C5=C4C(=CC=C5Br)N(C2=C(C14CCN(CC1)C(C)=O)C=C(C=C2)Br)CCC3=NN=NN3 |
| | | 1-[2,7-dichloro-10-[2-(1H-tetrazol-5-yl)ethyl]spiro[acridine-9,4'-piperidine]-1'-yl]ethanone | C5=C4C(=CC=C5C1)N(C2=C(C14CCN(CC1)C(C)=O)C=C(C=C2)C1)CCC3=NN=NN3 |
| | | 2,7-dichloro-1'-methyl-10-[2-(1H-tetrazol-5-yl)ethyl]spiro[acridine-9,4'-piperidine] | C5=C4C(=CC=C5C1)N(C2=C(C14CCN(CC1)C)C=C(C=C2)C1)CCC3=NN=NN3 |
| | | 2,7-dibromo-1'-methyl-10-[2-(1H-tetrazol-5-yl)ethyl]spiro[acridine-9,4'-piperidine] | C5=C4C(=CC=C5Br)N(C2=C(C14CCN(CC1)C)C=C(C=C2)Br)CCC3=NN=NN3 |
| | | 2-bromo-1'-prop-2-ynyl-10-[2-(1H-tetrazol-5-yl)ethyl]-7-[3-(trifluoromethyl)diazirin-3-yl]spiro[acridine-9,4'-piperidine] | C6=C5C(=CC=C6Br)N(C3=C(C15CCN(CC1)CC#C)C=C(C=C3)C2(N=N2)C(F)(F)F)CCC4=NN=NN4 |
| | | 2-chloro-1'-prop-2-ynyl-10-[2-(1H-tetrazol-5-yl)ethyl]-7-[3-(trifluoromethyl)diazirin-3-yl]spiro[acridine-9,4'-piperidine] | C6=C5C(=CC=C6C1)N(C3=C(C15CCN(CC1)CC#C)C=C(C=C3)C2(N=N2)C(F)(F)F)CCC4=NN=NN4 |
| | | 2-azido-7-chloro-1'-prop-2-ynyl-10-[2-(1H-tetrazol-5-yl)ethyl]spiro[acridine-9,4'-piperidine] | C5=C4C(=CC=C5C1)N(C2=C(C14CCN(CC1)CC#C)C=C(C=C2)N=[N+]=[N-])CCC3=NN=NN3 |
| | | 2-azido-7-bromo-1'-prop-2-ynyl-10-[2-(1H-tetrazol-5-yl)ethyl]spiro[acridine-9,4'-piperidine] | C5=C4C(=CC=C5Br)N(C2=C(C14CCN(CC1)CC#C)C=C(C=C2)N=[N+]=[N-])CCC3=NN=NN3 |
| | | 2-azido-7-prop-2-ynoxy-10-[2-(1H-tetrazol-5-yl)ethyl]-9H-acridine | C4=C3C(=CC=C4OCC#C)N(C1=C(C3)C=C(C=C1)N=[N+]=[N-])CCC2=NN=NN2 |
| | | 2-azido-7-prop-2-ynoxy-10-[2-(1H-tetrazol-5-yl)ethyl]spiro[acridine-9,1'-cyclopentane] | C5=C4C(=CC=C5OCC#C)N(C2=C(C14CCCC1)C=C(C=C2)N=[N+]=[N-])CCC3=NN=NN3 |
| | | 2-azido-9,9-dimethyl-7-prop-2-ynoxy-10-[2-(1H-tetrazol-5-yl)ethyl]acridine | C4=C3C(=CC=C4OCC#C)N(C1=C(C3(C)C)C=C(C=C1)N=[N+]=[N-])CCC2=NN=NN2 |
| | | 2-azido-7-prop-2-ynoxy-10-[2-(1H-tetrazol-5-yl)ethyl]spiro[acridine-9,1'-cyclohexane] | C5=C4C(=CC=C5OCC#C)N(C2=C(C14CCCCC1)C=C(C=C2)N=[N+]=[N-])CCC3=NN=NN3 |
| | | 3-(2,7-dichloro-9,9-dimethylacridin-10-yl)-N-hydroxypropanamide | C3=C2C(=CC=C3C1)N(C1=C(C2(C)C)C=C(C=C1)C1)CCC(=O)NO |
| | | 3-(2,7-dichloro-9,9-dimethylacridin-10-yl)-N-methylsulfonylpropanamide | C3=C2C(=CC=C3C1)N(C1=C(C2(C)C)C=C(C=C1)C1)CCC(=O)NS(C)(=O)=O |
| | | 3-(2,7-dichloro-9,9-dimethylacridin-10-yl)propanoic acid | C3=C2C(=CC=C3C1)N(C1=C(C2(C)C)C=C(C=C1)C1)CCC(=O)O |
| | | 3-(2,7-dichlorospiro[acridine-9,1'-cyclohexane]-10-yl)-N-hydroxypropanamide | C4=C3C(=CC=C4C1)N(C2=C(C13CCCCC1)C=C(C=C2)C1)CCC(=O)NO |

TABLE 2-continued

| name | name | IUPAC | Smiles |
|---|---|---|---|
| | | 3-(2,7-dichlorospiro[acridine-9,1'-cyclohexane]-10-yl)-N-methylsulfonylpropanamide | C4=C3C(=CC=C4C1)N(C2=C(C13CCCCC1)C=C(C=C2)C1)CCC(=O)NS(C)(=O)=O |
| | | N-[2-(2,7-dichlorospiro [acridine-9,1'-cyclohexane]-10-yl)ethylsulfonyl]acetamide | C4=C3C(=CC=C4C1)N(C2=C(C13CCCCC1)C=C(C=C2)C1)CCS(=O)(NC(C)=O)=O |
| | | N-[2-(2,7-dibromospiro[acridine-9,1'-cyclohexane]-10-yl)ethylsulfonyl]acetamide | C4=C3C(=CC=C4Br)N(C2=C(C13CCCCC1)C=C(C=C2)Br)CCS(=O)(NC(C)=O)=O |
| | | N-[2-(2,7-dibromo-9,9-dimethylacridin-10-yl)ethylsulfonyl]acetamide | C3=C2C(=CC=C3Br)N(C1=C(C2(C)C)C=C(C=C1)Br)CCS(=O)(NC(C)=O)=O |
| | | N-[2-(2,7-dichloro-9,9-dimethylacridin-10-yl)ethylsulfonyl]acetamide | C3=C2C(=CC=C3C1)N(C1=C(C2(C)C)C=C(C=C1)C1)CCS(=O)(NC(C)=O)=O |
| | | N-cyano-3-(2,7-dichloro-9,9-dimethylacridin-10-yl)propanamide | C3=C2C(=CC=C3C1)N(C1=C(C2(C)C)C=C(C=C1)C1)CCC(NC#N)=O |
| | | 2-(2,7-dichloro-9,9-dimethylacridin-10-yl)ethanesulfonic acid | C3=C2C(=CC=C3C1)N(C1=C(C2(C)C)C=C(C=C1)C1)CCS(O)(=O)=O |
| | | 3-[2-(2,7-dichloro-9,9-dimethylacridin-10-yl)ethyl]-4H-1,2,4-oxadiazol-5-one | C4=C3C(=CC=C4C1)N(C1=C(C3(C)C)C=C(C=C1)C1)CCC2=NOC(=O)N2 |
| | | 4-[2-(2,7-dichloro-9,9-dimethylacridin-10-yl)ethyl]-1H-tetrazol-5-one | C4=C3C(=CC=C4C1)N(C1=C(C3(C)C)C=C(C=C1)C1)CCN2N=NNC2=O |
| | | 2,7-dichloro-10-[2-(3-hydroxytriazol-4-yl)ethyl]-9,9-dimethylacridine | C4=C3C(=CC=C4C1)N(C1=C(C3(C)C)C=C(C=C1)C1)CCC2=CN=NN2O |
| | | 2,7-dichloro-10-[2-(2-hydroxypyrazol-3-yl)ethyl]-9,9-dimethylacridine | C4=C3C(=CC=C4C1)N(C1=C(C3(C)C)C=C(C=C1)C1)CCC2=CC=NN2O |
| | | 4-[2-(2,7-dichloro-9,9-dimethylacridin-10-yl)ethyl]-1,2,5-thiadiazol-3-ol | C4=C3C(=CC=C4C1)N(C1=C(C3(C)C)C=C(C=C1)C1)CCC2=NSN=C2O |
| | | 3,7-dichloro-10-[2-(1H-tetrazol-5-yl)ethyl]phenothiazine 5,5-dioxide | C4=C(C=CC3=C4S(=O)(=O)C2=CC(=CC=C2N3CCC1=NN=NN1)C1)C1 |
| | | 3,7-dichloro-10-[2-(1H-tetrazol-5-yl)ethyl]phenothiazine 5-oxide | C4=C(C=CC3=C4S(=O)C2=CC(=CC=C2N3CCC1=NN=NN1)C1)C1 |
| | | N-[2,7-dichloro-9-methyl-10-[2-(1H-tetrazol-5-yl)ethyl]acridin-9-yl]acetamide | C4=C(C=CC3=C4C(C2=CC(=CC=C2N3CCC1=NN=NN1)C1)(C)NC(C)=O)C1 |
| | | 2,7-dichloro-9-methyl-10-[2-(1H-tetrazol-5-yl)ethyl]acridin-9-amine | C4=C(C=CC3=C4C(C2=CC(=CC=C2N3CCC1=NN=NN1)C1)(C)N)C1 |
| | | 2,7-dichloro-9-methyl-10-[2-(1H-tetrazol-5-yl)ethyl]acridin-9-ol | C4=C(C=CC3=C4C(C2=CC(=CC=C2N3CCC1=NN=NN1)C1)(C)O)C1 |
| | | 2,7-dichloro-9-methoxy-9-methyl-10-[2-(1H-tetrazol-5-yl)ethyl]acridine | C4=C(C=CC3=C4C(C2=CC(=CC=C2N3CCC1=NN=NN1)C1)(C)OC)C1 |
| | | 2-azido-7-chloro-9-methyl-9-prop-2-ynoxy-10-[2-(1H-tetrazol-5-yl)ethyl]acridine | C4=C(C=CC3=C4C(C2=CC(=CC=C2N3CCC1=NN=NN1)N=[N+]=[N-])(C)OCC#C)C1 |
| | | 2-azido-7-chloro-9-methyl-N-prop-2-ynyl-10-[2-(1H-tetrazol-5-yl)ethyl]acridin-9-amine | C4=C(C=CC3=C4C(C2=CC(=CC=C2N3CCC1=NN=NN1)N=[N+]=[N-])(C)NCC#C)C1 |
| | | 2,7-dichloro-N,9-dimethyl-10-[2-(1H-tetrazol-5-yl)ethyl]acridin-9-amine | C4=C(C=CC3=C4C(C2=CC(=CC=C2N3CCC1=NN=NN1)C1)(C)NC)C1 |
| | | 2,7-dichloro-N,N,9-trimethyl-10-[2-(1H-tetrazol-5-yl)ethyl]acridin-9-amine | C4=C(C=CC3=C4C(C2=CC(=CC=C2N3CCC1=NN=NN1)C1)(C)N(C)C)C1 |
| | | N-[2,7-dichloro-9-methyl-10-[2-(1H-tetrazol-5-yl)ethyl]acridin-9-yl]methanesulfinamide | C4=C(C=CC3=C4C(C2=CC(=CC=C2N3CCC1=NN=NN1)C1)(C)NS(=O)C)C1 |
| | | 2,7-dichloro-10-[2-(1H-tetrazol-5-yl)ethyl]-9,9-bis(trifluoromethyl)acridine | C4=C(C=CC3=C4C(C2=CC(=CC=C2N3CCC1=NN=NN1)C1)(C(F)(F)F)C(F)(F)F)C1 |
| | ML-67 | 3-(3,6-dichlorocarbazol-9-yl)propanoic acid | C3=C2C(=CC=C3C1)N(C1=C2C=C(C=C1)C1)CCC(=O)O |

TABLE 3

Modulation of TREK-1 by select compounds (agonist activity).

| Compound number | Compound | Name | Active at 200 µM Yes | Active at 200 µM No | Active at 500 µM Yes | Active at 500 µM No | EC50 | comments |
|---|---|---|---|---|---|---|---|---|
| ML-67 | 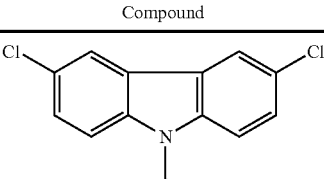 | 3-(3,6-dichlorocarbazol-9-yl)proanoic acid | | | X | | 213 µM | |

TABLE 3-continued

Modulation of TREK-1 by select compounds (agonist activity).

| Compound number | Compound | Name | Active at 200 μM Yes | Active at 200 μM No | Active at 500 μM Yes | Active at 500 μM No | EC50 | comments |
|---|---|---|---|---|---|---|---|---|
| ML67-1 | | 3-(3,6-dichlorocarbazol-9-yl)propanehydrazide | | | | X | | |
| ML67-2 | | 3-carbazol-9-ylpropanoic acid | | | | X | | |
| ML67-3 | | 3-(3,6-dichlorocarbazol-9-yl)propane-1,2-diol | | | | X | | |
| ML67-4 | | 3-carbazol-9-ylpropanehydrazide | | | | X | | |
| ML67-5 | | 3-phenothiazin-10-ylpropanoic acid | | | | X | | |

TABLE 3-continued

Modulation of TREK-1 by select compounds (agonist activity).

| Compound number | Compound | Name | Active at 200 µM Yes | No | Active at 500 µM Yes | No | EC50 | comments |
|---|---|---|---|---|---|---|---|---|
| ML67-8 | | 3-(2-chlorophenothiazin-10-yl)propanenitrile | | | | X | | |
| ML67-12 | | 3-(3,6-dichlorocarbazol-9-yl)propanenitrile | | | | X | | |
| ML67-13 | | 3-(3,6-dibromocarbazol-9-yl) propanoic acid | | | X | | 177 µM | |
| ML67-14 | | 3-(3-iodocarbazol-9-yl)propanoic acid | X | | | | >500 µM | No plateau |
| ML67-15 | | 4-(3,6-dichlorocarbazol-9-yl) butanoic acid | X | | | | | |

TABLE 3-continued

Modulation of TREK-1 by select compounds (agonist activity).

| Compound number | Compound | Name | Active at 200 µM Yes | Active at 200 µM No | Active at 500 µM Yes | Active at 500 µM No | EC50 | comments |
|---|---|---|---|---|---|---|---|---|
| ML67-16 | | (E)-3-(3,6-dichlorocarbazol-9-yl)prop-2-enoic acid | | X insoluble | | | | |
| ML67-17 | | 3-(3,6-dichlorocarbazol-9-yl)cyclobutane-1-carboxylic acid | X | | | | 162 µM | 85:15 t:c |
| ML67-18 | | 3,6-dichloro-9-[2-(1H-tetrazol-5-yl)ethyl]carbazole | X | | | | 125 µM | |
| ML67-19 | | 3-(3,6-dichlorocarbazol-9-yl)-N-hydroxy-propanamide | | X insoluble | | | | |
| ML67-20 | | 3-(3,6-difluorocarbazol-9-yl)propanoic acid | X | | | | | |

TABLE 3-continued

Modulation of TREK-1 by select compounds (agonist activity).

| Compound number | Compound | Name | Active at 200 μM Yes | No | Active at 500 μM Yes | No | EC50 | comments |
|---|---|---|---|---|---|---|---|---|
| ML67-21 | | 3-(3,6-dimethylcarbazol-9-yl)propanoic acid | X | | | | | |
| ML67-22 | | 3-(3-chlorocarbazol-9-yl)propanoic acid | X | | | | | |
| ML67-23 | | 3-(3-bromo-6-methylcarbazol-9-yl)propanoic acid | X | | | | | |
| Ml67-24 | | 3-(3-tert-butylcarbazol-9-yl)propanoic acid | X | | | | | |
| ML67-25 | | 3-[3,6-di(propan-2-yl)carbazol-9-yl]propanoic acid | X | | | | | |

TABLE 3-continued

Modulation of TREK-1 by select compounds (agonist activity).

| Compound number | Compound | Name | Active at 200 µM Yes | No | Active at 500 µM Yes | No | EC50 | comments |
|---|---|---|---|---|---|---|---|---|
| ML67-26 | | 3-(3,7-dichloro-phenothiazin-10-yl)propanoic acid | | | | | ~200 µM | No plateau |
| ML67-28 | | 3-(3,6-dichlorocarbazol-9-yl)cyclobutane-1-carboxylic acid (trans) | | | | | 162 µM | >98% trans |
| ML67-29 | | 3-(3,6-dichlorocarbazol-9-yl)cyclobutane-1-carboxylic acid (cis) | | | | | 162 µM | >95% cis |
| ML67-30 | | 3,6-dichloro-9-[3-(1H-tetrazol-5-yl)cyclobutyl]carbazole (trans) | | | | | Better than 125 µM | >99% trans |
| ML67-31 | | 3-(3,6-dichlorocarbazol-9-yl)cyclobutane-1-carboxamide (trans) | | | | | | >96% trans |

TABLE 3-continued

Modulation of TREK-1 by select compounds (agonist activity).

| Compound number | Compound | Name | Active at 200 µM Yes | Active at 200 µM No | Active at 500 µM Yes | Active at 500 µM No | EC50 | comments |
|---|---|---|---|---|---|---|---|---|
| ML67-33 (757254) | | 2,7-dichloro-9,9-dimethyl-10-[2-(1H-tetrazol-5-yl)ethyl]acridine | | | | | 38.5 µM | |
| ML67-34 (757083) | | 2,7-dibromo-9-[2-(1H-tetrazol-5-yl)ethyl]carbazole | | | | | EC50 greater than 38.5 µM | 13.4% activity at 50 µM Not better than ML67-33; |
| ML67-35 (75704) | | 10-[2-(1H-tetrazol-5-yl)ethyl]phenoxazine | | | | | EC50 greater than 38.5 µM | 17.8% activity at 50 µM Not better than ML67-33 |
| ML67-36 (757085) | | 10-[2-(1H-tetrazol-5-yl)ethyl]phenothiazine | | | | | EC50 greater than 38.5 µM | 19; .2% activity at 50 µM |
| ML67-37 (757134) | | 3,7-dibromo-10-[2-(1H-tetrazol-5-yl)ethyl]phenothiazine | | | | | EC50 greater than 38.5 µM | 96% activity at 50 µM Not better than ML67-33 |

TABLE 3-continued

Modulation of TREK-1 by select compounds (agonist activity).

| Compound number | Compound | Name | Active at 200 µM Yes | No | Active at 500 µM Yes | No | EC50 | comments |
|---|---|---|---|---|---|---|---|---|
| ML67-38 (757135) | | 3,7-dibromo-10-[2-(1H-tetrazol-5-yl)ethyl]phenoxazine | | | | | EC50 greater than 38.5 µM | 68.8% activity at 50 µM Not better than ML67-33 |
| ML67-39 (757136) | | 9,9-dimethyl-10-[2-(1H-tetrazol-5-yl)ethyl]acridine | | | | | EC50 greater than 38.5 µM | 29.2% activity at 50 µM Not better than ML67-33 |
| ML67-137 (757137) | | 2,7-dibromo-9,9-dimethyl-10-[2-(1H-tetrazol-5-yl)ethyl]acridine | | | | | | 100% activity of ML67-33 at 50 µM 80% activity at 10 µM |
| ML67-138 (835088) | | 2,7-dichloro-10-[2-(1H-tetrazol-5-yl)ethyl]spiro[acridine-9,1'-cyclopentane] | | | | | 18.3 µM | |

TABLE 3-continued

Modulation of TREK-1 by select compounds (agonist activity).

| Compound number | Compound | Name | Active at 200 μM Yes | Active at 200 μM No | Active at 500 μM Yes | Active at 500 μM No | EC50 | comments |
|---|---|---|---|---|---|---|---|---|
| ML67-139 (835115) | | 2,7-dichloro-10-[2-(1H-yl)ethyl]spiro[acridine-9,4'-oxane] | | | | | EC50 greater than 38.5 μM | 60.7% activity at 50 μM Not better than ML67-33 |
| ML67-140 (915114) | | 3-(2,5-dichlorospiro[acridine-9,1'-cyclohexane]-10-yl)propanoic acid | | | | | EC50 greater than 38.5 μM | 57.7% activity at 50 μM Not better than ML67-33 |
| ML67-141 (915120) | | 3-(2,7-dichlorospiro[acridine-9,1'-cyclohexane]-10-yl)propanoic acid | | | | | EC50 Between 38.5 μM and 8.6 μM | Better than ML67-33; not better than (ML67-142) |
| ML67-142 (910074) | | 2,7-dichloro-10-[2-(1H-tetrazol-5-yl)ethyl]spiro[acridine-9,1'-cyclohexane] | | | | | 8.6 μM | |

TABLE 3-continued

Modulation of TREK-1 by select compounds (agonist activity).

| Compound number | Compound | Name | Active at 200 µM Yes | Active at 200 µM No | Active at 500 µM Yes | Active at 500 µM No | EC50 | comments |
|---|---|---|---|---|---|---|---|---|
| ML67-143 (914581) | | 2,5-dichloro-10-[2-(1H-tetrazol-5-yl)ethyl]spiro[acridine-9,1'-cyclohexane] | | | | | EC50 Between 38.5 µM and 8.6 µM | Better than ML67-33; Not better than (ML67-142) |
| ML67-144 (910075) | | 10-[2-(1H-tetrazol-5-yl)ethyl]spiro[acridine-9,1'-cyclohexane] | | | | | EC50 greater than 38.5 µM | 32.3% activity at 50 µM Not better than ML67-33 |
| ML67-145 (916345) | | 2,7-dibromo-10-[2-(1H-1,2,3,4-tetrazol-5-yl)ethyl]-10H-spiro[acridine-9,1'-cyclohexane] | | | | | EC50 Between 38.5 µM and 8.6 µM | Better than ML67-33; Not better than (ML67-142) |
| ML67-146 (916356) | | 2-bromo-10-[2-(1H-1,2,3,4-tetrazol-5-yl)ethyl]-10H-spiro[acridine-9,1'-cyclohexane]-7-ylmethanol | | | | | EC50 greater than 38.5 µM | 25.9% activity at 50 µM Not better than ML67-33 |

TABLE 3-continued

Modulation of TREK-1 by select compounds (agonist activity).

| Compound number | Compound | Name | Active at 200 μM Yes | No | Active at 500 μM Yes | No | EC50 | comments |
|---|---|---|---|---|---|---|---|---|
| ML67-147 (916726) | | 3-{2,7-dibromo-10H-spiro[acridine-9,1'-cyclohexane]-10-yl}propanoic acid | | | | | EC50 greater than 38.5 μM | 84.1% activity at 50 μM; Not better than ML67-33 |
| ML67-148 (916730) | | 3-{2,7-dibromo-10H-spiro[acridine-9,1'-cyclohexane]-10-yl}-N-methanesulfonyl-propanamide | | | | | EC50 Between 38.5 μM and 8.6 μM | Better than ML67-33; Not better than (ML67-142) |
| ML67-149 (916760) | | 3-{2,7-dichloro-10H-spiro[acridine-9,1'-cyclohexane]-10-yl}propan-1-amine | | | | | | |
| ML67-150 (916761) | | 3-{2,7-dibromo-10H-spiro[acridine-9,1'-cyclohexane]-10-yl}-N-(4-ethynyl-benzenesulfonyl)propanamide | | | | | EC50 greater than 38.5 μM | Not better than ML67-33 |

TABLE 3-continued

Modulation of TREK-1 by select compounds (agonist activity).

| Compound number | Compound | Name | Active at 200 μM Yes | Active at 200 μM No | Active at 500 μM Yes | Active at 500 μM No | EC50 | comments |
|---|---|---|---|---|---|---|---|---|
| ML67-151 (918040) | | 1-(2-azido-10-{2-[(4-ethynylbenzene-sulfonyl)carbamoyl]ethyl}-10H-spiro[acridine-9,1'-cyclohexane]-7-yl)triaza-1,2-dien-2-ium | | | | | | About 50% activity of ML67-33 at 50 μM |
| ML67-152 (957890) | | 2-{2,7-dibromo-10H-spiro[acridine-9,1'-cyclohexane]-10-ylmethyl}pentanedioic acid | | | | | EC50 greater than 38.5 μM | 45% activity at 50 μM No better than ML67-33 |

TABLE 4

Small molecule screening data

| Category | Parameter | Description |
|---|---|---|
| Assay | Type of assay | cell-based (yeast strain SGY1528) |
| | Target | mouse two-pore potassium channel $K_{2P}2.1$ (TREK-1) |
| | Primary measurement | fluorometric detection of $K_{2P}2.1$-expressing yeast viability in the presence of library compounds in potassium-limiting conditions |
| | Key reagents | 'vital dye' Resazurin (Alamar Blue, Invitrogen) |
| | Assay protocol | see Methods section |
| | Additional comments | none |
| Library | Library size | 105,863 small molecule compounds |
| | Library composition | 103,868 - Diversity Collection (SPECS) |
| | | 1,995 - Bioactive Collection (Microsource) |
| | Source | Small Molecule Discovery Center, University of California, San Francisco |
| | Additional comments | none |
| Screen | Format | 384-square-well |
| | Concentration(s) tested | 10 μM, 1% DMSO |
| | Plate controls | 1% DMSO (0% growth inhibition control) |
| | | 0.1% SDS, 1% DMSO (100% growth inhibition control) |
| | Reagent/compound dispensing system | FXp Liquid Handler (Beckman) |
| | | WellMate Bulk Dispenser (Matrix) |
| | Detection instrument and software | Analyst HT Plate Reader (Molecular Devices) |
| | Assay validation/QC | Z' = 0.76 |
| | Correction factors | none |
| | Normalization | see Plate Controls |
| | Additional comments | Hit criteria: growth inhibition in the range 44-92%. 320 compounds were chosen for post-HTS analysis. |
| Post-HTS analysis | Hit criteria | $K_{2P}2.1$-specific growth inhibition. Reference: Trk1p-expressing yeast. Hit criteria: 2-fold difference in the apparent $IC_{50}$ required to inhibit the growth of yeast expressing $K_{2P}2.1$ (TREK-1) versus those expressing Trk1p |

TABLE 4-continued

Small molecule screening data

| Category | Parameter | Description |
|---|---|---|
| | Hit rate | 0.077% (81 compounds) |
| | Additional assay(s) | Direct electrophysiological measurements of the effect of the hit compounds on $K_{2P}2.1$ activity in *Xenopus* oocytes. |
| | Confirmation of hit purity and structure | resupplied as dry powders, QC by LC/MS >90% purity |
| | Additional comments | none |

TABLE 5

Antagonist compound examples. Modulation of TREK-1 by select compounds.

| | | | |
|---|---|---|---|
| ML45 | 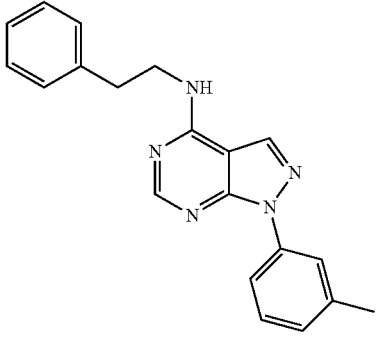 [SMILES: Cc1cccc(-n2ncc3c(NCCc4ccccc4)ncnc32)c1] | 1-(3-methylpyhenyl)-N-(2-phenylethyl)-1H-pyrazolo[3,4-d]pyrimidin-4-amine | ~30% current inhibition at 25 µM |
| ML45-1 (103624) | 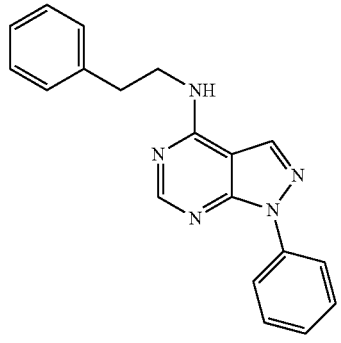 [SMILES: c1ccc(CCNc2ncnc3c2cnn3-c2ccccc2)cc1] | 1-phenyl-N-(2-phenylethyl)-1H-pyrazolo[3,4-d]pyrimidin-4-amine | 22.5% inhibition at 25 µM at 0 mV |
| ML45-2 (957903) | 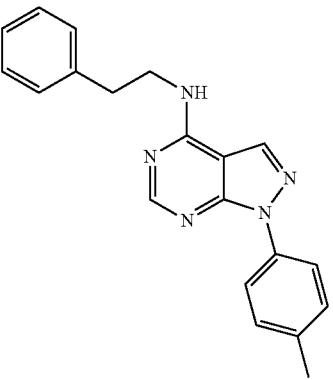 [SMILES: Cc1ccc(-n2ncc3c(NCCc4ccccc4)ncnc32)cc1] | 1-(4-methylphenyl)-N-(2-phenylethyl)-1H-pyrazolo[3,4-d]pyrimidin-4-amine | 25.2% inhibition at 25 µM at 0 mV |

TABLE 5-continued

Antagonist compound examples. Modulation of TREK-1 by select compounds.

| | | | |
|---|---|---|---|
| ML45-3 (957902) | 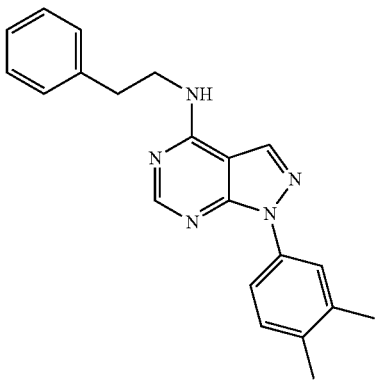 [SMILES: Cc1ccc(-n2ncc3c(NCCc4ccccc4)ncnc32)cc1C] | 1-(3,4-dimethylphenyl)-N-(2-phenylethyl)-1H-pyrazolo[3,4-d]pyrimidin-4-amine | 31.9% inhibition at 25 μM at 0 mV |
| ML45-4 (245199) | 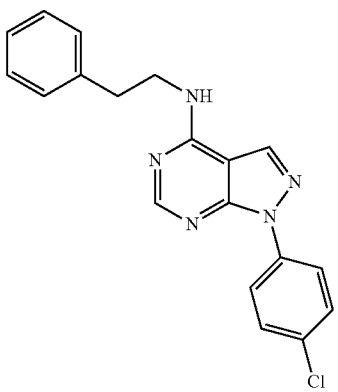 [SMILES: Clc1ccc(-n2ncc3c(NCCc4ccccc4)ncnc32)cc1] | 1-(4-chlorophenyl)-N-(2-phenylethyl)-1H-pyrazolo[3,4-d]pyrimidin-4-amine | 20.7% inhibition at 25 μM at 0 mV |
| ML45-5 (245480) | 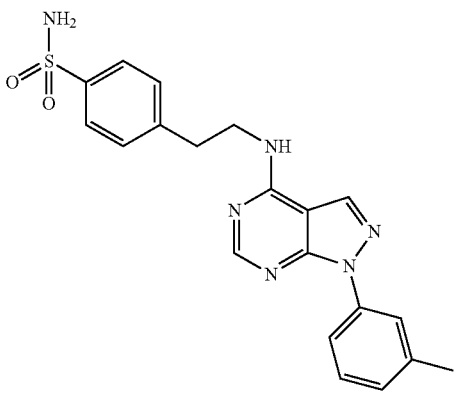 [SMILES: Cc1cccc(-n2ncc3c(NCCc4ccc(S(N)(=O)=O)cc4)ncnc32)c1] | 4-(2-{[1-(3-methylphenyl)-1H-pyrazolo[3,4-d]pyrimidin-4-yl]amino}ethyl)benzene-1-sulfonamide | 2.7% inhibition at 25 μM at 0 mV |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

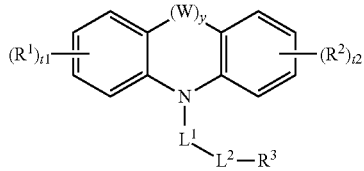

wherein

L¹ is an unsubstituted $C_1$-$C_{10}$ alkylene or unsubstituted $C_3$-$C_6$ cycloalkylene;

L² is a bond, —O—, —S—, —NH—, —C(O)—, —C(O)NH—, —NHC(O)—, —S(O)—, or —S(O)$_2$—;

R¹ and R² are independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

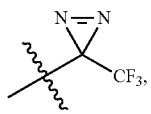

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁴ and R⁵ are independently hydrogen, halogen, —CF$_3$, —CCl$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

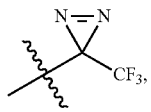

—C(CH$_3$)$_3$, —OCH$_2$CCH, —NHCH$_2$CCH, —NHCH$_3$, —N(CH$_3$)$_2$, —NHS(O)CH$_3$, —C(O)CH$_3$, —CH$_3$, —CH$_2$CCH, —NHC(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

where R⁴ and R⁵ may optionally be joined to form a substituted or unsubstituted cycloalkyl or substituted or unsubstituted heterocycloalkyl;

R³ is —C(O)OR⁹, —C(O)NR⁷R⁸, —SO$_2$R¹⁰, —OPO(OH)$_2$, —PO(OH)$_2$, —SO$_3$H, —SO$_4$H, —C(O)R⁹, substituted or unsubstituted sulfonate, substituted or unsubstituted phosphate, substituted or unsubstituted 2 to 10 membered heteroalkyl, substituted or unsubstituted cycloalkyl, substituted or unsubstituted heterocycloalkyl, or substituted or unsubstituted heteroaryl;

R⁷, R⁸, R⁹, and R¹⁰, are independently hydrogen, oxo, halogen, —C(O)CH$_3$, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)CH$_3$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl;

W is —O—, —S—, —S(O)—, —S(O)$_2$—, or —C(R⁴)(R⁵)—;

y is 0 or 1;

t1 and t2 are independently an integer from 1 to 4;

or a pharmaceutically acceptable salt thereof.

2. The compound of claim 1, having the formula:

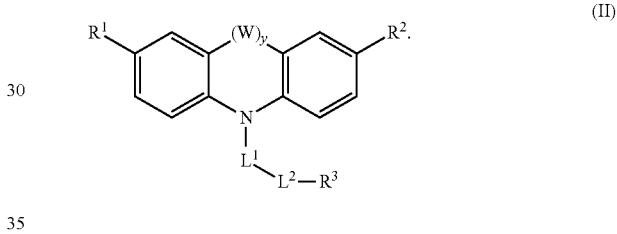

3. The compound, or a pharmaceutically acceptable salt thereof, of claim 1, wherein W is —C(R⁴)(R⁵)—.

4. The compound, or a pharmaceutically acceptable salt thereof, of claim 1, wherein R¹ is halogen.

5. The compound, or a pharmaceutically acceptable salt thereof, of claim 1, wherein R² is halogen.

6. The compound, or a pharmaceutically acceptable salt thereof, of claim 1, wherein R³ is substituted or unsubstituted heteroaryl.

7. The compound, or a pharmaceutically acceptable salt thereof, of claim 1, wherein R³ is —COOH, substituted or unsubstituted sulfonate, phosphate, or tetrazolyl.

8. A pharmaceutical composition comprising a pharmaceutically acceptable excipient and a compound, or a pharmaceutically acceptable salt thereof, of claim 1.

9. The compound, or a pharmaceutically acceptable salt thereof, of claim 1, wherein R⁴ and R⁵ are independently hydrogen, halogen, —CF$_3$, —CCl$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, —N$_3$,

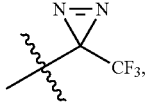 [SMILES: *C1(C(F)(F)F)N=N1]

—C(CH₃)₃, —OCH₂CCH, —NHCH₂CCH, —NHCH₃, —N(CH₃)₂, —NHS(O)CH₃, —C(O)CH₃, —CH₃, —CH₂CCH, —NHC(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

where R⁴ and R⁵ may optionally be joined to form a substituted or unsubstituted cycloalkyl or substituted or unsubstituted heterocycloalkyl.

10. The compound, or a pharmaceutically acceptable salt thereof, of claim 1, wherein R⁴ and R⁵ are independently hydrogen, halogen, —CF₃, —CCl₃, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCH₃, —OCF₃, —OCHF₂, —C(CH₃)₃, —OCH₂CCH, —NHCH₂CCH, —NHCH₃, —N(CH₃)₂, —NHS(O)CH₃, —C(O)CH₃, —CH₃, —CH₂CCH, or —NHC(O)CH₃;

where R⁴ and R⁵ may optionally be joined to form a substituted or unsubstituted cycloalkyl or substituted or unsubstituted heterocycloalkyl.

11. The compound, or a pharmaceutically acceptable salt thereof, of claim 1, wherein R⁴ and R⁵ are independently hydrogen, —CF₃, —CCl₃, or substituted or unsubstituted C₁-C₄ alkyl;

where R⁴ and R⁵ may optionally be joined to form a substituted or unsubstituted cycloalkyl or substituted or unsubstituted heterocycloalkyl.

12. The compound, or a pharmaceutically acceptable salt thereof, of claim 1, wherein R⁴ and R⁵ are joined to form a substituted or unsubstituted C₃-C₈ cycloalkyl or substituted or unsubstituted 3 to 8 membered heterocycloalkyl.

13. The compound, or a pharmaceutically acceptable salt thereof, of claim 1, wherein R⁴ and R⁵ are joined to form an unsubstituted C₃-C₆ cycloalkyl or unsubstituted 3 to 6 membered heterocycloalkyl.

14. The compound, or a pharmaceutically acceptable salt thereof, of claim 1, wherein R⁴ and R⁵ are joined to form an unsubstituted C₆ cycloalkyl.

15. The compound, or a pharmaceutically acceptable salt thereof, of claim 1, wherein R³ is substituted or unsubstituted

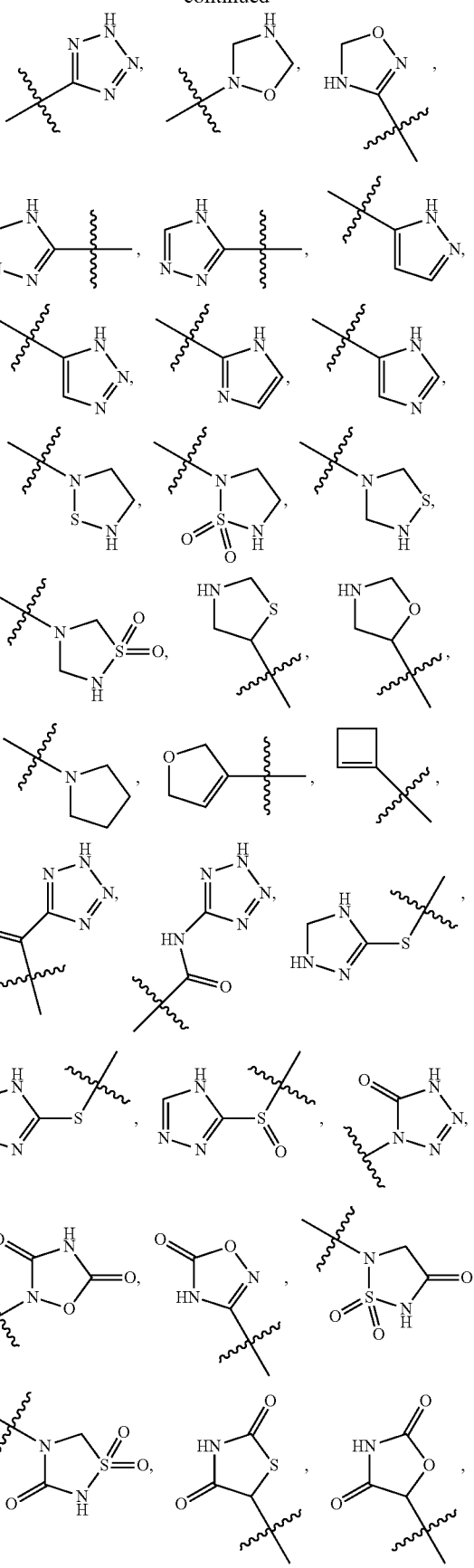

175
-continued
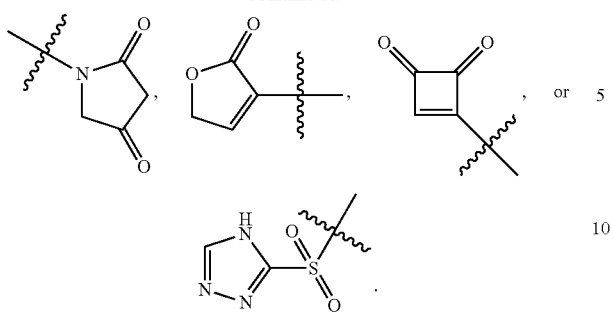
16. The compound, or a pharmaceutically acceptable salt thereof, of claim 1, having the formula:
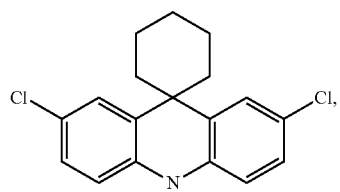
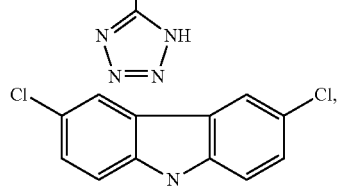
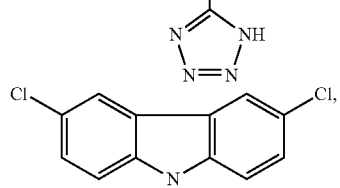
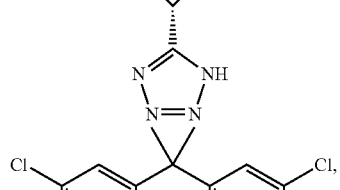
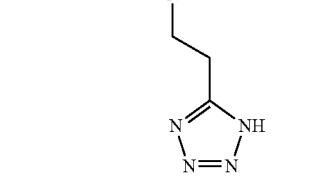
176
-continued
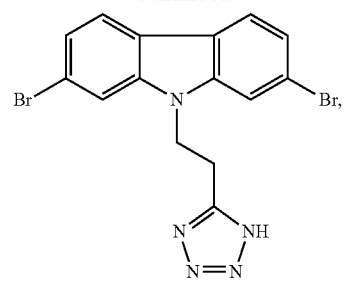
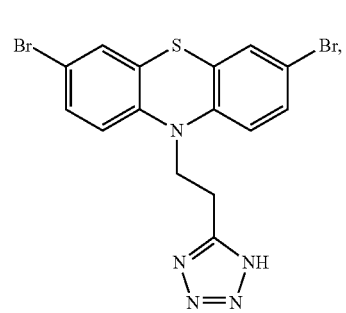
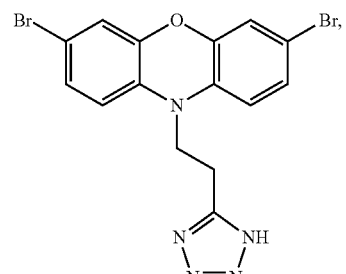
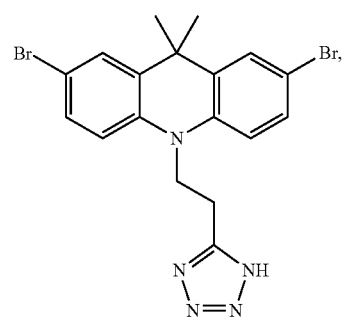
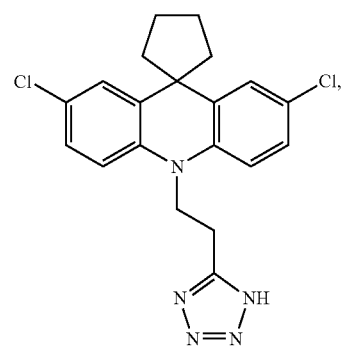

177
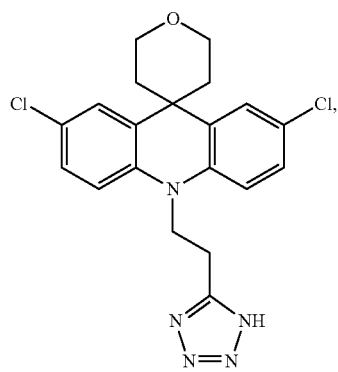
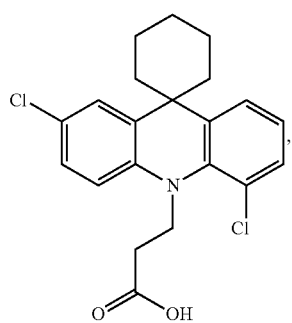
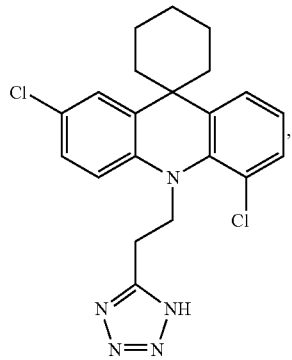
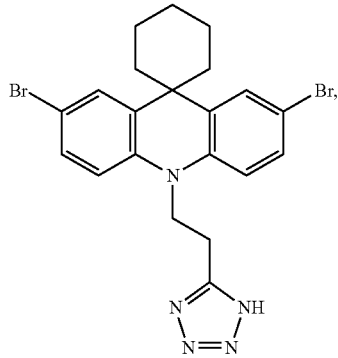
178
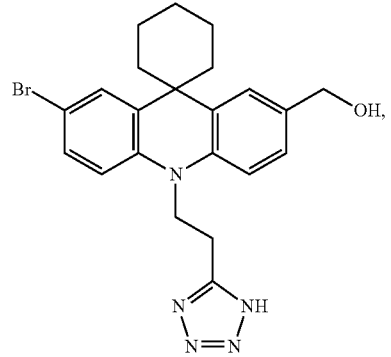
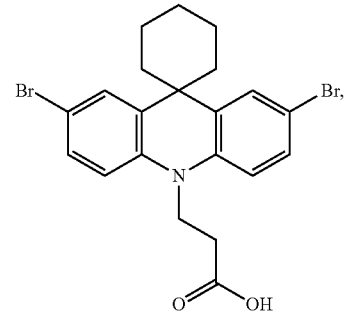
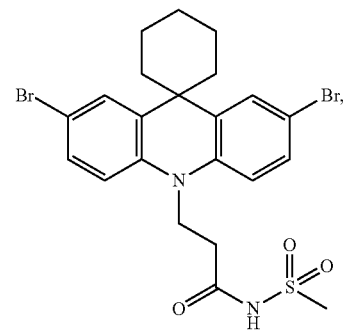
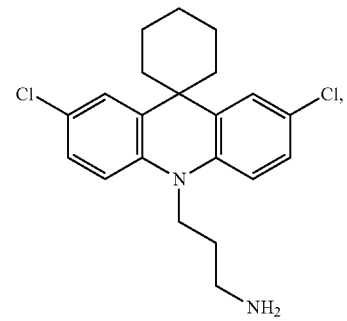
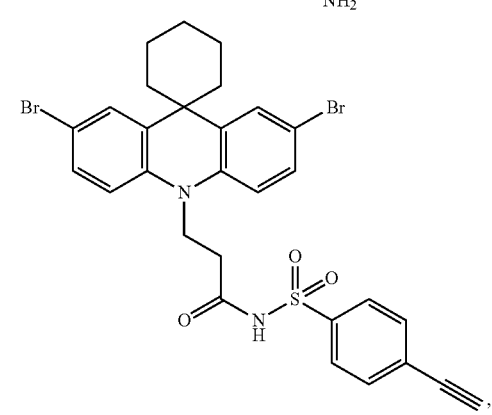

179
-continued
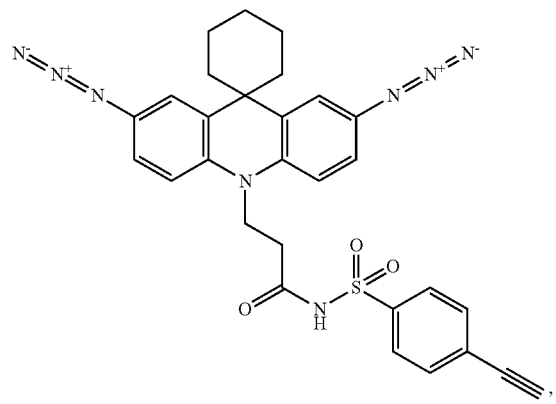
or
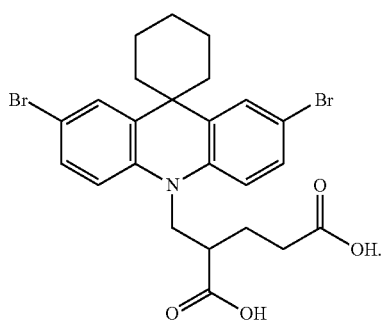 [SMILES: O=C(O)CCC(CN1c2ccc(Br)cc2C2(CCCCC2)c2cc(Br)ccc21)C(=O)O]
17. The compound, or a pharmaceutically acceptable salt thereof, of claim 1, having the formula
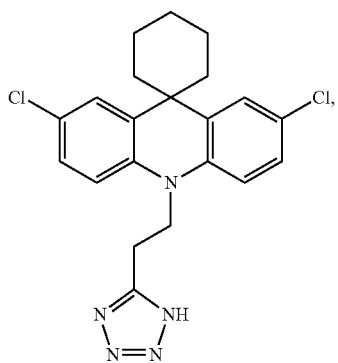
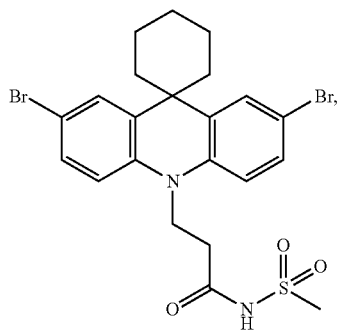
180
-continued
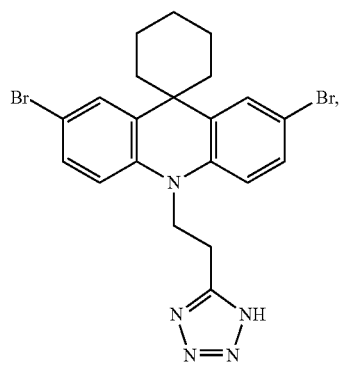
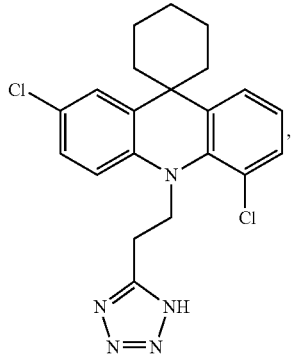
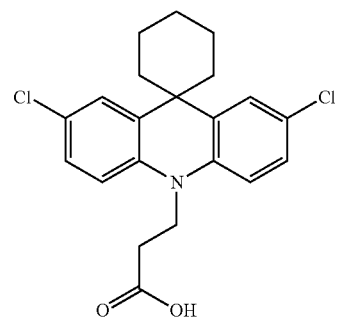
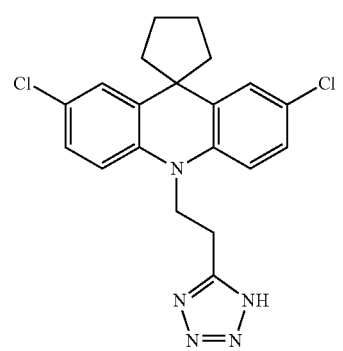

-continued

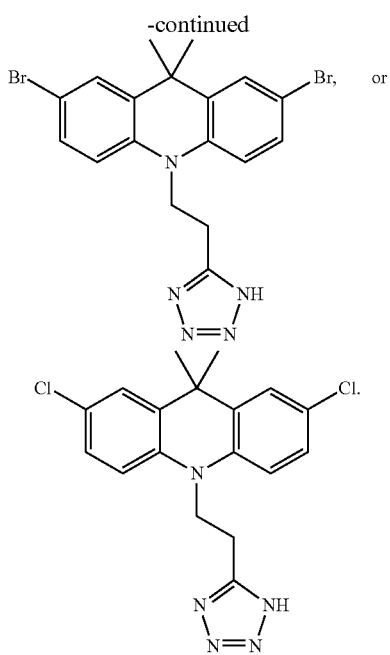

18. The compound, or a pharmaceutically acceptable salt thereof, of claim 1, having the formula

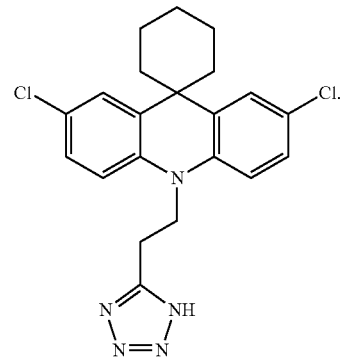 [SMILES: Clc1ccc2c(c1)C1(CCCCC1)c1cc(Cl)ccc1N2CCc1nnn[nH]1]

19. A method of treating a disease in a patient in need of such treatment, said method comprising administering a therapeutically effective amount of a compound of claim 1 to said patient, wherein said disease is selected from the group consisting of a neurological disease, pain, migraine, ischemic injury, brain ischemia, stroke, a neurodegenerative disease, a mood disorder, depression, and decompression sickness.

20. A method of increasing the level of activity of TREK-1 in a cell comprising contacting the cell with an effective amount of a compound of claim 1.

* * * * *